United States Patent
Baeuerle et al.

(10) Patent No.: US 11,242,376 B2
(45) Date of Patent: Feb. 8, 2022

(54) COMPOSITIONS AND METHODS FOR TCR REPROGRAMMING USING FUSION PROTEINS

(71) Applicant: TCR2 THERAPEUTICS INC., Cambridge, MA (US)

(72) Inventors: Patrick Baeuerle, Gauting (DE); Gregory Sieczkiewicz, Cambridge, MA (US); Robert Hofmeister, Scituate, MA (US)

(73) Assignee: TCR2 THERAPEUTICS INC., Cambridge, MA (US)

( * ) Notice: Subject to any disclaimer, the term of this patent is extended or adjusted under 35 U.S.C. 154(b) by 414 days.

(21) Appl. No.: 16/322,897

(22) PCT Filed: Aug. 2, 2017

(86) PCT No.: PCT/US2017/045159
§ 371 (c)(1),
(2) Date: Feb. 1, 2019

(87) PCT Pub. No.: WO2018/026953
PCT Pub. Date: Feb. 8, 2018

(65) Prior Publication Data
US 2019/0256571 A1    Aug. 22, 2019

Related U.S. Application Data

(60) Provisional application No. 62/370,189, filed on Aug. 2, 2016.

(51) Int. Cl.
| | | |
|---|---|---|
| *C07K 16/28* | (2006.01) | |
| *C07K 14/725* | (2006.01) | |
| *A61K 35/17* | (2015.01) | |
| *C07K 14/705* | (2006.01) | |
| *A61K 35/12* | (2015.01) | |
| *A61K 39/00* | (2006.01) | |

(52) U.S. Cl.
CPC .......... *C07K 14/7051* (2013.01); *A61K 35/17* (2013.01); *C07K 14/705* (2013.01); *C07K 14/70521* (2013.01); *C07K 16/2878* (2013.01); *A61K 2035/124* (2013.01); *A61K 2039/505* (2013.01); *C07K 2317/24* (2013.01); *C07K 2317/569* (2013.01); *C07K 2317/622* (2013.01); *C07K 2317/73* (2013.01); *C07K 2319/02* (2013.01); *C07K 2319/33* (2013.01); *C07K 2319/74* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,199,942 A | 4/1993 | Gillis |
| 5,225,539 A | 7/1993 | Winter |
| 5,350,674 A | 9/1994 | Boenisch et al. |
| 5,399,346 A | 3/1995 | Anderson et al. |
| 5,530,101 A | 6/1996 | Queen et al. |
| 5,565,332 A | 10/1996 | Hoogenboom et al. |
| 5,580,859 A | 12/1996 | Felgner et al. |
| 5,585,089 A | 12/1996 | Queen et al. |
| 5,585,362 A | 12/1996 | Wilson et al. |
| 5,589,466 A | 12/1996 | Felgner et al. |
| 5,766,886 A | 6/1998 | Studnicka et al. |
| 5,858,358 A | 1/1999 | June et al. |
| 5,883,223 A | 3/1999 | Gray |
| 6,120,766 A | 9/2000 | Hale et al. |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,534,055 B1 | 3/2003 | June et al. |
| 6,548,640 B1 | 4/2003 | Winter |
| 6,692,964 B1 | 2/2004 | June et al. |
| 6,797,514 B2 | 9/2004 | Berenson et al. |
| 6,867,041 B2 | 3/2005 | Berenson et al. |
| 6,887,466 B2 | 5/2005 | June et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,081,518 B1 | 7/2006 | Pastan et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 7,572,631 B2 | 8/2009 | Berenson et al. |

(Continued)

FOREIGN PATENT DOCUMENTS

| | | |
|---|---|---|
| EP | 0239400 A2 | 9/1987 |
| EP | 0519596 A1 | 12/1992 |

(Continued)

OTHER PUBLICATIONS

Koneru et al. IL-12 secreting tumor-targeted chimeric antigen receptor T cells eradicate ovarian tumors in vivo. OncoImmunology 4(3):e994446 (2015).
PCT/US2019/043690 International Search Report and Written Opinion dated Jan. 17, 2020.
Tully et al. The reconstruction of 2,631 draft metagenome-assembled genomes from the global oceans. Sci Data 5:170203 w/Supp. Information (2018).

(Continued)

*Primary Examiner* — Zachary S Skelding
(74) *Attorney, Agent, or Firm* — Wilson Sonsini Goodrich & Rosati

(57) ABSTRACT

Provided herein are T-cell receptor (TCR) fusion proteins (TFPs), T-cells engineered to express one or more TFPs, and methods of use thereof for the treatment of diseases, including cancer.

19 Claims, 28 Drawing Sheets

Specification includes a Sequence Listing.

(56) References Cited

U.S. PATENT DOCUMENTS

| | | |
|---|---|---|
| 7,695,936 B2 | 4/2010 | Carter et al. |
| 7,741,465 B1 | 6/2010 | Eshhar et al. |
| 8,206,710 B2 | 6/2012 | Ebel et al. |
| 8,389,282 B2 | 3/2013 | Sadelain et al. |
| 8,697,359 B1 | 4/2014 | Zhang |
| 8,911,732 B2 | 12/2014 | Dennis et al. |
| 9,023,351 B2 | 5/2015 | Kahnert et al. |
| 9,062,127 B2 | 6/2015 | Voss et al. |
| 9,102,736 B2 | 8/2015 | Hofmeister et al. |
| 9,115,197 B2 | 8/2015 | Ebel et al. |
| 9,181,527 B2 | 11/2015 | Sentman |
| 9,217,040 B2 | 12/2015 | Kipps et al. |
| 9,220,728 B2 | 12/2015 | Sadelain et al. |
| 9,272,002 B2 | 3/2016 | Powell, Jr. et al. |
| 9,316,646 B2 | 4/2016 | Rader et al. |
| 9,365,641 B2 | 6/2016 | June et al. |
| 9,393,257 B2 | 7/2016 | Osborn et al. |
| 9,416,190 B2 | 8/2016 | Ho et al. |
| 9,422,351 B2 | 8/2016 | Scholler et al. |
| 9,447,194 B2 | 9/2016 | Jensen et al. |
| 9,464,140 B2 | 10/2016 | June et al. |
| 9,758,586 B2 | 9/2017 | Rader et al. |
| 10,093,900 B2 | 10/2018 | Jantz et al. |
| 10,208,285 B2 | 2/2019 | Baeuerle et al. |
| 2002/0110855 A1 | 8/2002 | Sheppard et al. |
| 2004/0266390 A1 | 12/2004 | Faucher et al. |
| 2005/0042664 A1 | 2/2005 | Wu et al. |
| 2005/0048617 A1 | 3/2005 | Wu et al. |
| 2005/0100543 A1 | 5/2005 | Hansen et al. |
| 2005/0175606 A1 | 8/2005 | Huang et al. |
| 2006/0062780 A1 | 3/2006 | Zocher et al. |
| 2006/0121005 A1 | 6/2006 | Berenson et al. |
| 2007/0014794 A1 | 1/2007 | Carter et al. |
| 2008/0294058 A1 | 11/2008 | Shklarski |
| 2009/0047211 A1 | 2/2009 | Pastan et al. |
| 2009/0322513 A1 | 12/2009 | Hwang et al. |
| 2010/0003249 A1 | 1/2010 | Silence et al. |
| 2011/0189141 A1 | 8/2011 | Kieback et al. |
| 2013/0066283 A1 | 3/2013 | Alster et al. |
| 2013/0251642 A1 | 9/2013 | Rader et al. |
| 2013/0266551 A1 | 10/2013 | Campana et al. |
| 2013/0273073 A1 | 10/2013 | Kipps et al. |
| 2013/0280220 A1 | 10/2013 | Ahmed et al. |
| 2013/0295011 A1 | 11/2013 | Guise et al. |
| 2013/0315884 A1 | 11/2013 | Galetto et al. |
| 2013/0323214 A1 | 12/2013 | Gottschalk et al. |
| 2013/0323247 A1 | 12/2013 | Zugmaier et al. |
| 2014/0004132 A1 | 1/2014 | Brenner et al. |
| 2014/0050708 A1 | 2/2014 | Powell et al. |
| 2014/0099340 A1 | 4/2014 | June et al. |
| 2014/0227237 A1 | 8/2014 | June et al. |
| 2014/0271635 A1 | 9/2014 | Brogdon et al. |
| 2014/0286973 A1 | 9/2014 | Powell, Jr. et al. |
| 2014/0301993 A1 | 10/2014 | Powell, Jr. et al. |
| 2014/0308259 A1 | 10/2014 | Scholler et al. |
| 2014/0322212 A1 | 10/2014 | Brogdon et al. |
| 2014/0322216 A1 | 10/2014 | Kaplan |
| 2014/0370045 A1 | 12/2014 | June et al. |
| 2015/0031624 A1 | 1/2015 | Feldman et al. |
| 2015/0051266 A1 | 2/2015 | Kochenderfer |
| 2015/0093822 A1 | 4/2015 | June et al. |
| 2015/0190428 A1 | 7/2015 | June et al. |
| 2015/0203817 A1 | 7/2015 | Galetto et al. |
| 2015/0238631 A1 | 8/2015 | Kim et al. |
| 2015/0252110 A1 | 9/2015 | Hansen et al. |
| 2015/0284475 A1 | 10/2015 | Zhou et al. |
| 2015/0297640 A1 | 10/2015 | Cooper et al. |
| 2015/0306141 A1 | 10/2015 | Jensen et al. |
| 2015/0307564 A1 | 10/2015 | Young et al. |
| 2015/0322169 A1 | 11/2015 | June et al. |
| 2015/0329640 A1 | 11/2015 | Finer |
| 2015/0342993 A1 | 12/2015 | Kloss et al. |
| 2015/0344573 A1 | 12/2015 | Chang et al. |
| 2015/0344844 A1 | 12/2015 | Better et al. |
| 2015/0368360 A1 | 12/2015 | Liang et al. |
| 2015/0376287 A1 | 12/2015 | Vu et al. |
| 2015/0376296 A1 | 12/2015 | Fedorov et al. |
| 2016/0008398 A1 | 1/2016 | Sadelain et al. |
| 2016/0009813 A1 | 1/2016 | Themeli et al. |
| 2016/0015749 A1 | 1/2016 | Gottschalk et al. |
| 2016/0030479 A1 | 2/2016 | Abbot et al. |
| 2016/0039903 A1 | 2/2016 | Ring et al. |
| 2016/0040127 A1 | 2/2016 | Leventhal et al. |
| 2016/0045551 A1 | 2/2016 | Brentjens et al. |
| 2016/0046678 A1 | 2/2016 | Roschke et al. |
| 2016/0046724 A1 | 2/2016 | Brogdon et al. |
| 2016/0052990 A1 | 2/2016 | Ring et al. |
| 2016/0120906 A1 | 5/2016 | Galetto et al. |
| 2016/0120907 A1 | 5/2016 | Sentman |
| 2016/0122782 A1 | 5/2016 | Crisman et al. |
| 2016/0144026 A1 | 5/2016 | Lutteropp et al. |
| 2016/0145354 A1 | 5/2016 | Bacac et al. |
| 2016/0158359 A1 | 6/2016 | Gilbert |
| 2016/0168262 A1 | 6/2016 | Spriggs et al. |
| 2016/0176973 A1 | 6/2016 | Kufer et al. |
| 2016/0184362 A1 | 6/2016 | Duchateau et al. |
| 2016/0185861 A1 | 6/2016 | Bedoya et al. |
| 2016/0185862 A1 | 6/2016 | Wu et al. |
| 2016/0186165 A1 | 6/2016 | Dose et al. |
| 2016/0194375 A1 | 7/2016 | Kitchen et al. |
| 2016/0206656 A1 | 7/2016 | Gilbert |
| 2016/0207989 A1 | 7/2016 | Short |
| 2016/0208018 A1 | 7/2016 | Chen et al. |
| 2016/0215051 A1 | 7/2016 | Sharma et al. |
| 2016/0228547 A1 | 8/2016 | Wagner et al. |
| 2016/0235787 A1 | 8/2016 | June et al. |
| 2016/0237139 A1 | 8/2016 | Pulé et al. |
| 2016/0237407 A1 | 8/2016 | Wagner et al. |
| 2016/0256488 A1 | 9/2016 | Wu |
| 2016/0257762 A1 | 9/2016 | Kwon et al. |
| 2016/0264665 A1 | 9/2016 | Lim et al. |
| 2016/0272999 A1 | 9/2016 | Duchateau et al. |
| 2016/0289343 A1 | 10/2016 | Wu |
| 2016/0296633 A1 | 10/2016 | Goldenberg |
| 2016/0340406 A1 | 11/2016 | Zhao et al. |
| 2017/0166622 A1 | 6/2017 | Baeuerle et al. |
| 2017/0355766 A1 | 12/2017 | Zack et al. |
| 2018/0170992 A1 | 6/2018 | Balyasnikova et al. |
| 2018/0244747 A1 | 8/2018 | Baeuerle et al. |
| 2018/0251514 A1 | 9/2018 | Baeuerle et al. |
| 2019/0276540 A1 | 9/2019 | Baeuerle et al. |
| 2020/0207828 A1 | 7/2020 | Baeuerle et al. |
| 2020/0362011 A1 | 11/2020 | Baeuerle et al. |

FOREIGN PATENT DOCUMENTS

| | | |
|---|---|---|
| EP | 0592106 A1 | 4/1994 |
| EP | 0638119 A1 | 2/1995 |
| EP | 1075517 B1 | 7/2006 |
| EP | 2258719 A1 | 12/2010 |
| EP | 2258720 A1 | 12/2010 |
| EP | 2894164 A1 | 7/2015 |
| EP | 2342227 B1 | 10/2015 |
| EP | 2632954 B1 | 11/2015 |
| EP | 2953974 A1 | 12/2015 |
| EP | 2970472 A1 | 1/2016 |
| EP | 2982692 A1 | 2/2016 |
| EP | 2982696 A2 | 2/2016 |
| EP | 2361936 B1 | 4/2016 |
| EP | 3006459 A1 | 4/2016 |
| EP | 3018145 A1 | 5/2016 |
| EP | 3019622 A2 | 5/2016 |
| EP | 3023437 A1 | 5/2016 |
| EP | 2686417 B1 | 6/2016 |
| EP | 2982694 B1 | 6/2016 |
| EP | 3025719 A1 | 6/2016 |
| EP | 3029067 A1 | 6/2016 |
| EP | 3029068 A1 | 6/2016 |
| EP | 3057991 A1 | 8/2016 |
| EP | 3057994 A1 | 8/2016 |
| EP | 2370467 B1 | 9/2016 |
| EP | 3087101 A1 | 11/2016 |
| FR | 901228 A | 7/1945 |
| JP | H07505282 A | 6/1995 |

(56) References Cited

FOREIGN PATENT DOCUMENTS

| | | |
|---|---|---|
| JP | 2012508164 A | 4/2012 |
| KR | 20090092900 A | 9/2009 |
| WO | WO-9109967 A1 | 7/1991 |
| WO | WO-9317105 A1 | 9/1993 |
| WO | WO-0129058 A1 | 4/2001 |
| WO | WO-0196584 A2 | 12/2001 |
| WO | WO-2006020258 A2 | 2/2006 |
| WO | WO-2007024715 A2 | 3/2007 |
| WO | WO-2010052014 A1 | 5/2010 |
| WO | WO-2010104949 A2 | 9/2010 |
| WO | WO-2012076066 A1 | 6/2012 |
| WO | WO-2012138475 A1 | 10/2012 |
| WO | WO-2013040557 A2 | 3/2013 |
| WO | WO-2013063419 A2 | 5/2013 |
| WO | WO-2013072415 A1 | 5/2013 |
| WO | WO-2013126712 A1 | 8/2013 |
| WO | WO-2013154760 A1 | 10/2013 |
| WO | WO-2013176916 A1 | 11/2013 |
| WO | WO-2014153270 A1 | 9/2014 |
| WO | WO-2014184143 A1 | 11/2014 |
| WO | WO-2014190273 A1 | 11/2014 |
| WO | WO-2015092024 A2 | 6/2015 |
| WO | WO-2015095895 A1 | 6/2015 |
| WO | WO-2015107075 A1 | 7/2015 |
| WO | WO-2015112800 A1 | 7/2015 |
| WO | WO-2015112830 A1 | 7/2015 |
| WO | WO-2015121454 A1 | 8/2015 |
| WO | WO-2015123642 A1 | 8/2015 |
| WO | WO-2015124715 A1 | 8/2015 |
| WO | WO-2015142661 A1 | 9/2015 |
| WO | WO-2015142675 A2 | 9/2015 |
| WO | WO-2015158671 A1 | 10/2015 |
| WO | WO-2015164745 A1 | 10/2015 |
| WO | WO-2015168613 A2 | 11/2015 |
| WO | WO-2015177349 A1 | 11/2015 |
| WO | WO-2015179801 A1 | 11/2015 |
| WO | WO-2015188141 A2 | 12/2015 |
| WO | WO-2016011210 A2 | 1/2016 |
| WO | WO-2016014789 A2 | 1/2016 |
| WO | WO-2016016344 A1 | 2/2016 |
| WO | WO-2016019969 A1 | 2/2016 |
| WO | WO-2016025454 A2 | 2/2016 |
| WO | WO-2016030691 A1 | 3/2016 |
| WO | WO-2016036678 A1 | 3/2016 |
| WO | WO-2016040441 A1 | 3/2016 |
| WO | WO-2016044853 A1 | 3/2016 |
| WO | WO-2016054520 A2 | 4/2016 |
| WO | WO-2016055551 A1 | 4/2016 |
| WO | WO-2016070061 A1 | 5/2016 |
| WO | WO-2016073381 A1 | 5/2016 |
| WO | WO-2016079081 A1 | 5/2016 |
| WO | WO-2016087245 A1 | 6/2016 |
| WO | WO-2016090034 A2 | 6/2016 |
| WO | WO-2016090312 A1 | 6/2016 |
| WO | WO-2016090320 A1 | 6/2016 |
| WO | WO-2016090327 A2 | 6/2016 |
| WO | WO-2016097231 A2 | 6/2016 |
| WO | WO-2016115274 A1 | 7/2016 |
| WO | WO-2016115482 A1 | 7/2016 |
| WO | WO-2016116601 A1 | 7/2016 |
| WO | WO-2016123675 A1 | 8/2016 |
| WO | WO-2016126608 A1 | 8/2016 |
| WO | WO-2016127043 A1 | 8/2016 |
| WO | WO-2016127257 A1 | 8/2016 |
| WO | WO-2016132366 A1 | 8/2016 |
| WO | WO-2016151315 A1 | 9/2016 |
| WO | WO-2016161415 A2 | 10/2016 |
| WO | WO-2016187349 A1 | 11/2016 |
| WO | WO-2016203048 A1 | 12/2016 |
| WO | WO-2017112741 A1 | 6/2017 |
| WO | WO-2017173256 A1 | 10/2017 |
| WO | WO-2018026953 A1 | 2/2018 |
| WO | WO-2018067993 A1 | 4/2018 |
| WO | WO-2018098365 A2 | 5/2018 |
| WO | WO-2018119298 A1 | 6/2018 |
| WO | WO-2018200583 A1 | 11/2018 |
| WO | WO-2018232020 A1 | 12/2018 |
| WO | WO-2019173693 A1 | 9/2019 |
| WO | WO-2019222275 A2 | 11/2019 |
| WO | WO-2020023888 A2 | 1/2020 |
| WO | WO-2020047501 A1 | 3/2020 |

OTHER PUBLICATIONS

Abate-Daga et al. CAR models: next-generation CAR modifications for enhanced T-cell function. Mol Ther Oncolytics 3:16014 (2016).

Acuto et al. Tailoring T-cell receptor signals by proximal negative feedback mechanisms. Nat Rev Immunol 8(9):699-712 (2008).

Adusumilli et al. 342: A Phase 1 Clinical Trial of Malignant Pleural Disease Treated with Regionally Delivered Autologous Mesothelin-Targeted CAR T Cells: Safety and Efficacy—A Preliminary Report. Mol Therapy 26(5S1):158-159 (2018).

Adusumilli et al. Regional delivery of mesothelin-targeted CAR T cell therapy generates potent and long-lasting CD4-dependent tumor immunity. Sci Transl Med 6(261):261ra151 (2014) (w/Supplementary Data).

Agata et al. Expression of the PD-1 antigen on the surface of stimulated mouse T and B lymphocytes. Int Immunol 8:765-775 (1996).

Ager et al. Homing to solid cancers: a vascular checkpoint in adoptive cell therapy using CAR T-cells. Biochemical Society transactions. 44(2):377-385 (2016).

Almasbak et al. CAR T Cell Therapy: A Game Changer in Cancer Treatment. Journal of Immunology Research. 2016:1-10 (2016).

Al-Rawi et al. Interleukin-7 (IL-7) and IL-7 receptor (IL-7R) signalling complex in human solid tumours. Hist Histopathol 18:911-923 (2003).

Altschul et al. Basic local alignment search tool. J Mol Biol 215(3):403-410 (1990).

Altschul et al. Gapped BLAST and PSI-BLAST: a new generation of protein database search programs. Nucleic Acids Res 25:3389-3402 (1977).

Angelo et al. Antitumor Activity Associated with Prolonged Persistence of Adoptively Transferred NY-ESO-1c259 T cells in Synovial Sarcoma. Cancer Disov 8(8):944-957 (2018).

Ankri et al. Human T cells engineered to express a programmed death 1/28 costimulatory retargeting molecule display enhanced antitumor activity. J Immunol 191:4121-4129 (2013).

Baca et al. Antibody humanization using monovalent phage display. J Biol Chem 272(16):10678-10684 (1997).

Baeurle. Abstract No. A058. TRuC-T Cells Targeting CD19 or Mesothelin Demonstrate Superior Antitumor Activity in Preclinical Models Compared to CAR-T Cells (Poster session). Third CRI-CIMT-EATI-AACR International Cancer Immunotherapy Conference. URL:https://static1.squarespace.com/static/56dee-71e555986fb3ae583e2/t/59ad08b1b8a79b086c865d6c/1504512189107/CIMT_Abstracts_170904.pdf (1 pg.) (2017) [retrieved on Jan. 9, 2018].

Baeuerle et al. A Novel T Cell Therapy Engaging the Complete T Cell Receptor. (45 pgs) (2016).

Barretina et al. The Cancer Cell Line Encyclopedia enables predictive modelling of anticancer drug sensitivity. Nature 483:603-607 (2012).

Barrett et al. Eradication of established CD19-positive leukemia using a single injection of chimeric immunoreceptor modified lentiviral-transduced T cells in a xenograft NOG mouse model. Journal of Immunotherapy 32(9):941 (2009).

Barrett et al. Treatment of advanced leukemia in mice with mRNA engineered T cells. Hum Gene Ther 22:1575-1586 (2011).

Batlevi et al. Novel immunotherapies in lymphoid malignancies. Nat Rev Clin Oncol 13(1):25-40 (2016).

Batzer et al. Enhanced evolutionary PCR using oligonucleotides with inosine at the 3'-terminus. Nucleic Acid Res 19:5081 (1991).

Beatty et al. Activity of Mesothelin-specific Chimeric Antigen Receptor T cells Against Pancreatic Carcinoma Metastases in a Phase 1 Trial. Gastroenterology 5085(18)30323-30328 (accepted manuscript).

(56) References Cited

OTHER PUBLICATIONS

Beatty et al. Mesothelin-Specific Chimeric Antigen Receptor mRNA-Engineered T Cells Induce Antitumor Activity in Solid Malignancies. Cancer Immunol 3(2):217 (2015).
Beatty et al. Mesothelin-specific Chimeric Antigen Receptor mRNA-Engineered T cells Induce Anti-Tumor Activity in Solid Malignancies. Cancer Immunol Res 2(2):112-120 (2014).
Bezverbnaya et al. Tumor-targeting domains for chimeric antigen receptor T cells. Immunotherapy 9(1):33-46 (2017).
Billadeau et al. ITAMs versus ITIMs: striking a balance during cell regulation. J Clin Invest 109:161-168 (2002).
Bird et al. Single-chain antigen-binding proteins. Science 242(4877):423-426 (1988).
Blank et al. Interaction of PD-L1 on tumor cells with PD-1 on tumor-specific T cells as a mechanism of immune evasion: implications for tumor immunotherapy. Cancer Immunol Immunother 54:307-314 (2005).
Bonifant et al. Toxicity and management in CAR T-cell Therapy. Mol Ther Oncolytics 3:16011 (2016).
Brentjens et al. Genetically targeted T cells eradicate systemic acute lymphoblastic leukemia xenograft. Clin Cancer Res13:5426-5435 (2007).
Brentjens. Novel cellular therapies for leukemia: CAR-modified T cells targeted to the CD19 antigen. Hematology Am Soc Hematol Educ Program 2012:143-151 (2012).
Bridgeman et al. Building better chimeric antigen receptors for adoptive T cell therapy. Current Gene Therapy 10:77-90 (2010).
Bridgeman et al. Structural and biophysical determinants of αβ T-cell antigen recognition. Immunology 135(1):9-18 (2012).
Brudno et al. Allogeneic T cells that express an anti-CD19 chimeric antigen receptor induce remissions of B-cell malignancies that progress after allogeneic hematopoietic stem-cell transplantation without causing graft-versus-host disease. J Clin Oncol 34(10):1112-1121 (2016) .
Buck et al. Mitochondrial Dynamics Controls T Cell Fate through Metabolic Programming. Cell 166:63-76 (2016).
Budde et al. Combining a CD20 chimeric antigen receptor and an inducible caspase 9 suicide switch to improve the efficacy and safety of T cell adoptive immunotherapy for lymphoma. PLoS One 8(12):e82742 (2013).
Caldas et al. Design and synthesis of germline-based hemi-humanized single-chain Fv against the CD18 surface antigen. Protein Eng 13(5):353-360 (2000).
Call et al. The organizing principle in the formation of the T cell receptor-CD3 complex. Cell 111(7):967-979 (2002).
Carpenito et al. Control of large, established tumor xenografts with genetically retargeted human T cells containing CD28 and CD137 domains. PNAS USA 106(9):3360-3365 (2009).
Carpenter et al. B-cell maturation antigen is a promising target for adoptive T-cell therapy of multiple myeloma. Clin Cancer Res 19(8):2048-2060 (2013).
Cartellieri et al. Switching CAR T cells on and off: a novel modular platform for retargeting of T cells to AML blasts. Blood Cancer J 6(8):e458 (2016).
Carter et al. Humanization of an anti-p185HER2 antibody for human cancer therapy. PNAS USA 89(10):4285-4289 (1992).
Carter et al. PD-1: PD-L inhibitory pathway affects both CD4(+) and CD8(+) T cells and is overcome by IL-2. Eur J Immunol 32:634-643 (2002).
Chan et al. Chimeric antigen receptor-redirected CD45RA-negative T cells have potent antileukemia and pathogen memory response without graft-versus-host activity. Leukemia 29:387-395 (2015).
Chen et al. Novel anti-CD3 chimeric antigen receptor targeting of aggressive T cell malignancies. Oncotarget 7(35):56219-56232 (2016).
Chen et al. Oncology Meets Immunology: The Cancer-Immunity Cycle. Immunity 39(1):1-10 (2013).
Chhabra et al. TCR-Engineered, Customized, Antitumor T Cells for Cancer Immunotherapy: Advantages and Limitations. Scientific World Journal 11:121-129 (2011).

Chmielewski et al. Of CARs and TRUCKS: Chimeric antigen receptor (CAR) T cells engineered with an inducible cytokine to modulate the tumor stroma, Immunological Reviews 257(1):83-90 (2014).
Chothia et al. Canonical structures for the hypervariable regions of immunoglobulins. J Mol Biol. 196(4):901-917 (1987).
Chu et al. Targeting+ CD20 Aggressive B-cell Non-Hodgkin Lymphoma by Anti-CD20 CAR mRNA-Modified Expanded Natural Killer Cells In Vitro and in NSG Mice. Cancer Immunol Res 3(4):333-344 (2015).
Cieri et al. Adoptive immunotherapy with genetically modified lymphocytes in allogeneic stem cell transplantation. Immun Rev 257(1):165-180 (2014).
Cieri et al. IL-7 and IL-15 instruct the generation of human memory stem T cells from naive precursors. Blood 121(4):573-584 (2013).
Cooper. Adoptive transfer of T cells genetically modified using the Sleeping Beauty system. Adoptive Transfer Session. 24th iSBTc Annual Meeting (30 pgs) (Oct. 31, 2009).
Co-pending U.S. Appl. No. 16/222,846, filed Dec. 17, 2018.
Cougot et al. 'Cap-tabolism'. Trends in Biochem Sci 29:436-444 (2001).
Couto et al. Anti-BA46 monoclonal antibody Mc3: humanization using a novel positional consensus and in vivo and in vitro characterization. Cancer Res 55(8):1717-1722 (1995).
Couto et al. Designing human consensus antibodies with minimal positional templates. Cancer Res 55(23 Supp):5973s-5977s (1995).
Cristaudo et al. Clinical significance of serum mesothelin in patients with mesothelioma and lung cancer. Clin. Cancer Res. 13:5076-5081 (2007).
D'Agouges et al. Combination of rituximab with blinatumomab (MT103/MEDI-538), a T cell-engaging CD19-/CD3-bispecific antibody, for highly efficient lysis of human B lymphoma cells. Leukemia Res 33:465-473 (2009).
Davila. Efficacy and toxicity management of 19-28z CAR T cell therapy in B cell acute lymphoblastic leukemia. Sci Transl Med 6(224):224ra25 (2014).
Davila et al. How do CARs work? Early insights from recent clinical studies targeting CD19. Oncoimmunology 1(9):1577-1583 (2012).
Desmyter et al. Crystal structure of a camel single-domain VH antibody fragment in complex with lysozyme. Nat Struct Biol 3(9):803-811 (1996).
Dong et al. B7-H1 pathway and its role in the evasion of tumor immunity. J Mol Med 81:281-287 (2003).
Dopfer et al. The CD3 conformational change in the Gamma Delta T cell receptor is not triggered by antigens but can be enforced to enhance tumor killing. Cell Reports 7(5):1704-1715 (2014).
Dotti et al. Design and Development of Therapies using Chimeric Antigen Receptor-Expressing T cells. Immunol Rev. 257(1):35 pgs (2014).
Elango et al. Optimized transfection of mRNA transcribed from a d(A/T)100 tail-containing vector. Biochim Biophys Res Commun 330:958-966 (2005).
Eshhar et al. Chimeric T cell receptor which incorporates the anti-tumour specificity of a monoclonal antibody with the cytolytic activity of T cells: a model system for immunotherapeutical approach. Br J Cancer 62:27-29 (1990).
Eshhar et al., Design of cytotoxic T lymphocytes with antibody-type specificity against tumor cells using chimeric PCR. Journal of Cellular Biochemistry, A.R. Liss, Suppl. 14B: 70 (1990).
Fang et al. Immunotherapy for advanced melanoma. J Invest Derm 128(11):2596-2605 (2008).
Feng et al. A novel human monoclonal antibody that binds with high affinity to mesothelin-expressing cells and kills them by antibody-dependent cell-mediated cytotoxicity. Mol Cancer Ther 8(5):1113-1118.
Finney et al. Activation of resting human primary T cells with chimeric receptors: costimulation from CD28, inducible costimulator, CD134, and CD137 in series with signals from the TCR zeta chain. J Immunol 172:104-113 (2004).
Finney et al. Chimeric Receptors Providing Both Primary and Costimulatory Signaling in T Cells from a Single Gene Product. J Immunol 161:2791-2797 (1998).

(56) References Cited

OTHER PUBLICATIONS

Fraieitta et al. Ibrutinib enhances chimeric antigen receptor T-cell engraftment and efficacy in leukemia. Blood 127(9):1117-1127 (2016).
Freeman et al. Engagement of the PD-1 immunoinhibitory receptor by a novel B7 family member leads to negative regulation of lymphocyte activation. J Exp Med 192:1027-1034 (2000).
Frigault et al. Chimeric antigen receptor-modified T cells strike back. Int Immunol 28(7):355-363 (2016).
Gabrilovich et al. Myeloid-derived-suppressor cells as regulators of the immune system Nat Rev Immunol 9(3):162-174 (2009).
Garfall. Chimeric Antigen Receptor T Cells against CD19 for Multiple Myeloma. N Engl J Med 373(11):1040-1047 (2015).
Gargett et al. Different cytokine and stimulation conditions influence the expansion and immune phenotype of third-generation chimeric antigen receptor T cells specific for tumor antigen GD2. Cytotherapy 17(4):487-495 (2015).
Garland et al. The use of Teflon cell culture bags to expand functionally active CD8+ cytotoxic T lymphocytes. J Immunol Meth 227(1-2):53-63 (1999).
Garrido et al. The urgent need to recover MHC class I in cancers for effective immunotherapy. Current Opinion in Immunology 39:44-51 (2016).
Gattinoni et al. Paths to stemness: building the ultimate antitumour T cell. Nature Reviews Cancer 12(10):671-684 (2012).
Ghosh et al. Donor CD19 CAR T cells exert potent graft-versus-lymphoma activity with diminished graft-versus-host activity. Nature Medicine 23:242-249 (2017).
Gorochov et al. Functional assembly of chimeric T-cell receptor chains. Int J Cancer Supp 7:53-57 (1992).
Govers et al. TCRs Genetically Linked to CD28 and CD3ε Do Not Mispair with Endogenous TCR Chains and Mediate Enhanced T Cell Persistence and Anti-Melanoma Activity. J Immunol 193:5315-5326 (2014).
Griffin et al. Antibody fragments as tools in crystallography. Clin Exp Immunol 165(3):285-291 (2011).
Gross et al. Generation of effector T cells expressing chimeric T cell receptor with antibody type-specificity. Transplant Proc. 21(1 Pt 1):127-130 (1989).
Grupp et al. Chimeric antigen receptor-modified T cells for acute lymphoid leukemia. NEJM 368:1509-1518 (2013).
Guedan et al. ICOS-based chimeric antigen receptors program bipolar TH17/TH1 cells. Blood 124(7):1070-1080 (2014).
Guest et al. The role of extracellular spacer regions in the optimal design of chimeric immune receptors: evaluation of four different scFvs and antigens. J Immunother 28(3):203-211 (2005).
Guy et al. Distinct T cell receptor signaling pathways drive proliferation and cytokine production in T cells. Nat Immunol 14(3):262-270 (2013).
Haanen et al. Selective expansion of cross-reactive CD8(+) memory T cells by viral variants. J Exp Med 190(9):1319-1328 (1999).
Hassan et al. Major Cancer Regressions in Mesothelioma After Treatment with an Anti-Mesothelin Immunotoxin and Immune Suppression. Sci Transl Med 5:208ra147 (2013).
Hassan et al. Mesothelin: a new target for immunotherapy. Clin Cancer Res 10:3937-3942 (2004).
Hatzoglou et al. TNF receptor family member BCMA (B cell maturation) associates with TNF receptor-associated factor (TRAF) 1, TRAF2, and TRAF3 and activates NF-kappa B, elk-1, c-Jun N-terminal kinase, and p38 mitogen-activated protein kinase. Immunology 165(3):1322-1330 (2000).
Hicklin et al. HLA class I antigen downregulation in human cancers: T-cell immunotherapy revives and old story. Mol Med Today 5(4):178-186 (1999).
Ho et al. Mesothelin expression in human lung cancer. Clin Cancer Res 13:1571-1575 (2007).
Hollinger et al. "Diabodies": Small bivalent and bispeific antibody fragments. PNAS USA 90:6444 6448 (1993).

Holzinger et al. The growing world of CAR T cell trials: a systematic review, Cancer Immunology. Immunotherapy 65(12):1433-1450 (2016).
Hombach et al. T cell activation by antibody-like immunoreceptors: the position of the binding epitope within the target molecule determines the efficiency of activation of redirected T cells. J Immunol 178:4650-4657 (2007).
Huang et al. Driving an improved CAR for cancer immunotherapy. J Clin Invest 126(8):2795-2798 (2016).
Hudecek et al. The Nonsignaling Extracellular Spacer Domain of Chimeric Antigen Receptors Is Decisive for In Vivo Antitumor Activity. Cancer Immunol Res 3(2):125-135 (2015).
Huston et al. Protein engineering of antibody binding sites: recovery of specific activity in an anti-digoxin single-chain Fv analogue produced in *Escherichia coli*. PNAS USA 85(16):5879-5883 (1988).
Hwan et al. Universal Chimeric Antigen Receptors for Multiplexed and Logical Control of T Cell Responses. Cell 173(6):1426-1438. e11 (2018).
Hwu et al., The genetic modification of T cells for cancer therapy: an overview of laboratory and clinical trials. Cancer Detect Prev. 18(1):43-50 (1994).
Illei et al. Mesothelin Expression in Advanced Gastroesophageal Cancer Represents a Novel Target for Immunotherapy. Appl Immunohistochem Mol Morphol 24(4):246-252 (2016).
Institute for Clinical and Economic review (ICER). Chimeric Antigen Receptor T-Cell Therapy for B-Cell Cancers: Effectiveness and Value. Final Evidence Report dated Mar. 23, 2018 (185 pgs).
Iwahori et al. Engager T cells: a new class of antigen-specific T cells that redirect bystander T cells. Mol Ther 23(1):171-178 (2015).
Izumoto et al. Phase II clinical trial of Wilms tumor 1 peptide vaccination for patients with recurrent glioblastoma multiforme. J Neurosurg 108:963-971 (2008).
Jackson et al. Driving CAR T-cells forward. Nat Rev Clin Oncol 13(6):370-383 (2016).
Jacoby. CD19 CAR immune pressure induces B-precursor acute lymphoblastic leukaemia lineage switch exposing inherent leukaemic plasticity. Nat Commun 7:12320 (2016).
Jacoby et al. Murine models of acute leukemia: important tools in current pediatric leukemia research. Front Oncol 4:95 (2014).
James et al. Antigen sensitivity of CD22-specific chimeric TCR is modulated by target epitope distance from the cell membrane. J Immunol 180:7028-7038 (2008).
Jamnani et al. T cells expressing VHH-directed oligoclonal chimeric HER2 antigen receptors: towards tumor-directed oligoclonal T cell therapy. Biochim Biophys Acta 1840(1):378-386 (2014).
Jena et al. Chimeric antigen receptor (CAR)-specific monoclonal antibody to detect CD19-specific T cells in clinical trials. PLoS One. 8(3):e57838 (2013).
Jin et al. Safe engineering of CAR T cells for adoptive cell therapy of cancer using long-term episomal gene transfer. EMBO Mol Med 8(7):702-711 (2016).
John et al. Anti-PD-1 antibody therapy potently enhances the eradication of established tumors by gene-modified T cells. Clin Cancer Res 19(20):5636-5646 (2013).
Johnson et al. Rational development and characterization of humanized anti-EGFR variant III chimeric antigen receptor T cells for glioblastoma. Immunotherapy 7(275):275ra22 (2015).
Jones et al. Replacing the complementarity-determining regions in a human antibody with those from a mouse. Nature 321:522-525 (1986).
Jonnalagadda et al. Chimeric Antigen Receptors With Mutated IgG4 Fc Spacer Avoid Fc Receptor Binding and Improve T Cell Persistence and Antitumor Efficacy. Mol Ther 23(4):757-768 (2015).
June et al. Chimeric Antigen Receptor Therapy. N Engl J Med 379:64-73 (2018).
June et al. Engineering lymphocyte subsets: tools, trials and tribulations. Nat Rev Immunol 9.10:704-716 (2009).
June et al. Is autoimmunity the Achilles' heel of cancer immunotherapy? Nat Med 23(5):540-547 (2017).
Junghans. The challenges of solid tumor for designer CAR-T therapies: a 25-year perspective. Cancer Gene Ther 24(3):89-99 (2017).

(56) References Cited

OTHER PUBLICATIONS

Kabat et al. Sequences of Proteins of Immunological Interest. NIH Pub. No. 91-3242. Public Health Service, National Institutes of Health. 1:647-669 (1991).
Kachala et al. Mesothelin Overexpression Is a Marker of Tumor Aggressiveness and Is Associated with Reduced Recurrence-Free and Overall Survival in Early-Stage Lung Adenocarcinoma. Clin Cancer Res 20(4):1020-1028 (2013).
Kaiser. Towards a commercial process for the manufacture of genetically modified T cells for therapy. Cancer Gene Thera 22(2):72-78 (2015).
Kalos et al. T cells with chimeric antigen receptors have potent antitumor effects and can establish memory in patients with advanced leukemia. Sci Transl Med 3(95):95ra73 (2011).
Karlsson et al. Evaluation of Intracellular Signaling Downstream Chimeric Antigen Receptors. PLoS One 10(12):e0144787 (2015).
Kawalekar et al. Distinct Signaling of Coreceptors Regulates Specific Metabolism Pathways and Impacts Memory Development in CAR T Cells. Immunity 44(2):380-390 (2016).
Kawalekar et al. Supplemental Information. Distinct Signaling of Coreceptors Regulates Specific Metabolism Pathways and Impacts Memory Development in CAR T Cells. Immunity 44(2):380-390 (2016).
Kebriaei et al. Phase I trials using Sleeping Beauty to generate CD19-specific CAR T cells. J Clin Invest 126(9):3363-3376 (2016).
Kershaw et al. Gene-engineered T cells for cancer therapy. Nat Rev Cancer 13(8):525-541 (2013).
Klebanoff et al. Memory T cell-driven differentiation of naive cells impairs adoptive immunotherapy. J Clin Invest 126(1):318-334 (2016).
Klebanoff et al. Prospects for gene-engineered T cell immunotherapy for solid cancers. Nat Med 22(1):26-36 (2016).
Knies et al. An optimized single chain TCR scaffold relying on the assembly with the native CD3-complex prevents residual mispairing with endogenous TCRs in human T-cells. Oncotarget 7(16):21199-211221 (2016).
Kochenderfer et al. B-cell depletion and remissions of malignancy along with cytokine-associated toxicity in a clinical trial of anti-CD19 chimeric-antigen-receptor-transduced T cells. Blood 119(12):2709-2720 (2012).
Kochenderfer et al. Construction and Pre-clinical Evaluation of an Anti-CD19 Chimeric Antigen Receptor. Immunotherapy 32(7):689-702 (2010).
Kojima et al. Molecular cloning and expression of megakaryocyte potentiating factor cDNA. J Biol Chem 270:21984-21990 (1995).
Konishi et al. B7-H1 expression on non-small cell lung cancer cells and its relationship with tumor-infiltrating lymphocytes and their PD-1 expression. Clin Cancer Res 10:5094-5100 (2004).
Kowolik et al. CD28 costimulation provided through a CD19-specific chimeric antigen receptor enhances in vivo persistence and antitumor efficacy of adoptively transferred T cells. Cancer Res 66(22):10995-11004 (2006).
Krenciute et al. Characterization and Functional Analysis of scFv-based Chimeric Antigen Receptors to Redirect T Cells to IL13Rα2-positive Glioma. Mol Ther 24(2):354-363 (2016).
Kuhns et al. TCR Signaling Emerges from the Sum of Many Parts. Front. Immunol. 3:159 (2012).
Kunert et al. TCR-engineered T cells meet new challenges to treat solid tumors: Choice of antigen, T cell fitness, and sensitization of tumor milieu. Front Immun 4:363 (2013).
Kunkele et al. Functional Tuning of CARs Reveals Signaling Threshold above Which CD8+ CTL Antitumor Potency Is Attenuated due to Cell Fas-FasL-Dependent AICD. Cancer Immunol Res 3(4):368-379 (2015).
Laabi et al. A new gene, BCM, on chromosome 16 is fused to the interleukin 2 gene by a t(4;16)(q26;p13) translocation in a malignant T cell lymphoma. EMBO 11(11):3897-3904 (1992).
Laabi et al. The BCMA gene, preferentially expressed during B lymphoid maturation, is bidirectionally transcribed. Nucleic Acids Res 22(7):1147-1154 (1994).
Langer. Comparative Evaluation of Peripheral Blood T Cells and Resultant Engineered Anti-CD19 CAR T-Cell Products From Patients With Relapsed / Refractory Non-Hodgkin Lymphoma (NHL). Abstract 2305 AACR Apr. 16-20, 2016 (1 pg.).
Lanier. NKG2D Receptor and Its Ligands in Host Defense. Cancer Immunol Res. 3(6):575-582 (2015).
Lanitis et al. Chimeric antigen receptor T Cells with dissociated signaling domains exhibit focused antitumor activity with reduced potential for toxicity in vivo. Cancer Immunol Res 1(1):45-53 (2013).
Lanitis et al. Redirected Antitumor Activity of Primary Human Lymphocytes Transduced With a Fully Human Anti-mesothelin Chimeric Receptor. Mol Ther 20(3):633-643 (2012).
Lanzavecchia et al. The use of hybrid hybridomas to target human cytotoxic T lymphocytes. Eur J Immunol. 17(1):105-111 (1987).
Latchman et al. PD-L2 is a second ligand for PD-1 and inhibits T cell activation. Nat Immunol 2:261-268 (2001).
Lee et al. Current concepts in the diagnosis and management of cytokine release syndrome. Blood 124(2):188-196 (2014).
Lee et al. T cells expressing CD19 chimeric antigen receptors for acute lymphoblastic leukaemia in children and young adults: A phase 1 dose-escalation trial. The Lancet 385(9967):517-528 (2014).
Lee. Solid-state target CAR-T, 'TRUC platform' (KR). Biol.co.kr Retrieved from the Internet: URL:http://www.biospectator.com/view/news_ print.php?varAtcId=4037 (7 pgs.) (2017) [retrieved on Jan. 9, 2018] (Machine translation).
Leone et al. MHC Class I Antigen Processing and Presenting Machinery: Organization, Function, and Defects in Tumor Cells. J Natl Cancer Inst 105:1172-1187 (2013).
Li et al. Adoptive immunotherapy using T lymphocytes redirected to glypican-3 for the treatment of lung squamous cell carcinoma. Oncotarget 7(3):2496-2507 (2015).
Li et al. Enhanced Cancer Immunotherapy by Chimeric Antigen Receptor-Modified T Cells Engineered to Secrete Checkpoint Inhibitors. Clin Cancer Res 23(22):6982-6992 (2017).
Lipowska-Bhalla et al. Targeted immunotherapy of cancer with CAR T cells: Achievements and challenges. Cancer Immunol Immuno 61(7):953-962 (2012).
Liu et al. A Chimeric Switch-Receptor Targeting PD1 Augments the Efficacy of Second-Generation CAR T Cells in Advanced Solid Tumors. Cancer Res 76(6):1578-1590 (2016).
Liu et al. Affinity-Tuned ErbB2 or EGFR Chimeric Antigen Receptor T Cells Exhibit an Increased Therapeutic Index against Tumors in Mice. Cancer Res 75(17):3596-3607 (2015).
Liu et al. Improved anti-leukemia activities of adoptively transferred T cells expressing bispecific T-cell engager in mice. Blood Cancer J 6:e430 (2016).
Liu et al. Supplemental Information. A Chimeric Switch-Receptor Targeting PD1 Augments the Efficacy of Second-Generation CAR T Cells in Advanced Solid Tumors. Cancer Res 76(6):1578-1590 (2016).
Long et al. 4-1BB Costimulation Ameliorates T Cell Exhaustion Induced by Tonic Signaling of Chimeric Antigen Receptors. Nat Med 21(6):581-590 (2015).
Lu et al. Treatment of Patients With Metastatic Cancer Using a Major Histocompatibility Complex Class II-Restricted T-Cell Receptor Targeting the Cancer Germline Antigen MAGE-A3. J Clin Oncol 35(29):3322-3329.
Ma et al. Recognition of mesothelin by the therapeutic antibody MORAb-009: structural and mechanistic insights. J Biol Chem 287:33123-33131(2012).
Ma et al. Versatile strategy for controlling the specificity and activity of engineered T cells. PNAS 113(4):E450-E458 (2016).
Maher et al. Human T-lymphocyte cytotoxicity and proliferation directed by a single chimeric TCRzeta /CD28 receptor. Nat Biotech 20(1):70-75 (2002).
Mahmoud et al. Enforced CD19 expression leads to growth inhibition and reduced tumorigenicity. Blood 94(10):3551-3558 (1999).
Maude et al. CD19-targeted chimeric antigen receptor T-cell therapy for acute lymphoblastic leukemia. Blood 125(26):4017-4024 (2015).
Maus et al. Adoptive immunotherapy for cancer of viruses. Annual Review of Immunology 32:189-225 (2014).

(56) References Cited

OTHER PUBLICATIONS

Maus et al. Ex vivo expansion of polyclonal and antigen-specific cytotoxic T lymphocytes by artificial APCs expressing ligands for the T-cell receptor, CD28 and 4-1BB. Nature Biotech 20(2):143-148 (2002).
Maus et al. Making Better Chimeric Antigen Receptors for Adoptive T-cell Therapy. Clin Cancer Res 22(8):1875-1884 (2016).
Maus et al. T Cells Expressing Chimeric Antigen Receptors Can Cause Anaphylaxis in Humans. Cancer Immunol Res. 1:26-31 (2013).
Maus et al. Zoom zoom: Racing CARs for multiple myeloma. Clin Cancer Res 19(8):1917-1919 (2013).
Menk et al. 4-1BB costimulation induces T cell mitochondrial function and biogenesis enabling cancer immunotherapeutic responses. J Exp Med 215(4):1091-1100 (2018).
Merry et al. O-glycan sialylation and the structure of the stalk-like region of the T cell co-receptor CD8. J Biol Chem 278(29):27119-27128 (2003).
Miller et al. CD19-Targeted CAR T Cells: A New Tool in the Fight against B Cell Malignancies. Oncol Res Treat 38(12):683-690 (2015).
Milone et al. Chimeric receptors containing CD137 signal transduction domains mediate enhanced survival of T cells and increased antileukemic efficacy in vivo. Mol Ther 17(8):1453-1464 (2009).
Minguet et al. A permissive geometry model for TCR-CD3 activation. Trends in Biochemical Sciences 33(2):51-57 (2008).
Minguet et al. Full Activation of the T Cell Receptor Requires Both Clustering and Conformational Changes at CD3. Immunity 26(1):43-54 (2007).
Moon et al. Expression of a functional CCR2 receptor enhances tumor localization and tumor eradication by retargeted human T cells expressing a mesothelin-specific chimeric antibody receptor. Clin Cancer Res 17(14):4719-4730 (2011).
Morea et al. Antibody modeling: implications for engineering and design. Methods 20(3):267-279 (2000).
Morello et al. Mesothelin-Targeted CARs: Driving T Cells to Solid Tumors. Cancer Discov 6(2):133-146 (2016).
Morton et al. Establishment of human tumor xenografts in immunodeficient mice. Nat Procol 2:247 (2007).
Moynihan et al. Eradication of large established tumors in mice by combination immunotherapy that engages innate and adaptive immune responses. Nat Med 12(22):1402-1410 (2016).
Mumtaz et al. Design of liposomes for circumventing the reticuloendothelial cells. Glycobiology 5:505-510 (1991).
Nacheva et al. Preventing nondesired RNA-primed RNA extension catalyzed by T7 RNA polymerase. Eur J Biochem 270:1458-1465 (2003).
Needleman et al. A general method applicable to the search for similarities in the amino acid sequence of two proteins. J. Mol. Biol. 48:443-453 (1970).
Newick et al. Chimeric antigen receptor T-cell therapy for solid tumors. Molecular Therapy—Oncolytics 3:16006 (2016).
Nicholson et al. Construction and characterisation of a functional CD19 specific single chain Fv fragment for immunotherapy of B lineage leukaemia and lymphoma. Mol Immun 34(16-17):1157-1165 (1997).
Nishikawa et al. Nonviral vectors in the new millennium: delivery barriers in gene transfer. Human Gene Therapy. 12:861-870 (2001).
Nolan et al. Bypassing immunization: optimized design of "designer T cells" against carcinoembryonic antigen (CEA)-expressing tumors, and lack of suppression by soluble CEA. Clin Cancer Res 5:3928-3941 (1999).
Oden et al. Potent anti-tumor response by targeting B cell maturation antigen (BCMA) in a mouse model of multiple myeloma. Mole Oncol 9(7):1348-1358 (2015).
O'Hare et al. Mesothelin as a target for chimeric antigen receptor-modified T cells as anticancer therapy. Immunotherapy 8(4):449-460 (2016).
Ohtsuka et al. An alternative approach to deoxyoligonucleotides as hybridization probes by insertion of Deoxyinosine at Ambiguous Codon Positions. J Biol Chem 260(5):2605-2608 (Mar. 10, 1985).
Onda et al. Megakaryocyte potentiation factor cleaved from mesothelin precursor is a useful tumor marker in the serum of patients with mesothelioma. Clin Cancer Res. 12:4225-4231 (2006).
Onda et al. New Monoclonal Antibodies to Mesothelin Useful for Immunohistochemistry, Fluorescence-Activated Cell Sorting, Western Blotting, and ELISA. Clin Cancer Res 11(16):5840-5846 (2005).
Padlan. A possible procedure for reducing the immunogenicity of antibody variable domains while preserving their ligand-binding properties. Mol Immunol 28(4-5):489-498 (1991).
Park et al. Adoptive Immunotherapy for B-cell Malignancies with Autologous Chimeric Antigen Receptor Modified Tumor Targeted T Cells. Disc Med 9(47)277-288 (2010).
Pastan et al. Discovery of Mesothelin and Exploiting It as a Target for Immunotherapy. Cancer Res 74(11):2907-2912 (2014).
Patel et al. Engineering an APRIL-specific B Cell Maturation Antigen. J Bio Chem 279(16):16727-16735 (2004).
Patel et al. PDL-1 Expression as a Predictive Biomarker in cancer Immunotherapy. Mol Cancer Ther 14(4):847-856 (2015).
PCT/US2016/033146 International Preliminary Report on Patentability dated Nov. 30, 2017.
PCT/US2016/033146 International Search Report and Written Opinion dated Oct. 20, 2016.
PCT/US2017/045159 International Search Report and Written Opinion dated Nov. 3, 2017.
PCT/US2017/055628 International Search Report and Written Opinion dated Jan. 24, 2018.
PCT/US2017/063137 International Search Report and Written Opinion dated Jun. 14, 2018.
PCT/US2017/068002 International Search Report and Written Opinion dated Apr. 12, 2018.
PCT/US2018/037387 International Search Report and Written Opinion dated Sep. 17, 2018.
Pearson, et al. Improved Tools for Biological Sequence Comparison. Proc. Nat'l Acad. Sci. USA. 85 (1988): 2444-48.
Pedersen et al. Comparison of surface accessible residues in human and murine immunoglobulin Fv domains. Implication for humanization of murine antibodies. J Mol Biol 235(3):959-973 (1994).
Philip et al. A highly compact epitope-based marker suicide gene for safer and easier adoptive T-cell gene therapy. Blood 124:1277-1287 (2014).
Porter et al. Chimeric antigen receptor T cells persist and induce sustained remissions in relapsed refractory chronic lymphocytic leukemia. Sci Trans Med 7(303):303ra319 (2015).
Porter et al. Chimeric antigen receptor-modified T cells in chronic lymphoid leukemia. NEJM 365:725-733 (2011).
Porter et al. Pilot study of redirected autologous t cells engineered to contain anti-CD19 attached to TCRZ and 4-1BB signaling domains in patients with chemotherapy resistant or refractory CD19+ leukemia and lymphoma. NCT02374333. Available at https://www.clinicaltrials.gov/ct2/show/NCT02374333?term=13BT022 (3 pgs.) (2016).
Posey et al. Engineered CAR T Cells Targeting the Cancer-Associated Tn-Glycoform of theMembraneMucinMUC1 Control Adenocarcinoma. Immunity 44:1444-1454 (2016).
Presta. Antibody Engineering. Curr Op Struct Biol 2:593-596 (1992).
Presta et al. Humanization of an antibody directed against IgE. J Immunol 151:2623-2632 (1993).
Pule et al. A chimeric T cell antigen receptor that augments cytokine release and supports clonal expansion of primary human T cells. Mol Ther 12(5):933-941 (2005).
Punt et al. Stoichiometry of the T cell antigen receptor (TCR) complex: each TCR/CD3 complex contains one TCR alpha, one TCR beta, and two CD3 epsilon chains. J Exp Med 180(2):587-593 (1994).
Riechmann et al. Reshaping human antibodies for therapy. Nature, 332.6162 (1988): 323-7.
Rivadeneira et al. Antitumor T cell reconditioning: improving metabolic fitness for optimal cancer immunotherapy. Clin Cancer Res 24(11):2473-2481 (2018).

(56) References Cited

OTHER PUBLICATIONS

Rodgers et al. Switch-mediated activation and retargeting of CAR-T cells for B-cell malignancies. PNAS USA 113(4):E459-E468 (2016).
Roguska et al. A comparison of two murine monoclonal antibodies humanized by CDR-grafting and variable domain resurfacing. Protein Eng 9(10):895-904 (1996).
Roguska et al. Humanization of murine monoclonal antibodies through variable domain resurfacing. PNAS 91:969-973 (1994).
Rosenberg. Cell transfer immunotherapy for metastatic solid cancer—what clinicians need to know. Nat Rev Clin Oncol 8(10):577-585 (2011).
Rosenberg et al. Adoptive cell transfer as personalized immunotherapy for human cancer. Science 348(6230):62-68 (2015).
Rosenberg et al. Use of tumor-infiltrating lymphocytes and interleukin-2 in the immunotherapy of patients with metastatic melanoma. A preliminary report. NEJM 319:1676 (1988).
Rossolini et al. Use of deoxyinosine-containing primers vs degenerate primers for polymerase chain reaction based on ambiguous sequence information. Mol Cell Probes 8(2):91-98 (1994).
Roybal et al. Precision Tumor Recognition by T Cells With Combinatorial Antigen-Sensing Circuits. Cell 164:1-10 (2016).
Ruella et al. Smart CARS: optimized development of a chimeric antigen receptor (CAR) T cell targeting epidermal growth factor receptor variant III (EGFRvIII) for glioblastoma. Ann Transl Med 4(1):13 (2016).
Rump et al. Binding of ovarian cancer antigen CA125/MUC16 to mesothelin mediates cell adhesion. J Biol Chem 279:9190-9198 (2004).
Rushworth et al. Universal Artificial Antigen Presenting Cells to Selectively Propagate T Cells Expressing Chimeric Antigen Receptor Independent of Specificity. J Immunother 37(4):204-213 (2014).
Sadelain. CAR therapy: The CD19 paradigm. J Clin Invest 135(9):3392-3400 (2015).
Sadelain et al. Tales of Antigen Evasion from CAR Therapy. Cancer Immunol Res 4(6):473 (2016).
Sadelain et al. The Basic Principles of Chimeric Antigen Receptor Design. Cancer Discov 3(4):388-398 (2013).
Sadelain et al. Therapeutic T cell engineering. Nature 545:423-431 (2017).
Sakemura et al. A Tet-On Inducible System for Controlling CD19-Chimeric Antigen Receptor Expression upon Drug Administration. Cancer Immunol Res 4(8):658-668 (2016).
Sander et al. CRISPR-Cas systems for editing, regulating and targeting genomes. Nat. Biotechnol 32:347-355 (2014).
Sandhu. A rapid procedure for the humanization of monoclonal antibodies. Gene 150(2):409-410 (1994).
Sapede et al. Aberrant splicing and protease involvement in mesothelin release from epithelioid mesothelioma cells. Cancer Sci 99(3):590-594 (2008).
Schenborn et al. A novel transcription property of SP6 and T7 RNA polymerases: dependence on template structure. Nuc Acids Res 13:6223-6236 (1985).
Servais et al. An In Vivo Platform for Tumor Biomarker Assessment. PloS One 6(10):e26772.
Sharpe et al. Genetically modified T cells in cancer therapy: opportunities and challenges. Dis Model Mech 8(4):337-350 (2015).
Shin et al. Positive conversion of negative signaling of CTLA4 potentiates antitumor efficacy of adoptive T-cell therapy in murine tumor models. Blood 119(24):5678-5687 (2012).
Simon et al. PD-1 expression conditions T cell avidity within an antigen-specific repertoire. Oncoimmunology 5(1):e1104448 (2015).
Sims et al. A humanized CD18 antibody can block function without cell destruction. J Immunol., 151 (1993): 2296-2308.
Smith, et al. Comparison of Biosequences. Advances in Applied Mathematics. 1981;2: 482-489.
Sommers et al. Function of CD3ε-mediated Signals in T Cell Development. J Exper Med 192(6):913-920 (2000).
Song et al. CD27 costimulation augments the survival and antitumor activity of redirected human T cells in vivo. Blood 119(3):696-706 (2012).
Song et al. In Vivo Persistence, Tumor Localization, and Antitumor Activity of CAR-Engineered T Cells Is Enhanced by Costimulatory Signaling through CD137 (4-1BB). Cancer Res 71(13):4617-4627 (2011).
Spear et al. Collaboration of chimeric antigen receptor (CAR)-expressing T cells and host T cells for optimal elimination of established ovarian tumors. Oncoimmunology 2(4):e23564 (2013).
Srivastava et al. Engineering CAR-T cells: Design concepts. Trends Immunol 36(8):494-502 (2015).
Stepinski et al. Synthesis and properties of mRNAs containing the novel 'anti-reverse' cap analogs 7-methyl(3'0-methyl)GpppG and 7-methyl(e'-deoxy)GpppG. RNA 7:1486-1495 (2001).
Stone et al. A novel T cell receptor single-chain signaling complex mediates antigen-specific T cell activity and tumor control. Cancer Immunol Immunother 63(11):1163-1176 (2014).
Stromnes et al. T Cells Engineered against a Native Antigen Can Surmount Immunologic and Physical Barriers to Treat Pancreatic Ductal Adenocarcinoma. Cancer Cell 28:638-652 (2015).
Studnicka et al. Human-engineered monoclonal antibodies retain full specific binding activity by preserving non-CDR complementarity-modulating residues. Pro Eng 7(6):805-814 (1994).
Sun et al. The quest for spatio-temporal control of CAR T cells. Cell Res 25(12):1281-1282 (2015).
Tan et al. "Superhumanized" antibodies: reduction of immunogenic potential by complementarity-determining region grafting with human germline sequences: application to an anti-CD28. J Immunol 169:1119-1125 (2002).
Tang et al. A human single-domain antibody elicits potent antitumor activity by targeting an epitope in mesothelin close to the cancer cell surface. Mol. Cancer Thera 12(4):416-426 (2013).
Tanyi et al. Possible Compartmental Cytokine Release Syndrome in a Patient With Recurrent Ovarian Cancer After Treatment With Mesothelin-targeted CAR-T Cells. J Immunother 40(3):104-107 (2017).
Tchou et al. Safety and efficacy of intratumoral injections of chimeric antigen receptor (CAR) T cells in metastatic breast cancer. Cancer Immunol Res 5(12):1152-1161 (2017).
TCR2 Therapeutics Presents Positive Solid Tumor Data for its Novel TRuC™ Engineered T Cell Therapies at the World Preclinical Congress. PRNewswire. Available at http://www.prnewswire.com/news-releases/tcr2-therapeutics-presents-positive-solid-tumor-data-for-its-novel-truc-engineered-t-cell-therapies-at-the-world-preclinical-congress-300472629.html (Jun. 13, 2017) (2 pgs.).
Teachey. Identification of Predictive Biomarkers for Cytokine Release Syndrome after Chimeric Antigen Receptor T cell Therapy for Acute Lymphoblastic Leukemia. Cancer Disc 6(6):664-679 (2016).
Ten Berg et al. Selective expansion of a peripheral blood CD8+ memory T cell subset expressing both granzyme B and L-selectin during primary viral infection in renal allograft recipients. Transplant Proc 30(8):3975-3977 (1998).
Themeli et al. Generation of tumor-targeted human T lymphocytes from induced pluripotent stem cells for cancer therapy. Nat Biotech 31:928-933 (2013).
Themeli et al. New cell sources for T cell engineering and adoptive immunotherapy. Cell Stem Cell 16(4):357-366 (2015).
Thokala et al. Redirecting Specificity of T cells Using the Sleeping Beauty System to Express Chimeric Antigen Receptors by Mix-and-Matching of VL and VH Domains Targeting CD123+ Tumors. PLoS One 11(8):e0159477 (2016).
Torikai et al. A foundation for universal T-cell based immunotherapy: T cells engineered to express a CD19-specific chimeric-antigen-receptor and eliminate expression of endogenous TCR. Blood 119(24):5697-5705 (2012).
Torikai et al. Translational Implications for Off-the-shelf Immune Cells Expressing Chimeric Antigen Receptors. Mol Ther 24(7):1178-1186 (2016).
Tran et al. Cancer Immunotherapy Based on Mutation-Specific CD4+ T Cells in a Patient with Epithelial Cancer. Science 9:641-645 (2014).
Tsai et al. Producer T cells: Using genetically engineered T cells as vehicles to generate and deliver therapeutics to tumors. Oncoimmunol 5(5):e1122158 (2016).

(56) References Cited

OTHER PUBLICATIONS

Tumaini et al. Simplified process for the production of anti-CD19-CAR engineered T cells. Cytotherapy 15(11):1406-1415 (2014).
Turtle et al. CD19 CAR-T cells of defined CD4+:CD8+ composition in adult B cell ALL patients. J Clin Invest 126(6):2123-2138 (2016).
UI-TEI et al. Sensitive assay of RNA interference in *Drosophila* and Chinese hamster cultured cells using firefly luciferase gene as target. FEBS Letters 479: 79-82 (2000).
U.S. Appl. No. 15/419,398 1st Action Interview dated Jul. 3, 2017.
U.S. Appl. No. 15/419,398 Office Action dated Mar. 7, 2018.
U.S. Appl. No. 15/419,398 Office Action dated Nov. 9, 2017.
U.S. Appl. No. 15/965,738 Preinterview First Action dated Nov. 15, 2018.
U.S. Appl. No. 15/965,739 Preinterview First Action dated Nov. 15, 2018.
Valton et al. A Multidrug-resistant Engineered CAR T Cell for Allogeneic Combination Immunotherapy. Mol Ther 23(9):1507-1518 (2015).
Van Der Stegen et al. The pharmacology of second-generation chimeric antigen receptors. Nat Rev Drug Discov 14(7):499-509 (2015).
Velasquez. T cells expressing CD19-specific Engager Molecules for the Immunotherapy of CD19-positive Malignancies. Sci Rep 6:27130 (2016).
Verhoeyen et al. Reshaping human antibodies: grafting an antilysozyme activity. Science 239:1534-1536 (1988).
Wang et al. Generation of Potent T-cell Immunotherapy for Cancer Using DAP12-Based, Multichain, Chimeric Immunoreceptors. Cancer Immunol Res 3(7):815-826 (2015).
Wang et al. Manufacture of tumor- and virus-specific T lymphocytes for adoptive cell therapies. Cancer Gene Therapy 22(2):85-94 (2015).
Wang et al. VISTA, a novel mouse Ig superfamily ligand that negatively regulates T cell responses. J Exp Med 208(3):577-592 (2011).
Watanabe et al. Fine-tuning the CAR spacer improves T-cell potency. Oncoimmunology. 5(2):e1253656 (2016).
Weekes et al. Phase I Study of DMOT4039A, an Antibody-Drug Conjugate Targeting Mesothelin, in Patients with Unresectable Pancreatic or Platinum-Resistant Ovarian Cancer. Mol Cancer Ther 15(3):439-447 (2016).
Wegener et al. The T cell receptor/CD3 complex is composed of at least two autonomous transduction modules. Cell 68:83-95 (1992).
Whittington et al. Accounting for All Costs in the Total Cost of Chimeric Antigen Receptor T-Cell Immunotherapy. JAMA Oncol. Published online Oct. 11, 2018 (1 pg.).
Wilkie et al. Selective Expansion of Chimeric Antigen Receptor-targeted T-cells with Potent Effector Function using Interleukin-4. J Biol Chem 285(33):25538-25544 (2010).
Wu et al. Protein design of IgG/TCR chimeras for the co-expression of Fab-like moieties within bispecific antibodies. MABS 7(2):364-376 (2015).
Wucherpfennig et al. Structural Biology of the T-cell Receptor: Insights into Receptor Assembly, Ligand Recognition, and Initiation of Signaling. Cold Spring Harb Perspect Biol 2(4):a005140 (2010).
Xu et al. The basics of CAR T design and challenges in immunotherapy of solid tumors—Ovarian cancer as a model. Hum Vaccin Immunother 13(7):1548-1555 (2017).
Yun et al. Targeting of T Lymphocytes to Melanoma Cells Through Chimeric Anti-GD3 Immunoglobulin T-Cell Receptors. Neoplasia 2(5):449-459 (2000).
Zah et al. T cells expressing CD19/CD20 bi-specific chimeric antigen receptors prevent antigen escape by malignant B cells. Cancer Immunol Res 4(6)498-509 (2016) .
Zhang et al. 4-1BB is superior to CD28 costimulation for generating CD8+ cytotoxic lymphocytes for adoptive immunotherapy. J Immunol 179:4910-4918 (2007).
Zhang et al. New High Affinity Monoclonal Antibodies Recognize Non-Overlapping Epitopes On Mesothelin For Monitoring And Treating Mesothelioma. Sci Rep 5:9928 (2015).
Zhang et al. Phase I Escalating-Dose Trial of CAR-T Therapy Targeting CEA+ Metastatic Colorectal Cancers. Mol Ther 25:1248-1258 (2017).
Zhao et al. A herceptin-based chimeric antigen receptor with modified signaling domains leads to enhanced survival of transduced T lymphocytes and antitumor activity. J Immunol 183:5563-5574 (2009).
Zhao et al. Multiple injections of electroporated autologous T cells expressing a chimeric antigen receptor mediate regression of human disseminated tumor. Cancer Res 70(22):9053-9061 w/Supplemental Information (2010).
Zhao et al. Structural Design of Engineered Costimulation Determines Tumor Rejection Kinetics and Persistence of CAR T cells. Cancer Cell 28(4):415-428 (2015).
Zhou et al. Exclusive Transduction of Human CD4+ T Cells upon Systemic Delivery of CD4-Targeted Lentiviral Vectors. J Immunol 195:2493-2501 (2015).
Brocker et al. Redirecting the complete T cell receptor/CD3 signaling machinery towards native antigen via modified T cell receptor. Eur J. Immunol 26:1770-1774 (1996).
Brocker et al. Signals through T cell receptor-zeta chain alone are insufficient to prime resting T lymphocytes. J Med Chem 181:1653-1659 (1995).
Brocker. Chimeric Fv-zeta or Fv-epsilon receptors are not sufficient to induce activation or cytokine production in peripheral T cells. Blood 96(5):1999-2001 (2000).
Mosquera et al. In vitro and in vivo characterization of a novel antibody-like single-chain TCR human IgG1 fusion protein. J Immunol 174(7):4381-4388 (2005).
Sommermeyer et al. Designer T cells by T cell receptor replacement. Eur J Immunol 36(11):3052-3059 (2006).
Pipeline. A Broad Pipeline of T Cell Therapies For Solid And Hematologi Cancers. TCR2 Therapeutics. Available at https://www.tcr2.com/pipeline (Accessed Apr. 15, 2020) (5 pgs).
Rafiq et al. Targeted delivery of a PD-1-blocking scFv by CAR-T cells enhances anti-tumor efficacy in vivo. Nat Biotechnol 36(9):847-856 (2018).
Abate-Daga et al. Expression profiling of TCR-engineered T cells demonstrates overexpression of multiple inhibitory receptors in persisting lymphocytes. Blood 122(8):1399-410 (2013).
Badoual et al. PD-1-expressing tumor-infiltrating T cells are a favorable prognostic biomarker in HPV-associated head and neck cancer. Cancer Res. 73(1):128-138 (2013).
Bahram et al. A second lineage of mammalian major histocompatibility complex class I genes. PNAS USA 91:6259-6263 (1994).
Bauer et al. Activation of NK cells and T cells by NKG2D, a receptor for stress-inducible MICA. Science 285(5428):727-9 (1999).
Borcherding et al. ROR1, an embryonic protein with an emerging role in cancer biology. Protein Cell 5(7):496-502 (2014).
Borroto et al. Crammed signaling motifs in the T-cell receptor. Immunol Lett 161:113-117 (2014).
Brahmer et al. Safety and activity of anti-PD-L1 antibody in patients with advanced cancer. N Engl J Med 366(26):2455-2465 (2012).
Bruhns et al. Specificity and Affinity of Human Fc Receptors and Their Polymorphic Variants for Human IgG Subclasses. Blood 113(16):3716-3725 (2009).
Chen et al. In situ expression and significance of B7 costimulatory molecules within tissues of human gastric carcinoma. World J Gastroenterol. 9(6):1370-1373 (2003).
Chen et al. Mesothelin Binding to CA125/MUC16 Promotes Pancreatic Cancer Cell Motility and Invasion via MMP-7 Activation. Scientific Reports 3(1):4-8 (2013).
Choi et al. Pre-clinical Specificity and Safety of UC-961, a First-In-Class Monoclonal Antibody Targeting ROR1 Clinical Lymphoma, Myeloma & Leukemia 15(Supp):SI67-S169 (2015).
Cui et al. Targeting ROR1 inhibits epithelial-mesenchymal transition and metastasis. Cancer Research 73(12):3649-3660 (2015).
D'Aloia et al. T Lymphocytes Engineered to Express a CD16-Chimeric Antigen Receptor Redirect T-cell Immune Responses Against Immunoglobulin G-Opsonized Target Cells. Cytotherapy 18(2):278-290 (2016).

(56) References Cited

OTHER PUBLICATIONS

Dangaj et al. In vivo blocking of CA125/mesothelin-dependent cell adhesion prevents ovarian cancer peritoneal metastasis. Gynecologic Oncology 116(3):S2-S169 (2010).
Darce et al. Regulated expression of BAFF-binding receptors during human B cell differentiation. J Immunol 179(11):7276-7286 (2007).
Deniger et al. Sleeping Beauty Transposition of Chimeric Antigen Receptors Targeting Receptor Tyrosine Kinase-Like Orphan Receptor-1 (ROR1) into Diverse Memory T-Cell Populations. PLoS ONE 10(6):e0128151 (2015).
Ding et al. CBP loss cooperates with PTEN haploinsufficiency to drive prostate cancer: implications for epigenetic therapy. Cancer Res 74(7):2050-2061 (2014).
Dong et al. Tumor-associated B7-H1 promotes T-cell apoptosis: a potential mechanism of immune evasion. Nat Med 8:793-800 (2002).
Dudley et al. Adoptive cell therapy for patients with metastatic melanoma: evaluation of intensive myeloablative chemoradiation preparative regimens. J Clin Oncol 26(32):5233-5239 (2008).
Eagle et al. Cellular expression, trafficking, and function of two isoforms of human ULBP5/RAET1G. PLoS One 4:e4503 (2009).
Eagle et al. ULBP6/RAET1L is an additional human NKG2D ligand. Eur J Immunol 39:3207-3216 (2009).
Ellyard et al. Antigen-selected, immunoglobulin-secreting cells persist in human spleen and bone marrow. Blood 103(10):3805-3812 (2004).
Gao et al. Overexpression of PD-L1 significantly associates with tumor aggressiveness and postoperative recurrence in human hepatocellular carcinoma. Clin Cancer Res. 15(3):971-979 (2009).
Gattinoni et al. Adoptive immunotherapy for cancer: building on success. Nature Reviews Immunology 6(5):383-393 (2006).
Geng et al. B7-H1 up-regulated expression in human pancreatic carcinoma tissue associates with tumor progression. J Cancer Res Clin Oncol. 134(9):1021-1027 (2008).
Ghebeh et al. The B7-H1 (PD-L1) T Lymphocyte-Inhibitory Molecule Is Expressed in Breast Cancer Patients with Infiltrating Ductal Carcinoma: Correlation with Important High-Risk Prognostic Factors. Neoplasia 8(3):190-198 (2006).
Goding et al. Restoring immune function of tumor-specific CD4+ T cells during recurrence of melanoma. J Immunol 190(9):4899-4909 (2013).
Gros et al. PD-1 identifies the patient-specific CD8+ tumor-reactive repertoire infiltrating human tumors. The Journal of clinical investigation, 124(5):2246-2259 (2014).
Guy et al. Distinct T cell receptor signaling pathways drive proliferation and cytokine production in T cells. Nat Immunol 14(3):262-270 and Supp pp. 1-9 (2013).
Han et al. Masked Chimeric Antigen Receptor for Tumor-Specific Activation. Molecular Therapy 25(1):274-284 (2017).
Holst et al. Scalable signaling mediated by T cell antigen receptor-CD3 ITAMs ensures effective negative selection and prevents autoimmunity. Nat Immunol 9(6):658-666 and Supp pp. 1-21 (2008).
Hudecek et al. Receptor affinity and extracellular domain modifications affect tumor recognition by ROR1-specific chimeric antigen receptor T cells. Clin Cancer Res 19(12):3153-3164 (2013).
Hudecek et al. The B-cell tumor-associated antigen ROR1 can be targeted with T cells modified to express a ROR1-specific chimeric antigen receptor. Blood 116(22):4532-4541 (2010).
James et al. Antibody-mediated B-cell depletion before adoptive immunotherapy with T cells expressing CD20-specific chimeric T-cell receptors facilitates eradication of leukemia in immunocompetent mice. Blood 114(27):5454-5463 (2009).
Karim et al. Tumor-expressed B7-H1 and B7-DC in relation to PD-1+ T-cell infiltration and survival of patients with cervical carcinoma. Clin Cancer Res. 15(20):6341-6347 (2009).
Karyampudi et al. Accumulation of Memory Precursor CD8 T Cells in Regressing Tumors following Combination Therapy with Vaccine and Anti-PD-1 Antibody. Cancer Res 74(11):2974-85 (2014).

Kozako et al. PD-1/PD-L1 expression in human T-cell leukemia virus type 1 carriers and adult T-cell leukemia/lymphoma patients. Leukemia 23(2):375-382 (2009).
Kudo et al. T lymphocytes expressing a CD16 signaling receptor exert antibody-dependent cancer cell killing. Cancer Res 74(1):93-103 (2013).
Leen et al. Improving T cell therapy for cancer. Annu Rev Immunol 25:243-265 (2007).
Liu et al. Plasma cells from multiple myeloma patients express B7-H1 (PD-L1) and increase expression after stimulation with IFN-{gamma} and TLR ligands via a MyD88-, TRAF6-, and MEK-dependent pathway. Blood 110(1):296-304 (2007).
Love et al. ITAM-mediated signaling by the T-cell antigen receptor. Cold Spring Harb Perspect Biol. 2(6):a002485 (2010).
Malaspina et al. Enhanced programmed death 1 (PD-1) and PD-1 ligand (PD-L1) expression in patients with actinic cheilitis and oral squamous cell carcinoma. Cancer Immunol Immunother. 60(7):965-974 (2011).
Mansfield et al. B7-H1 expression in malignant pleural mesothelioma is associated with sarcomatoid histology and poor prognosis. J Thorac Oncol. 9(7):1036-1040 (2014).
Mato et al. A drive through cellular therapy for CLL in 2015: allogeneic cell transplantation and CARs. Blood 126(4):478-485 (2015).
Mumtaz et al. Design of liposomes for circumventing the reticuloendothelial cells. Glycobiology 5:505-10 (1991).
Nakanishi et al. Overexpression of B7-H1 (PD-L1) significantly associates with tumor grade and postoperative prognosis in human urothelial cancers. Cancer Immunol Immunother. 56(8):1173-1182 (2007).
Nicolaides et al. CA125 suppresses amatuximab immune-effector function and elevated serum levels are associated with reduced clinical response in first line mesothelioma patients. Cancer Biology & Therapy 19(7):622-630 (2018).
Nimmerjahn et al. FcγRIV: a Novel FcR with Distinct IgG Subclass Specificity. Immunity 23(1):41-51 (2005).
Novak et al. Expression of BCMA, TACI, and BAFF-R in multiple myeloma: a mechanism for growth and survival. Blood 103(2):689-94 (2004).
Novak et al. Expression of BLyS and its receptors in B-cell non-Hodgkin lymphoma: correlation with disease activity and patient outcome. Blood 104(8):2247-53 (2004).
NP 000064, human T-cell surface glycoprotein CD3 gamma chain precursor, NCBI, pp. 1-4, May 4, 2019.
NP 000724, human T-cell surface glycoprotein CD3 epsilon chain precursor, NCBI, pp. 1-4, May 4, 2019.
O'Connor et al. BCMA Is Essential for the Survival of Long-lived Bone Marrow Plasma Cells. J Exp Med 199(1):91-8 (2004).
Ohigashi et al. Clinical significance of programmed death-1 ligand-1 and programmed death-1 ligand-2 expression in human esophageal cancer. Clin Cancer Res 11(8):2947-2953 (2005).
PCT/US2019/021315 International Search Report and Written Opinion dated Jun. 13, 2019.
PCT/US2019/032298 International Search Report and Written Opinion dated Nov. 21, 2019.
PCT/US2019/043690 Invitation to Pay Additional Fees dated Nov. 4, 2019.
Poirot et al. Multiplex Genome-Edited T-cell Manufacturing Platform for Off-the-Shelf Adoptive T-cell Immunotherapies. Cancer Research 75(18):3853-3864 (2015).
Rodriguez-Garcia et al. T-cell target antigens across major gynecologic cancers. Gynecologic Oncology 145(3):426-435 (2017).
Rosenberg et al. Durable complete responses in heavily pretreated patients with metastatic melanoma using T-cell transfer immunotherapy. Clin Cancer Res 17(13):4550-4557 (2011).
Shimabukuro-Vornhagen et al. Cytokine release syndrome. J Immunother Cancer 6:56 (2018).
Spear et al. NKG2D ligands as therapeutic targets. Cancer Immunity 13:8 (2013).
Thompson et al. Costimulatory molecule B7-H1 in primary and metastatic clear cell renal cell carcinoma. Cancer 104(10):2084-2091 (2005).

(56) References Cited

OTHER PUBLICATIONS

Topalian et al. Safety, Activity, and Immune Correlates of Anti-PD-1 Antibody in Cancer. N Engl J Med 366:2443-2454 (2012).
Urnov et al. Genome editing with engineered zinc finger nucleases. Nature Reviews Genetics 11:636-646 (2010).
U.S. Appl. No. 15/419,398 Office Action dated Jul. 17, 2019.
U.S. Appl. No. 15/419,398 Office Action dated May 24, 2019.
Usui et al. Expression of costimulatory molecules on human retinoblastoma cells Y-79: functional expression of CD40 and B7H1. Invest Ophthalmol Vis Sci. 47(10):4607-4613 (2006).
Vanseggelen et al. T Cells Engineered With Chimeric Antigen Receptors Targeting NKG2D Ligands Display Lethal Toxicity in Mice. Molecular Therapy 23(10):1600-1610 (2015).
Vermeire et al. Signal peptide-binding drug as a selective inhibitor of co-translational protein translocation. PLoS Biol 12(12):e1002011 (2014).
Wintterle et al. Expression of the B7-related molecule B7-H1 by glioma cells: a potential mechanism of immune paralysis. Cancer Res. 63(21):7462-7467 (2003).
Xerri et al. Programmed death 1 is a marker of angioimmunoblastic T-cell lymphoma and B-cell small lymphocytic lymphoma/chronic lymphocytic leukemia. Hum Pathol. 39(7):1050-1058 (2008).
Yamamoto et al. PD-1-PD-1 ligand interaction contributes to immunosuppressive microenvironment of Hodgkin lymphoma. Blood 111(6):3220-3224 (2008).
Yao et al. CyTOF supports efficient detection of immune cell subsets from small samples. J Immunol Methods 415:1-5 (2014).
Ye et al. Interaction of B7-H1 on intrahepatic cholangiocarcinoma cells with PD-1 on tumor-infiltrating T cells as a mechanism of immune evasion. J Surg Oncol. 100(6):500-504 (2009).
Yokosuka et al. Programmed cell death 1 forms negative costimulatory microclusters that directly inhibit T cell receptor signaling by recruiting phosphatase SHP2. J Exp Med 209(6):1201-1217 (2012).
Yu et al. Wnt5a induces ROR1/ROR2 heterooligomerization to enhance leukemia chemotaxis and proliferation. J Clin Invest 126(2):585-98 (2016).
Zhang et al. The onco-embryonic antigen ROR1 is expressed by a variety of human cancers. Am J Path 181(6):1903-1910 (2012).

FIG. 7B
E:T 5:1
HeLa-BCMA (BCMA+ tumor targets)
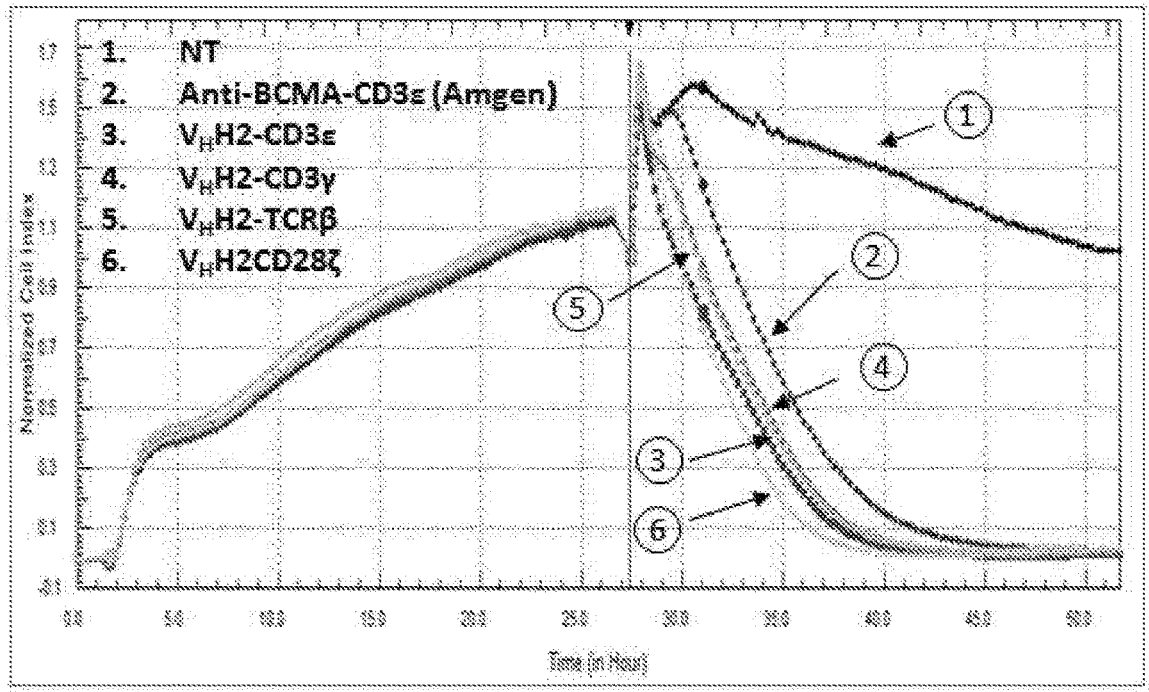
HeLa-CD19 (BCMA- tumor targets)
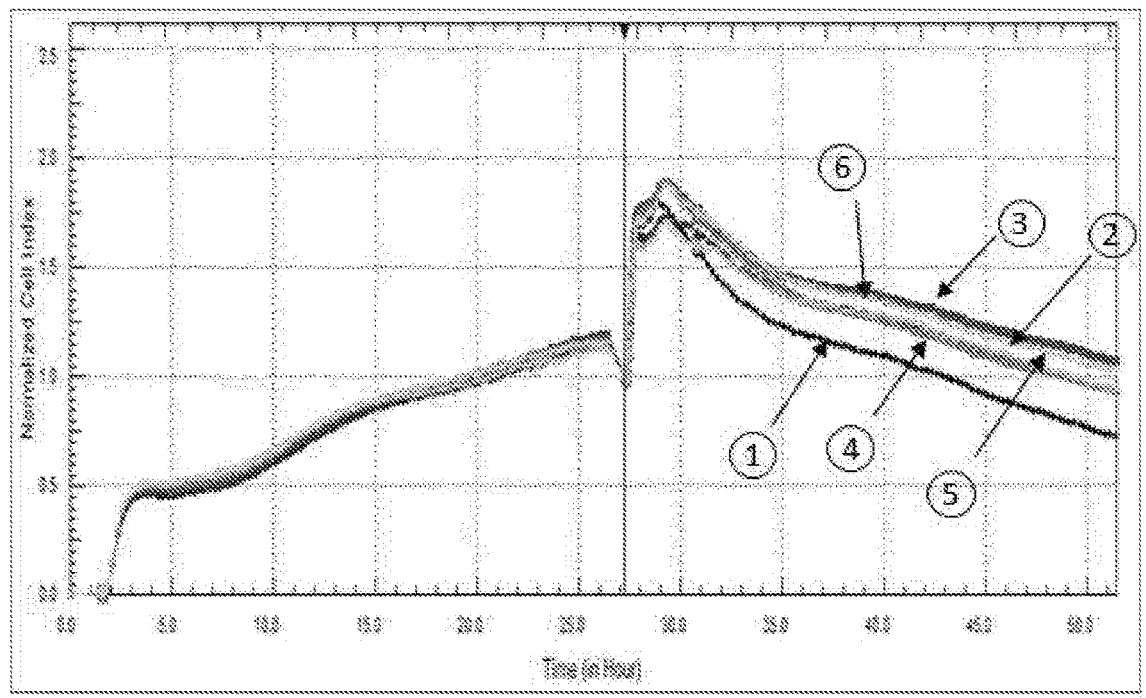

FIG. 7C
E:T 1:1
HeLa-BCMA (BCMA+ tumor targets)
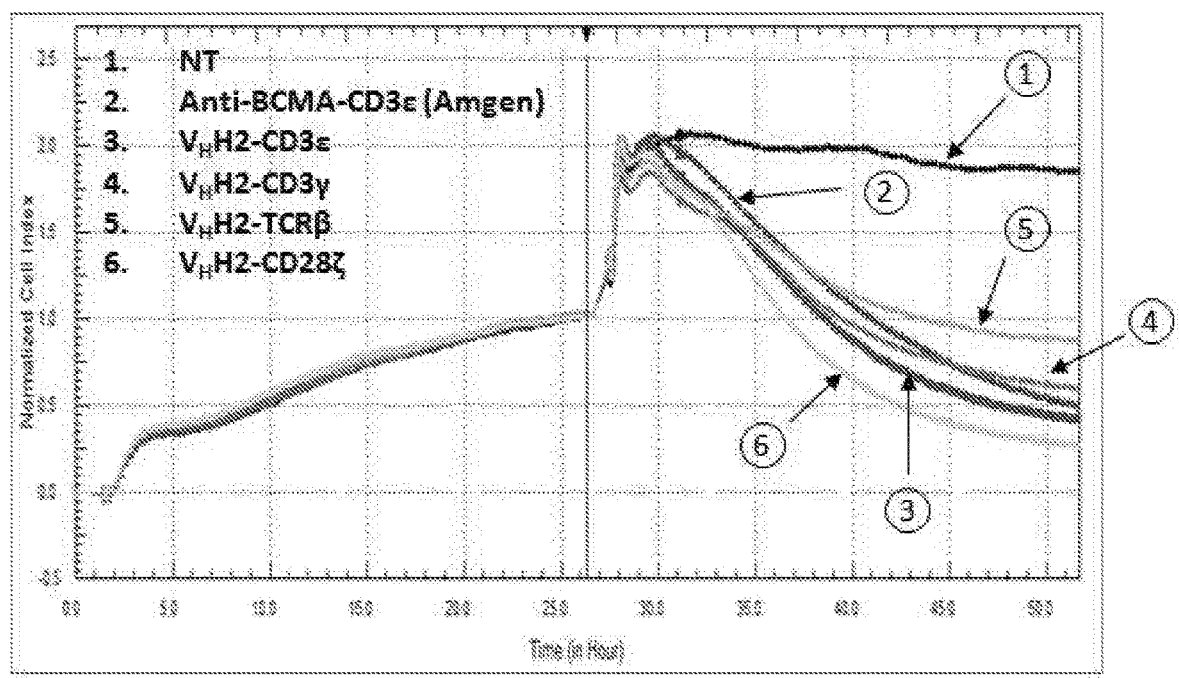
HeLa-CD19 (BCMA- tumor targets)
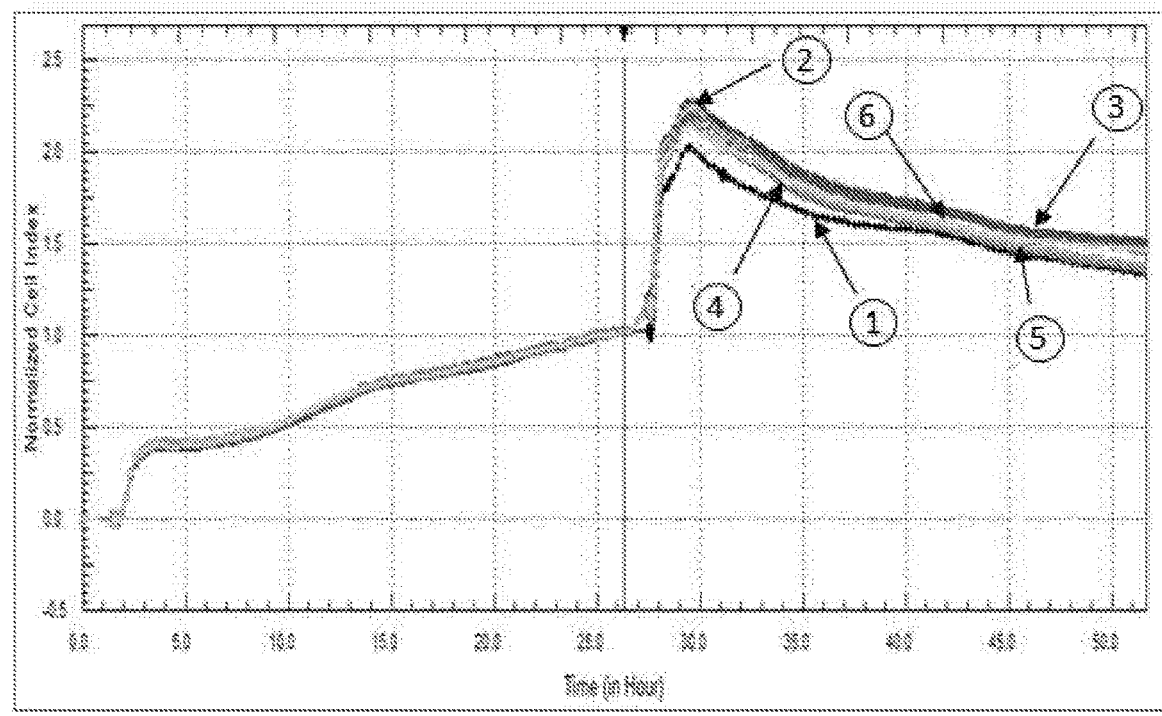

FIG. 7D
E:T 1:5
HeLa-BCMA (BCMA+ tumor targets)
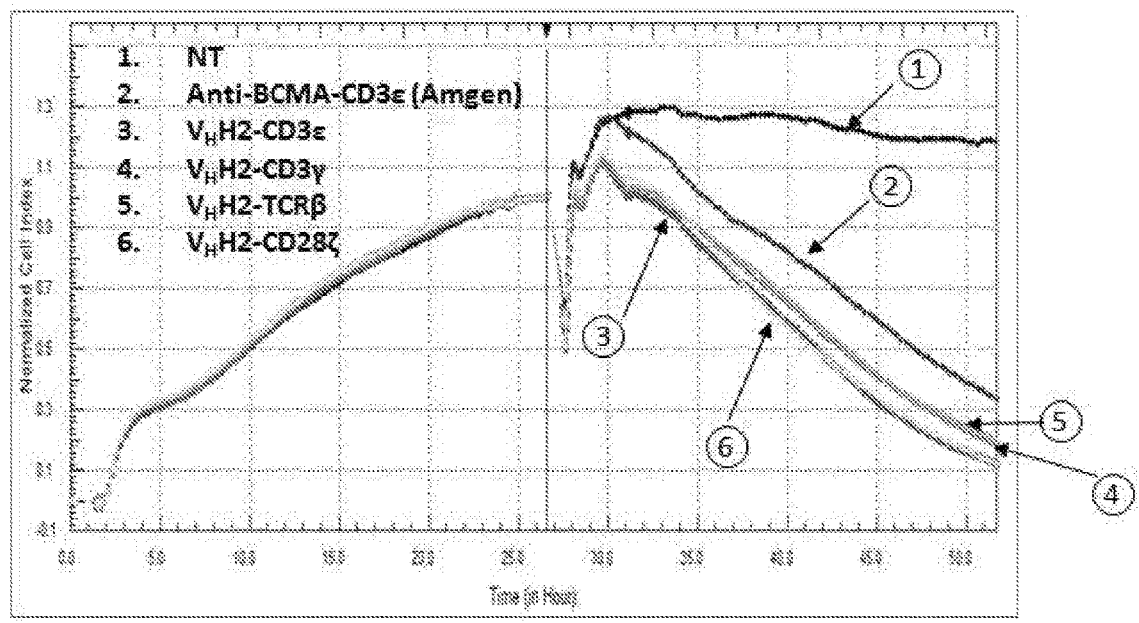
1. NT
2. Anti-BCMA-CD3ε (Amgen)
3. $V_HH2$-CD3ε
4. $V_HH2$-CD3γ
5. $V_HH2$-TCRβ
6. $V_HH2$-CD28ζ
HeLa-CD19 (BCMA- tumor targets)
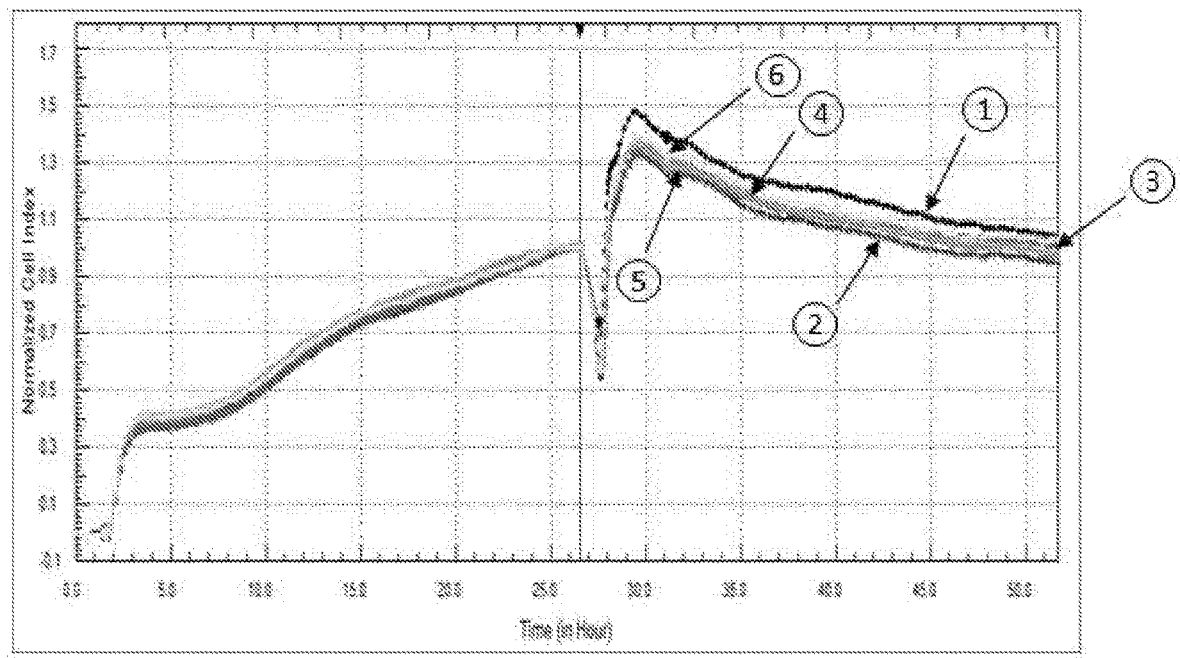

FIG. 7E
E:T 5:1
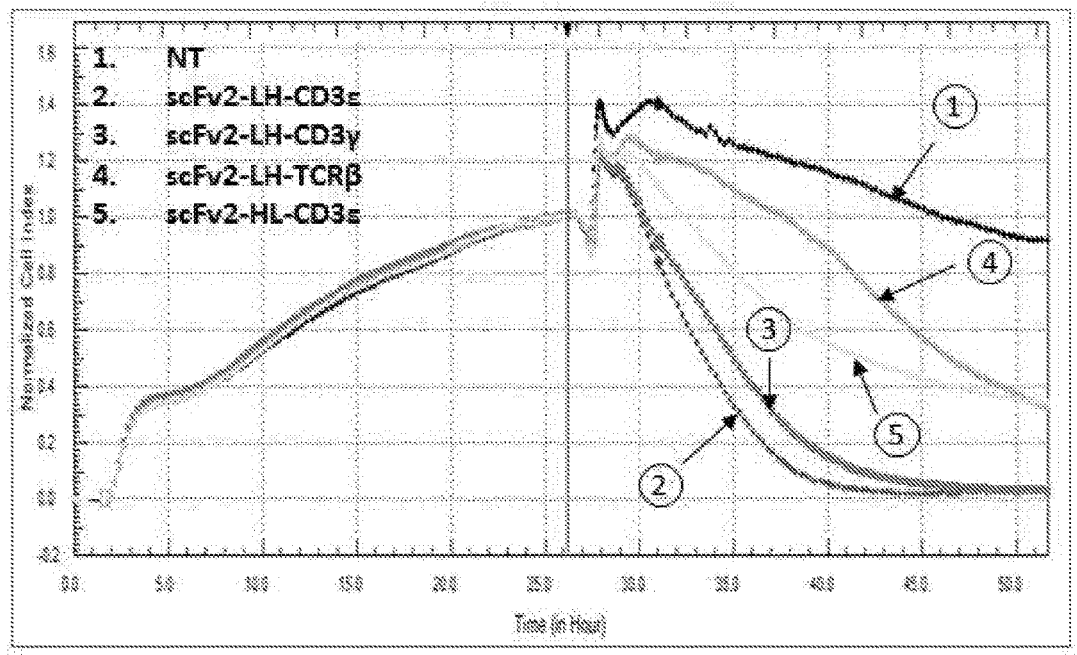
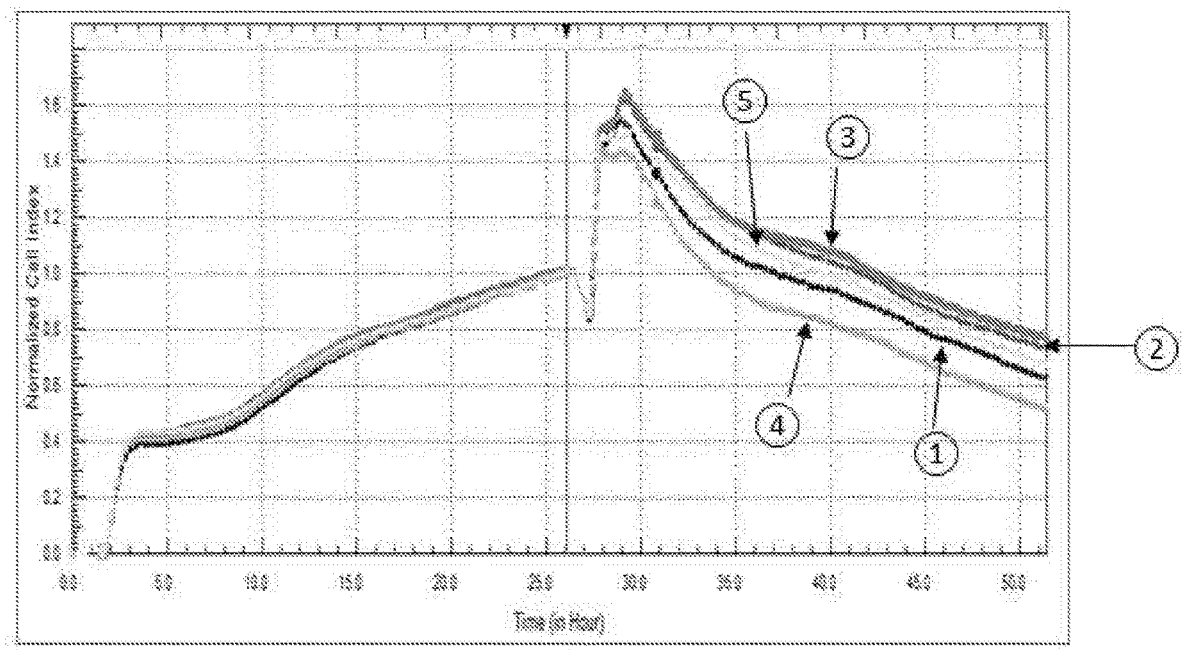

FIG. 7F
E:T 1:1
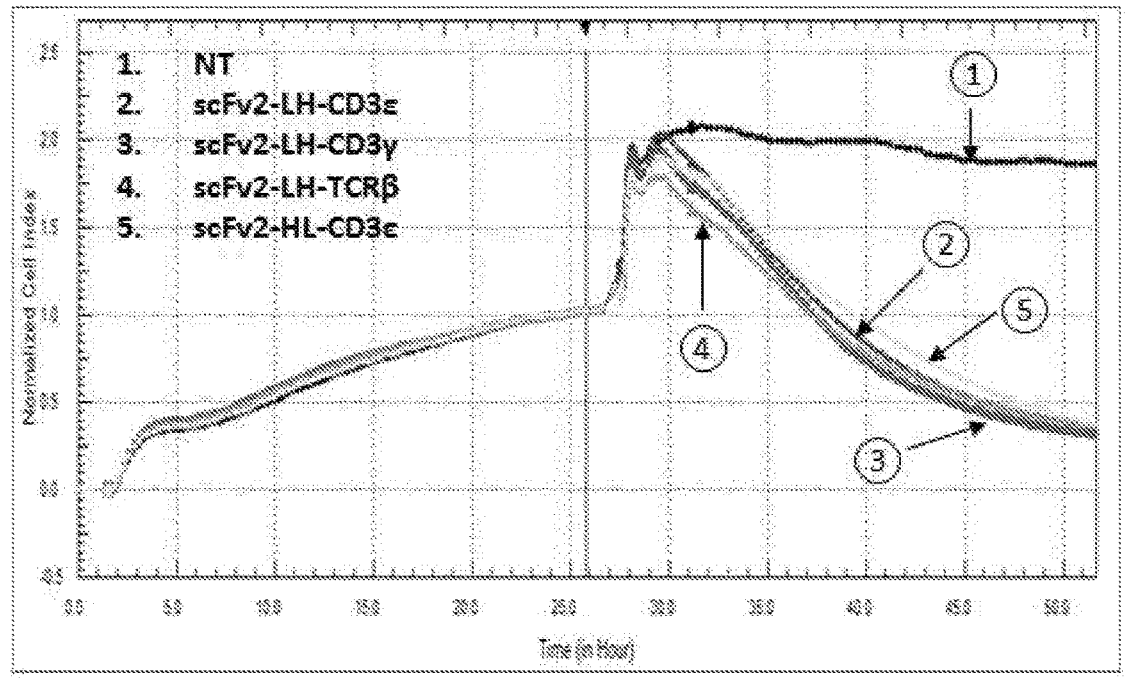
HeLa-BCMA (BCMA+ tumor targets)
1. NT
2. scFv2-LH-CD3ε
3. scFv2-LH-CD3γ
4. scFv2-LH-TCRβ
5. scFv2-HL-CD3ε
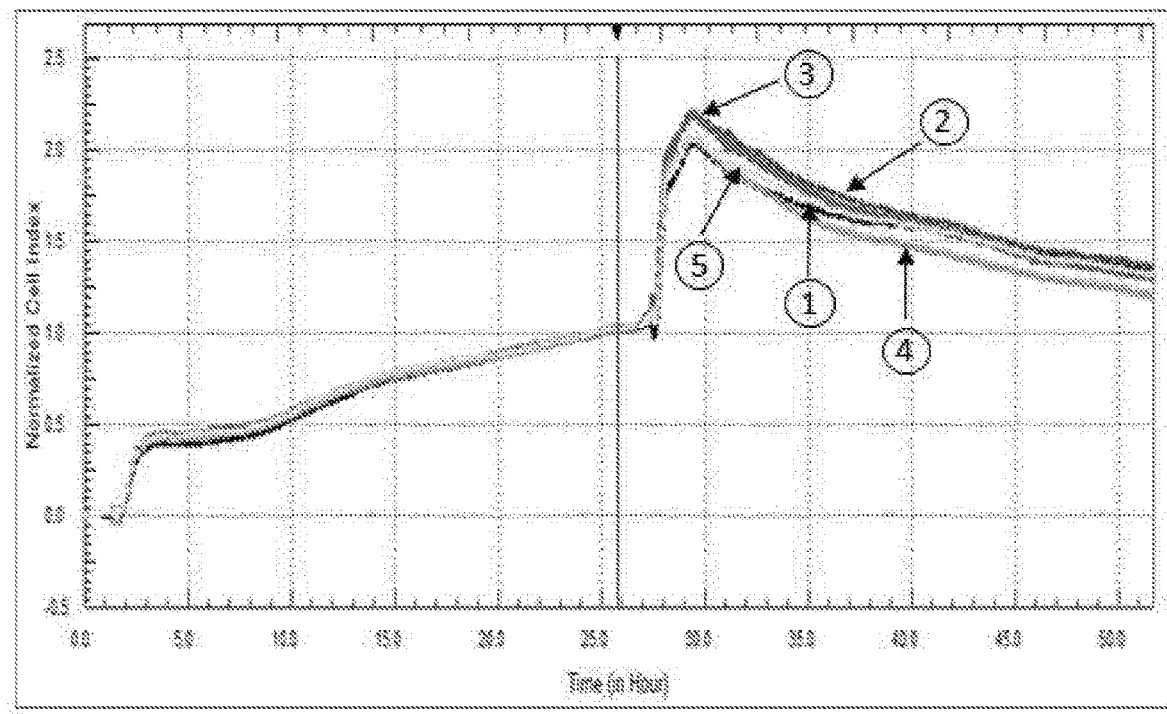
HeLa-CD19 (BCMA- tumor targets)

FIG. 7G
E:T 1:5
HeLa-BCMA (BCMA+ tumor targets)
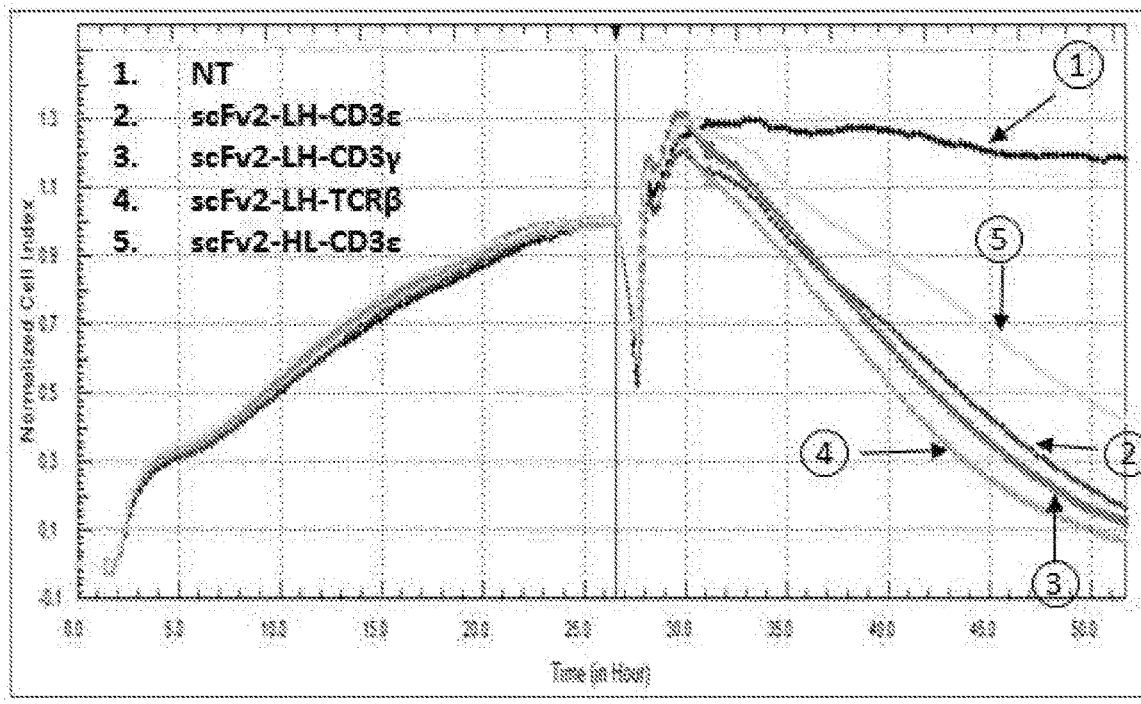
HeLa-CD19 (BCMA- tumor targets)
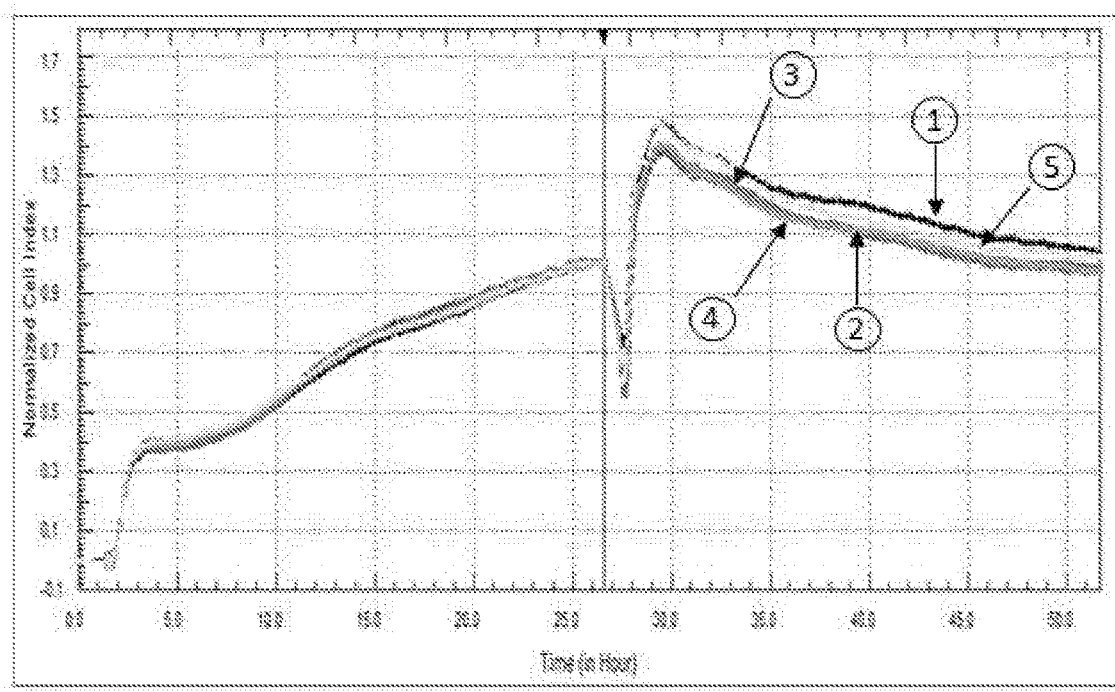

E:T 1:1

FIG. 11C
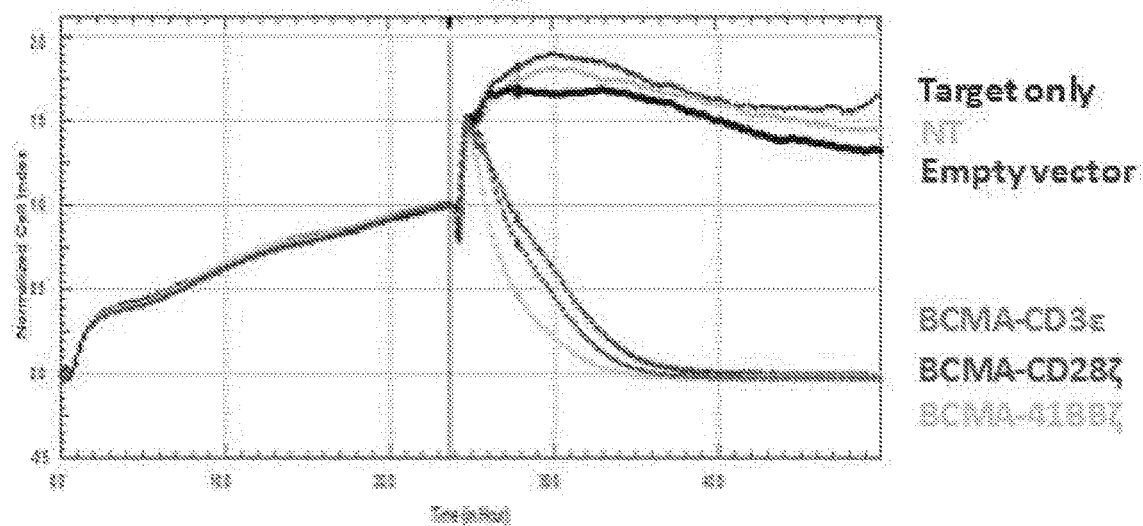
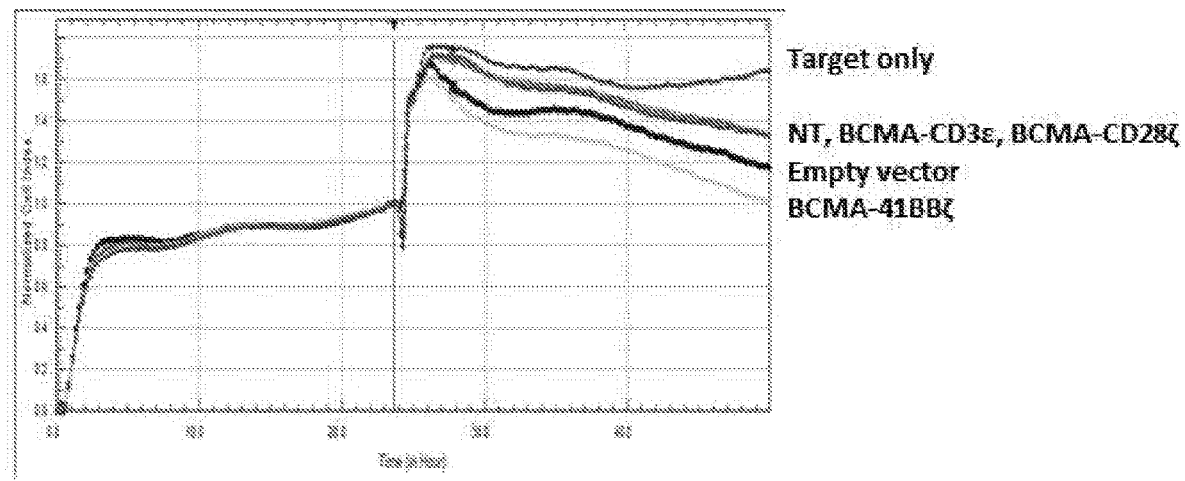

SEQUENCE LISTING

<160> NUMBER OF SEQ ID NOS: 63

<210> SEQ ID NO 1
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ala Ala Ala Gly Gly Gly Gly Ser Gly Gly Gly Gly Ser Gly Gly Gly
1               5                   10                  15

Gly Ser Leu Glu
            20

<210> SEQ ID NO 2
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 2

Ala Ala Ala Ile Glu Val Met Tyr Pro Pro Pro Tyr Leu Gly Gly Gly
1               5                   10                  15

Gly Ser Gly Gly Gly Gly Ser Gly Gly Gly Gly Ser Leu Glu
            20                  25                  30

<210> SEQ ID NO 3
<211> LENGTH: 10
<212> TYPE: PRT
<213> ORGANISM: Artificial Sequence
<220> FEATURE:
<221> NAME/KEY: source -continued

```
<223> OTHER INFORMATION: /note="Description of Artificial Sequence:
      Synthetic peptide"

<400> SEQUENCE: 3

Gly Gly Gly Gly Ser Gly Gly Gly Gly Ser
1               5                   10

<210> SEQ ID NO 4
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 4
ggtggcggag gttctggagg tggaggttcc                                        30

<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gly Gly Gly Gly Ser Gly Gly Gly Ser Gly Gly Gly Gly Ser Leu
1               5                   10                  15

Glu

<210> SEQ ID NO 6
<211> LENGTH: 8147
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 6
acgcgtgtag tcttatgcaa tactcttgta gtcttgcaac atggtaacga tgagttagca      60
acatgcctta caaggagaga aaaagcaccg tgcatgccga ttggtggaag taaggtggta     120
cgatcgtgcc ttattaggaa ggcaacagac gggtctgaca tggattggac gaaccactga    180
attgccgcat tgcagagata ttgtatttaa gtgcctagct cgatacataa acgggtctct    240
ctggttagac cagatctgag cctgggagct ctctggctaa ctagggaacc cactgcttaa    300
gcctcaataa agcttgcctt gagtgcttca agtagtgtgt gcccgtctgt tgtgtgactc    360
tggtaactag agatccctca gacccttta gtcagtgtgg aaaatctcta gcagtggcgc     420
ccgaacaggg acctgaaagc gaagggaaa ccagagctct ctcgacgcag gactcggctt     480
gctgaagcgc gcacggcaag aggcgagggg cggcgactgg tgagtacgcc aaaaattttg    540
actagcggag gctagaagga gagagatggg tgcgagagcg tcagtattaa gcggggagag   600
attagatcgc gatgggaaaa aattcggtta aggccagggg gaaagaaaaa atataaatta   660
aaacatatag tatgggcaag cagggagcta gaacgattcg cagttaatcc tggcctgtta   720
gaaacatcag aaggctgtag acaaatactg ggacagctac aaccatccct tcagacagga   780
tcagaagaac ttagatcatt atataataca gtagcaaccc tctattgtgt gcatcaaagg   840
```

```
atagagataa aagacaccaa ggaagcttta gacaagatag aggaagagca aaacaaaagt      900
aagaccaccg cacagcaagc ggccactgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg gagcagcagg aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta acataacaaa     1560
ttggctgtgg tatataaaat tattcataat gatagtagga ggcttggtag gtttaagaat     1620
agttttgct gtactttcta tagtgaatag agttaggcag ggatattcac cattatcgtt     1680
tcagacccac ctcccaaccc cgaggggacc cgacaggccc gaaggaatag aagaagaagg     1740
tggagagaga gacagagaca gatccattcg attagtgaac ggatctcgac ggtatcggtt     1800
aacttttaaa agaaaagggg ggattggggg gtacagtgca ggggaaagaa tagtagacat     1860
aatagcaaca gacatacaaa ctaaagaatt acaaaaacaa attacaaaat tcaaaatttt     1920
atcgatacta gtattatgcc cagtacatga cctatgggca ctttcctact ggcagtaca      1980
tctacgtatt agtcatcgct attaccatgg tgatgcggtt ttggcagtac atcaatgggc     2040
gtggatagcg gtttgactca cggggatttc caagtctcca ccccattgac gtcaatggga     2100
gtttgttttg gcaccaaaat caacgggact ttccaaaatg tcgtaacaac tccgcccat      2160
tgacgcaaat gggcggtagg cgtgtacggt gggaggttta taagcaga gctcgtttag      2220
tgaaccgtca gatcgcctgg agacgccatc cacgctgttt tgacctccat agaagattct     2280
agagctagcg ccgccaccat gctccagatg gctggccagt gcagccagaa cgagtacttc     2340
gacagcctgc tgcacgcctg catcccttgc cagctgcggt gcagcagcaa caccccaccc     2400
ctgacctgcc agcggtactg caacgccagc gtgaccaaca gcgtgaaggg caccaacgcc     2460
atcctgtgga cctgcctggg cctgagcctg atcatcagcc tggccgtgtt cgtgctgatg     2520
ttcctgctgc ggaagatcaa cagcgagccc ctgaaggacg agttcaagaa caccggcagc     2580
ggcctgctgg gcatggccaa catcgacctg gaaaagagcc ggaccggcga cgagatcatc     2640
ctgcccagag gctggagta caccgtggaa gagtgtacct gcgaggactg catcaagagc     2700
aagcccaagg tggacagcga ccactgcttc cctctgcccg ccatggaaga gggcgccacc     2760
atcctggtga caacaaagac caacgactac tgcaagagcc tgcctgccgc cctgagcgcc     2820
accgagatcg agaagtccat cagcgccaga tgaggatccg cggccgcaag gatctgcgat     2880
cgctccggtg cccgtcagtg ggcagagcgc acatcgccca cagtccccga gaagttgggg     2940
ggaggggtcg gcaattgaac gggtgcctag agaaggtggc gcggggtaaa ctgggaaagt     3000
gatgtcgtgt actggctccg cctttttccc gagggtgggg gagaaccgta tataagtgca     3060
gtagtcgccg tgaacgttct ttttcgcaac gggtttgccg ccagaacaca gctgaagctt     3120
cgaggggctc gcatctctcc ttcacgcgcc cgccgcccta cctgaggccg ccatccacgc     3180
cggttgagtc gcgttctgcc gcctcccgcc tgtggtgcct cctgaactgc gtccgccgtc     3240
```

```
taggtaagtt taaagctcag gtcgagaccg ggcctttgtc cggcgctccc ttggagccta    3300
cctagactca gccggctctc cacgctttgc ctgaccctgc ttgctcaact ctacgtcttt    3360
gtttcgtttt ctgttctgcg ccgttacaga tccaagctgt gaccggcgcc tacgtcgaga    3420
tgattgaaca agatggattg cacgcaggtt ctccggccgc ttgggtggag aggctattcg    3480
gctatgactg ggcacaacag acaatcggct gctctgatgc cgccgtgttc cggctgtcag    3540
cgcaggggcg cccggttctt tttgtcaaga ccgacctgtc cggtgccctg aatgaactgc    3600
aggacgaggc agcgcggcta tcgtggctgg ccgcgacggg cgttccttgc gcagctgtgc    3660
tcgacgttgt cactgaagcg ggaagggact ggctgctatt gggcgaagtg ccggggcagg    3720
atctcctgtc atctcacctt gctcctgccg agaaagtatc catcatggct gatgcaatgc    3780
ggcggctgca tacgcttgat ccggctacct gcccattcga ccaccaagcg aaacatcgca    3840
tcgagcgagc acgtactcgg atggaagccg gtcttgtcga tcaggatgat ctggacgaag    3900
agcatcaggg gctcgcgcca gccgaactgt tcgccaggct caaggcgcgc atgcccgacg    3960
gcgaggatct cgtcgtgacc catggcgatg cctgcttgcc gaatatcatg gtggaaaatg    4020
gccgcttttc tggattcatc gactgtggcc ggctgggtgt ggcggaccgc tatcaggaca    4080
tagcgttggc tacccgtgat attgctgaag agcttggcgg cgaatgggct gaccgcttcc    4140
tcgtgcttta cggtatcgcc gctcccgatt cgcagcgcat cgccttctat cgccttcttg    4200
acgagttctt ctgactcgac aatcaacctc tggattacaa aatttgtgaa agattgactg    4260
gtattcttaa ctatgttgct ccttttacgc tatgtggata cgctgcttta atgcctttgt    4320
atcatgctat tgcttcccgt atggctttca ttttctcctc cttgtataaa tcctggttgc    4380
tgtctcttta tgaggagttg tggcccgttg tcaggcaacg tggcgtggtg tgcactgtgt    4440
ttgctgacgc aacccccact ggttggggca ttgccaccac ctgtcagctc ctttccggga    4500
ctttcgcttt ccccctccct attgccacgc ggaactcatc gccgcctgcc ttgcccgct    4560
gctggacagg ggctcggctg ttgggcactg acaattccgt ggtgttgtcg gggaaatcat    4620
cgtcctttcc ttggctgctc gcctgtgttg ccacctggat tctgcgcggg acgtccttct    4680
gctacgtccc ttcggccctc aatccagcgg accttccttc ccgcggcctg ctgccggctc    4740
tgcggcctct tccgcgtctt cgccttcgcc ctcagacgag tcggatctcc ctttgggccg    4800
cctccccgcc tggtaccttt aagaccaatg acttacaagg cagctgtaga tcttagccac    4860
tttttaaaag aaaaggggg actggaaggg ctaattcact cccaacgaag ataagatctg    4920
cttttttgctt gtactgggtc tctctggtta gaccagatct gagcctggga gctctctggc    4980
taactaggga acccactgct taagcctcaa taaagcttgc cttgagtgct tcaagtagtg    5040
tgtgcccgtc tgttgtgtga ctctggtaac tagagatccc tcagaccctt ttagtcagtg    5100
tggaaaatct ctagcagtag tagttcatgt catcttatta ttcagtattt ataacttgca    5160
aagaaatgaa tatcagagag tgagaggaac ttgtttattg cagcttataa tggttacaaa    5220
taaagcaata gcatcacaaa tttcacaaat aaagcatttt tttcactgca ttctagttgt    5280
ggtttgtcca aactcatcaa tgtatcttat catgtctggc tctagctatc ccgcccctaa    5340
ctccgcccat cccgcccta actccgccca gttccgccca ttctccgccc catggctgac    5400
taattttttt tatttatgca gaggccgagg ccgcctcggc ctctgagcta ttccagaagt    5460
agtgaggagg cttttttgga ggcctagact tttgcagaga cggcccaaat tcgtaatcat    5520
ggtcatagct gtttcctgtg tgaaattgtt atccgctcac aattccacac aacatacgag    5580
```

```
ccggaagcat aaagtgtaaa gcctggggtg cctaatgagt gagctaactc acattaattg   5640
cgttgcgctc actgcccgct ttccagtcgg gaaacctgtc gtgccagctg cattaatgaa   5700
tcggccaacg cgcggggaga ggcggtttgc gtattgggcg ctcttccgct tcctcgctca   5760
ctgactcgct gcgctcggtc gttcggctgc ggcgagcgg atcagctcac tcaaaggcgg   5820
taatacggtt atccacagaa tcaggggata acgcaggaaa gaacatgtga gcaaaaggcc   5880
agcaaaaggc caggaaccgt aaaaaggccg cgttgctggc gttttttcat aggctccgcc   5940
cccctgacga gcatcacaaa aatcgacgct caagtcagag gtggcgaaac ccgacaggac   6000
tataaagata ccaggcgttt ccccctggaa gctccctcgt gcgctctcct gttccgaccc   6060
tgccgcttac cggatacctg tccgcctttc tcccttcggg aagcgtggcg ctttctcata   6120
gctcacgctg taggtatctc agttcggtgt aggtcgttcg ctccaagctg gctgtgtgc   6180 acgaaccccc cgttcagccc gaccgctgcg ccttatccgg taactatcgt cttgagtcca   6240
acccggtaag acacgactta tcgccactgg cagcagccac tggtaacagg attagcagag   6300
cgaggtatgt aggcggtgct acagagttct tgaagtggtg cctaactac ggctacacta   6360 gaaggacagt atttggtatc tgcgctctgc tgaagccagt taccttcgga aaaagagttg   6420
gtagctcttg atccggcaaa caaaccaccg ctggtagcgg tggtttttt gtttgcaagc   6480 agcagattac gcgcagaaaa aaaggatctc aagaagatcc tttgatcttt tctacggggt   6540
ctgacgctca gtggaacgaa aactcacgtt aagggatttt ggtcatgaga ttatcaaaaa   6600
ggatcttcac ctagatcctt ttaaattaaa aatgaagttt taaatcaatc taaagtatat   6660
atgagtaaac ttggtctgac agttaccaat gcttaatcag tgaggcacct atctcagcga   6720
tctgtctatt tcgttcatcc atagttgcct gactccccgt cgtgtagata actacgatac   6780
gggagggctt accatctggc cccagtgctg caatgatacc gcgagaccca cgctcaccgg   6840
ctccagattt atcagcaata aaccagccag ccggaagggc cgagcgcaga agtggtcctg   6900
caactttatc cgcctccatc cagtctatta attgttgccg gaagctaga gtaagtagtt   6960 cgccagttaa tagtttgcgc aacgttgttg ccattgctac aggcatcgtg gtgtcacgct   7020
cgtcgtttgg tatggcttca ttcagctccg gttcccaacg atcaaggcga gttacatgat   7080
cccccatgtt gtgcaaaaaa gcggttagct ccttcggtcc tccgatcgtt gtcagaagta   7140
agttggccgc agtgttatca ctcatggtta tggcagcact gcataattct cttactgtca   7200
tgccatccgt aagatgcttt tctgtgactg gtgagtactc aaccaagtca ttctgagaat   7260
agtgtatgcg gcgaccgagt tgctcttgcc cggcgtcaat acgggataat accgcgccac   7320
atagcagaac tttaaaagtg ctcatcattg gaaaacgttc ttcggggcga aaactctcaa   7380
ggatcttacc gctgttgaga tccagttcga tgtaacccac tcgtgcaccc aactgatctt   7440
cagcatcttt tactttcacc agcgtttctg ggtgagcaaa aacaggaagg caaaatgccg   7500
caaaaaaggg aataagggcg acacggaaat gttgaatact catactcttc ctttttcaat   7560
attattgaag catttatcag ggttattgtc tcatgagcgg atacatattt gaatgtattt   7620
agaaaaataa acaaataggg gttccgcgca catttccccg aaaagtgcca cctgacgtct   7680
aagaaaccat tattatcatg acattaacct ataaaaatag gcgtatcacg aggccctttc   7740
gtctcgcgcg tttcggtgat gacggtgaaa acctctgaca catgcagctc ccggagacgg   7800
tcacagcttg tctgtaagcg gatgccggga gcagacaagc ccgtcagggc gcgtcagcgg   7860
gtgttggcgg gtgtcgggc tggcttaact atgcggcatc agagcagatt gtactgagag   7920
tgcaccatat gcggtgtgaa ataccgcaca gatgcgtaag gagaaaatac cgcatcaggc   7980
```

```
gccattcgcc attcaggctg cgcaactgtt gggaagggcg atcggtgcgg gcctcttcgc      8040
tattacgcca gctggcgaaa gggggatgtg ctgcaaggcg attaagttgg gtaacgccag      8100
ggttttccca gtcacgacgt tgtaaaacga cggccagtgc caagctg                    8147
```

<210> SEQ ID NO 7
<211> LENGTH: 48
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 7

```
aaaagcagcc agagcctggt gcatagcaac ggcaacacct atctgcat                   48
```

<210> SEQ ID NO 8
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Lys Ser Ser Gln Ser Leu Val His Ser Asn Gly Asn Thr Tyr Leu His
 1               5                  10                  15

<210> SEQ ID NO 9
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 9

```
aaagtgagca accgctttag c                                                21
```

<210> SEQ ID NO 10
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Lys Val Ser Asn Arg Phe Ser
 1               5

<210> SEQ ID NO 11
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 11

```
gcggaaacca gccatgtgcc gtggacc                                          27
```

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Ala Glu Thr Ser His Val Pro Trp Thr
1               5

<210> SEQ ID NO 13
<211> LENGTH: 39
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 13
aaagcgagcg gctatagctt tccggattat tatattaac                              39

<210> SEQ ID NO 14
<211> LENGTH: 13
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Lys Ala Ser Gly Tyr Ser Phe Pro Asp Tyr Tyr Ile Asn
1               5                   10

<210> SEQ ID NO 15
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
tggatttatt ttgcgagcgg caacagcgaa tataaccaga aatttaccgg c                51

<210> SEQ ID NO 16
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Trp Ile Tyr Phe Ala Ser Gly Asn Ser Glu Tyr Asn Gln Lys Phe Thr
1               5                   10                  15

Gly

<210> SEQ ID NO 17
<211> LENGTH: 30
<212> TYPE: DNA

<213> ORGANISM: Artificial Sequence
<220> FEATURE:
<221> NAME/KEY: source
<223> OTHER INFORMATION: /note="Description of Artificial Sequence:
     Synthetic oligonucleotide"

<400> SEQUENCE: 17
ctgtatgatt atgattggta ttttgatgtg                               30

<210> SEQ ID NO 18
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic peptide"

<400> SEQUENCE: 18

Leu Tyr Asp Tyr Asp Trp Tyr Phe Asp Val
1               5                   10

<210> SEQ ID NO 19
<211> LENGTH: 339
<212> TYPE: DNA
<213> ORGANISM: Artificial Sequence
<220> FEATURE:
<221> NAME/KEY: source
<223> OTHER INFORMATION: /note="Description of Artificial Sequence:
     Synthetic polynucleotide"

<400> SEQUENCE: 19
gatattgtga tgacccagac cccgctgagc ctgagcgtga ccccgggcga accggcgagc      60
attagctgca aaagcagcca gagcctggtg catagcaacg gcaacaccta tctgcattgg     120
tatctgcaga aaccgggcca gagcccgcag ctgctgattt ataaagtgag caaccgcttt     180
agcggcgtgc cggatcgctt tagcggcagc ggcagcggcg cggattttac cctgaaaatt     240
agccgcgtgg aagcggaaga tgtgggcgtg tattattgcg cggaaaccag ccatgtgccg     300
tggacctttg gccagggcac caaactggaa attaaaagc                            339

<210> SEQ ID NO 20
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
     Synthetic polypeptide"

<400> SEQUENCE: 20

Asp Ile Val Met Thr Gln Thr Pro Leu Ser Leu Ser Val Thr Pro Gly
1               5                   10                  15

Glu Pro Ala Ser Ile Ser Cys Lys Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Ala Asp Phe Thr Leu Lys Ile
65                  70                  75                  80

Ser Arg Val Glu Ala Glu Asp Val Gly Val Tyr Tyr Cys Ala Glu Thr
                85                  90                  95

Ser His Val Pro Trp Thr Phe Gly Gln Gly Thr Lys Leu Glu Ile Lys
                100                 105                 110

Ser

<210> SEQ ID NO 21
<211> LENGTH: 357
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 21
caggtgcagc tggtgcagag cggcgcggaa gtgaaaaaac cgggcgcgag cgtgaaagtg    60
agctgcaaag cgagcggcta tagctttccg gattattata ttaactgggt gcgccaggcg   120
ccgggccagg gcctggaatg gatgggctgg atttattttg cgagcggcaa cagcgaatat   180
aaccagaaat ttaccggccg cgtgaccatg acccgcgata ccagcagcag caccgcgtat   240
atggaactga gcagcctgcg cagcgaagat accgcggtgt atttttgcgc gagcctgtat   300
gattatgatt ggtattttga tgtgtggggc cagggcacca tggtgaccgt gagcagc     357

<210> SEQ ID NO 22
<211> LENGTH: 119
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 22

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser
        115

<210> SEQ ID NO 23
<211> LENGTH: 567
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 23
atggcggtgg tcctggctgc tctactacaa ggtgtccagg ctcaggtgca cccggtggag    60

-continued

```
tctgggggag gcttggtgca gactgggggg tctctgagac tctcctgtgc agcctctgct    120
ggtatcttca gtatcaatgt catgggctgg taccgccagg ctccagggaa gcagcgcgaa    180
ttggtcgcga gtataactag tcgtggtgat acaacgtatg cgaactccgt gaagggccga    240
ttcaccatct ccagagacaa cgccaagaac acggtatatc tgcaaatgaa cgccctgaaa    300
cctgaggaca cagccgtcta ttactgtaat ttaaagggga cagactatag tggtacatcc    360
acccagacct cgacagaca gggccagggg acccaggtca ccgtctcttc ggaacccaag     420
acaccaaaac cacaaccaca accacaacca caaccacaac ccaatcctac aacagaatcc    480
aagtgtccca atgtccagc ccctgagctc ctgggagggc cctcagtctt catcttcccc     540
ccgaaaccca aggacgtcct ctccatc                                        567
```

<210> SEQ ID NO 24
<211> LENGTH: 189
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Met Ala Val Val Leu Ala Ala Leu Leu Gln Gly Val Gln Ala Gln Val
1               5                   10                  15

His Pro Val Glu Ser Gly Gly Gly Leu Val Gln Thr Gly Gly Ser Leu
            20                  25                  30

Arg Leu Ser Cys Ala Ala Ser Ala Gly Ile Phe Ser Ile Asn Val Met
        35                  40                  45

Gly Trp Tyr Arg Gln Ala Pro Gly Lys Gln Arg Glu Leu Val Ala Ser
    50                  55                  60

Ile Thr Ser Arg Gly Asp Thr Thr Tyr Ala Asn Ser Val Lys Gly Arg
65                  70                  75                  80

Phe Thr Ile Ser Arg Asp Asn Ala Lys Asn Thr Val Tyr Leu Gln Met
                85                  90                  95

Asn Ala Leu Lys Pro Glu Asp Thr Ala Val Tyr Tyr Cys Asn Leu Lys
            100                 105                 110

Gly Thr Asp Tyr Ser Gly Thr Ser Thr Gln Thr Phe Asp Arg Gln Gly
        115                 120                 125

Gln Gly Thr Gln Val Thr Val Ser Ser Glu Pro Lys Thr Pro Lys Pro
    130                 135                 140

Gln Pro Gln Pro Gln Pro Gln Pro Gln Pro Asn Pro Thr Thr Glu Ser
145                 150                 155                 160

Lys Cys Pro Lys Cys Pro Ala Pro Glu Leu Leu Gly Gly Pro Ser Val
                165                 170                 175

Phe Ile Phe Pro Pro Lys Pro Lys Asp Val Leu Ser Ile
            180                 185

<210> SEQ ID NO 25
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Ile Asn Val Met Gly

<210> SEQ ID NO 26
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 26

```
Ser Ile Thr Ser Arg Gly Asp Thr Thr Tyr Ala Asn Ser Val Lys Gly
1               5                   10                  15
```

<210> SEQ ID NO 27
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 27

```
Leu Lys Gly Thr Asp Tyr Ser Gly Thr Ser Thr Gln Thr Phe Asp Arg
1               5                   10                  15
```

<210> SEQ ID NO 28
<211> LENGTH: 173
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 28

```
Gln Val Gln Leu Val Glu Ser Gly Gly Gly Leu Val Gln Pro Gly Glu
1               5                   10                  15

Ser Leu Arg Leu Ser Cys Ala Ala Ser Thr Asn Ile Phe Ser Ile Ser
                20                  25                  30

Pro Met Gly Trp Tyr Arg Gln Ala Pro Gly Lys Gln Arg Glu Leu Val
            35                  40                  45

Ala Ala Ile His Gly Phe Ser Thr Leu Tyr Ala Asp Ser Val Lys Gly
        50                  55                  60

Arg Phe Thr Ile Ser Arg Asp Asn Ala Lys Asn Thr Ile Tyr Leu Gln
65                  70                  75                  80

Met Asn Ser Leu Lys Pro Glu Asp Thr Ala Val Tyr Tyr Cys Asn Lys
                85                  90                  95

Val Pro Trp Gly Asp Tyr His Pro Arg Asn Val Tyr Trp Gly Gln Gly
            100                 105                 110

Thr Gln Val Thr Val Ser Ser Glu Pro Lys Thr Pro Lys Pro Gln Pro
        115                 120                 125

Gln Pro Gln Pro Gln Pro Gln Pro Asn Pro Thr Thr Glu Ser
    130                 135                 140

Lys Cys Pro Lys Cys Pro Ala Pro Glu Leu Leu Gly Gly Pro Ser Val
145                 150                 155                 160

Phe Ile Phe Pro Pro Lys Pro Lys Asp Val Leu Ser Ile
                165                 170
```

<210> SEQ ID NO 29

```
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ile Ser Pro Met Gly
1               5

<210> SEQ ID NO 30
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 30

Ala Ile His Gly Phe Ser Thr Leu Tyr Ala Asp Ser Val Lys Gly
1               5                  10                  15

<210> SEQ ID NO 31
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Val Pro Trp Gly Asp Tyr His Pro Arg Asn Val Tyr
1               5                  10

<210> SEQ ID NO 32
<211> LENGTH: 207
<212> TYPE: PRT
<213> ORGANISM: Homo sapiens

<400> SEQUENCE: 32

Met Gln Ser Gly Thr His Trp Arg Val Leu Gly Leu Cys Leu Leu Ser
1               5                  10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
```

```
                145                 150                 155                 160
Pro Val Thr Arg Gly Ala Gly Gly Arg Gln Arg Gly Gln Asn
                    165                 170                 175
Lys Glu Arg Pro Pro Val Pro Asn Pro Asp Tyr Glu Pro Ile Arg
                180                 185                 190
Lys Gly Gln Arg Asp Leu Tyr Ser Gly Leu Asn Gln Arg Ile
                195                 200                 205
```

<210> SEQ ID NO 33
<211> LENGTH: 182
<212> TYPE: PRT
<213> ORGANISM: Homo sapiens

<400> SEQUENCE: 33

```
Met Glu Gln Gly Lys Gly Leu Ala Val Leu Ile Leu Ala Ile Ile Leu
1               5                   10                  15
Leu Gln Gly Thr Leu Ala Gln Ser Ile Lys Gly Asn His Leu Val Lys
                20                  25                  30
Val Tyr Asp Tyr Gln Glu Asp Gly Ser Val Leu Leu Thr Cys Asp Ala
            35                  40                  45
Glu Ala Lys Asn Ile Thr Trp Phe Lys Asp Gly Lys Met Ile Gly Phe
        50                  55                  60
Leu Thr Glu Asp Lys Lys Lys Trp Asn Leu Gly Ser Asn Ala Lys Asp
65                  70                  75                  80
Pro Arg Gly Met Tyr Gln Cys Lys Gly Ser Gln Asn Lys Ser Lys Pro
                85                  90                  95
Leu Gln Val Tyr Tyr Arg Met Cys Gln Asn Cys Ile Glu Leu Asn Ala
                100                 105                 110
Ala Thr Ile Ser Gly Phe Leu Phe Ala Glu Ile Val Ser Ile Phe Val
            115                 120                 125
Leu Ala Val Gly Val Tyr Phe Ile Ala Gly Gln Asp Gly Val Arg Gln
        130                 135                 140
Ser Arg Ala Ser Asp Lys Gln Thr Leu Leu Pro Asn Asp Gln Leu Tyr
145                 150                 155                 160
Gln Pro Leu Lys Asp Arg Glu Asp Asp Gln Tyr Ser His Leu Gln Gly
                165                 170                 175
Asn Gln Leu Arg Arg Asn
            180
```

<210> SEQ ID NO 34
<211> LENGTH: 172
<212> TYPE: PRT
<213> ORGANISM: Homo sapiens

<400> SEQUENCE: 34

```
Met Glu His Ser Thr Phe Leu Ser Gly Leu Val Leu Ala Thr Leu Leu
1               5                   10                  15
Ser Gln Val Ser Pro Phe Lys Ile Pro Ile Glu Glu Leu Glu Asp Arg
                20                  25                  30
Val Phe Val Asn Cys Asn Thr Ser Ile Thr Trp Val Glu Gly Thr Val
            35                  40                  45
Gly Thr Leu Leu Ser Asp Ile Thr Arg Leu Asp Leu Gly Lys Arg Ile
        50                  55                  60
Leu Asp Pro Arg Gly Ile Tyr Arg Cys Asn Gly Thr Asp Ile Tyr Lys
65                  70                  75                  80
Asp Lys Glu Ser Thr Val Gln Val His Tyr Arg Met Cys Gln Ser Cys
```

```
                 85                  90                  95

Val Glu Leu Asp Pro Ala Thr Val Ala Gly Ile Ile Val Thr Asp Val
            100                 105                 110

Ile Ala Thr Leu Leu Ala Leu Gly Val Phe Cys Phe Ala Gly His
            115                 120                 125

Glu Thr Gly Arg Leu Ser Gly Ala Ala Asp Thr Gln Ala Leu Leu Arg
            130                 135                 140

Asn Asp Gln Val Tyr Gln Pro Leu Arg Asp Arg Asp Ala Gln Tyr
145                 150                 155                 160

Ser His Leu Gly Gly Asn Trp Ala Arg Asn Lys Ser
                165                 170

<210> SEQ ID NO 35
<211> LENGTH: 164
<212> TYPE: PRT
<213> ORGANISM: Homo sapiens

<400> SEQUENCE: 35

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
            115                 120                 125

Lys Gly Glu Arg Arg Arg Gly Lys Gly His Asp Gly Leu Tyr Gln Gly
            130                 135                 140

Leu Ser Thr Ala Thr Lys Asp Thr Tyr Asp Ala Leu His Met Gln Ala
145                 150                 155                 160

Leu Pro Pro Arg

<210> SEQ ID NO 36
<211> LENGTH: 280
<212> TYPE: PRT
<213> ORGANISM: Homo sapiens

<400> SEQUENCE: 36

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
            20                  25                  30

Ile Met Leu Leu Val Asp Gly Lys Gln Gln Met Val Val Cys Leu
            35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80
```

```
Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
            100                 105                 110

Ala Glu Gly His Ser Arg Ser Thr Gln Pro Met His Leu Ser Gly Glu
        115                 120                 125

Ala Ser Thr Ala Arg Thr Cys Pro Gln Glu Pro Leu Arg Gly Thr Pro
    130                 135                 140

Gly Gly Ala Leu Trp Leu Gly Val Leu Arg Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
            180                 185                 190

Ser His Arg Leu His Pro Ala Thr Glu Thr Gly Gly Arg Glu Ala Thr
        195                 200                 205

Ser Ser Pro Arg Pro Gln Pro Arg Asp Arg Arg Trp Gly Asp Thr Pro
    210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Ala
                245                 250                 255

Leu Arg Ala Pro Ser Ser Ser Leu Gly Ala Phe Phe Ala Gly Asp Leu
            260                 265                 270

Pro Pro Pro Leu Gln Ala Gly Ala
        275                 280

<210> SEQ ID NO 37
<211> LENGTH: 142
<212> TYPE: PRT
<213> ORGANISM: Homo sapiens

<400> SEQUENCE: 37

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
            20                  25                  30

Thr Asn Val Ser Gln Ser Lys Asp Ser Asp Val Tyr Ile Thr Asp Lys
        35                  40                  45

Thr Val Leu Asp Met Arg Ser Met Asp Phe Lys Ser Asn Ser Ala Val
    50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
            100                 105                 110

Phe Gln Asn Leu Ser Val Ile Gly Phe Arg Ile Leu Leu Leu Lys Val
        115                 120                 125

Ala Gly Phe Asn Leu Leu Met Thr Leu Arg Leu Trp Ser Ser
    130                 135                 140

<210> SEQ ID NO 38
<211> LENGTH: 139
<212> TYPE: PRT
```

<213> ORGANISM: Homo sapiens

<400> SEQUENCE: 38

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
        35                  40                  45

Cys Asp Tyr Thr Asn Ser Met Phe Asp Tyr Phe Leu Trp Tyr Lys Lys
 50                  55                  60

Tyr Pro Ala Glu Gly Pro Thr Phe Leu Ile Ser Ile Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Lys Gly Ala Gly Thr Ala Ser Lys Leu Thr
        115                 120                 125

Phe Gly Thr Gly Thr Arg Leu Gln Val Thr Leu
    130                 135

<210> SEQ ID NO 39
<211> LENGTH: 177
<212> TYPE: PRT
<213> ORGANISM: Homo sapiens

<400> SEQUENCE: 39

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 40
<211> LENGTH: 133
<212> TYPE: PRT
<213> ORGANISM: Homo sapiens

<400> SEQUENCE: 40

Met Gly Thr Ser Leu Leu Cys Trp Met Ala Leu Cys Leu Leu Gly Ala
1               5                   10                  15

Asp His Ala Asp Thr Gly Val Ser Gln Asn Pro Arg His Asn Ile Thr
            20                  25                  30

Lys Arg Gly Gln Asn Val Thr Phe Arg Cys Asp Pro Ile Ser Glu His
        35                  40                  45

Asn Arg Leu Tyr Trp Tyr Arg Gln Thr Leu Gly Gln Gly Pro Glu Phe
    50                  55                  60

Leu Thr Tyr Phe Gln Asn Glu Ala Gln Leu Glu Lys Ser Arg Leu Leu
65                  70                  75                  80

Ser Asp Arg Phe Ser Ala Glu Arg Pro Lys Gly Ser Phe Ser Thr Leu
            85                  90                  95

Glu Ile Gln Arg Thr Glu Gln Gly Asp Ser Ala Met Tyr Leu Cys Ala
            100                 105                 110

Ser Ser Leu Ala Gly Leu Asn Gln Pro Gln His Phe Gly Asp Gly Thr
        115                 120                 125

Arg Leu Ser Ile Leu
    130

<210> SEQ ID NO 41
<211> LENGTH: 135
<212> TYPE: PRT
<213> ORGANISM: Homo sapiens

<400> SEQUENCE: 41

Met Asp Ser Trp Thr Phe Cys Cys Val Ser Leu Cys Ile Leu Val Ala
1               5                   10                  15

Lys His Thr Asp Ala Gly Val Ile Gln Ser Pro Arg His Glu Val Thr
            20                  25                  30

Glu Met Gly Gln Glu Val Thr Leu Arg Cys Lys Pro Ile Ser Gly His
        35                  40                  45

Asn Ser Leu Phe Trp Tyr Arg Gln Thr Met Met Arg Gly Leu Glu Leu
    50                  55                  60

Leu Ile Tyr Phe Asn Asn Asn Val Pro Ile Asp Asp Ser Gly Met Pro
65                  70                  75                  80

Glu Asp Arg Phe Ser Ala Lys Met Pro Asn Ala Ser Phe Ser Thr Leu
            85                  90                  95

Lys Ile Gln Pro Ser Glu Pro Arg Asp Ser Ala Val Tyr Phe Cys Ala
            100                 105                 110

Ser Ser Phe Ser Thr Cys Ser Ala Asn Tyr Gly Tyr Thr Phe Gly Ser
        115                 120                 125

Gly Thr Arg Leu Thr Val Val
    130                 135

<210> SEQ ID NO 42
<211> LENGTH: 184
<212> TYPE: PRT
<213> ORGANISM: Homo sapiens

<400> SEQUENCE: 42

Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

```
Pro Pro Leu Thr Cys Gln Arg Tyr Cys Asn Ala Ser Val Thr Asn Ser
            35                  40                  45

Val Lys Gly Thr Asn Ala Ile Leu Trp Thr Cys Leu Gly Leu Ser Leu
 50                  55                  60

Ile Ile Ser Leu Ala Val Phe Val Leu Met Phe Leu Leu Arg Lys Ile
 65                  70                  75                  80

Asn Ser Glu Pro Leu Lys Asp Glu Phe Lys Asn Thr Gly Ser Gly Leu
            85                  90                  95

Leu Gly Met Ala Asn Ile Asp Leu Glu Lys Ser Arg Thr Gly Asp Glu
                100                 105                 110

Ile Ile Leu Pro Arg Gly Leu Glu Tyr Thr Val Glu Glu Cys Thr Cys
            115                 120                 125

Glu Asp Cys Ile Lys Ser Lys Pro Lys Val Asp Ser Asp His Cys Phe
130                 135                 140

Pro Leu Pro Ala Met Glu Glu Gly Ala Thr Ile Leu Val Thr Thr Lys
145                 150                 155                 160

Thr Asn Asp Tyr Cys Lys Ser Leu Pro Ala Ala Leu Ser Ala Thr Glu
                165                 170                 175

Ile Glu Lys Ser Ile Ser Ala Arg
            180
```

<210> SEQ ID NO 43
<211> LENGTH: 242
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 43

```
Asp Ile Val Met Thr Gln Ser Gln Arg Phe Met Thr Thr Ser Val Gly
 1               5                  10                  15

Asp Arg Val Ser Val Thr Cys Lys Ala Ser Gln Ser Val Asp Ser Asn
            20                  25                  30

Val Ala Trp Tyr Gln Gln Lys Pro Arg Gln Ser Pro Lys Ala Leu Ile
            35                  40                  45

Phe Ser Ala Ser Leu Arg Phe Ser Gly Val Pro Ala Arg Phe Thr Gly
 50                  55                  60

Ser Gly Ser Gly Thr Asp Phe Thr Leu Thr Ile Ser Asn Leu Gln Ser
 65                  70                  75                  80

Glu Asp Leu Ala Glu Tyr Phe Cys Gln Gln Tyr Asn Asn Tyr Pro Leu
            85                  90                  95

Thr Phe Gly Ala Gly Thr Lys Leu Glu Leu Lys Gly Gly Gly Gly Ser
                100                 105                 110

Gly Gly Gly Gly Ser Ser Gly Gly Ser Gln Val Gln Leu Gln Gln
            115                 120                 125

Ser Gly Gly Gly Leu Val Gln Pro Gly Gly Ser Leu Lys Leu Ser Cys
            130                 135                 140

Ala Ala Ser Gly Ile Asp Phe Ser Arg Tyr Trp Met Ser Trp Val Arg
145                 150                 155                 160

Arg Ala Pro Gly Lys Gly Leu Glu Trp Ile Gly Glu Ile Asn Pro Asp
                165                 170                 175

Ser Ser Thr Ile Asn Tyr Ala Pro Ser Leu Lys Asp Lys Phe Ile Ile
                180                 185                 190

Ser Arg Asp Asn Ala Lys Asn Thr Leu Tyr Leu Gln Met Ser Lys Val
```

```
                   195                 200                 205
Arg Ser Glu Asp Thr Ala Leu Tyr Tyr Cys Ala Ser Leu Tyr Tyr Asp
    210                 215                 220

Tyr Gly Asp Ala Met Asp Tyr Trp Gly Gln Gly Thr Ser Val Thr Val
225                 230                 235                 240

Ser Ser

<210> SEQ ID NO 44
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Gly Gly Gly Gly Ser Gly Gly Gly Ser Gly Gly Gly Ser
1               5                   10                  15

<210> SEQ ID NO 45
<211> LENGTH: 247
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Pro Asp Tyr
            20                  25                  30

Tyr Ile Asn Trp Val Arg Gln Ala Pro Gly Gln Gly Leu Glu Trp Met
        35                  40                  45

Gly Trp Ile Tyr Phe Ala Ser Gly Asn Ser Glu Tyr Asn Gln Lys Phe
    50                  55                  60

Thr Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Phe Cys
                85                  90                  95

Ala Ser Leu Tyr Asp Tyr Asp Trp Tyr Phe Asp Val Trp Gly Gln Gly
            100                 105                 110

Thr Met Val Thr Val Ser Ser Gly Gly Gly Ser Gly Gly Gly Gly
            115                 120                 125

Ser Gly Gly Gly Ser Asp Ile Val Met Thr Gln Thr Pro Leu Ser
    130                 135                 140

Leu Ser Val Thr Pro Gly Glu Pro Ala Ser Ile Ser Cys Lys Ser Ser
145                 150                 155                 160

Gln Ser Leu Val His Ser Asn Gly Asn Thr Tyr Leu His Trp Tyr Leu
                165                 170                 175

Gln Lys Pro Gly Gln Ser Pro Gln Leu Leu Ile Tyr Lys Val Ser Asn
            180                 185                 190

Arg Phe Ser Gly Val Pro Asp Arg Phe Ser Gly Ser Gly Ser Gly Ala
        195                 200                 205

Asp Phe Thr Leu Lys Ile Ser Arg Val Glu Ala Glu Asp Val Gly Val
    210                 215                 220
```

```
Tyr Tyr Cys Ala Glu Thr Ser His Val Pro Trp Thr Phe Gly Gln Gly
225                 230                 235                 240

Thr Lys Leu Glu Ile Lys Ser
                245
```

<210> SEQ ID NO 46
<211> LENGTH: 175
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

```
Gln Val His Pro Val Glu Ser Gly Gly Gly Leu Val Gln Thr Gly Gly
1               5                   10                  15

Ser Leu Arg Leu Ser Cys Ala Ala Ser Ala Gly Ile Phe Ser Ile Asn
                20                  25                  30

Val Met Gly Trp Tyr Arg Gln Ala Pro Gly Lys Gln Arg Glu Leu Val
            35                  40                  45

Ala Ser Ile Thr Ser Arg Gly Asp Thr Thr Tyr Ala Asn Ser Val Lys
        50                  55                  60

Gly Arg Phe Thr Ile Ser Arg Asp Asn Ala Lys Asn Thr Val Tyr Leu
65                  70                  75                  80

Gln Met Asn Ala Leu Lys Pro Glu Asp Thr Ala Val Tyr Tyr Cys Asn
                85                  90                  95

Leu Lys Gly Thr Asp Tyr Ser Gly Thr Ser Thr Gln Thr Phe Asp Arg
            100                 105                 110

Gln Gly Gln Gly Thr Gln Val Thr Val Ser Ser Glu Pro Lys Thr Pro
        115                 120                 125

Lys Pro Gln Pro Gln Pro Gln Pro Gln Pro Asn Pro Thr Thr
    130                 135                 140

Glu Ser Lys Cys Pro Lys Cys Pro Ala Pro Glu Leu Leu Gly Gly Pro
145                 150                 155                 160

Ser Val Phe Ile Phe Pro Pro Lys Pro Lys Asp Val Leu Ser Ile
                165                 170                 175
```

<210> SEQ ID NO 47
<211> LENGTH: 171
<212> TYPE: PRT
<213> ORGANISM: Homo sapiens

<400> SEQUENCE: 47

```
Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
                20                  25                  30

Val Phe Val Asn Cys Asn Thr Ser Ile Thr Trp Val Glu Gly Thr Val
            35                  40                  45

Gly Thr Leu Leu Ser Asp Ile Thr Arg Leu Asp Leu Gly Lys Arg Ile
        50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110
```

-continued

```
Ile Ala Thr Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Ala Gln Tyr
145                 150                 155                 160

Ser His Leu Gly Gly Asn Trp Ala Arg Asn Lys
                165                 170

<210> SEQ ID NO 48
<211> LENGTH: 281
<212> TYPE: PRT
<213> ORGANISM: Homo sapiens

<400> SEQUENCE: 48

Met Ala Gly Thr Trp Leu Leu Leu Leu Ala Leu Gly Cys Pro Ala
1               5                   10                  15

Leu Pro Thr Gly Val Gly Gly Thr Pro Phe Pro Ser Leu Ala Pro Pro
                20                  25                  30

Ile Met Leu Leu Val Asp Gly Lys Gln Gln Met Val Val Cys Leu
        35                  40                  45

Val Leu Asp Val Ala Pro Pro Gly Leu Asp Ser Pro Ile Trp Phe Ser
50                  55                  60

Ala Gly Asn Gly Ser Ala Leu Asp Ala Phe Thr Tyr Gly Pro Ser Pro
65                  70                  75                  80

Ala Thr Asp Gly Thr Trp Thr Asn Leu Ala His Leu Ser Leu Pro Ser
                85                  90                  95

Glu Glu Leu Ala Ser Trp Glu Pro Leu Val Cys His Thr Gly Pro Gly
                100                 105                 110

Ala Glu Gly His Ser Arg Ser Thr Gln Pro Met His Leu Ser Gly Glu
            115                 120                 125

Ala Ser Thr Ala Arg Thr Cys Pro Gln Glu Pro Leu Arg Gly Thr Pro
        130                 135                 140

Gly Gly Ala Leu Trp Leu Gly Val Leu Arg Leu Leu Leu Phe Lys Leu
145                 150                 155                 160

Leu Leu Phe Asp Leu Leu Leu Thr Cys Ser Cys Leu Cys Asp Pro Ala
                165                 170                 175

Gly Pro Leu Pro Ser Pro Ala Thr Thr Thr Arg Leu Arg Ala Leu Gly
                180                 185                 190

Ser His Arg Leu His Pro Ala Thr Glu Thr Gly Gly Arg Glu Ala Thr
            195                 200                 205

Ser Ser Pro Arg Pro Gln Pro Arg Asp Arg Arg Trp Gly Asp Thr Pro
210                 215                 220

Pro Gly Arg Lys Pro Gly Ser Pro Val Trp Gly Glu Gly Ser Tyr Leu
225                 230                 235                 240

Ser Ser Tyr Pro Thr Cys Pro Ala Gln Ala Trp Cys Ser Arg Ser Ala
                245                 250                 255

Leu Arg Ala Pro Ser Ser Ser Leu Gly Ala Phe Phe Ala Gly Asp Leu
            260                 265                 270

Pro Pro Pro Leu Gln Ala Gly Ala Ala
            275                 280

<210> SEQ ID NO 49
<211> LENGTH: 20
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This sequence may encompass 1-4
      'Gly Gly Gly Gly Ser' repeating units"

<400> SEQUENCE: 49

Gly Gly Gly Gly Ser Gly Gly Gly Gly Ser Gly Gly Gly Gly Ser Gly
1               5                   10                  15

Gly Gly Gly Ser
            20

<210> SEQ ID NO 50
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

Gly Gly Gly Gly Ser Gly Gly Gly Gly Ser Gly Gly Gly Gly Ser
1               5                   10                  15

<210> SEQ ID NO 51
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(40)
<223> OTHER INFORMATION: /note="This sequence may encompass 1-10
      'Gly Gly Gly Ser' repeating units"

<400> SEQUENCE: 51

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser
        35                  40

<210> SEQ ID NO 52
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 50-5000
      nucleotides"

<400> SEQUENCE: 52
aaaaaaaaaa aaaaaaaaaa aaaaaaaaaa aaaaaaaaaa aaaaaaaaaa aaaaaaaaaa    60
```

```
aaaaaaaaaa aaaaaaaaaa aaaaaaaaaa aaaaaaaaaa aaaaaaaaaa aaaaaaaaaa      120
aaaaaaaaaa aaaaaaaaaa aaaaaaaaaa aaaaaaaaaa aaaaaaaaaa aaaaaaaaaa      180
aaaaaaaaaa aaaaaaaaaa aaaaaaaaaa aaaaaaaaaa aaaaaaaaaa aaaaaaaaaa      240
aaaaaaaaaa aaaaaaaaaa aaaaaaaaaa aaaaaaaaaa aaaaaaaaaa aaaaaaaaaa      300
aaaaaaaaaa aaaaaaaaaa aaaaaaaaaa aaaaaaaaaa aaaaaaaaaa aaaaaaaaaa      360
aaaaaaaaaa aaaaaaaaaa aaaaaaaaaa aaaaaaaaaa aaaaaaaaaa aaaaaaaaaa      420
aaaaaaaaaa aaaaaaaaaa aaaaaaaaaa aaaaaaaaaa aaaaaaaaaa aaaaaaaaaa      480
aaaaaaaaaa aaaaaaaaaa aaaaaaaaaa aaaaaaaaaa aaaaaaaaaa aaaaaaaaaa      540
aaaaaaaaaa aaaaaaaaaa aaaaaaaaaa aaaaaaaaaa aaaaaaaaaa aaaaaaaaaa      600
aaaaaaaaaa aaaaaaaaaa aaaaaaaaaa aaaaaaaaaa aaaaaaaaaa aaaaaaaaaa      660
aaaaaaaaaa aaaaaaaaaa aaaaaaaaaa aaaaaaaaaa aaaaaaaaaa aaaaaaaaaa      720
aaaaaaaaaa aaaaaaaaaa aaaaaaaaaa aaaaaaaaaa aaaaaaaaaa aaaaaaaaaa      780
aaaaaaaaaa aaaaaaaaaa aaaaaaaaaa aaaaaaaaaa aaaaaaaaaa aaaaaaaaaa      840
aaaaaaaaaa aaaaaaaaaa aaaaaaaaaa aaaaaaaaaa aaaaaaaaaa aaaaaaaaaa      900
aaaaaaaaaa aaaaaaaaaa aaaaaaaaaa aaaaaaaaaa aaaaaaaaaa aaaaaaaaaa      960
aaaaaaaaaa aaaaaaaaaa aaaaaaaaaa aaaaaaaaaa aaaaaaaaaa aaaaaaaaaa     1020
aaaaaaaaaa aaaaaaaaaa aaaaaaaaaa aaaaaaaaaa aaaaaaaaaa aaaaaaaaaa     1080
aaaaaaaaaa aaaaaaaaaa aaaaaaaaaa aaaaaaaaaa aaaaaaaaaa aaaaaaaaaa     1140
aaaaaaaaaa aaaaaaaaaa aaaaaaaaaa aaaaaaaaaa aaaaaaaaaa aaaaaaaaaa     1200
aaaaaaaaaa aaaaaaaaaa aaaaaaaaaa aaaaaaaaaa aaaaaaaaaa aaaaaaaaaa     1260
aaaaaaaaaa aaaaaaaaaa aaaaaaaaaa aaaaaaaaaa aaaaaaaaaa aaaaaaaaaa     1320
aaaaaaaaaa aaaaaaaaaa aaaaaaaaaa aaaaaaaaaa aaaaaaaaaa aaaaaaaaaa     1380
aaaaaaaaaa aaaaaaaaaa aaaaaaaaaa aaaaaaaaaa aaaaaaaaaa aaaaaaaaaa     1440
aaaaaaaaaa aaaaaaaaaa aaaaaaaaaa aaaaaaaaaa aaaaaaaaaa aaaaaaaaaa     1500
aaaaaaaaaa aaaaaaaaaa aaaaaaaaaa aaaaaaaaaa aaaaaaaaaa aaaaaaaaaa     1560
aaaaaaaaaa aaaaaaaaaa aaaaaaaaaa aaaaaaaaaa aaaaaaaaaa aaaaaaaaaa     1620
aaaaaaaaaa aaaaaaaaaa aaaaaaaaaa aaaaaaaaaa aaaaaaaaaa aaaaaaaaaa     1680
aaaaaaaaaa aaaaaaaaaa aaaaaaaaaa aaaaaaaaaa aaaaaaaaaa aaaaaaaaaa     1740
aaaaaaaaaa aaaaaaaaaa aaaaaaaaaa aaaaaaaaaa aaaaaaaaaa aaaaaaaaaa     1800
aaaaaaaaaa aaaaaaaaaa aaaaaaaaaa aaaaaaaaaa aaaaaaaaaa aaaaaaaaaa     1860
aaaaaaaaaa aaaaaaaaaa aaaaaaaaaa aaaaaaaaaa aaaaaaaaaa aaaaaaaaaa     1920
aaaaaaaaaa aaaaaaaaaa aaaaaaaaaa aaaaaaaaaa aaaaaaaaaa aaaaaaaaaa     1980
aaaaaaaaaa aaaaaaaaaa aaaaaaaaaa aaaaaaaaaa aaaaaaaaaa aaaaaaaaaa     2040
aaaaaaaaaa aaaaaaaaaa aaaaaaaaaa aaaaaaaaaa aaaaaaaaaa aaaaaaaaaa     2100
aaaaaaaaaa aaaaaaaaaa aaaaaaaaaa aaaaaaaaaa aaaaaaaaaa aaaaaaaaaa     2160
aaaaaaaaaa aaaaaaaaaa aaaaaaaaaa aaaaaaaaaa aaaaaaaaaa aaaaaaaaaa     2220
aaaaaaaaaa aaaaaaaaaa aaaaaaaaaa aaaaaaaaaa aaaaaaaaaa aaaaaaaaaa     2280
aaaaaaaaaa aaaaaaaaaa aaaaaaaaaa aaaaaaaaaa aaaaaaaaaa aaaaaaaaaa     2340
aaaaaaaaaa aaaaaaaaaa aaaaaaaaaa aaaaaaaaaa aaaaaaaaaa aaaaaaaaaa     2400
aaaaaaaaaa aaaaaaaaaa aaaaaaaaaa aaaaaaaaaa aaaaaaaaaa aaaaaaaaaa     2460
```

```
aaaaaaaaaa aaaaaaaaaa aaaaaaaaaa aaaaaaaaaa aaaaaaaaaa aaaaaaaaaa     2520
aaaaaaaaaa aaaaaaaaaa aaaaaaaaaa aaaaaaaaaa aaaaaaaaaa aaaaaaaaaa     2580
aaaaaaaaaa aaaaaaaaaa aaaaaaaaaa aaaaaaaaaa aaaaaaaaaa aaaaaaaaaa     2640
aaaaaaaaaa aaaaaaaaaa aaaaaaaaaa aaaaaaaaaa aaaaaaaaaa aaaaaaaaaa     2700
aaaaaaaaaa aaaaaaaaaa aaaaaaaaaa aaaaaaaaaa aaaaaaaaaa aaaaaaaaaa     2760
aaaaaaaaaa aaaaaaaaaa aaaaaaaaaa aaaaaaaaaa aaaaaaaaaa aaaaaaaaaa     2820
aaaaaaaaaa aaaaaaaaaa aaaaaaaaaa aaaaaaaaaa aaaaaaaaaa aaaaaaaaaa     2880
aaaaaaaaaa aaaaaaaaaa aaaaaaaaaa aaaaaaaaaa aaaaaaaaaa aaaaaaaaaa     2940
aaaaaaaaaa aaaaaaaaaa aaaaaaaaaa aaaaaaaaaa aaaaaaaaaa aaaaaaaaaa     3000
aaaaaaaaaa aaaaaaaaaa aaaaaaaaaa aaaaaaaaaa aaaaaaaaaa aaaaaaaaaa     3060
aaaaaaaaaa aaaaaaaaaa aaaaaaaaaa aaaaaaaaaa aaaaaaaaaa aaaaaaaaaa     3120
aaaaaaaaaa aaaaaaaaaa aaaaaaaaaa aaaaaaaaaa aaaaaaaaaa aaaaaaaaaa     3180
aaaaaaaaaa aaaaaaaaaa aaaaaaaaaa aaaaaaaaaa aaaaaaaaaa aaaaaaaaaa     3240
aaaaaaaaaa aaaaaaaaaa aaaaaaaaaa aaaaaaaaaa aaaaaaaaaa aaaaaaaaaa     3300
aaaaaaaaaa aaaaaaaaaa aaaaaaaaaa aaaaaaaaaa aaaaaaaaaa aaaaaaaaaa     3360
aaaaaaaaaa aaaaaaaaaa aaaaaaaaaa aaaaaaaaaa aaaaaaaaaa aaaaaaaaaa     3420
aaaaaaaaaa aaaaaaaaaa aaaaaaaaaa aaaaaaaaaa aaaaaaaaaa aaaaaaaaaa     3480
aaaaaaaaaa aaaaaaaaaa aaaaaaaaaa aaaaaaaaaa aaaaaaaaaa aaaaaaaaaa     3540
aaaaaaaaaa aaaaaaaaaa aaaaaaaaaa aaaaaaaaaa aaaaaaaaaa aaaaaaaaaa     3600
aaaaaaaaaa aaaaaaaaaa aaaaaaaaaa aaaaaaaaaa aaaaaaaaaa aaaaaaaaaa     3660
aaaaaaaaaa aaaaaaaaaa aaaaaaaaaa aaaaaaaaaa aaaaaaaaaa aaaaaaaaaa     3720
aaaaaaaaaa aaaaaaaaaa aaaaaaaaaa aaaaaaaaaa aaaaaaaaaa aaaaaaaaaa     3780
aaaaaaaaaa aaaaaaaaaa aaaaaaaaaa aaaaaaaaaa aaaaaaaaaa aaaaaaaaaa     3840
aaaaaaaaaa aaaaaaaaaa aaaaaaaaaa aaaaaaaaaa aaaaaaaaaa aaaaaaaaaa     3900
aaaaaaaaaa aaaaaaaaaa aaaaaaaaaa aaaaaaaaaa aaaaaaaaaa aaaaaaaaaa     3960
aaaaaaaaaa aaaaaaaaaa aaaaaaaaaa aaaaaaaaaa aaaaaaaaaa aaaaaaaaaa     4020
aaaaaaaaaa aaaaaaaaaa aaaaaaaaaa aaaaaaaaaa aaaaaaaaaa aaaaaaaaaa     4080
aaaaaaaaaa aaaaaaaaaa aaaaaaaaaa aaaaaaaaaa aaaaaaaaaa aaaaaaaaaa     4140
aaaaaaaaaa aaaaaaaaaa aaaaaaaaaa aaaaaaaaaa aaaaaaaaaa aaaaaaaaaa     4200
aaaaaaaaaa aaaaaaaaaa aaaaaaaaaa aaaaaaaaaa aaaaaaaaaa aaaaaaaaaa     4260
aaaaaaaaaa aaaaaaaaaa aaaaaaaaaa aaaaaaaaaa aaaaaaaaaa aaaaaaaaaa     4320
aaaaaaaaaa aaaaaaaaaa aaaaaaaaaa aaaaaaaaaa aaaaaaaaaa aaaaaaaaaa     4380
aaaaaaaaaa aaaaaaaaaa aaaaaaaaaa aaaaaaaaaa aaaaaaaaaa aaaaaaaaaa     4440
aaaaaaaaaa aaaaaaaaaa aaaaaaaaaa aaaaaaaaaa aaaaaaaaaa aaaaaaaaaa     4500
aaaaaaaaaa aaaaaaaaaa aaaaaaaaaa aaaaaaaaaa aaaaaaaaaa aaaaaaaaaa     4560
aaaaaaaaaa aaaaaaaaaa aaaaaaaaaa aaaaaaaaaa aaaaaaaaaa aaaaaaaaaa     4620
aaaaaaaaaa aaaaaaaaaa aaaaaaaaaa aaaaaaaaaa aaaaaaaaaa aaaaaaaaaa     4680
aaaaaaaaaa aaaaaaaaaa aaaaaaaaaa aaaaaaaaaa aaaaaaaaaa aaaaaaaaaa     4740
aaaaaaaaaa aaaaaaaaaa aaaaaaaaaa aaaaaaaaaa aaaaaaaaaa aaaaaaaaaa     4800
```

```
aaaaaaaaaa aaaaaaaaaa aaaaaaaaaa aaaaaaaaaa aaaaaaaaaa aaaaaaaaaa    4860
aaaaaaaaaa aaaaaaaaaa aaaaaaaaaa aaaaaaaaaa aaaaaaaaaa aaaaaaaaaa    4920
aaaaaaaaaa aaaaaaaaaa aaaaaaaaaa aaaaaaaaaa aaaaaaaaaa aaaaaaaaaa    4980
aaaaaaaaaa aaaaaaaaaa                                                5000

<210> SEQ ID NO 53
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Gly Gly Gly Gly Ser
1               5

<210> SEQ ID NO 54
<211> LENGTH: 2000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(2000)
<223> OTHER INFORMATION: /note="This sequence may encompass 50-2000
      nucleotides"

<400> SEQUENCE: 54
aaaaaaaaaa aaaaaaaaaa aaaaaaaaaa aaaaaaaaaa aaaaaaaaaa aaaaaaaaaa      60
aaaaaaaaaa aaaaaaaaaa aaaaaaaaaa aaaaaaaaaa aaaaaaaaaa aaaaaaaaaa     120
aaaaaaaaaa aaaaaaaaaa aaaaaaaaaa aaaaaaaaaa aaaaaaaaaa aaaaaaaaaa     180
aaaaaaaaaa aaaaaaaaaa aaaaaaaaaa aaaaaaaaaa aaaaaaaaaa aaaaaaaaaa     240
aaaaaaaaaa aaaaaaaaaa aaaaaaaaaa aaaaaaaaaa aaaaaaaaaa aaaaaaaaaa     300
aaaaaaaaaa aaaaaaaaaa aaaaaaaaaa aaaaaaaaaa aaaaaaaaaa aaaaaaaaaa     360
aaaaaaaaaa aaaaaaaaaa aaaaaaaaaa aaaaaaaaaa aaaaaaaaaa aaaaaaaaaa     420
aaaaaaaaaa aaaaaaaaaa aaaaaaaaaa aaaaaaaaaa aaaaaaaaaa aaaaaaaaaa     480
aaaaaaaaaa aaaaaaaaaa aaaaaaaaaa aaaaaaaaaa aaaaaaaaaa aaaaaaaaaa     540
aaaaaaaaaa aaaaaaaaaa aaaaaaaaaa aaaaaaaaaa aaaaaaaaaa aaaaaaaaaa     600
aaaaaaaaaa aaaaaaaaaa aaaaaaaaaa aaaaaaaaaa aaaaaaaaaa aaaaaaaaaa     660
aaaaaaaaaa aaaaaaaaaa aaaaaaaaaa aaaaaaaaaa aaaaaaaaaa aaaaaaaaaa     720
aaaaaaaaaa aaaaaaaaaa aaaaaaaaaa aaaaaaaaaa aaaaaaaaaa aaaaaaaaaa     780
aaaaaaaaaa aaaaaaaaaa aaaaaaaaaa aaaaaaaaaa aaaaaaaaaa aaaaaaaaaa     840
aaaaaaaaaa aaaaaaaaaa aaaaaaaaaa aaaaaaaaaa aaaaaaaaaa aaaaaaaaaa     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaaa    1020
aaaaaaaaaa aaaaaaaaaa aaaaaaaaaa aaaaaaaaaa aaaaaaaaaa aaaaaaaaaa    1080
aaaaaaaaaa aaaaaaaaaa aaaaaaaaaa aaaaaaaaaa aaaaaaaaaa aaaaaaaaaa    1140
aaaaaaaaaa aaaaaaaaaa aaaaaaaaaa aaaaaaaaaa aaaaaaaaaa aaaaaaaaaa    1200
```

| | |
|---|---|
| aaaaaaaaaa aaaaaaaaaa aaaaaaaaaa aaaaaaaaaa aaaaaaaaaa aaaaaaaaaa | 1260 |
| aaaaaaaaaa aaaaaaaaaa aaaaaaaaaa aaaaaaaaaa aaaaaaaaaa aaaaaaaaaa | 1320 |
| aaaaaaaaaa aaaaaaaaaa aaaaaaaaaa aaaaaaaaaa aaaaaaaaaa aaaaaaaaaa | 1380 |
| aaaaaaaaaa aaaaaaaaaa aaaaaaaaaa aaaaaaaaaa aaaaaaaaaa aaaaaaaaaa | 1440 |
| aaaaaaaaaa aaaaaaaaaa aaaaaaaaaa aaaaaaaaaa aaaaaaaaaa aaaaaaaaaa | 1500 |
| aaaaaaaaaa aaaaaaaaaa aaaaaaaaaa aaaaaaaaaa aaaaaaaaaa aaaaaaaaaa | 1560 |
| aaaaaaaaaa aaaaaaaaaa aaaaaaaaaa aaaaaaaaaa aaaaaaaaaa aaaaaaaaaa | 1620 |
| aaaaaaaaaa aaaaaaaaaa aaaaaaaaaa aaaaaaaaaa aaaaaaaaaa aaaaaaaaaa | 1680 |
| aaaaaaaaaa aaaaaaaaaa aaaaaaaaaa aaaaaaaaaa aaaaaaaaaa aaaaaaaaaa | 1740 |
| aaaaaaaaaa aaaaaaaaaa aaaaaaaaaa aaaaaaaaaa aaaaaaaaaa aaaaaaaaaa | 1800 |
| aaaaaaaaaa aaaaaaaaaa aaaaaaaaaa aaaaaaaaaa aaaaaaaaaa aaaaaaaaaa | 1860 |
| aaaaaaaaaa aaaaaaaaaa aaaaaaaaaa aaaaaaaaaa aaaaaaaaaa aaaaaaaaaa | 1920 |
| aaaaaaaaaa aaaaaaaaaa aaaaaaaaaa aaaaaaaaaa aaaaaaaaaa aaaaaaaaaa | 1980 |
| aaaaaaaaaa aaaaaaaaaa | 2000 |

<210> SEQ ID NO 55
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"
<220> FEATURE:
<221> NAME/KEY: misc_feature
<222> LOCATION: (1)..(5000)
<223> OTHER INFORMATION: /note="This sequence may encompass 50-5000 nucleotides"

<400> SEQUENCE: 55

| | |
|---|---|
| tttttttttt tttttttttt tttttttttt tttttttttt tttttttttt tttttttttt | 60 |
| tttttttttt tttttttttt tttttttttt tttttttttt tttttttttt tttttttttt | 120 |
| tttttttttt tttttttttt tttttttttt tttttttttt tttttttttt tttttttttt | 180 |
| tttttttttt tttttttttt tttttttttt tttttttttt tttttttttt tttttttttt | 240 |
| tttttttttt tttttttttt tttttttttt tttttttttt tttttttttt tttttttttt | 300 |
| tttttttttt tttttttttt tttttttttt tttttttttt tttttttttt tttttttttt | 360 |
| tttttttttt tttttttttt tttttttttt tttttttttt tttttttttt tttttttttt | 420 |
| tttttttttt tttttttttt tttttttttt tttttttttt tttttttttt tttttttttt | 480 |
| tttttttttt tttttttttt tttttttttt tttttttttt tttttttttt tttttttttt | 540 |
| tttttttttt tttttttttt tttttttttt tttttttttt tttttttttt tttttttttt | 600 |
| tttttttttt tttttttttt tttttttttt tttttttttt tttttttttt tttttttttt | 660 |
| tttttttttt tttttttttt tttttttttt tttttttttt tttttttttt tttttttttt | 720 |
| tttttttttt tttttttttt tttttttttt tttttttttt tttttttttt tttttttttt | 780 |
| tttttttttt tttttttttt tttttttttt tttttttttt tttttttttt tttttttttt | 840 |
| tttttttttt tttttttttt tttttttttt tttttttttt tttttttttt tttttttttt | 900 |
| tttttttttt tttttttttt tttttttttt tttttttttt tttttttttt tttttttttt | 960 |
| tttttttttt tttttttttt tttttttttt tttttttttt tttttttttt tttttttttt | 1020 |

| | |
|---|---|
| tttttttttt tttttttttt tttttttttt tttttttttt tttttttttt tttttttttt | 1080 |
| tttttttttt tttttttttt tttttttttt tttttttttt tttttttttt tttttttttt | 1140 |
| tttttttttt tttttttttt tttttttttt tttttttttt tttttttttt tttttttttt | 1200 |
| tttttttttt tttttttttt tttttttttt tttttttttt tttttttttt tttttttttt | 1260 |
| tttttttttt tttttttttt tttttttttt tttttttttt tttttttttt tttttttttt | 1320 |
| tttttttttt tttttttttt tttttttttt tttttttttt tttttttttt tttttttttt | 1380 |
| tttttttttt tttttttttt tttttttttt tttttttttt tttttttttt tttttttttt | 1440 |
| tttttttttt tttttttttt tttttttttt tttttttttt tttttttttt tttttttttt | 1500 |
| tttttttttt tttttttttt tttttttttt tttttttttt tttttttttt tttttttttt | 1560 |
| tttttttttt tttttttttt tttttttttt tttttttttt tttttttttt tttttttttt | 1620 |
| tttttttttt tttttttttt tttttttttt tttttttttt tttttttttt tttttttttt | 1680 |
| tttttttttt tttttttttt tttttttttt tttttttttt tttttttttt tttttttttt | 1740 |
| tttttttttt tttttttttt tttttttttt tttttttttt tttttttttt tttttttttt | 1800 |
| tttttttttt tttttttttt tttttttttt tttttttttt tttttttttt tttttttttt | 1860 |
| tttttttttt tttttttttt tttttttttt tttttttttt tttttttttt tttttttttt | 1920 |
| tttttttttt tttttttttt tttttttttt tttttttttt tttttttttt tttttttttt | 1980 |
| tttttttttt tttttttttt tttttttttt tttttttttt tttttttttt tttttttttt | 2040 |
| tttttttttt tttttttttt tttttttttt tttttttttt tttttttttt tttttttttt | 2100 |
| tttttttttt tttttttttt tttttttttt tttttttttt tttttttttt tttttttttt | 2160 |
| tttttttttt tttttttttt tttttttttt tttttttttt tttttttttt tttttttttt | 2220 |
| tttttttttt tttttttttt tttttttttt tttttttttt tttttttttt tttttttttt | 2280 |
| tttttttttt tttttttttt tttttttttt tttttttttt tttttttttt tttttttttt | 2340 |
| tttttttttt tttttttttt tttttttttt tttttttttt tttttttttt tttttttttt | 2400 |
| tttttttttt tttttttttt tttttttttt tttttttttt tttttttttt tttttttttt | 2460 |
| tttttttttt tttttttttt tttttttttt tttttttttt tttttttttt tttttttttt | 2520 |
| tttttttttt tttttttttt tttttttttt tttttttttt tttttttttt tttttttttt | 2580 |
| tttttttttt tttttttttt tttttttttt tttttttttt tttttttttt tttttttttt | 2640 |
| tttttttttt tttttttttt tttttttttt tttttttttt tttttttttt tttttttttt | 2700 |
| tttttttttt tttttttttt tttttttttt tttttttttt tttttttttt tttttttttt | 2760 |
| tttttttttt tttttttttt tttttttttt tttttttttt tttttttttt tttttttttt | 2820 |
| tttttttttt tttttttttt tttttttttt tttttttttt tttttttttt tttttttttt | 2880 |
| tttttttttt tttttttttt tttttttttt tttttttttt tttttttttt tttttttttt | 2940 |
| tttttttttt tttttttttt tttttttttt tttttttttt tttttttttt tttttttttt | 3000 |
| tttttttttt tttttttttt tttttttttt tttttttttt tttttttttt tttttttttt | 3060 |
| tttttttttt tttttttttt tttttttttt tttttttttt tttttttttt tttttttttt | 3120 |
| tttttttttt tttttttttt tttttttttt tttttttttt tttttttttt tttttttttt | 3180 |
| tttttttttt tttttttttt tttttttttt tttttttttt tttttttttt tttttttttt | 3240 |
| tttttttttt tttttttttt tttttttttt tttttttttt tttttttttt tttttttttt | 3300 |
| tttttttttt tttttttttt tttttttttt tttttttttt tttttttttt tttttttttt | 3360 |

| | |
|---|---|
| tttttttttt tttttttttt tttttttttt tttttttttt tttttttttt tttttttttt | 3420 |
| tttttttttt tttttttttt tttttttttt tttttttttt tttttttttt tttttttttt | 3480 |
| tttttttttt tttttttttt tttttttttt tttttttttt tttttttttt tttttttttt | 3540 |
| tttttttttt tttttttttt tttttttttt tttttttttt tttttttttt tttttttttt | 3600 |
| tttttttttt tttttttttt tttttttttt tttttttttt tttttttttt tttttttttt | 3660 |
| tttttttttt tttttttttt tttttttttt tttttttttt tttttttttt tttttttttt | 3720 |
| tttttttttt tttttttttt tttttttttt tttttttttt tttttttttt tttttttttt | 3780 |
| tttttttttt tttttttttt tttttttttt tttttttttt tttttttttt tttttttttt | 3840 |
| tttttttttt tttttttttt tttttttttt tttttttttt tttttttttt tttttttttt | 3900 |
| tttttttttt tttttttttt tttttttttt tttttttttt tttttttttt tttttttttt | 3960 |
| tttttttttt tttttttttt tttttttttt tttttttttt tttttttttt tttttttttt | 4020 |
| tttttttttt tttttttttt tttttttttt tttttttttt tttttttttt tttttttttt | 4080 |
| tttttttttt tttttttttt tttttttttt tttttttttt tttttttttt tttttttttt | 4140 |
| tttttttttt tttttttttt tttttttttt tttttttttt tttttttttt tttttttttt | 4200 |
| tttttttttt tttttttttt tttttttttt tttttttttt tttttttttt tttttttttt | 4260 |
| tttttttttt tttttttttt tttttttttt tttttttttt tttttttttt tttttttttt | 4320 |
| tttttttttt tttttttttt tttttttttt tttttttttt tttttttttt tttttttttt | 4380 |
| tttttttttt tttttttttt tttttttttt tttttttttt tttttttttt tttttttttt | 4440 |
| tttttttttt tttttttttt tttttttttt tttttttttt tttttttttt tttttttttt | 4500 |
| tttttttttt tttttttttt tttttttttt tttttttttt tttttttttt tttttttttt | 4560 |
| tttttttttt tttttttttt tttttttttt tttttttttt tttttttttt tttttttttt | 4620 |
| tttttttttt tttttttttt tttttttttt tttttttttt tttttttttt tttttttttt | 4680 |
| tttttttttt tttttttttt tttttttttt tttttttttt tttttttttt tttttttttt | 4740 |
| tttttttttt tttttttttt tttttttttt tttttttttt tttttttttt tttttttttt | 4800 |
| tttttttttt tttttttttt tttttttttt tttttttttt tttttttttt tttttttttt | 4860 |
| tttttttttt tttttttttt tttttttttt tttttttttt tttttttttt tttttttttt | 4920 |
| tttttttttt tttttttttt tttttttttt tttttttttt tttttttttt tttttttttt | 4980 |
| tttttttttt tttttttttt | 5000 |

```
<210> SEQ ID NO 56
<211> LENGTH: 400
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(400)
<223> OTHER INFORMATION: /note="This sequence may encompass 100-400
      nucleotides"
```

<400> SEQUENCE: 56

| | |
|---|---|
| aaaaaaaaaa aaaaaaaaaa aaaaaaaaaa aaaaaaaaaa aaaaaaaaaa aaaaaaaaaa | 60 |
| aaaaaaaaaa aaaaaaaaaa aaaaaaaaaa aaaaaaaaaa aaaaaaaaaa aaaaaaaaaa | 120 |
| aaaaaaaaaa aaaaaaaaaa aaaaaaaaaa aaaaaaaaaa aaaaaaaaaa aaaaaaaaaa | 180 |

```
aaaaaaaaaa aaaaaaaaaa aaaaaaaaaa aaaaaaaaaa aaaaaaaaaa aaaaaaaaaa    240
aaaaaaaaaa aaaaaaaaaa aaaaaaaaaa aaaaaaaaaa aaaaaaaaaa aaaaaaaaaa    300
aaaaaaaaaa aaaaaaaaaa aaaaaaaaaa aaaaaaaaaa aaaaaaaaaa aaaaaaaaaa    360
aaaaaaaaaa aaaaaaaaaa aaaaaaaaaa aaaaaaaaaa                          400

<210> SEQ ID NO 57
<211> LENGTH: 100
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 57
tttttttttt tttttttttt tttttttttt tttttttttt tttttttttt tttttttttt    60
tttttttttt tttttttttt tttttttttt tttttttttt                          100

<210> SEQ ID NO 58
<211> LENGTH: 30
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(30)
<223> OTHER INFORMATION: /note="This sequence may encompass 1-6
      'Gly Gly Gly Gly Ser' repeating units"

<400> SEQUENCE: 58

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 59
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MISC_FEATURE
<222> LOCATION: (1)..(20)
<223> OTHER INFORMATION: /note="This sequence may encompass 2-4
      'Gly Gly Gly Gly Ser' repeating units"

<400> SEQUENCE: 59

Gly Gly Gly Gly Ser Gly Gly Gly Gly Ser Gly Gly Gly Gly Ser Gly
1               5                   10                  15

Gly Gly Gly Ser
            20

<210> SEQ ID NO 60
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<220> FEATURE:
<221> NAME/KEY: MISC_FEATURE
<222> LOCATION: (1)..(15)
<223> OTHER INFORMATION: /note="This sequence may encompass 1-3
      'Gly Gly Gly Gly Ser' repeating units"

<400> SEQUENCE: 60

Gly Gly Gly Gly Ser Gly Gly Gly Gly Ser Gly Gly Gly Gly Ser
1               5                   10                  15

<210> SEQ ID NO 61
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gly Gly Gly Gly Ser Gly Gly Gly Gly Ser Gly Gly Gly Gly Ser Gly
1               5                   10                  15

Gly Gly Gly Ser
            20

<210> SEQ ID NO 62
<211> LENGTH: 5000
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"
<220> FEATURE:
<221> NAME/KEY: misc_feature
<222> LOCATION: (1)..(5000)
<223> OTHER INFORMATION: /note="This sequence may encompass 100-5000
      nucleotides"

<400> SEQUENCE: 62
aaaaaaaaaa aaaaaaaaaa aaaaaaaaaa aaaaaaaaaa aaaaaaaaaa aaaaaaaaaa        60
aaaaaaaaaa aaaaaaaaaa aaaaaaaaaa aaaaaaaaaa aaaaaaaaaa aaaaaaaaaa       120
aaaaaaaaaa aaaaaaaaaa aaaaaaaaaa aaaaaaaaaa aaaaaaaaaa aaaaaaaaaa       180
aaaaaaaaaa aaaaaaaaaa aaaaaaaaaa aaaaaaaaaa aaaaaaaaaa aaaaaaaaaa       240
aaaaaaaaaa aaaaaaaaaa aaaaaaaaaa aaaaaaaaaa aaaaaaaaaa aaaaaaaaaa       300
aaaaaaaaaa aaaaaaaaaa aaaaaaaaaa aaaaaaaaaa aaaaaaaaaa aaaaaaaaaa       360
aaaaaaaaaa aaaaaaaaaa aaaaaaaaaa aaaaaaaaaa aaaaaaaaaa aaaaaaaaaa       420
aaaaaaaaaa aaaaaaaaaa aaaaaaaaaa aaaaaaaaaa aaaaaaaaaa aaaaaaaaaa       480
aaaaaaaaaa aaaaaaaaaa aaaaaaaaaa aaaaaaaaaa aaaaaaaaaa aaaaaaaaaa       540
aaaaaaaaaa aaaaaaaaaa aaaaaaaaaa aaaaaaaaaa aaaaaaaaaa aaaaaaaaaa       600
aaaaaaaaaa aaaaaaaaaa aaaaaaaaaa aaaaaaaaaa aaaaaaaaaa aaaaaaaaaa       660
aaaaaaaaaa aaaaaaaaaa aaaaaaaaaa aaaaaaaaaa aaaaaaaaaa aaaaaaaaaa       720
aaaaaaaaaa aaaaaaaaaa aaaaaaaaaa aaaaaaaaaa aaaaaaaaaa aaaaaaaaaa       780
aaaaaaaaaa aaaaaaaaaa aaaaaaaaaa aaaaaaaaaa aaaaaaaaaa aaaaaaaaaa       840
aaaaaaaaaa aaaaaaaaaa aaaaaaaaaa aaaaaaaaaa aaaaaaaaaa aaaaaaaaaa       900
aaaaaaaaaa aaaaaaaaaa aaaaaaaaaa aaaaaaaaaa aaaaaaaaaa aaaaaaaaaa       960
aaaaaaaaaa aaaaaaaaaa aaaaaaaaaa aaaaaaaaaa aaaaaaaaaa aaaaaaaaaa      1020
```

```
aaaaaaaaaa aaaaaaaaaa aaaaaaaaaa aaaaaaaaaa aaaaaaaaaa aaaaaaaaaa      1080
aaaaaaaaaa aaaaaaaaaa aaaaaaaaaa aaaaaaaaaa aaaaaaaaaa aaaaaaaaaa      1140
aaaaaaaaaa aaaaaaaaaa aaaaaaaaaa aaaaaaaaaa aaaaaaaaaa aaaaaaaaaa      1200
aaaaaaaaaa aaaaaaaaaa aaaaaaaaaa aaaaaaaaaa aaaaaaaaaa aaaaaaaaaa      1260
aaaaaaaaaa aaaaaaaaaa aaaaaaaaaa aaaaaaaaaa aaaaaaaaaa aaaaaaaaaa      1320
aaaaaaaaaa aaaaaaaaaa aaaaaaaaaa aaaaaaaaaa aaaaaaaaaa aaaaaaaaaa      1380
aaaaaaaaaa aaaaaaaaaa aaaaaaaaaa aaaaaaaaaa aaaaaaaaaa aaaaaaaaaa      1440
aaaaaaaaaa aaaaaaaaaa aaaaaaaaaa aaaaaaaaaa aaaaaaaaaa aaaaaaaaaa      1500
aaaaaaaaaa aaaaaaaaaa aaaaaaaaaa aaaaaaaaaa aaaaaaaaaa aaaaaaaaaa      1560
aaaaaaaaaa aaaaaaaaaa aaaaaaaaaa aaaaaaaaaa aaaaaaaaaa aaaaaaaaaa      1620
aaaaaaaaaa aaaaaaaaaa aaaaaaaaaa aaaaaaaaaa aaaaaaaaaa aaaaaaaaaa      1680
aaaaaaaaaa aaaaaaaaaa aaaaaaaaaa aaaaaaaaaa aaaaaaaaaa aaaaaaaaaa      1740
aaaaaaaaaa aaaaaaaaaa aaaaaaaaaa aaaaaaaaaa aaaaaaaaaa aaaaaaaaaa      1800
aaaaaaaaaa aaaaaaaaaa aaaaaaaaaa aaaaaaaaaa aaaaaaaaaa aaaaaaaaaa      1860
aaaaaaaaaa aaaaaaaaaa aaaaaaaaaa aaaaaaaaaa aaaaaaaaaa aaaaaaaaaa      1920
aaaaaaaaaa aaaaaaaaaa aaaaaaaaaa aaaaaaaaaa aaaaaaaaaa aaaaaaaaaa      1980
aaaaaaaaaa aaaaaaaaaa aaaaaaaaaa aaaaaaaaaa aaaaaaaaaa aaaaaaaaaa      2040
aaaaaaaaaa aaaaaaaaaa aaaaaaaaaa aaaaaaaaaa aaaaaaaaaa aaaaaaaaaa      2100
aaaaaaaaaa aaaaaaaaaa aaaaaaaaaa aaaaaaaaaa aaaaaaaaaa aaaaaaaaaa      2160
aaaaaaaaaa aaaaaaaaaa aaaaaaaaaa aaaaaaaaaa aaaaaaaaaa aaaaaaaaaa      2220
aaaaaaaaaa aaaaaaaaaa aaaaaaaaaa aaaaaaaaaa aaaaaaaaaa aaaaaaaaaa      2280
aaaaaaaaaa aaaaaaaaaa aaaaaaaaaa aaaaaaaaaa aaaaaaaaaa aaaaaaaaaa      2340
aaaaaaaaaa aaaaaaaaaa aaaaaaaaaa aaaaaaaaaa aaaaaaaaaa aaaaaaaaaa      2400
aaaaaaaaaa aaaaaaaaaa aaaaaaaaaa aaaaaaaaaa aaaaaaaaaa aaaaaaaaaa      2460
aaaaaaaaaa aaaaaaaaaa aaaaaaaaaa aaaaaaaaaa aaaaaaaaaa aaaaaaaaaa      2520
aaaaaaaaaa aaaaaaaaaa aaaaaaaaaa aaaaaaaaaa aaaaaaaaaa aaaaaaaaaa      2580
aaaaaaaaaa aaaaaaaaaa aaaaaaaaaa aaaaaaaaaa aaaaaaaaaa aaaaaaaaaa      2640
aaaaaaaaaa aaaaaaaaaa aaaaaaaaaa aaaaaaaaaa aaaaaaaaaa aaaaaaaaaa      2700
aaaaaaaaaa aaaaaaaaaa aaaaaaaaaa aaaaaaaaaa aaaaaaaaaa aaaaaaaaaa      2760
aaaaaaaaaa aaaaaaaaaa aaaaaaaaaa aaaaaaaaaa aaaaaaaaaa aaaaaaaaaa      2820
aaaaaaaaaa aaaaaaaaaa aaaaaaaaaa aaaaaaaaaa aaaaaaaaaa aaaaaaaaaa      2880
aaaaaaaaaa aaaaaaaaaa aaaaaaaaaa aaaaaaaaaa aaaaaaaaaa aaaaaaaaaa      2940
aaaaaaaaaa aaaaaaaaaa aaaaaaaaaa aaaaaaaaaa aaaaaaaaaa aaaaaaaaaa      3000
aaaaaaaaaa aaaaaaaaaa aaaaaaaaaa aaaaaaaaaa aaaaaaaaaa aaaaaaaaaa      3060
aaaaaaaaaa aaaaaaaaaa aaaaaaaaaa aaaaaaaaaa aaaaaaaaaa aaaaaaaaaa      3120
aaaaaaaaaa aaaaaaaaaa aaaaaaaaaa aaaaaaaaaa aaaaaaaaaa aaaaaaaaaa      3180
aaaaaaaaaa aaaaaaaaaa aaaaaaaaaa aaaaaaaaaa aaaaaaaaaa aaaaaaaaaa      3240
```

| | |
|---|---|
| aaaaaaaaaa aaaaaaaaaa aaaaaaaaaa aaaaaaaaaa aaaaaaaaaa aaaaaaaaaa | 3300 |
| aaaaaaaaaa aaaaaaaaaa aaaaaaaaaa aaaaaaaaaa aaaaaaaaaa aaaaaaaaaa | 3360 |
| aaaaaaaaaa aaaaaaaaaa aaaaaaaaaa aaaaaaaaaa aaaaaaaaaa aaaaaaaaaa | 3420 |
| aaaaaaaaaa aaaaaaaaaa aaaaaaaaaa aaaaaaaaaa aaaaaaaaaa aaaaaaaaaa | 3480 |
| aaaaaaaaaa aaaaaaaaaa aaaaaaaaaa aaaaaaaaaa aaaaaaaaaa aaaaaaaaaa | 3540 |
| aaaaaaaaaa aaaaaaaaaa aaaaaaaaaa aaaaaaaaaa aaaaaaaaaa aaaaaaaaaa | 3600 |
| aaaaaaaaaa aaaaaaaaaa aaaaaaaaaa aaaaaaaaaa aaaaaaaaaa aaaaaaaaaa | 3660 |
| aaaaaaaaaa aaaaaaaaaa aaaaaaaaaa aaaaaaaaaa aaaaaaaaaa aaaaaaaaaa | 3720 |
| aaaaaaaaaa aaaaaaaaaa aaaaaaaaaa aaaaaaaaaa aaaaaaaaaa aaaaaaaaaa | 3780 |
| aaaaaaaaaa aaaaaaaaaa aaaaaaaaaa aaaaaaaaaa aaaaaaaaaa aaaaaaaaaa | 3840 |
| aaaaaaaaaa aaaaaaaaaa aaaaaaaaaa aaaaaaaaaa aaaaaaaaaa aaaaaaaaaa | 3900 |
| aaaaaaaaaa aaaaaaaaaa aaaaaaaaaa aaaaaaaaaa aaaaaaaaaa aaaaaaaaaa | 3960 |
| aaaaaaaaaa aaaaaaaaaa aaaaaaaaaa aaaaaaaaaa aaaaaaaaaa aaaaaaaaaa | 4020 |
| aaaaaaaaaa aaaaaaaaaa aaaaaaaaaa aaaaaaaaaa aaaaaaaaaa aaaaaaaaaa | 4080 |
| aaaaaaaaaa aaaaaaaaaa aaaaaaaaaa aaaaaaaaaa aaaaaaaaaa aaaaaaaaaa | 4140 |
| aaaaaaaaaa aaaaaaaaaa aaaaaaaaaa aaaaaaaaaa aaaaaaaaaa aaaaaaaaaa | 4200 |
| aaaaaaaaaa aaaaaaaaaa aaaaaaaaaa aaaaaaaaaa aaaaaaaaaa aaaaaaaaaa | 4260 |
| aaaaaaaaaa aaaaaaaaaa aaaaaaaaaa aaaaaaaaaa aaaaaaaaaa aaaaaaaaaa | 4320 |
| aaaaaaaaaa aaaaaaaaaa aaaaaaaaaa aaaaaaaaaa aaaaaaaaaa aaaaaaaaaa | 4380 |
| aaaaaaaaaa aaaaaaaaaa aaaaaaaaaa aaaaaaaaaa aaaaaaaaaa aaaaaaaaaa | 4440 |
| aaaaaaaaaa aaaaaaaaaa aaaaaaaaaa aaaaaaaaaa aaaaaaaaaa aaaaaaaaaa | 4500 |
| aaaaaaaaaa aaaaaaaaaa aaaaaaaaaa aaaaaaaaaa aaaaaaaaaa aaaaaaaaaa | 4560 |
| aaaaaaaaaa aaaaaaaaaa aaaaaaaaaa aaaaaaaaaa aaaaaaaaaa aaaaaaaaaa | 4620 |
| aaaaaaaaaa aaaaaaaaaa aaaaaaaaaa aaaaaaaaaa aaaaaaaaaa aaaaaaaaaa | 4680 |
| aaaaaaaaaa aaaaaaaaaa aaaaaaaaaa aaaaaaaaaa aaaaaaaaaa aaaaaaaaaa | 4740 |
| aaaaaaaaaa aaaaaaaaaa aaaaaaaaaa aaaaaaaaaa aaaaaaaaaa aaaaaaaaaa | 4800 |
| aaaaaaaaaa aaaaaaaaaa aaaaaaaaaa aaaaaaaaaa aaaaaaaaaa aaaaaaaaaa | 4860 |
| aaaaaaaaaa aaaaaaaaaa aaaaaaaaaa aaaaaaaaaa aaaaaaaaaa aaaaaaaaaa | 4920 |
| aaaaaaaaaa aaaaaaaaaa aaaaaaaaaa aaaaaaaaaa aaaaaaaaaa aaaaaaaaaa | 4980 |
| aaaaaaaaaa aaaaaaaaaa | 5000 |

<210> SEQ ID NO 63
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 63

Gly Gly Gly Ser
1

COMPOSITIONS AND METHODS FOR TCR REPROGRAMMING USING FUSION PROTEINS

CROSS-REFERENCE

This patent application is the national phase entry of International Application No. PCT/US2017/045159, filed on Aug. 2, 2017, which claims the benefit of U.S. Provisional Application No. 62/370,189, filed Aug. 2, 2016, both of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Oct. 4, 2017, is named "48538705831_SL.txt" and is 81,431 bytes in size.

BACKGROUND OF THE INVENTION

Most patients with hematological malignancies or with late-stage solid tumors are incurable with standard therapy. In addition, traditional treatment options often have serious side effects. Numerous attempts have been made to engage a patient's immune system for rejecting cancerous cells, an approach collectively referred to as cancer immunotherapy. However, several obstacles make it rather difficult to achieve clinical effectiveness. Although hundreds of so-called tumor antigens have been identified, these are often derived from self and thus can direct the cancer immunotherapy against healthy tissue, or are poorly immunogenic. Furthermore, cancer cells use multiple mechanisms to render themselves invisible or hostile to the initiation and propagation of an immune attack by cancer immunotherapies.

Recent developments using chimeric antigen receptor (CAR) modified autologous T-cell therapy, which relies on redirecting genetically engineered T-cells to a suitable cell-surface molecule on cancer cells, show promising results in harnessing the power of the immune system to treat cancers. For example, the clinical results from an ongoing trial with B-cell maturation antigen (BCMA)-specific CAR T-cells have shown partial remission in some multiple myeloma patients (one such trial may be found via clinicaltrials.gov identifier NCT02215967). An alternative approach is the use of T-cell receptor (TCR) alpha and beta chains selected for a tumor-associated peptide antigen for genetically engineering autologous T-cells. These TCR chains will form complete TCR complexes and provide the T-cells with a TCR for a second defined specificity. Encouraging results were obtained with engineered autologous T-cells expressing NY-ESO-1-specific TCR alpha and beta chains in patients with synovial carcinoma.

Besides the ability of genetically modified T-cells expressing a CAR or a second TCR to recognize and destroy respective target cells in vitro/ex vivo, successful patient therapy with engineered T-cells requires the T-cells to be capable of strong activation, expansion, persistence over time, and, in case of relapsing disease, to enable a 'memory' response. High and manageable clinical efficacy of CAR T-cells is currently limited to mesothelin-positive B cell malignancies and to NY-ESO-1-peptide-expressing synovial sarcoma patients expressing HLA-A2. There is a clear need to improve genetically engineered T-cells to more broadly act against various human malignancies. Described herein are novel fusion proteins of TCR subunits, including CD3 epsilon, CD3gamma and CD3 delta, and of TCR alpha and TCR beta chains with binding domains specific for cell surface antigens that have the potential to overcome limitations of existing approaches. Described herein are novel fusion proteins that more efficiently kill target cells than CARs, but release comparable or lower levels of pro-inflammatory cytokines. These fusion proteins and methods of their use represent an advantage for TFPs relative to CARs because elevated levels of these cytokines have been associated with dose-limiting toxicities for adoptive CAR-T therapies.

SUMMARY OF THE INVENTION

Provided herein are BCMA binding proteins, and antibodies and T-cell receptor (TCR) fusion proteins (TFPs) comprising such BCMA binding proteins. In addition are provided T-cells engineered to express one or more TFPs, and methods of use thereof for the treatment of diseases.

In one aspect, provided herein is an isolated recombinant nucleic acid molecule encoding a T-cell receptor (TCR) fusion protein (TFP) comprising a TCR subunit and a human or humanized antibody domain comprising an anti-BCMA binding domain.

In one aspect, provided herein is an isolated recombinant nucleic acid molecule or molecules encoding an antibody, e.g., a bispecific antibody, comprising a BCMA binding region. In some instances, the antibody is an affinity matured antibody. In some instances, the BCMA binding protein is a camelid or single domain antibody (sdAb). In some instances, the antibody has a $V_H H$ region comprising SEQ ID NO:24. In other instances, the antibody has a $V_H H$ region comprising SEQ ID NO:28. In some instances, the antibody is a single domain antibody having CDR sequences set forth in SEQ ID NO:25, SEQ ID NO:26, and SEQ ID NO:27. In some instances, the antibody is a single domain antibody having CDR sequences as set forth in SEQ ID NO:29, SEQ ID NO:30, and SEQ ID NO:31.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 epsilon; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 gamma; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of CD3 delta; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of TCR alpha; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit comprising at least a portion of a TCR extracellular domain, and a TCR intracellular domain comprising a stimulatory domain from an intracellular signaling domain of TCR beta; and a human or humanized antibody domain comprising an antigen binding domain wherein the TCR subunit and the antibody domain are operatively linked, and wherein the TFP incorporates into a TCR when expressed in a T-cell.

In one aspect, provided herein is an isolated recombinant nucleic acid molecule encoding a T-cell receptor (TCR) fusion protein (TFP) comprising a TCR subunit and a human or humanized antibody domain comprising an antigen binding domain that is an anti-BCMA binding domain.

In some instances, the TCR subunit and the antibody domain are operatively linked. In some instances, the TFP incorporates into a TCR when expressed in a T-cell. In some instances, the encoded antigen binding domain is connected to the TCR extracellular domain by a linker sequence. In some instances, the encoded linker sequence comprises $(G_4S)_n$, wherein n=1 to 4. In some instances, the TCR subunit comprises a TCR extracellular domain. In some instances, the TCR subunit comprises a TCR transmembrane domain. In some instances, the TCR subunit comprises a TCR intracellular domain. In some instances, the TCR subunit comprises (i) a TCR extracellular domain, (ii) a TCR transmembrane domain, and (iii) a TCR intracellular domain, wherein at least two of (i), (ii), and (iii) are from the same TCR subunit. In some instances, the TCR subunit comprises a TCR intracellular domain comprising a stimulatory domain selected from an intracellular signaling domain of CD3 epsilon, CD3 gamma or CD3 delta, or an amino acid sequence having at least one, two or three modifications thereto. In some instances, the TCR subunit comprises an intracellular domain comprising a stimulatory domain selected from a functional signaling domain of 4-1BB and/or a functional signaling domain of CD3 zeta, or an amino acid sequence having at least one modification thereto. In some instances, the human or humanized antibody domain comprises an antibody fragment. In some instances, the human or humanized antibody domain comprises a scFv or a $V_H$ domain. In some instances, the isolated nucleic acid molecule encodes (i) a light chain (LC) CDR1, LC CDR2 and LC CDR3 of an anti-BCMA light chain binding domain amino acid sequence with 70-100% sequence identity to a light chain (LC) CDR1, LC CDR2 and LC CDR3 of an anti-BCMA light chain binding domain provided herein, respectively, and/or (ii) a heavy chain (HC) CDR1, HC CDR2 and HC CDR3 of an anti-BCMA heavy chain binding domain amino acid sequence with 70-100% sequence identity to a heavy chain (HC) CDR1, HC CDR2 and HC CDR3 of an anti-BCMA heavy chain binding domain provided herein, respectively. In some instances, the isolated nucleic acid molecule encodes a light chain variable region, wherein the light chain variable region comprises an amino acid sequence having at least one but not more than 30 modifications of a light chain variable region amino acid sequence of a light chain variable region provided herein, or a sequence with 95-99% identity to a light chain variable region amino acid sequence of a light chain variable region provided herein. In some instances, the isolated nucleic acid molecule encodes a heavy chain variable region, wherein the heavy chain variable region comprises an amino acid sequence having at least one but not more than 30 modifications of a heavy chain variable region amino acid sequence of a heavy chain variable region provided herein, or a sequence with 95-99% identity to a heavy chain variable region amino acid sequence of a heavy chain variable region provided herein.

In some instances, the TFP includes an extracellular domain of a TCR subunit that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the encoded TFP includes a transmembrane domain that comprises a transmembrane domain of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the encoded TFP includes a transmembrane domain that comprises a transmembrane domain of a protein selected from the group consisting of a TCR alpha chain, a TCR beta chain, a TCR zeta chain, a CD3 epsilon TCR subunit, a CD3 gamma TCR subunit, a CD3 delta TCR subunit, CD45, CD4, CD5, CD8, CD9, CD16, CD22, CD33, CD28, CD37, CD64, CD80, CD86, CD134, CD137, CD154, functional fragments thereof, and amino acid sequences thereof having at least one but not more than 20 modifications. In some instances, the isolated nucleic acid molecule further comprises a sequence encoding a costimulatory domain. In some instances, the costimulatory domain is a functional signaling domain obtained from a protein selected from the group consisting of OX40, CD2, CD27, CD28, CDS, ICAM-1, LFA-1 (CD11a/CD18), ICOS (CD278), and 4-1BB (CD137), and amino acid sequences thereof having at least one but not more than 20 modifications thereto. In some instances, the isolated nucleic acid molecule further comprises a leader sequence. In some instances, the isolated nucleic acid molecule is mRNA.

In some instances, the TFP includes an immunoreceptor tyrosine-based activation motif (ITAM) of a TCR subunit that comprises an ITAM or portion thereof of a protein selected from the group consisting of CD3 zeta TCR subunit, CD3 epsilon TCR subunit, CD3 gamma TCR subunit, CD3 delta TCR subunit, TCR zeta chain, Fc epsilon receptor 1 chain, Fc epsilon receptor 2 chain, Fc gamma receptor 1 chain, Fc gamma receptor 2a chain, Fc gamma receptor 2b1 chain, Fc gamma receptor 2b2 chain, Fc gamma receptor 3a chain, Fc gamma receptor 3b chain, Fc beta receptor 1 chain, TYROBP (DAP12), CD5, CD16a, CD16b, CD22, CD23, CD32, CD64, CD79a, CD79b, CD89, CD278, CD66d, functional fragments thereof, and amino acid sequences thereof having at least one but not more than 20 modifications thereto. In some instances, the ITAM replaces an ITAM of CD3 gamma, CD3 delta, or CD3 epsilon. In some instances, the ITAM is selected from the group consisting of CD3 zeta TCR subunit, CD3 epsilon TCR subunit, CD3 gamma TCR subunit, and CD3 delta TCR subunit and replaces a different ITAM selected from the group consisting of CD3 zeta TCR subunit, CD3 epsilon TCR subunit, CD3 gamma TCR subunit, and CD3 delta TCR subunit.

In some instances, the nucleic acid comprises a nucleotide analog. In some instances, the nucleotide analog is selected from the group consisting of 2'-O-methyl, 2'-O-methoxyethyl (2'-O-MOE), 2'-O-aminopropyl, 2'-deoxy, T-deoxy-2'-fluoro, 2'-O-aminopropyl (2'-O-AP), 2'-O-dimethylaminoethyl (2'-O-DMAOE), 2'-O-dimethylaminopropyl (2'-O-DMAP), T-O-dimethylaminoethyloxyethyl (2'-O-DMAEOE), 2'-O—N-methylacetamido (2'-O-NMA) modified, a locked nucleic acid (LNA), an ethylene nucleic acid (ENA), a peptide nucleic acid (PNA), a 1',5'-anhydrohexitol nucleic acid (HNA), a morpholino, a methylphosphonate nucleotide, a thiolphosphonate nucleotide, and a 2'-fluoro N3-P5'-phosphoramidite In one aspect, provided herein is an isolated polypeptide molecule encoded by a nucleic acid molecule provided herein.

In one aspect, provided herein is an isolated TFP molecule comprising a human or humanized anti-BCMA binding domain, a TCR extracellular domain, a transmembrane domain, and an intracellular domain.

In one aspect, provided herein is an isolated TFP molecule comprising a human or humanized anti-BCMA binding domain, a TCR extracellular domain, a transmembrane domain, and an intracellular signaling domain, wherein the TFP molecule is capable of functionally interacting with an endogenous TCR complex and/or at least one endogenous TCR polypeptide.

In one aspect, provided herein is an isolated TFP molecule comprising a human or humanized anti-BCMA binding domain, a TCR extracellular domain, a transmembrane domain, and an intracellular signaling domain, wherein the TFP molecule is capable of functionally integrating into an endogenous TCR complex In some instances, the isolated TFP molecule comprises an antibody or antibody fragment comprising a human or humanized anti-BCMA binding domain, a TCR extracellular domain, a transmembrane domain, and an intracellular domain. In some instances, the anti-BCMA binding domain is a scFv or a $V_H$ domain. In some instances, the anti-BCMA binding domain comprises a heavy chain with 95-100% identity to an amino acid sequence of a heavy chain provided herein, a functional fragment thereof, or an amino acid sequence thereof having at least one but not more than 30 modifications. In some instances, the anti-BCMA binding domain comprises a light chain with 95-100% identity to an amino acid sequence of a light chain provided herein, a functional fragment thereof, or an amino acid sequence thereof having at least one but not more than 30 modifications. In some instances, the isolated TFP molecule comprises a TCR extracellular domain that comprises an extracellular domain or portion thereof of a protein selected from the group consisting of a TCR alpha chain, a TCR beta chain, a CD3 epsilon TCR subunit, a CD3 gamma TCR subunit, a CD3 delta TCR subunit, functional fragments thereof, and amino acid sequences thereof having at least one but not more than 20 modifications. In some instances, the anti-BCMA binding domain is connected to the TCR extracellular domain by a linker sequence. In some instances, the linker region comprises $(G_4S)_n$, wherein n=1 to 4.

In some instances, the isolated TFP molecule further comprises a sequence encoding a costimulatory domain. In some instances, the isolated TFP molecule further comprises a sequence encoding an intracellular signaling domain. In some instances, the isolated TFP molecule further comprises a leader sequence.

In one aspect, provided herein is a vector comprising a nucleic acid molecule encoding a TFP provided herein. In some instances, the vector is selected from the group consisting of a DNA, a RNA, a plasmid, a lentivirus vector, adenoviral vector, a Rous sarcoma viral (RSV) vector, or a retrovirus vector. In some instances, the vector further comprises a promoter. In some instances, the vector is an in vitro transcribed vector. In some instances, a nucleic acid sequence in the vector further comprises a poly(A) tail. In some instances, a nucleic acid sequence in the vector further comprises a 3'UTR.

In one aspect, provided herein is a cell comprising a vector provided herein. In some instances, the cell is a human T-cell. In some instances, the T-cell is a CD8+ or CD4+ T-cell. In some instances, the cell further comprises a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprises a first polypeptide that comprises at least a portion of PD1 and a second polypeptide comprising a costimulatory domain and primary signaling domain.

In one aspect, provided herein is a human CD8+ or CD4+ T-cell comprising at least two TFP molecules, the TFP molecules comprising a human or humanized anti-BCMA binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In one aspect, provided herein is a protein complex comprising: a TFP molecule comprising a human or humanized anti-BCMA binding domain, a TCR extracellular domain, a transmembrane domain, and an intracellular domain; and at least one endogenous TCR complex.

In some instances, the TCR comprises an extracellular domain or portion thereof of a protein selected from the group consisting of TCR alpha chain, a TCR beta chain, a CD3 epsilon TCR subunit, a CD3 gamma TCR subunit, and a CD3 delta TCR subunit. In some instances, the anti-BCMA binding domain is connected to the TCR extracellular domain by a linker sequence. In some instances, the linker region comprises $(G_4S)_n$, wherein n=1 to 4.

In some instances, the TFP molecule comprises one or more chimeric domains comprising sequences from multiple TCR or CD3 subunits. In some instances, the chimeric TFP is engineered via gene editing techniques.

In one aspect, provided herein is a human CD8+ or CD4+ T-cell comprising at least two different TFP proteins per a protein complex provided herein.

In one aspect, provided herein is a method of making a cell comprising transducing a T-cell with a vector provided herein.

In one aspect, provided herein is a method of generating a population of RNA-engineered cells comprising introducing an in vitro transcribed RNA or synthetic RNA into a cell, where the RNA comprises a nucleic acid encoding a TFP molecule provided herein.

In one aspect, provided herein is a method of providing an anti-tumor immunity in a mammal comprising administering to the mammal an effective amount of a cell expressing a TFP molecule provided herein, or expressing a polypeptide molecule provided herein.

In some instances, the cell is an autologous T-cell. In some instances, the cell is an allogeneic T-cell. In some instances, the mammal is a human.

In one aspect, provided herein is a method of treating a mammal having a disease associated with expression of BCMA comprising administering to the mammal an effective amount of a TFP molecule provided herein, a cell provided herein, or a polypeptide molecule provided herein. In some instances, the disease associated with BCMA expression is selected from the group consisting of a proliferative disease, a cancer, a malignancy, and a non-cancer related indication associated with expression of BCMA, e.g., systemic lupus erythematosus, hypertension, or renal disorders. In some instances, the disease is a cancer selected from the group consisting of renal cell carcinoma, multiple myeloma, breast cancer, lung cancer, ovarian cancer, prostate cancer, colon cancer, cervical cancer, brain cancer, liver cancer, pancreatic cancer, kidney, endometrial, and stomach cancer.

In some instances, the disease is a cancer selected from the group consisting of a plasma cell disorder, a B-cell carcinoma, leukemia, lymphoma, or a disease associated with BCMA expression, and combinations thereof.

In some instances, the cells expressing a TFP molecule are administered in combination with an agent that increases the efficacy of a cell expressing a TFP molecule. Such an agent may be, e.g., a chemotherapeutic agent and/or an agent that increases the efficacy of a cell expressing a TFP molecule by increasing the permeability of a tumor or tumors in a mammal. In some instances, an agent that increases the efficacy of a cell expressing a TFP molecule is cyclophosphamide. In some instances, less cytokines are released in the mammal compared a mammal administered an effective amount of a T-cell expressing an anti-BCMA chimeric antigen receptor (CAR). In some instances, the cells expressing a TFP molecule are administered in combination with an agent that ameliorates one or more side effects associated with administration of a cell expressing a TFP molecule. In some instances, the cells expressing a TFP molecule are administered in combination with an agent that treats the disease associated with BCMA.

In one aspect, an isolated nucleic acid molecule provided herein, an isolated polypeptide molecule provided herein, an isolated TFP provided herein, a complex provided herein, a vector provided herein, or a cell provided herein, is for use as a medicament.

In one aspect, provided herein is a method of treating a mammal having a disease associated with expression of BCMA comprising administering to the mammal an effective amount of a TFP molecule provided herein, a cell provided herein, or a polypeptide molecule provided herein, wherein less cytokines are released in the mammal compared to a mammal administered an effective amount of a T-cell expressing an anti-BCMA chimeric antigen receptor (CAR).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
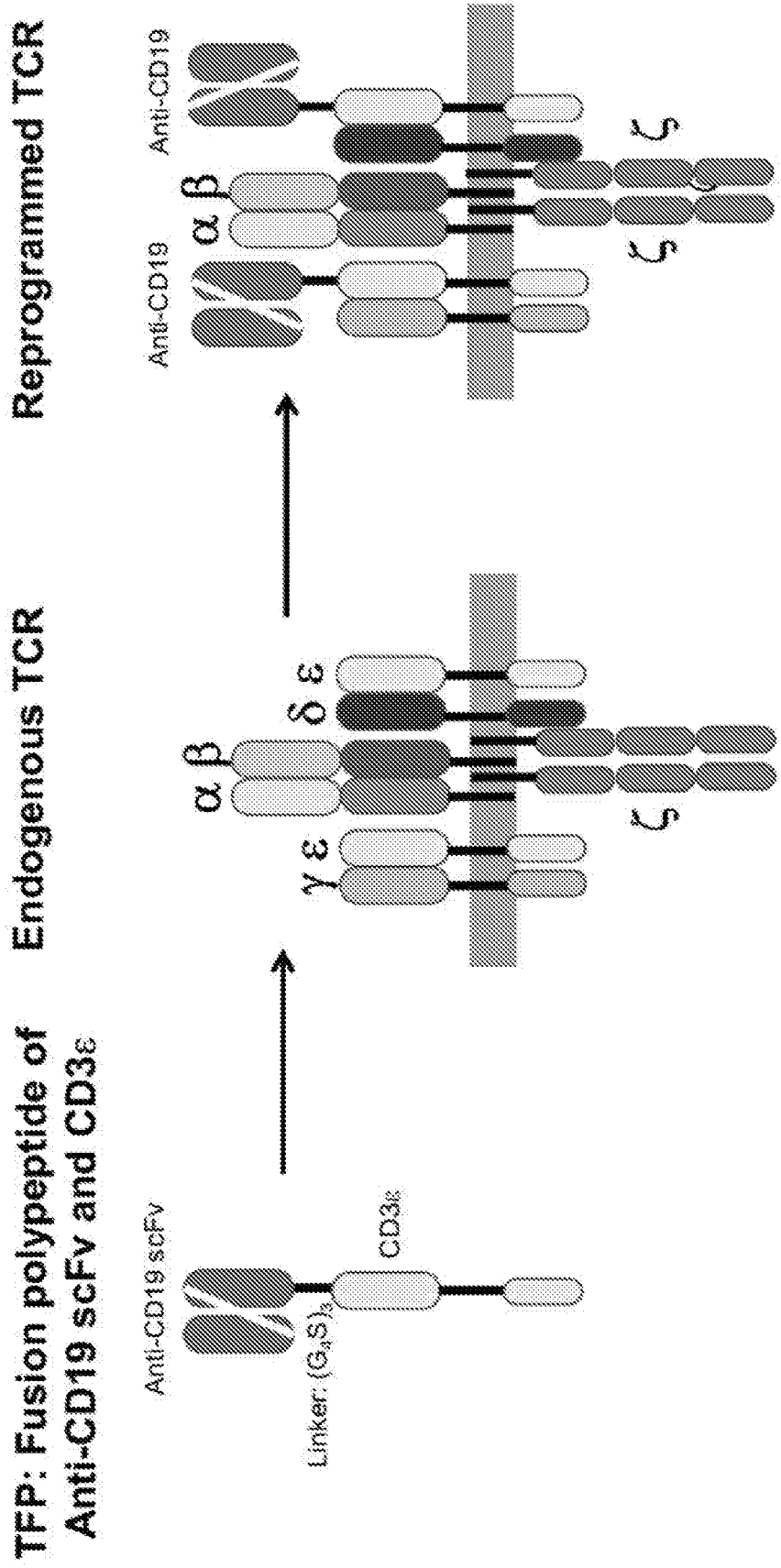
FIG. 1 is a schematic illustration demonstrating the use of T-cell receptor fusion polypeptides (TFPs) of the invention. An exemplary TFP contains an anti-BCMA scFv and a full-length CD3 epsilon polypeptide fused via a $(G_4S)_3$ linker sequence. When produced by or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.
Figure 2:
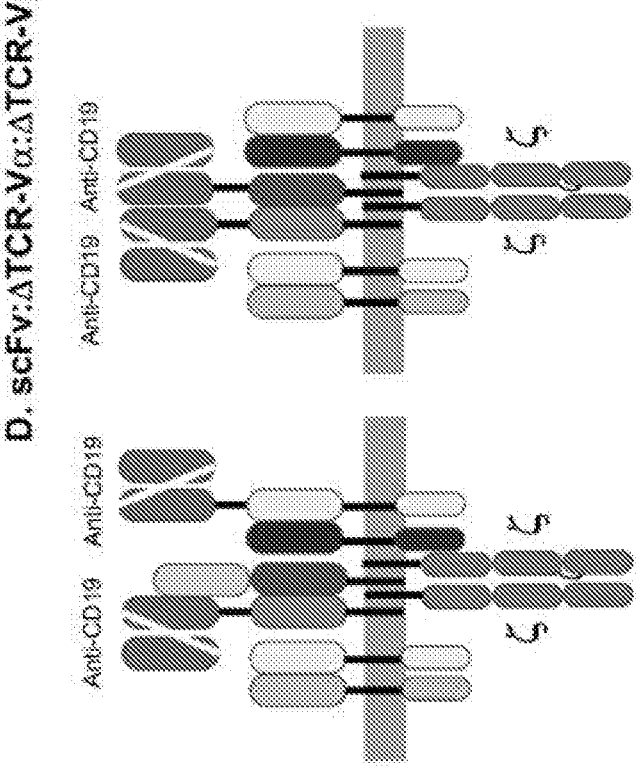
FIG. 2A represents schematic illustrations demonstrating exemplary variations of reprogrammed T-cell receptor fusion polypeptides (TFPs) of the invention.
FIG. 2B illustrates an exemplary reprogrammed TCR containing a TFP that contains an anti-BCMA TFPs including i) an anti-BCMA $V_HH$ and a full-length TCR Vα polypeptide fused via a $(G_4S)_3$ linker sequence and ii) an anti-BCMA $V_HH$ and a full-length TCR Vβ polypeptide fused via a $(G_4S)_3$ linker sequence.
FIG. 2C illustrates an exemplary reprogrammed TCR that contains multiple TFPs including i) an anti-BCMA $V_HH$ and a truncated (Δ) TCR polypeptide fused via a $(G_4S)_3$ linker sequence and ii) an BCMA $V_HH$ and a full-length CD3 epsilon polypeptide fused via a $(G_4S)_3$ linker sequence. The truncated (Δ) TCR polypeptide is truncated by the deletion of the Vα.
FIG. 2D illustrates an exemplary reprogrammed TCR that contains multiple TFPs including i) an anti-BCMA $V_HH$ and a truncated (Δ) TCR Vα polypeptide fused via a $(G_4S)_3$ linker sequence and ii) an anti-BCMA $V_HH$ and a truncated (Δ) TCR Vβ polypeptide fused via a $(G_4S)_3$ linker sequence. The truncated (Δ) TCR polypeptide is truncated by the deletion of the Vβ.
Figure 3:
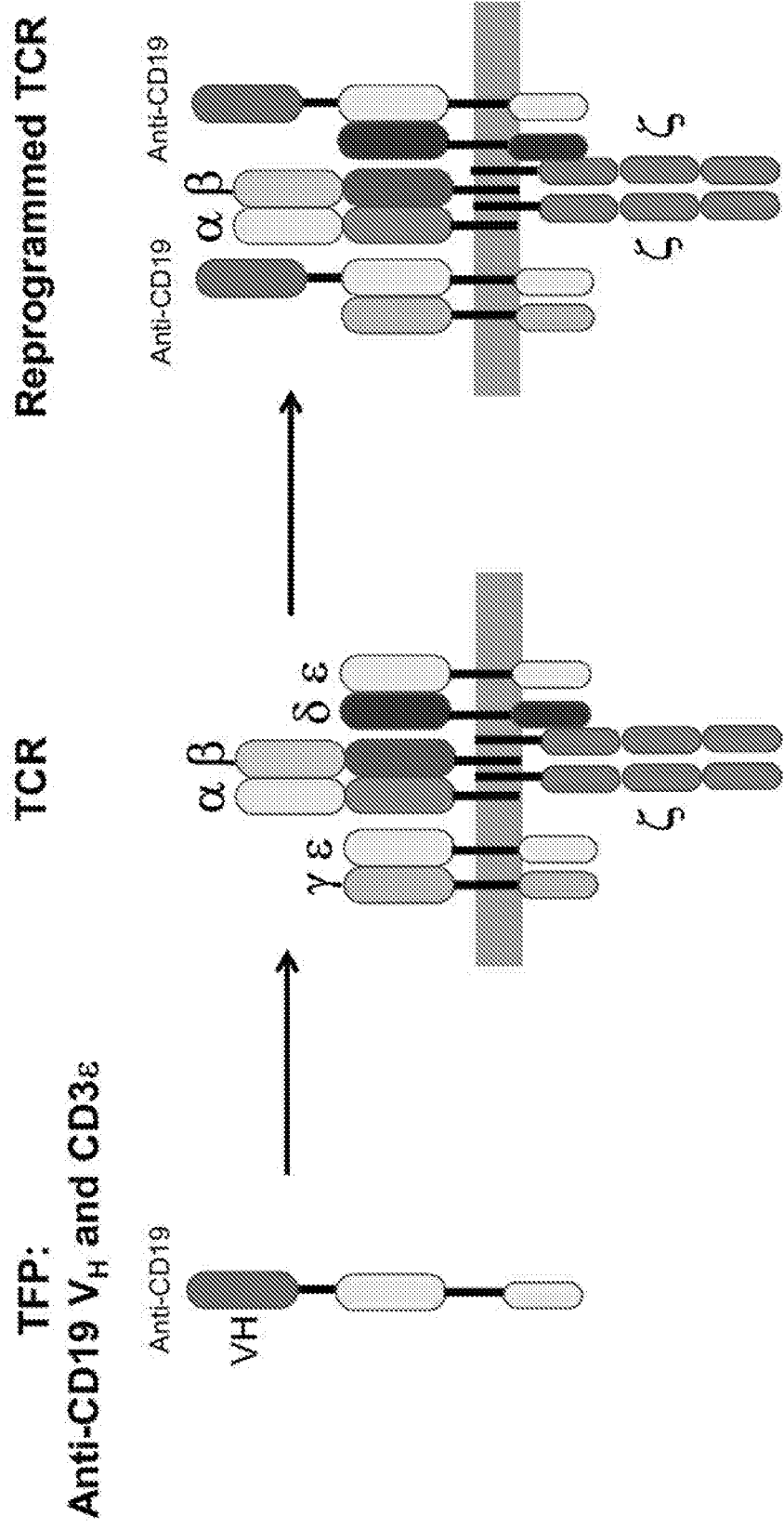
FIG. 3 is a schematic illustration demonstrating the use of T-cell receptor fusion polypeptides (TFPs) of the invention. An exemplary TFP contains an anti-BCMA $V_H$ domain and a full-length CD3 epsilon polypeptide fused via a $(G_4S)_3$ linker sequence. When produced by a T-cell or introduced into a T-cell, the TFP associates with other polypeptides of the endogenous T-cell receptor (TCR) (shown to include two CD3 epsilon polypeptides, one CD3 gamma polypeptide, one CD3 delta polypeptide, two CD3 zeta polypeptides, one TCR alpha subunit and one TCR beta subunit, where the horizontal grey segment represents the plasma membrane) to form a reprogrammed TCR in which one or both of the endogenous CD3 epsilon polypeptides are substituted by the TFP.
Figure 4:
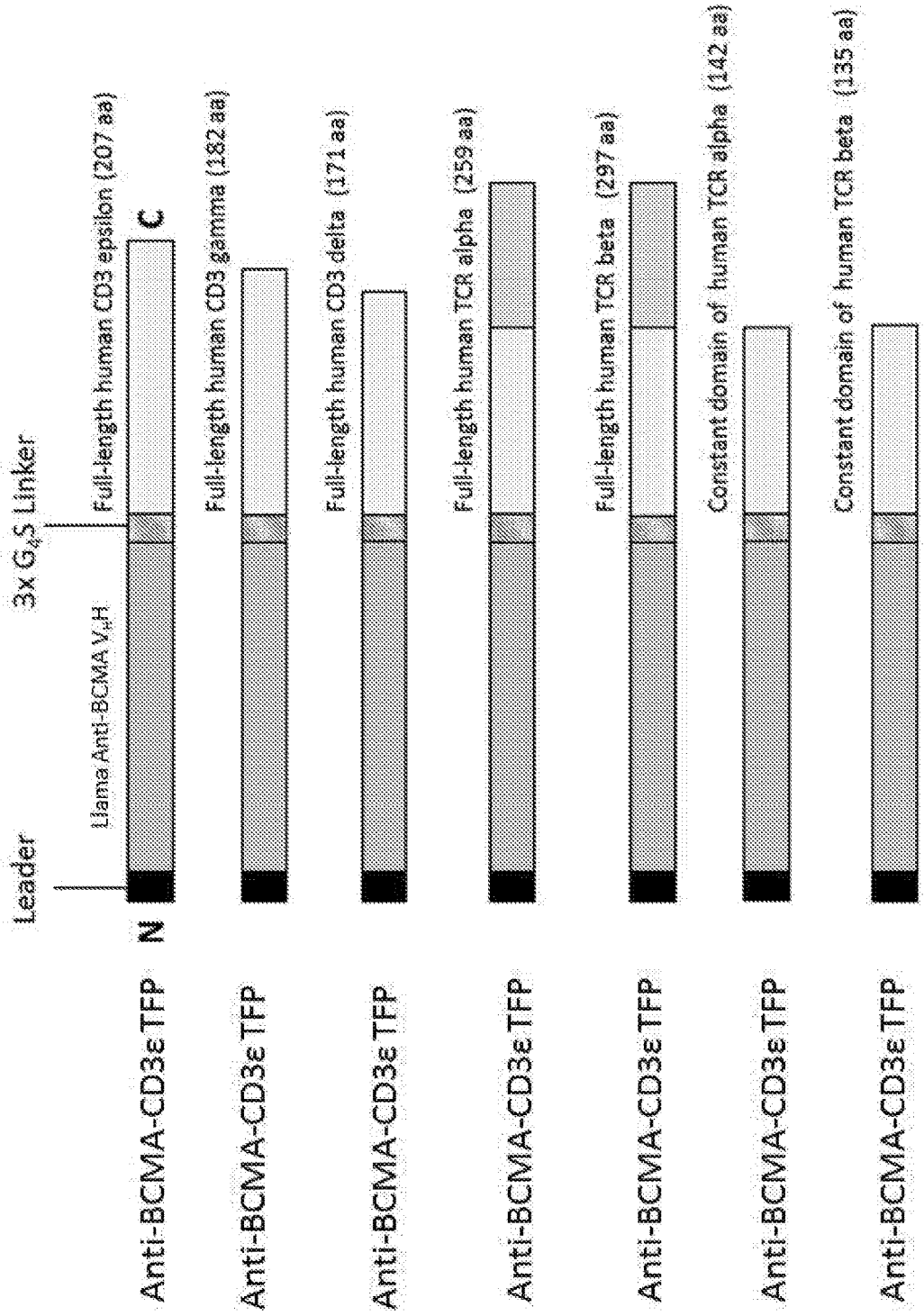
FIG. 4 is a series of schematic illustrations demonstrating DNA constructs encoding various TFPs.

In one aspect, described herein are isolated nucleic acid molecules encoding a T-cell Receptor (TCR) fusion protein (TFP) that comprise a TCR subunit and a human or humanized antibody domain comprising an anti-BCMA binding domain. In some embodiments, the TCR subunit comprises a TCR extracellular domain. In other embodiments, the TCR subunit comprises a TCR transmembrane domain. In yet other embodiments, the TCR subunit comprises a TCR intracellular domain. In further embodiments, the TCR subunit comprises (i) a TCR extracellular domain, (ii) a TCR transmembrane domain, and (iii) a TCR intracellular domain, wherein at least two of (i), (ii), and (iii) are from the same TCR subunit. In yet further embodiments, the TCR subunit comprises a TCR intracellular domain comprising a stimulatory domain selected from an intracellular signaling domain of CD3 epsilon, CD3 gamma or CD3 delta, or an amino acid sequence having at least one, two or three modifications thereto. In yet further embodiments, the TCR subunit comprises an intracellular domain comprising a stimulatory domain selected from a functional signaling domain of 4-1BB and/or a functional signaling domain of CD3 zeta, or an amino acid sequence having at least one, two or three modifications thereto.

In some embodiments, the human or humanized antibody domain comprises an antibody fragment. In some embodiments, the human or humanized antibody domain comprises a scFv or a $V_H$ domain.

In some embodiments, the isolated nucleic acid molecules comprise (i) a light chain (LC) CDR1, LC CDR2 and LC CDR3 of any anti-BCMA light chain binding domain amino acid sequence provided herein, and/or (ii) a heavy chain (HC) CDR1, HC CDR2 and HC CDR3 of any anti-BCMA heavy chain binding domain amino acid sequence provided herein.

In some embodiments, the light chain variable region comprises an amino acid sequence having at least one, two or three modifications but not more than 30, 20 or 10 modifications of an amino acid sequence of a light chain variable region provided herein, or a sequence with 95-99% identity to an amino acid sequence provided herein. In other embodiments, the heavy chain variable region comprises an amino acid sequence having at least one, two or three modifications but not more than 30, 20 or 10 modifications of an amino acid sequence of a heavy chain variable region provided herein, or a sequence with 95-99% identity to an amino acid sequence provided herein.

In some embodiments, the TFP includes an extracellular domain of a TCR subunit that comprises an extracellular domain or portion thereof of a protein selected from the group consisting of the alpha or beta chain of the T-cell receptor, CD3 delta, CD3 epsilon, or CD3 gamma, or a functional fragment thereof, or an amino acid sequence having at least one, two or three modifications but not more than 20, 10 or 5 modifications thereto. In other embodiments, the encoded TFP includes a transmembrane domain that comprises a transmembrane domain of a protein selected from the group consisting of the alpha, beta chain of the TCR or TCR subunits CD3 epsilon, CD3 gamma and CD3 delta, or a functional fragment thereof, or an amino acid sequence having at least one, two or three modifications but not more than 20, 10 or 5 modifications thereto.

In some embodiments, the encoded TFP includes a transmembrane domain that comprises a transmembrane domain of a protein selected from the group consisting of the alpha, beta or zeta chain of the TCR or CD3 epsilon, CD3 gamma and CD3 delta CD45, CD4, CD5, CD8, CD9, CD16, CD22, CD33, CD28, CD37, CD64, CD80, CD86, CD134, CD137 and CD154, or a functional fragment thereof, or an amino acid sequence having at least one, two or three modifications but not more than 20, 10 or 5 modifications thereto.

In some embodiments, the encoded anti-BCMA binding domain is connected to the TCR extracellular domain by a linker sequence. In some instances, the encoded linker sequence comprises $(G_4S)_n$, wherein n=1 to 4. In some instances, the encoded linker sequence comprises a long linker (LL) sequence. In some instances, the encoded long linker sequence comprises $(G_4S)_n$, wherein n=2 to 4. In some instances, the encoded linker sequence comprises a short linker (SL) sequence. In some instances, the encoded short linker sequence comprises $(G_4S)_n$, wherein n=1 to 3.

In some embodiments, the isolated nucleic acid molecules further comprise a sequence encoding a costimulatory domain. In some instances, the costimulatory domain is a functional signaling domain obtained from a protein selected from the group consisting of OX40, CD2, CD27, CD28, CDS, ICAM-1, LFA-1 (CD11a/CD18), ICOS (CD278), and 4-1BB (CD137), or an amino acid sequence having at least one, two or three modifications but not more than 20, 10 or 5 modifications thereto.

In some embodiments, the isolated nucleic acid molecules further comprise a leader sequence.

Also provided herein are isolated polypeptide molecules encoded by any of the previously described nucleic acid molecules.

Also provided herein in another aspect, are isolated T-cell receptor fusion protein (TFP) molecules that comprise a human or humanized anti-BCMA binding domain, a TCR extracellular domain, a transmembrane domain, and an intracellular domain. In some embodiments, the isolated TFP molecules comprises an antibody or antibody fragment comprising a human or humanized anti-BCMA binding domain, a TCR extracellular domain, a transmembrane domain, and an intracellular domain.

In some embodiments, the anti-BCMA binding domain is a scFv or a $V_H$ domain. In other embodiments, the anti-BCMA binding domain comprises a light chain and a heavy chain of an amino acid sequence provided herein, or a functional fragment thereof, or an amino acid sequence having at least one, two or three modifications but not more than 30, 20 or 10 modifications of an amino acid sequence of a light chain variable region provided herein, or a sequence with 95-99% identity with an amino acid sequence provided herein. In some embodiments, the isolated TFP molecules comprise a TCR extracellular domain that comprises an extracellular domain or portion thereof of a protein selected from the group consisting of the alpha or beta chain of the T-cell receptor, CD3 delta, CD3 epsilon, or CD3 gamma, or an amino acid sequence having at least one, two or three modifications but not more than 20, 10 or 5 modifications thereto.

In some embodiments, the anti-BCMA binding domain is connected to the TCR extracellular domain by a linker sequence. In some instances, the linker region comprises $(G_4S)_n$, wherein n=1 to 4. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

In some embodiments, the isolated TFP molecules further comprise a sequence encoding a costimulatory domain. In other embodiments, the isolated TFP molecules further comprise a sequence encoding an intracellular signaling domain. In yet other embodiments, the isolated TFP molecules further comprise a leader sequence.

Also provided herein are vectors that comprise a nucleic acid molecule encoding any of the previously described TFP molecules. In some embodiments, the vector is selected from the group consisting of a DNA, an RNA, a plasmid, a lentivirus vector, adenoviral vector, or a retrovirus vector. In some embodiments, the vector further comprises a promoter. In some embodiments, the vector is an in vitro transcribed vector. In some embodiments, a nucleic acid sequence in the vector further comprises a poly(A) tail. In some embodiments, a nucleic acid sequence in the vector further comprises a 3'UTR.

Also provided herein are cells that comprise any of the described vectors. In some embodiments, the cell is a human T-cell. In some embodiments, the cell is a CD8+ or CD4+ T-cell. In other embodiments, the cells further comprise a nucleic acid encoding an inhibitory molecule that comprises a first polypeptide that comprises at least a portion of an inhibitory molecule, associated with a second polypeptide that comprises a positive signal from an intracellular signaling domain. In some instances, the inhibitory molecule comprises a first polypeptide that comprises at least a portion of PD1 and a second polypeptide comprising a costimulatory domain and primary signaling domain.

In another aspect, provided herein are isolated TFP molecules that comprise a human or humanized anti-BCMA binding domain, a TCR extracellular domain, a transmembrane domain, and an intracellular signaling domain, wherein the TFP molecule is capable of functionally interacting with an endogenous TCR complex and/or at least one endogenous TCR polypeptide.

In another aspect, provided herein are isolated TFP molecules that comprise a human or humanized anti-BCMA binding domain, a TCR extracellular domain, a transmembrane domain, and an intracellular signaling domain, wherein the TFP molecule is capable of functionally integrating into an endogenous TCR complex.

In another aspect, provided herein are human CD8+ or CD4+ T-cells that comprise at least two TFP molecules, the TFP molecules comprising a human or humanized anti-BCMA binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In another aspect, provided herein are protein complexes that comprise i) a TFP molecule comprising a human or humanized anti-BCMA binding domain, a TCR extracellular domain, a transmembrane domain, and an intracellular domain; and ii) at least one endogenous TCR complex.

In some embodiments, the TCR comprises an extracellular domain or portion thereof of a protein selected from the group consisting of the alpha or beta chain of the T-cell receptor, CD3 delta, CD3 epsilon, or CD3 gamma. In some embodiments, the anti-BCMA binding domain is connected to the TCR extracellular domain by a linker sequence. In some instances, the linker region comprises $(G_4S)_n$, wherein n=1 to 4. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

Also provided herein are human CD8+ or CD4+ T-cells that comprise at least two different TFP proteins per any of the described protein complexes.

In another aspect, provided herein is a population of human CD8+ or CD4+ T-cells, wherein the T-cells of the population individually or collectively comprise at least two TFP molecules, the TFP molecules comprising a human or humanized anti-BCMA binding domain, a TCR extracellular domain, a transmembrane domain, and an intracellular domain, wherein the TFP molecule is capable of functionally interacting with an endogenous TCR complex and/or at least one endogenous TCR polypeptide in, at and/or on the surface of the human CD8+ or CD4+ T-cell.

In another aspect, provided herein is a population of human CD8+ or CD4+ T-cells, wherein the T-cells of the population individually or collectively comprise at least two TFP molecules encoded by an isolated nucleic acid molecule provided herein.

In another aspect, provided herein are methods of making a cell comprising transducing a T-cell with any of the described vectors.

In another aspect, provided herein are methods of generating a population of RNA-engineered cells that comprise introducing an in vitro transcribed RNA or synthetic RNA into a cell, where the RNA comprises a nucleic acid encoding any of the described TFP molecules.

In another aspect, provided herein are methods of providing an anti-tumor immunity in a mammal that comprise administering to the mammal an effective amount of a cell expressing any of the described TFP molecules. In some embodiments, the cell is an autologous T-cell. In some embodiments, the cell is an allogeneic T-cell. In some embodiments, the mammal is a human.

In another aspect, provided herein are methods of treating a mammal having a disease associated with expression of BCMA that comprise administering to the mammal an effective amount of the cell comprising any of the described TFP molecules. In some embodiments, the disease associated with BCMA expression is selected from a proliferative disease such as a cancer or malignancy or a precancerous condition such as a myelodysplasia, a myelodysplastic syndrome or a preleukemia, or is a non-cancer related indication associated with expression of BCMA. In some embodiments, the disease is a hematologic cancer selected from the group consisting of one or more acute leukemias including but not limited to B-cell acute lymphoid leukemia ("B-ALL"), T-cell acute lymphoid leukemia ("T-ALL"), acute lymphoblastic leukemia (ALL); one or more chronic leukemias including but not limited to chronic myelogenous leukemia (CML), chronic lymphocytic leukemia (CLL); additional hematologic cancers or hematologic conditions including, but not limited to B cell prolymphocytic leukemia, blastic plasmacytoid dendritic cell neoplasm, Burkitt's lymphoma, diffuse large B cell lymphoma, follicular lymphoma, hairy cell leukemia, small cell- or a large cell-follicular lymphoma, malignant lymphoproliferative conditions, MALT lymphoma, mantle cell lymphoma, marginal zone lymphoma, multiple myeloma, smoldering multiple myeloma, solitary plasmacytoma, lymphoplasmacytic lymphoma, plasma cell leukemia, myelodysplasia and myelodysplastic syndrome, non-Hodgkin's lymphoma, plasmablastic lymphoma, plasmacytoid dendritic cell neoplasm, Waldenstrom's macroglobulinemia, and "preleukemia" which are a diverse collection of hematological conditions united by ineffective production (or dysplasia) of myeloid blood cells, and to disease associated with BCMA expression include, but not limited to atypical and/or non-classical cancers, malignancies, precancerous conditions or proliferative diseases expressing BCMA; and combinations thereof.

In some embodiments, the cells expressing any of the described TFP molecules are administered in combination with an agent that ameliorates one or more side effects associated with administration of a cell expressing a TFP molecule. In some embodiments, the cells expressing any of the described TFP molecules are administered in combination with an agent that treats the disease associated with BCMA.

Also provided herein are any of the described isolated nucleic acid molecules, any of the described isolated polypeptide molecules, any of the described isolated TFPs, any of the described protein complexes, any of the described vectors or any of the described cells for use as a medicament.

Definitions

Unless defined otherwise, all technical and scientific terms used herein have the same meaning as commonly understood by one of ordinary skill in the art to which the invention pertains.

The term "a" and "an" refers to one or to more than one (i.e., to at least one) of the grammatical object of the article. By way of example, "an element" means one element or more than one element.

As used herein, "about" can mean plus or minus less than 1 or 1, 2, 3, 4, 5, 6, 7, 8, 9, 10, 11, 12, 13, 14, 15, 16, 17, 18, 19, 20, 25, 30, or greater than 30 percent, depending upon the situation and known or knowable by one skilled in the art.

As used herein the specification, "subject" or "subjects" or "individuals" may include, but are not limited to, mammals such as humans or non-human mammals, e.g., domesticated, agricultural or wild, animals, as well as birds, and aquatic animals. "Patients" are subjects suffering from or at risk of developing a disease, disorder or condition or otherwise in need of the compositions and methods provided herein.

As used herein, "treating" or "treatment" refers to any indicia of success in the treatment or amelioration of the disease or condition. Treating can include, for example, reducing, delaying or alleviating the severity of one or more symptoms of the disease or condition, or it can include reducing the frequency with which symptoms of a disease, defect, disorder, or adverse condition, and the like, are experienced by a patient. As used herein, "treat or prevent" is sometimes used herein to refer to a method that results in some level of treatment or amelioration of the disease or condition, and contemplates a range of results directed to that end, including but not restricted to prevention of the condition entirely.

As used herein, "preventing" refers to the prevention of the disease or condition, e.g., tumor formation, in the patient. For example, if an individual at risk of developing a tumor or other form of cancer is treated with the methods of the present invention and does not later develop the tumor or other form of cancer, then the disease has been prevented, at least over a period of time, in that individual.

As used herein, a "therapeutically effective amount" is the amount of a composition or an active component thereof sufficient to provide a beneficial effect or to otherwise reduce a detrimental non-beneficial event to the individual to whom the composition is administered. By "therapeutically effective dose" herein is meant a dose that produces one or more desired or desirable (e.g., beneficial) effects for which it is administered, such administration occurring one or more times over a given period of time. The exact dose will depend on the purpose of the treatment, and will be ascertainable by one skilled in the art using known techniques (see, e.g. Lieberman, Pharmaceutical Dosage Forms (vols. 1-3, 1992); Lloyd, The Art, Science and Technology of Pharmaceutical Compounding (1999); and Pickar, Dosage Calculations (1999))

As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell.

As used herein, the term "B cell As used herein, the term "BCMA" refers to the B-cell maturation antigen" or "BCMA" or "BCM," also known as tumor necrosis factor receptor superfamily member 17 (TNFRSF17) and Cluster of Differentiation 269 protein (CD269), or TNFRSF13A, is a protein that in humans is encoded by the TNFRSF17 gene. BCMA is a cell surface receptor of the TNF receptor superfamily which recognizes B-cell activating factor (BAFF). The receptor is preferentially expressed in mature B lymphocytes, and may be important for B cell development and autoimmune response. This receptor has been shown to specifically bind to the tumor necrosis factor (ligand) superfamily, member 13b (TNFSF13B/TALL-1/BAFF), and to lead to NF-kappaB and MAPK8/JNK activation. It is a non-glycosylated integral membrane receptor for the ligands BAFF and APRIL. BCMA's ligands can also bind additional receptors: TACI (Transmembrane Activator and Calcium modulator and cyclophilin ligand Interactor), which binds APRIL and BAFF; as well as BAFF-R (BAFF Receptor or BR3), which shows restricted but high affinity for BAFF. Together, these receptors and their corresponding ligands regulate different aspects of humoral immunity, B-cell development and homeostasis.

BCMA's expression is typically restricted to the B-cell lineage and is reported to increase in terminal B-cell differentiation. BCMA is expressed by human plasma blasts, plasma cells from tonsils, spleen and bone marrow, but also by tonsillar memory B cells and by germinal centre B cells, which have a TACI-BAFFR low phenotype (Darce et al, 2007). BCMA is virtually absent on naive and memory B-cells (Novak et al., 2004a and b). The BCMA antigen is expressed on the cell surface so is accessible to the antibody, but is also expressed in the golgi. As suggested by its expression profile, BCMA signalling, typically linked with B-cell survival and proliferation, is important in the late stages of B-cell differentiation, as well as the survival of long lived bone marrow plasma cells (O'Connor et al., 2004) and plasmablasts (Avery et al., 2003). Furthermore, as BCMA binds APRIL with high affinity, the BCMA-APRIL signalling axis is suggested to predominate at the later stages of B-cell differentiation, perhaps being the most physiologically relevant interaction.

The human and murine amino acid and nucleic acid sequences can be found in a public database, such as GenBank, UniProt and Swiss-Prot. For example, the amino acid sequence of human BCMA can be found as UniProt/Swiss-Prot Accession No. Q02223. The human BCMA polypeptide canonical sequence is UniProt Accession No. Q02223-1 (herein, SEQ ID NO:42, see Appendix A).

The term "antibody," as used herein, refers to a protein, or polypeptide sequences derived from an immunoglobulin molecule, which specifically binds to an antigen. Antibodies can be intact immunoglobulins of polyclonal or monoclonal origin, or fragments thereof and can be derived from natural or from recombinant sources.

The terms "antibody fragment" or "antibody binding domain" refer to at least one portion of an antibody, or recombinant variants thereof, that contains the antigen binding domain, i.e., an antigenic determining variable region of an intact antibody, that is sufficient to confer recognition and specific binding of the antibody fragment to a target, such as an antigen and its defined epitope. Examples of antibody fragments include, but are not limited to, Fab, Fab', F(ab')$_2$, and Fv fragments, single-chain (sc)Fv ("scFv") antibody fragments, linear antibodies, single domain antibodies (abbreviated "sdAb") (either $V_L$ or $V_H$), camelid $V_{HH}$ domains, and multi-specific antibodies formed from antibody fragments.

The term "scFv" refers to a fusion protein comprising at least one antibody fragment comprising a variable region of a light chain and at least one antibody fragment comprising a variable region of a heavy chain, wherein the light and heavy chain variable regions are contiguously linked via a short flexible polypeptide linker, and capable of being expressed as a single polypeptide chain, and wherein the scFv retains the specificity of the intact antibody from which it is derived.

"Heavy chain variable region" or "$V_H$" (or, in the case of single domain antibodies, e.g., nanobodies, "$V_{HH}$") with regard to an antibody refers to the fragment of the heavy chain that contains three CDRs interposed between flanking stretches known as framework regions, these framework regions are generally more highly conserved than the CDRs and form a scaffold to support the CDRs.

Unless specified, as used herein an scFv may have the $V_L$ and $V_H$ regions in either order, e.g., with respect to the N-terminal and C-terminal ends of the polypeptide, the scFv may comprise $V_L$-linker-$V_H$ or may comprise $V_H$-linker-$V_L$.

The portion of the TFP composition of the invention comprising an antibody or antibody fragment thereof may exist in a variety of forms where the antigen binding domain is expressed as part of a contiguous polypeptide chain including, for example, a single domain antibody fragment (sdAb) or heavy chain antibodies HCAb 242:423-426). In one aspect, the antigen binding domain of a TFP composition of the invention comprises an antibody fragment. In a further aspect, the TFP comprises an antibody fragment that comprises a scFv or a sdAb.

The term "antibody heavy chain," refers to the larger of the two types of polypeptide chains present in antibody molecules in their naturally occurring conformations, and which normally determines the class to which the antibody belongs.

The term "antibody light chain," refers to the smaller of the two types of polypeptide chains present in antibody molecules in their naturally occurring conformations. Kappa ("κ") and lambda ("λ") light chains refer to the two major antibody light chain isotypes.

The term "recombinant antibody" refers to an antibody that is generated using recombinant DNA technology, such as, for example, an antibody expressed by a bacteriophage or yeast expression system. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using recombinant DNA or amino acid sequence technology which is available and well known in the art.

The term "antigen" or "Ag" refers to a molecule that is capable of being bound specifically by an antibody, or otherwise provokes an immune response. This immune response may involve either antibody production, or the activation of specific immunologically-competent cells, or both.

The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample, or might be macromolecule besides a polypeptide. Such a biological sample can include, but is not limited to a tissue sample, a tumor sample, a cell or a fluid with other biological components.

The term "anti-tumor effect" refers to a biological effect which can be manifested by various means, including but not limited to, e.g., a decrease in tumor volume, a decrease in the number of tumor cells, a decrease in the number of metastases, an increase in life expectancy, decrease in tumor cell proliferation, decrease in tumor cell survival, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autologous" refers to any material derived from the same individual to whom it is later to be re-introduced into the individual.

The term "allogeneic" refers to any material derived from a different animal of the same species or different patient as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "xenogeneic" refers to a graft derived from an animal of a different species.

The term "cancer" refers to a disease characterized by the rapid and uncontrolled growth of aberrant cells. Cancer cells can spread locally or through the bloodstream and lymphatic system to other parts of the body. Examples of various cancers are described herein and include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The phrase "disease associated with expression of BCMA" includes, but is not limited to, a disease associated with expression of BCMA or condition associated with cells which express BCMA including, e.g., proliferative diseases such as a cancer or malignancy or a precancerous condition, or a defect of B-cell development/immunoglobulin production (immunodeficiencies). In one aspect, the cancer is non-Hodgkin's lymphoma, B-cell leukemia, Hodgkin's lymphoma, chronic lyphocytic leukemia, multiple myeloma, non-secretory multiple myeloma, smoldering multiple myeloma, POEMS syndrome/osteosclerotic melanoma, Non-cancer related indications associated with expression of BCMA include, but are not limited to, e.g., autoimmune disease, (e.g., lupus, systemic lupus erythematosus, rheumatoid arthritis, colitis, Type I and II cryoglobulinemia, light chain deposition disease, Goodpasture's syndrome, idiopathic thrombocytopenic purpura, acute glomerulonephritis, pemphigus and pemphigoid disorders, or epidermolysis bullosa acquisita), inflammatory disorders (allergy and asthma), and transplantation.

The term "conservative sequence modifications" refers to amino acid modifications that do not significantly affect or alter the binding characteristics of the antibody or antibody fragment containing the amino acid sequence. Such conservative modifications include amino acid substitutions, additions and deletions. Modifications can be introduced into an antibody or antibody fragment of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a TFP of the invention can be replaced with other amino acid residues from the same side chain family and the altered TFP can be tested using the functional assays described herein.

The term "stimulation" refers to a primary response induced by binding of a stimulatory domain or stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, and/or reorganization of cytoskeletal structures, and the like.

The term "stimulatory molecule" or "stimulatory domain" refers to a molecule or portion thereof expressed by a T-cell that provides the primary cytoplasmic signaling sequence(s) that regulate primary activation of the TCR complex in a stimulatory way for at least some aspect of the T-cell signaling pathway. In one aspect, the primary signal is initiated by, for instance, binding of a TCR/CD3 complex with an MHC molecule loaded with peptide, and which leads to mediation of a T-cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or "ITAM". Examples of an ITAM containing primary cytoplasmic signaling sequence that is of particular use in the invention includes, but is not limited to, those derived from TCR zeta, FcR gamma, FcR beta, CD3 gamma, CD3 delta, CD3 epsilon, CD5, CD22, CD79a, CD79b, CD278 (also known as "ICOS") and CD66d.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

An "intracellular signaling domain," as the term is used herein, refers to an intracellular portion of a molecule. The intracellular signaling domain generates a signal that promotes an immune effector function of the TFP containing cell, e.g., a TFP-expressing T-cell. Examples of immune effector function, e.g., in a TFP-expressing T-cell, include cytolytic activity and T helper cell activity, including the secretion of cytokines. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation.

A primary intracellular signaling domain can comprise an ITAM ("immunoreceptor tyrosine-based activation motif"). Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, and CD66d DAP10 and DAP12.

The term "costimulatory molecule" refers to the cognate binding partner on a T-cell that specifically binds with a costimulatory ligand, thereby mediating a costimulatory response by the T-cell, such as, but not limited to, proliferation. Costimulatory molecules are cell surface molecules other than antigen receptors or their ligands that are required for an efficient immune response. Costimulatory molecules include, but are not limited to an MHC class 1 molecule, BTLA and a Toll ligand receptor, as well as OX40, CD2, CD27, CD28, CDS, ICAM-1, LFA-1 (CD11a/CD18) and 4-1BB (CD137). A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, lymphocyte function-associated antigen-1 (LFA-1), CD2, CD7, LIGHT, NKG2C, SLAMF7, NKp80, CD160, B7-H3, and a ligand that specifically binds with CD83, and the like. The intracellular signaling domain can comprise the entire intracellular portion, or the entire native intracellular signaling domain, of the molecule from which it is derived, or a functional fragment thereof. The term "4-1BB" refers to a member of the TNFR superfamily with an amino acid sequence provided as GenBank Acc. No. AAA62478.2, or the equivalent residues from a non-human species, e.g., mouse, rodent, monkey, ape and the like; and a "4-1BB costimulatory domain" is defined as amino acid residues 214-255 of GenBank Acc. No. AAA62478.2, or equivalent residues from non-human species, e.g., mouse, rodent, monkey, ape and the like.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain one or more introns.

The term "effective amount" or "therapeutically effective amount" are used interchangeably herein, and refer to an amount of a compound, formulation, material, or composition, as described herein effective to achieve a particular biological or therapeutic result.

The term "endogenous" refers to any material from or produced inside an organism, cell, tissue or system.

The term "exogenous" refers to any material introduced from or produced outside an organism, cell, tissue or system.

The term "expression" refers to the transcription and/or translation of a particular nucleotide sequence driven by a promoter.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a polylysine compound, liposome, and the like. Examples of viral transfer vectors include, but are not limited to, adenoviral vectors, adeno-associated virus vectors, retroviral vectors, lentiviral vectors, and the like.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, e.g., the LENTIVECTOR™ gene delivery technology from Oxford BioMedica, the LENTIMAX™ vector system from Lentigen, and the like. Nonclinical types of lentiviral vectors are also available and would be known to one skilled in the art.

The term "homologous" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Human" or "fully human" refers to an immunoglobulin, such as an antibody or antibody fragment, where the whole molecule is of human origin or consists of an amino acid sequence identical to a human form of the antibody or immunoglobulin.

The term "isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "operably linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The term "parenteral" administration of an immunogenic composition includes, e.g., subcutaneous (s.c.), intravenous (i.v.), intramuscular (i.m.), or intrasternal injection, intratumoral, or infusion techniques.

The term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "promoter" refers to a DNA sequence recognized by the transcription machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "constitutive" promoter refers to a nucleotide sequence which, when operably linked with a polynucleotide which encodes or specifies a gene product, causes the gene product to be produced in a cell under most or all physiological conditions of the cell.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

The term "tissue-specific" promoter refers to a nucleotide sequence which, when operably linked with a polynucleotide encodes or specified by a gene, causes the gene product to be produced in a cell substantially only if the cell is a cell of the tissue type corresponding to the promoter.

The terms "linker" and "flexible polypeptide linker" as used in the context of a scFv refers to a peptide linker that consists of amino acids such as glycine and/or serine residues used alone or in combination, to link variable heavy and variable light chain regions together. In one embodiment, the flexible polypeptide linker is a Gly/Ser linker and comprises the amino acid sequence (Gly-Gly-Gly-Ser)$_n$, where n is a positive integer equal to or greater than 1. For example, n=1, n=2, n=3, n=4, n=5, n=6, n=7, n=8, n=9 and n=10. In one embodiment, the flexible polypeptide linkers include, but are not limited to, (Gly$_4$Ser)$_4$ or (Gly$_4$Ser)$_3$. In another embodiment, the linkers include multiple repeats of (Gly$_2$Ser), (GlySer) or (Gly$_3$Ser). Also included within the scope of the invention are linkers described in WO2012/138475 (incorporated herein by reference). In some instances, the linker sequence comprises a long linker (LL) sequence. In some instances, the long linker sequence comprises (G$_4$S)$_n$, wherein n=2 to 4. In some instances, the linker sequence comprises a short linker (SL) sequence. In some instances, the short linker sequence comprises (G$_4$S)$_n$, wherein n=1 to 3.

As used herein, a 5' cap (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

As used herein, "in vitro transcribed RNA" refers to RNA, preferably mRNA, which has been synthesized in vitro. Generally, the in vitro transcribed RNA is generated from an in vitro transcription vector. The in vitro transcription vector comprises a template that is used to generate the in vitro transcribed RNA.

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. Poly(A) sequences can be modified chemically or enzymatically to modulate mRNA functionality such as localization, stability or efficiency of translation.

As used herein, "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly(A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

The term "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

The term "subject" is intended to include living organisms in which an immune response can be elicited (e.g., mammals, human).

The term, a "substantially purified" cell refers to a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some aspects, the cells are cultured in vitro. In other aspects, the cells are not cultured in vitro.

The term "therapeutic" as used herein means a treatment. A therapeutic effect is obtained by reduction, suppression, remission, or eradication of a disease state.

The term "prophylaxis" as used herein means the prevention of or protective treatment for a disease or disease state.

In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, NHL, leukemias, uterine cancer, cervical cancer, bladder cancer, kidney cancer and adenocarcinomas such as breast cancer, prostate cancer, ovarian cancer, pancreatic cancer, and the like.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "specifically binds," refers to an antibody, an antibody fragment or a specific ligand, which recognizes and binds a cognate binding partner (e.g., BCMA) present in a sample, but which does not necessarily and substantially recognize or bind other molecules in the sample.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. As another example, a range such as 95-99% identity, includes something with 95%, 96%, 97%, 98% or 99% identity, and includes subranges such as 96-99%, 96-98%, 96-97%, 97-99%, 97-98% and 98-99% identity. This applies regardless of the breadth of the range.

DETAILED DESCRIPTION

Provided herein are compositions of matter and methods of use for the treatment of a disease such as cancer, using T-cell receptor (TCR) fusion proteins. As used herein, a "T-cell receptor (TCR) fusion protein" or "TFP" includes a recombinant polypeptide derived from the various polypeptides comprising the TCR that is generally capable of i) binding to a surface antigen on target cells and ii) interacting with other polypeptide components of the intact TCR complex, typically when co-located in or on the surface of a T-cell. As provided herein, TFPs provide substantial benefits as compared to Chimeric Antigen Receptors. The term "Chimeric Antigen Receptor" or alternatively a "CAR" refers to a recombinant polypeptide comprising an extracellular antigen binding domain in the form of a scFv, a transmembrane domain, and cytoplasmic signaling domains (also referred to herein as "an intracellular signaling domains") comprising a functional signaling domain derived from a stimulatory molecule as defined below. Generally, the central intracellular signaling domain of a CAR is derived from the CD3 zeta chain that is normally found associated with the TCR complex. The CD3 zeta signaling domain can be fused with one or more functional signaling domains derived from at least one costimulatory molecule such as 4-1BB (i.e., CD137), CD27 and/or CD28.

T-Cell Receptor (TCR) Fusion Proteins (TFP)

The present invention encompasses recombinant DNA constructs encoding TFPs, wherein the TFP comprises an antibody fragment that binds specifically to BCMA, e.g., human BCMA, wherein the sequence of the antibody fragment is contiguous with and in the same reading frame as a nucleic acid sequence encoding a TCR subunit or portion thereof. The TFPs provided herein are able to associate with one or more endogenous (or alternatively, one or more exogenous, or a combination of endogenous and exogenous) TCR subunits in order to form a functional TCR complex.

In one aspect, the TFP of the invention comprises a target-specific binding element otherwise referred to as an antigen binding domain. The choice of moiety depends upon the type and number of target antigen that define the surface of a target cell. For example, the antigen binding domain may be chosen to recognize a target antigen that acts as a cell surface marker on target cells associated with a particular disease state. Thus, examples of cell surface markers that may act as target antigens for the antigen binding domain in a TFP of the invention include those associated with viral, bacterial and parasitic infections; autoimmune diseases; and cancerous diseases (e.g., malignant diseases).

In one aspect, the TFP-mediated T-cell response can be directed to an antigen of interest by way of engineering an antigen-binding domain into the TFP that specifically binds a desired antigen.

In one aspect, the portion of the TFP comprising the antigen binding domain comprises an antigen binding domain that targets BCMA. In one aspect, the antigen binding domain targets human BCMA.

The antigen binding domain can be any domain that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain ($V_H$), a light chain variable domain ($V_L$) and a variable domain ($V_{HH}$) of a camelid derived nanobody, and to an alternative scaffold known in the art to function as antigen binding domain, such as a recombinant fibronectin domain, anticalin, DARPIN and the like. Likewise, a natural or synthetic ligand specifically recognizing and binding the target antigen can be used as antigen binding domain for the TFP. In some instances, it is beneficial for the antigen binding domain to be derived from the same species in which the TFP will ultimately be used in. For example, for use in humans, it may be beneficial for the antigen binding domain of the TFP to comprise human or humanized residues for the antigen binding domain of an antibody or antibody fragment.

Thus, in one aspect, the antigen-binding domain comprises a humanized or human antibody or an antibody fragment, or a murine antibody or antibody fragment. In one embodiment, the humanized or human anti-BCMA binding domain comprises one or more (e.g., all three) light chain complementary determining region 1 (LC CDR1), light chain complementary determining region 2 (LC CDR2), and light chain complementary determining region 3 (LC CDR3) of a humanized or human anti-BCMA binding domain described herein, and/or one or more (e.g., all three) heavy chain complementary determining region 1 (HC CDR1), heavy chain complementary determining region 2 (HC CDR2), and heavy chain complementary determining region 3 (HC CDR3) of a humanized or human anti-BCMA binding domain described herein, e.g., a humanized or human anti-BCMA binding domain comprising one or more, e.g., all three, LC CDRs and one or more, e.g., all three, HC CDRs. In one embodiment, the humanized or human anti-BCMA binding domain comprises one or more (e.g., all three) heavy chain complementary determining region 1 (HC CDR1), heavy chain complementary determining region 2 (HC CDR2), and heavy chain complementary determining region 3 (HC CDR3) of a humanized or human anti-BCMA binding domain described herein, e.g., the humanized or human anti-BCMA binding domain has two variable heavy chain regions, each comprising a HC CDR1, a HC CDR2 and a HC CDR3 described herein. In one embodiment, the humanized or human anti-BCMA binding domain comprises a humanized or human light chain variable region described herein and/or a humanized or human heavy chain variable region described herein. In one embodiment, the humanized or human anti-BCMA binding domain comprises a humanized heavy chain variable region described herein, e.g., at least two humanized or human heavy chain variable regions described herein. In one embodiment, the anti-BCMA binding domain is a scFv comprising a light chain and a heavy chain of an amino acid sequence provided herein. In an embodiment, the anti-BCMA binding domain (e.g., an scFv or $V_H$H nb) comprises: a light chain variable region comprising an amino acid sequence having at least one, two or three modifications (e.g., substitutions) but not more than 30, 20 or 10 modifications (e.g., substitutions) of an amino acid sequence of a light chain variable region provided herein, or a sequence with 95-99% identity with an amino acid sequence provided herein; and/or a heavy chain variable region comprising an amino acid sequence having at least one, two or three modifications (e.g., substitutions) but not more than 30, 20 or 10 modifications (e.g., substitutions) of an amino acid sequence of a heavy chain variable region provided herein, or a sequence with 95-99% identity to an amino acid sequence provided herein. In one embodiment, the humanized or human anti-BCMA binding domain is a scFv, and a light chain variable region comprising an amino acid sequence described herein, is attached to a heavy chain variable region comprising an amino acid sequence described herein, via a linker, e.g., a linker described herein. In one embodiment, the humanized anti-BCMA binding domain includes a $(Gly_4\text{-}Ser)_n$ linker, wherein n is 1, 2, 3, 4, 5, or 6, preferably 3 or 4. The light chain variable region and heavy chain variable region of a scFv can be, e.g., in any of the following orientations: light chain variable region-linker-heavy chain variable region or heavy chain variable region-linker-light chain variable region. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

In some aspects, a non-human antibody is humanized, where specific sequences or regions of the antibody are modified to increase similarity to an antibody naturally produced in a human or fragment thereof. In one aspect, the antigen binding domain is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. 20050042664, U.S. Patent Application Publication No. 20050048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions (see, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; and 6,548,640, the contents of which are incorporated herein by reference in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (see, e.g., Nicholson et al. Mol. Immun. 34 (16-17): 1157-1165 (1997); Carter et al., Proc. Natl. Acad. Sci. USA, 89:4285 (1992); Presta et al., J. Immunol., 151:2623 (1993), the contents of which are incorporated herein by reference herein in their entirety). In some embodiments, the framework region, e.g., all four framework regions, of the heavy chain variable region are derived from a $V_H$4-4-59 germline sequence. In one embodiment, the framework region can comprise, one, two, three, four or five modifications, e.g., substitutions, e.g., from the amino acid at the corresponding murine sequence. In one embodiment, the framework region, e.g., all four framework regions of the light chain variable region are derived from a VK3-1.25 germline sequence. In one embodiment, the framework region can comprise, one, two, three, four or five modifications, e.g., substitutions, e.g., from the amino acid at the corresponding murine sequence.

In some aspects, the portion of a TFP composition of the invention that comprises an antibody fragment is humanized with retention of high affinity for the target antigen and other favorable biological properties. According to one aspect of the invention, humanized antibodies and antibody fragments are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, e.g., the analysis of residues that influence the ability of the candidate immunoglobulin to bind the target antigen. In this way, FR residues can be selected and combined from the recipient and import sequences so that the desired antibody or antibody fragment characteristic, such as increased affinity for the target antigen, is achieved. In general, the CDR residues are directly and most substantially involved in influencing antigen binding.

A humanized antibody or antibody fragment may retain a similar antigenic specificity as the original antibody, e.g., in the present invention, the ability to bind human BCMA. In some embodiments, a humanized antibody or antibody fragment may have improved affinity and/or specificity of binding to human BCMA.

In one aspect, the anti-BCMA binding domain is characterized by particular functional features or properties of an antibody or antibody fragment. For example, in one aspect, the portion of a TFP composition of the invention that comprises an antigen binding domain specifically binds human BCMA. In one aspect, the invention relates to an antigen binding domain comprising an antibody or antibody fragment (e.g., a $V_HH$), wherein the antibody binding domain specifically binds to a BCMA protein or fragment thereof, wherein the antibody or antibody fragment comprises a variable light chain and/or a variable heavy chain that includes an amino acid sequence provided herein. In certain aspects, the scFv is contiguous with and in the same reading frame as a leader sequence.

In one aspect, the anti-BCMA binding domain is a fragment, e.g., a single chain variable fragment (scFv) or a camelid heavy chain ($V_HH$). In one aspect, the anti-BCMA binding domain is a Fv, a Fab, a (Fab')$_2$, or a bi-functional (e.g. bi-specific) hybrid antibody (e.g., Lanzavecchia et al., Eur. J. Immunol. 17, 105 (1987)). In one aspect, the antibodies and fragments thereof of the invention binds a BCMA protein with wild-type or enhanced affinity.

Also provided herein are methods for obtaining an antibody antigen binding domain specific for a target antigen (e.g., BCMA or any target antigen described elsewhere herein for targets of fusion moiety binding domains), the method comprising providing by way of addition, deletion, substitution or insertion of one or more amino acids in the amino acid sequence of a $V_H$ (or $V_HH$) domain set out herein a $V_H$ domain which is an amino acid sequence variant of the $V_H$ domain, optionally combining the $V_H$ domain thus provided with one or more $V_L$ domains, and testing the $V_H$ domain or $V_H/V_L$ combination or combinations to identify a specific binding member or an antibody antigen binding domain specific for a target antigen of interest (e.g., BCMA) and optionally with one or more desired properties.

In some instances, $V_H$ domains and scFvs can be prepared according to method known in the art (see, for example, Bird et al., (1988) Science 242:423-426 and Huston et al., (1988) Proc. Natl. Acad. Sci. USA 85:5879-5883). scFv molecules can be produced by linking $V_H$ and $V_L$ regions together using flexible polypeptide linkers. The scFv molecules comprise a linker (e.g., a Ser-Gly linker) with an optimized length and/or amino acid composition. The linker length can greatly affect how the variable regions of a scFv fold and interact. In fact, if a short polypeptide linker is employed (e.g., between 5-10 amino acids) intra-chain folding is prevented. Inter-chain folding is also required to bring the two variable regions together to form a functional epitope binding site. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3. For examples of linker orientation and size see, e.g., Hollinger et al. 1993 Proc Natl Acad. Sci. U.S.A. 90:6444-6448, U.S. Patent Application Publication Nos. 20050100543 and 20050175606, U.S. Pat. No. 7,695,936, and PCT Publication Nos. WO2006/020258 and WO2007/024715, is incorporated herein by reference.

A scFv can comprise a linker of about 10, 11, 12, 13, 14, 15 or greater than 15 residues between its $V_L$ and $V_H$ regions. The linker sequence may comprise any naturally occurring amino acid. In some embodiments, the linker sequence comprises amino acids glycine and serine. In another embodiment, the linker sequence comprises sets of glycine and serine repeats such as $(Gly_4Ser)_n$, where n is a positive integer equal to or greater than 1. In one embodiment, the linker can be $(Gly_4Ser)_4$ or $(Gly_4Ser)_3$. Variation in the linker length may retain or enhance activity, giving rise to superior efficacy in activity studies. In some instances, the linker sequence comprises a long linker (LL) sequence. In some instances, the long linker sequence comprises $(G_4S)_n$, wherein n=2 to 4. In some instances, the linker sequence comprises a short linker (SL) sequence. In some instances, the short linker sequence comprises $(G_4S)_n$, wherein n=1 to 3.

Stability and Mutations

The stability of an anti-BCMA binding domain, e.g., scFv molecules (e.g., soluble scFv) can be evaluated in reference to the biophysical properties (e.g., thermal stability) of a conventional control scFv molecule or a full-length antibody. In one embodiment, the humanized or human scFv has a thermal stability that is greater than about 0.1, about 0.25, about 0.5, about 0.75, about 1, about 1.25, about 1.5, about 1.75, about 2, about 2.5, about 3, about 3.5, about 4, about 4.5, about 5, about 5.5, about 6, about 6.5, about 7, about 7.5, about 8, about 8.5, about 9, about 9.5, about 10 degrees, about 11 degrees, about 12 degrees, about 13 degrees, about 14 degrees, or about 15 degrees Celsius than a parent scFv in the described assays.

The improved thermal stability of the anti-BCMA binding domain, e.g., scFv is subsequently conferred to the entire BCMA-TFP construct, leading to improved therapeutic properties of the anti-BCMA TFP construct. The thermal stability of the anti-BCMA binding domain, e.g., scFv can be improved by at least about 2° C. or 3° C. as compared to a conventional antibody. In one embodiment, the anti-BCMA binding domain, e.g., scFv has a 1° C. improved thermal stability as compared to a conventional antibody. In another embodiment, the anti-BCMA binding domain, e.g., scFv has a 2° C. improved thermal stability as compared to a conventional antibody. In another embodiment, the scFv has a 4° C., 5° C., 6° C., 7° C., 8° C., 9° C., 10° C., 11° C., 12° C., 13° C., 14° C., or 15° C. improved thermal stability as compared to a conventional antibody. Comparisons can be made, for example, between the scFv molecules disclosed herein and scFv molecules or Fab fragments of an antibody from which the scFv $V_H$ and $V_L$ were derived. Thermal stability can be measured using methods known in the art. For example, in one embodiment, $T_M$ can be measured. Methods for measuring $T_M$ and other methods of determining protein stability are described below.

Mutations in scFv (arising through humanization or mutagenesis of the soluble scFv) alter the stability of the scFv and improve the overall stability of the scFv and the anti-BCMA TFP construct. Stability of the humanized scFv is compared against the murine scFv using measurements such as $T_M$, temperature denaturation and temperature aggregation. In one embodiment, the anti-BCMA binding domain, e.g., a scFv, comprises at least one mutation arising from the humanization process such that the mutated scFv confers improved stability to the anti-BCMA TFP construct. In another embodiment, the anti-BCMA binding domain, e.g., scFv comprises at least 1, 2, 3, 4, 5, 6, 7, 8, 9, 10 mutations arising from the humanization process such that the mutated scFv confers improved stability to the BCMA-TFP construct.

In one aspect, the antigen binding domain of the TFP comprises an amino acid sequence that is homologous to an antigen binding domain amino acid sequence described herein, and the antigen binding domain retains the desired functional properties of the anti-BCMA antibody fragments described herein. In one specific aspect, the TFP composition of the invention comprises an antibody fragment. In a further aspect, that antibody fragment comprises a scFv.

In various aspects, the antigen binding domain of the TFP is engineered by modifying one or more amino acids within one or both variable regions (e.g., $V_H$ and/or $V_L$), for example within one or more CDR regions and/or within one or more framework regions. In one specific aspect, the TFP composition of the invention comprises an antibody fragment. In a further aspect, that antibody fragment comprises a scFv.

It will be understood by one of ordinary skill in the art that the antibody or antibody fragment of the invention may further be modified such that they vary in amino acid sequence (e.g., from wild-type), but not in desired activity. For example, additional nucleotide substitutions leading to amino acid substitutions at "non-essential" amino acid residues may be made to the protein. For example, a nonessential amino acid residue in a molecule may be replaced with another amino acid residue from the same side chain family. In another embodiment, a string of amino acids can be replaced with a structurally similar string that differs in order and/or composition of side chain family members, e.g., a conservative substitution, in which an amino acid residue is replaced with an amino acid residue having a similar side chain, may be made.

Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Percent identity in the context of two or more nucleic acids or polypeptide sequences refers to two or more sequences that are the same. Two sequences are "substantially identical" if two sequences have a specified percentage of amino acid residues or nucleotides that are the same (e.g., 60% identity, optionally 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, (1970) Adv. Appl. Math. 2:482c, by the homology alignment algorithm of Needleman and Wunsch, (1970) J. Mol. Biol. 48:443, by the search for similarity method of Pearson and Lipman, (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., (2003) Current Protocols in Molecular Biology). Two examples of algorithms that are suitable for determining percent sequence identity and sequence similarity are the BLAST and BLAST 2.0 algorithms, which are described in Altschul et al., (1977) Nuc. Acids Res. 25:3389-3402; and Altschul et al., (1990) J. Mol. Biol. 215:403-410, respectively. Software for performing BLAST analyses is publicly available through the National Center for Biotechnology Information.

In one aspect, the present invention contemplates modifications of the starting antibody or fragment (e.g., scFv) amino acid sequence that generate functionally equivalent molecules. For example, the $V_H$ or $V_L$ of an anti-BCMA binding domain, e.g., scFv, comprised in the TFP can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity of the starting $V_H$ or $V_L$ framework region of the anti-BCMA binding domain, e.g., scFv. The present invention contemplates modifications of the entire TFP construct, e.g., modifications in one or more amino acid sequences of the various domains of the TFP construct in order to generate functionally equivalent molecules. The TFP construct can be modified to retain at least about 70%, 71%. 72%. 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity of the starting TFP construct.

Extracellular Domain

The extracellular domain may be derived either from a natural or from a recombinant source. Where the source is natural, the domain may be derived from any protein, but in particular a membrane-bound or transmembrane protein. In one aspect the extracellular domain is capable of associating with the transmembrane domain. An extracellular domain of particular use in this invention may include at least the extracellular region(s) of e.g., the alpha, beta or zeta chain of the T-cell receptor, or CD3 epsilon, CD3 gamma, or CD3 delta, or in alternative embodiments, CD28, CD45, CD4, CD5, CD8, CD9, CD16, CD22, CD33, CD37, CD64, CD80, CD86, CD134, CD137, CD154.

Transmembrane Domain

In general, a TFP sequence contains an extracellular domain and a transmembrane domain encoded by a single genomic sequence. In alternative embodiments, a TFP can be designed to comprise a transmembrane domain that is heterologous to the extracellular domain of the TFP. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region). In one aspect, the transmembrane domain is one that is associated with one of the other domains of the TFP is used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another TFP on the TFP-T-cell surface. In a different aspect the amino acid sequence of the transmembrane domain may be modified or substituted so as to minimize interactions with the binding domains of the native binding partner present in the same TFP.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the TFP has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154.

In some instances, the transmembrane domain can be attached to the extracellular region of the TFP, e.g., the antigen binding domain of the TFP, via a hinge, e.g., a hinge from a human protein. For example, in one embodiment, the hinge can be a human immunoglobulin (Ig) hinge, e.g., an IgG4 hinge, or a CD8a hinge.

Linkers

Optionally, a short oligo- or polypeptide linker, between 2 and 10 amino acids in length may form the linkage between the transmembrane domain and the cytoplasmic region of the TFP. A glycine-serine doublet provides a particularly suitable linker. For example, in one aspect, the linker comprises the amino acid sequence of GGGGSGGGGS (SEQ ID NO:3). In some embodiments, the linker is encoded by a nucleotide sequence of GGTGGCGGAGGTTCTGGAGGTGGAGGTTCC (SEQ ID NO:4).

Cytoplasmic Domain

The cytoplasmic domain of the TFP can include an intracellular signaling domain, if the TFP contains CD3 gamma, delta or epsilon polypeptides; TCR alpha and TCR beta subunits are generally lacking in a signaling domain. An intracellular signaling domain is generally responsible for activation of at least one of the normal effector functions of the immune cell in which the TFP has been introduced. The term "effector function" refers to a specialized function of a cell. Effector function of a T-cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular signaling domains for use in the TFP of the invention include the cytoplasmic sequences of the T-cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of naive T-cells and that a secondary and/or costimulatory signal is required. Thus, naïve T-cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs (ITAMs).

Examples of ITAMs containing primary intracellular signaling domains that are of particular use in the invention include those of CD3 zeta, FcR gamma, FcR beta, CD3 gamma, CD3 delta, CD3 epsilon, CD5, CD22, CD79a, CD79b, and CD66d. In one embodiment, a TFP of the invention comprises an intracellular signaling domain, e.g., a primary signaling domain of CD3-epsilon. In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the TFP can comprise the CD3 zeta signaling domain by itself or it can be combined with any other desired intracellular signaling domain(s) useful in the context of a TFP of the invention. For example, the intracellular signaling domain of the TFP can comprise a CD3 epsilon chain portion and a costimulatory signaling domain. The costimulatory signaling domain refers to a portion of the TFP comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human TFP-T-cells in vitro and augments human T-cell persistence and antitumor activity in vivo (Song et al. Blood. 2012; 119(3):696-706).

The intracellular signaling sequences within the cytoplasmic portion of the TFP of the invention may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequences.

In one embodiment, a glycine-serine doublet can be used as a suitable linker. In one embodiment, a single amino acid, e.g., an alanine, a glycine, can be used as a suitable linker.

In one aspect, the TFP-expressing cell described herein can further comprise a second TFP, e.g., a second TFP that includes a different antigen binding domain, e.g., to the same target (BCMA) or a different target (e.g., CD123). In one embodiment, when the TFP-expressing cell comprises two or more different TFPs, the antigen binding domains of the different TFPs can be such that the antigen binding domains do not interact with one another. For example, a cell expressing a first and second TFP can have an antigen binding domain of the first TFP, e.g., as a fragment, e.g., a scFv, that does not associate with the antigen binding domain of the second TFP, e.g., the antigen binding domain of the second TFP is a $V_H H$.

In another aspect, the TFP-expressing cell described herein can further express another agent, e.g., an agent which enhances the activity of a TFP-expressing cell. For example, in one embodiment, the agent can be an agent which inhibits an inhibitory molecule. Inhibitory molecules, e.g., PD1, can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4 and TIGIT, or a fragment of any of these (e.g., at least a portion of an extracellular domain of any of these), and a second polypeptide which is an intracellular signaling domain described herein (e.g., comprising a costimulatory domain (e.g., 4-1BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T-cells and myeloid cells (Agata et al. 1996 Int. Immunol 8:765-75). Two ligands for PD1, PD-L1 and PD-L2 have been shown to downregulate T-cell activation upon binding to PD1 (Freeman et al. 2000 J Exp Med 192:1027-34; Latchman et al. 2001 Nat Immunol 2:261-8; Carter et al. 2002 Eur J Immunol 32:634-43). PD-L1 is abundant in human cancers (Dong et al. 2003 J Mol Med 81:281-7; Blank et al. 2005 Cancer Immunol. Immunother 54:307-314; Konishi et al. 2004 Clin Cancer Res 10:5094). Immune suppression can be reversed by inhibiting the local interaction of PD1 with PD-L1.

In one embodiment, the agent comprises the extracellular domain (ECD) of an inhibitory molecule, e.g., Programmed Death 1 (PD1) can be fused to a transmembrane domain and optionally an intracellular signaling domain such as 41BB and CD3 zeta (also referred to herein as a PD1 TFP). In one embodiment, the PD1 TFP, when used in combinations with an anti-BCMA TFP described herein, improves the persistence of the T-cell. In one embodiment, the TFP is a PD1 TFP comprising the extracellular domain of PD1. Alternatively, provided are TFPs containing an antibody or antibody fragment such as a scFv that specifically binds to the Programmed Death-Ligand 1 (PD-L1) or Programmed Death-Ligand 2 (PD-L2).

In another aspect, the present invention provides a population of TFP-expressing T-cells, e.g., TFP-T-cells. In some embodiments, the population of TFP-expressing T-cells comprises a mixture of cells expressing different TFPs. For example, in one embodiment, the population of TFP-T-cells can include a first cell expressing a TFP having an anti-BCMA binding domain described herein, and a second cell expressing a TFP having a different anti-BCMA binding domain, e.g., an anti-BCMA binding domain described herein that differs from the anti-BCMA binding domain in the TFP expressed by the first cell. As another example, the population of TFP-expressing cells can include a first cell expressing a TFP that includes an anti-BCMA binding domain, e.g., as described herein, and a second cell expressing a TFP that includes an antigen binding domain to a target other than BCMA (e.g., another tumor-associated antigen).

In another aspect, the present invention provides a population of cells wherein at least one cell in the population expresses a TFP having an anti-BCMA domain described herein, and a second cell expressing another agent, e.g., an agent which enhances the activity of a TFP-expressing cell. For example, in one embodiment, the agent can be an agent which inhibits an inhibitory molecule. Inhibitory molecules, e.g., can, in some embodiments, decrease the ability of a TFP-expressing cell to mount an immune effector response. Examples of inhibitory molecules include PD1, PD-L1, PD-L2, CTLA4, TIM3, LAG3, VISTA, BTLA, TIGIT, LAIR1, CD160, 2B4 and TGFR beta. In one embodiment, the agent that inhibits an inhibitory molecule comprises a first polypeptide, e.g., an inhibitory molecule, associated with a second polypeptide that provides a positive signal to the cell, e.g., an intracellular signaling domain described herein.

Disclosed herein are methods for producing in vitro transcribed RNA encoding TFPs. The present invention also includes a TFP encoding RNA construct that can be directly transfected into a cell. A method for generating mRNA for use in transfection can involve in vitro transcription (IVT) of a template with specially designed primers, followed by polyA addition, to produce a construct containing 3' and 5' untranslated sequence ("UTR"), a 5' cap and/or Internal Ribosome Entry Site (IRES), the nucleic acid to be expressed, and a polyA tail, typically 50-2000 bases in length. RNA so produced can efficiently transfect different kinds of cells. In one aspect, the template includes sequences for the TFP.

In one aspect, the anti-BCMA TFP is encoded by a messenger RNA (mRNA). In one aspect the mRNA encoding the anti-BCMA TFP is introduced into a T-cell for production of a TFP-T-cell. In one embodiment, the in vitro transcribed RNA TFP can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a TFP of the present invention. In one embodiment, the DNA to be used for PCR contains an open reading frame. The DNA can be from a naturally occurring DNA sequence from the genome of an organism. In one embodiment, the nucleic acid can include some or all of the 5' and/or 3' untranslated regions (UTRs). The nucleic acid can include exons and introns. In one embodiment, the DNA to be used for PCR is a human nucleic acid sequence. In another embodiment, the DNA to be used for PCR is a human nucleic acid sequence including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary," as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a nucleic acid that is normally transcribed in cells (the open reading frame), including 5' and 3' UTRs. The primers can also be designed to amplify a portion of a nucleic acid that encodes a particular domain of interest. In one embodiment, the primers are designed to amplify the coding region of a human cDNA, including all or portions of the 5' and 3' UTRs. Primers useful for PCR can be generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5' to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between one and 3,000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the nucleic acid of interest. Alternatively, UTR sequences that are not endogenous to the nucleic acid of interest can be added by incorporating the UTR sequences into the forward and reverse primers or by any other modifications of the template. The use of UTR sequences that are not endogenous to the nucleic acid of interest can be useful for modifying the stability and/or translation efficiency of the RNA. For example, it is known that AU-rich elements in 3'UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous nucleic acid. Alternatively, when a 5' UTR that is not endogenous to the nucleic acid of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be 5'UTR of an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However, polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100 T tail (size can be 50-5000 Ts), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Nucleic Acid Constructs Encoding a TFP

The present invention also provides nucleic acid molecules encoding one or more TFP constructs described herein. In one aspect, the nucleic acid molecule is provided as a messenger RNA transcript. In one aspect, the nucleic acid molecule is provided as a DNA construct.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

In one embodiment, one or more domains of the TFP construct (e.g., extracellular, transmembrane, and intracellular signaling domain) are engineered using a gene editing technique such as clustered regularly interspaced short palindromic repeats (CRISPR®, see, e.g., U.S. Pat. No. 8,697, 359), transcription activator-like effector nucleases (TALEN, see, e.g., U.S. Pat. No. 9,393,257), meganucleases (naturally occurring endodeoxyribonucleases having large recognition sites comprising double-stranded DNA sequences of 12 to 40 base pairs), or zinc finger nuclease (ZFN, see, e.g., Umov et al., Nat. Rev. Genetics (2010) v11, 636-646) methods. In this way, a chimeric construct may be engineered to combine desirable characteristics of each subunit, such as conformation or signaling capabilities. See also Sander & Joung, Nat. Biotech. (2014) v32, 347-55, herein incorporated by reference.

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In another embodiment, the vector comprising the nucleic acid encoding the desired TFP of the invention is an adeno-viral vector (A5/35). In another embodiment, the expression of nucleic acids encoding TFPs can be accomplished using of transposons such as sleeping beauty, crisper, CAS9, and zinc finger nucleases (See, June et al. 2009 Nature Reviews Immunol. 9.10: 704-716, incorporated herein by reference).

The expression constructs of the present invention may also be used for nucleic acid immunization and gene therapy, using standard gene delivery protocols. Methods for gene delivery are known in the art (see, e.g., U.S. Pat. Nos. 5,399,346, 5,580,859, 5,589,466, incorporated by reference herein in their entireties). In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, e.g., in Sambrook et al., 2012, Molecular Cloning: A Laboratory Manual, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (e.g., WO 01/96584; WO 01/29058; and U.S. Pat. No. 6,326,193).

A number of virally based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter that is capable of expressing a TFP transgene in a mammalian T-cell is the EF1a promoter. The native EF1a promoter drives expression of the alpha subunit of the elongation factor-1 complex, which is responsible for the enzymatic delivery of aminoacyl tRNAs to the ribosome. The EF1a promoter has been extensively used in mammalian expression plasmids and has been shown to be effective in driving TFP expression from transgenes cloned into a lentiviral vector (see, e.g., Milone et al., Mol. Ther. 17(8): 1453-1464 (2009)). Another example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the elongation factor-1a promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline-regulated promoter.

In order to assess the expression of a TFP polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art (see, e.g., Sambrook et al., 2012, Molecular Cloning: A Laboratory Manual, volumes 1-4, Cold Spring Harbor Press, NY). One method for the introduction of a polynucleotide into a host cell is calcium phosphate transfection Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like (see, e.g., U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Other methods of state-of-the-art targeted delivery of nucleic acids are available, such as delivery of polynucleotides with targeted nanoparticles or other suitable submicron sized delivery system.

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

The present invention further provides a vector comprising a TFP encoding nucleic acid molecule. In one aspect, a TFP vector can be directly transduced into a cell, e.g., a T-cell. In one aspect, the vector is a cloning or expression vector, e.g., a vector including, but not limited to, one or more plasmids (e.g., expression plasmids, cloning vectors, minicircles, minivectors, double minute chromosomes), retroviral and lentiviral vector constructs. In one aspect, the vector is capable of expressing the TFP construct in mammalian T-cells. In one aspect, the mammalian T-cell is a human T-cell.

Sources of T-Cells

Prior to expansion and genetic modification, a source of T-cells is obtained from a subject. The term "subject" is intended to include living organisms in which an immune response can be elicited (e.g., mammals). Examples of subjects include humans, dogs, cats, mice, rats, and transgenic species thereof. T-cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain aspects of the present invention, any number of T-cell lines available in the art, may be used. In certain aspects of the present invention, T-cells can be obtained from a unit of blood collected from a subject using any number of techniques known to the skilled artisan, such as Ficoll™ separation. In one preferred aspect, cells from the circulating blood of an individual are obtained by apheresis. The apheresis product typically contains lymphocytes, including T-cells, monocytes, granulocytes, B cells, other nucleated white blood cells, red blood cells, and platelets. In one aspect, the cells collected by apheresis may be washed to remove the plasma fraction and to place the cells in an appropriate buffer or media for subsequent processing steps. In one aspect of the invention, the cells are washed with phosphate buffered saline (PBS). In an alternative aspect, the wash solution lacks calcium and may lack magnesium or may lack many if not all divalent cations. Initial activation steps in the absence of calcium can lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In one aspect, T-cells are isolated from peripheral blood lymphocytes by lysing the red blood cells and depleting the monocytes, for example, by centrifugation through a PERCOLL gradient or by counterflow centrifugal elutriation. A specific subpopulation of T-cells, such as CD3+, CD28+, CD4+, CD8+, CD45RA+, and CD45RO+ T-cells, can be further isolated by positive or negative selection techniques. For example, in one aspect, T-cells are isolated by incubation with anti-CD3/anti-CD28 (e.g., 3×28)-conjugated beads, such as DYNABEADS™ M-450 CD3/CD28 T, for a time period sufficient for positive selection of the desired T-cells. In one aspect, the time period is about 30 minutes. In a further aspect, the time period ranges from 30 minutes to 36 hours or longer and all integer values there between. In a further aspect, the time period is at least 1, 2, 3, 4, 5, or 6 hours. In yet another preferred aspect, the time period is 10 to 24 hours. In one aspect, the incubation time period is 24 hours. Longer incubation times may be used to isolate T-cells in any situation where there are few T-cells as compared to other cell types, such in isolating tumor infiltrating lymphocytes (TIL) from tumor tissue or from immunocompromised individuals. Further, use of longer incubation times can increase the efficiency of capture of CD8+ T-cells. Thus, by simply shortening or lengthening the time T-cells are allowed to bind to the CD3/CD28 beads and/or by increasing or decreasing the ratio of beads to T-cells (as described further herein), subpopulations of T-cells can be preferentially selected for or against at culture initiation or at other time points during the process. Additionally, by increasing or decreasing the ratio of anti-CD3 and/or anti-CD28 antibodies on the beads or other surface, subpopulations of T-cells can be preferentially selected for or against at culture initiation or at other desired time points. The skilled artisan would recognize that multiple rounds of selection can also be used in the context of this invention. In certain aspects, it may be desirable to perform the selection procedure and use the "unselected" cells in the activation and expansion process. "Unselected" cells can also be subjected to further rounds of selection.

Enrichment of a T-cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain aspects, it may be desirable to enrich for or positively select for regulatory T-cells which typically express CD4+, CD25+, CD62Lhi, GITR+, and FoxP3+. Alternatively, in certain aspects, T regulatory cells are depleted by anti-C25 conjugated beads or other similar method of selection.

In one embodiment, a T-cell population can be selected that expresses one or more of IFN-γ☐☐TNF-α, IL-17A, IL-2, IL-3, IL-4, GM-CSF, IL-10, IL-13, granzyme B, and perforin, or other appropriate molecules, e.g., other cytokines. Methods for screening for cell expression can be determined, e.g., by the methods described in PCT Publication No.: WO 2013/126712.

For isolation of a desired population of cells by positive or negative selection, the concentration of cells and surface (e.g., particles such as beads) can be varied. In certain aspects, it may be desirable to significantly decrease the volume in which beads and cells are mixed together (e.g., increase the concentration of cells), to ensure maximum contact of cells and beads. For example, in one aspect, a concentration of 2 billion cells/mL is used. In one aspect, a concentration of 1 billion cells/mL is used. In a further aspect, greater than 100 million cells/mL is used. In a further aspect, a concentration of cells of 10, 15, 20, 25, 30, 35, 40, 45, or 50 million cells/mL is used. In yet one aspect, a concentration of cells from 75, 80, 85, 90, 95, or 100 million cells/mL is used. In further aspects, concentrations of 125 or 150 million cells/mL can be used. Using high concentrations can result in increased cell yield, cell activation, and cell expansion. Further, use of high cell concentrations allows more efficient capture of cells that may weakly express target antigens of interest, such as CD28-negative T-cells, or from samples where there are many tumor cells present (e.g., leukemic blood, tumor tissue, etc.). Such populations of cells may have therapeutic value and would be desirable to obtain. For example, using high concentration of cells allows more efficient selection of CD8+ T-cells that normally have weaker CD28 expression.

In a related aspect, it may be desirable to use lower concentrations of cells. By significantly diluting the mixture of T-cells and surface (e.g., particles such as beads), interactions between the particles and cells is minimized. This selects for cells that express high amounts of desired antigens to be bound to the particles. For example, CD4+ T-cells express higher levels of CD28 and are more efficiently captured than CD8+ T-cells in dilute concentrations. In one aspect, the concentration of cells used is $5 \times 10^6$/mL. In other aspects, the concentration used can be from about $1 \times 10^5$/mL to $1 \times 10^6$/mL, and any integer value in between. In other aspects, the cells may be incubated on a rotator for varying lengths of time at varying speeds at either 2-10° C. or at room temperature.

T-cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1 per minute and stored in the vapor phase of a liquid nitrogen storage tank. Other methods of controlled freezing may be used as well as uncontrolled freezing immediately at −20° C. or in liquid nitrogen. In certain aspects, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T-cells, isolated and frozen for later use in T-cell therapy for any number of diseases or conditions that would benefit from T-cell therapy, such as those described herein. In one aspect, a blood sample or an apheresis is taken from a generally healthy subject. In certain aspects, a blood sample or an apheresis is taken from a generally healthy subject who is at risk of developing a disease, but who has not yet developed a disease, and the cells of interest are isolated and frozen for later use. In certain aspects, the T-cells may be expanded, frozen, and used at a later time. In certain aspects, samples are collected from a patient shortly after diagnosis of a particular disease as described herein but prior to any treatments. In a further aspect, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation.

In a further aspect of the present invention, T-cells are obtained from a patient directly following treatment that leaves the subject with functional T-cells. In this regard, it has been observed that following certain cancer treatments, in particular treatments with drugs that damage the immune system, shortly after treatment during the period when patients would normally be recovering from the treatment, the quality of T-cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T-cells, dendritic cells, or other cells of the hematopoietic lineage, during this recovery phase. Further, in certain aspects, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T-cells, B cells, dendritic cells, and other cells of the immune system.

Activation and Expansion of T Cells

T-cells may be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and 7,572,631.

Generally, the T-cells of the invention may be expanded by contact with a surface having attached thereto an agent that stimulates a CD3/TCR complex associated signal and a ligand that stimulates a costimulatory molecule on the surface of the T-cells. In particular, T-cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol. Meth. 227(1-2):53-63, 1999).

T-cells that have been exposed to varied stimulation times may exhibit different characteristics. For example, typical blood or apheresed peripheral blood mononuclear cell products have a helper T-cell population (TH, CD4+) that is greater than the cytotoxic or suppressor T-cell population (TC, CD8+). Ex vivo expansion of T-cells by stimulating CD3 and CD28 receptors produces a population of T-cells that prior to about days 8-9 consists predominately of TH cells, while after about days 8-9, the population of T-cells comprises an increasingly greater population of TC cells. Accordingly, depending on the purpose of treatment, infusing a subject with a T-cell population comprising predominately of TH cells may be advantageous. Similarly, if an antigen-specific subset of TC cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T-cell product for specific purposes.

Once an anti-BCMA TFP is constructed, various assays can be used to evaluate the activity of the molecule, such as but not limited to, the ability to expand T-cells following antigen stimulation, sustain T-cell expansion in the absence of re-stimulation, and anti-cancer activities in appropriate in vitro and animal models. Assays to evaluate the effects of an anti-BCMA TFP are described in further detail below Western blot analysis of TFP expression in primary T-cells can be used to detect the presence of monomers and dimers (see, e.g., Milone et al., Molecular Therapy 17(8): 1453-1464 (2009)). Very briefly, T-cells (1:1 mixture of $CD4^+$ and $CD8^+$ T-cells) expressing the TFPs are expanded in vitro for more than 10 days followed by lysis and SDS-PAGE under reducing conditions. TFPs are detected by Western blotting using an antibody to a TCR chain. The same T-cell subsets are used for SDS-PAGE analysis under non-reducing conditions to permit evaluation of covalent dimer formation.

In vitro expansion of $TFP^+$ T-cells following antigen stimulation can be measured by flow cytometry. For example, a mixture of $CD4^+$ and $CD8^+$ T-cells are stimulated with alphaCD3/alphaCD28 and APCs followed by transduction with lentiviral vectors expressing GFP under the control of the promoters to be analyzed. Exemplary promoters include the CMV IE gene, EF-1α, ubiquitin C, or phosphoglycerokinase (PGK) promoters. GFP fluorescence is evaluated on day 6 of culture in the CD4+ and/or CD8+ T-cell subsets by flow cytometry (see, e.g., Milone et al., Molecular Therapy 17(8): 1453-1464 (2009)). Alternatively, a mixture of CD4+ and CD8+ T-cells are stimulated with alphaCD3/alphaCD28 coated magnetic beads on day 0, and transduced with TFP on day 1 using a bicistronic lentiviral vector expressing TFP along with eGFP using a 2A ribosomal skipping sequence. Cultures are re-stimulated with either BCMA+K562 cells (K562-BCMA), wild-type K562 cells (K562 wild type) or K562 cells expressing hCD32 and 4-1BBL in the presence of antiCD3 and anti-CD28 antibody (K562-BBL-3/28) following washing. Exogenous IL-2 is added to the cultures every other day at 100 IU/mL. GFP+ T-cells are enumerated by flow cytometry using bead-based counting (see, e.g., Milone et al., Molecular Therapy 17(8): 1453-1464 (2009)).

Sustained TFP+ T-cell expansion in the absence of re-stimulation can also be measured (see, e.g., Milone et al., Molecular Therapy 17(8): 1453-1464 (2009)). Briefly, mean T-cell volume (fl) is measured on day 8 of culture using a Coulter Multisizer III particle counter following stimulation with alphaCD3/alphaCD28 coated magnetic beads on day 0, and transduction with the indicated TFP on day 1.

Animal models can also be used to measure a TFP-T activity. For example, xenograft model using human BCMA-specific TFP+ T-cells to treat a cancer in immunodeficient mice (see, e.g., Milone et al., Molecular Therapy 17(8): 1453-1464 (2009)). Very briefly, after establishment of cancer, mice are randomized as to treatment groups. Different numbers of engineered T-cells are injected at a 1:1 ratio into NOD/SCID/γ-/- mice bearing cancer. The number of copies of each vector in spleen DNA from mice is evaluated at various times following T-cell injection. Animals are assessed for cancer at weekly intervals. Peripheral blood BCMA+ cancer cell counts are measured in mice that are injected with alphaBCMA-zeta TFP+ T-cells or mock-transduced T-cells. Survival curves for the groups are compared using the log-rank test. In addition, absolute peripheral blood CD4+ and CD8+ T-cell counts 4 weeks following T-cell injection in NOD/SCID/γ-/- mice can also be analyzed. Mice are injected with cancer cells and 3 weeks later are injected with T-cells engineered to express TFP by a bicistronic lentiviral vector that encodes the TFP linked to eGFP. T-cells are normalized to 45-50% input GFP+ T-cells by mixing with mock-transduced cells prior to injection, and confirmed by flow cytometry. Animals are assessed for cancer at 1-week intervals. Survival curves for the TFP+ T-cell groups are compared using the log-rank test.

Dose dependent TFP treatment response can be evaluated (see, e.g., Milone et al., Molecular Therapy 17(8): 1453-1464 (2009)). For example, peripheral blood is obtained 35-70 days after establishing cancer in mice injected on day 21 with TFP T-cells, an equivalent number of mock-transduced T-cells, or no T-cells. Mice from each group are randomly bled for determination of peripheral blood BCMA+ cancer cell counts and then killed on days 35 and 49. The remaining animals are evaluated on days 57 and 70.

Assessment of cell proliferation and cytokine production has been previously described, e.g., at Milone et al., Molecular Therapy 17(8): 1453-1464 (2009). Briefly, assessment of TFP-mediated proliferation is performed in microtiter plates by mixing washed T-cells with cells expressing BCMA or CD32 and CD137 (KT32-BBL) for a final T-cell:cell expressing BCMA ratio of 2:1. Cells expressing BCMA cells are irradiated with gamma-radiation prior to use. Anti-CD3 (clone OKT3) and anti-CD28 (clone 9.3) monoclonal antibodies are added to cultures with KT32-BBL cells to serve as a positive control for stimulating T-cell proliferation since these signals support long-term CD8+ T-cell expansion ex vivo. T-cells are enumerated in cultures using Count-Bright™ fluorescent beads (Invitrogen) and flow cytometry as described by the manufacturer. TFP+ T-cells are identified by GFP expression using T-cells that are engineered with eGFP-2A linked TFP-expressing lentiviral vectors. For TFP+ T-cells not expressing GFP, the TFP+ T-cells are detected with biotinylated recombinant BCMA protein and a secondary avidin-PE conjugate. CD4+ and CD8+ expression on T-cells are also simultaneously detected with specific monoclonal antibodies (BD Biosciences). Cytokine measurements are performed on supernatants collected 24 hours following re-stimulation using the human TH1/TH2 cytokine cytometric bead array kit (BD Biosciences) according the manufacturer's instructions. Fluorescence is assessed using a FACScalibur flow cytometer, and data is analyzed according to the manufacturer's instructions.

Cytotoxicity can be assessed by a standard $^{51}$Cr-release assay (see, e.g., Milone et al., Molecular Therapy 17(8): 1453-1464 (2009)). Briefly, target cells are loaded with $^{51}$Cr (as NaCrO$_4$, New England Nuclear) at 37° C. for 2 hours with frequent agitation, washed twice in complete RPMI and plated into microtiter plates. Effector T-cells are mixed with target cells in the wells in complete RPMI at varying ratios of effector cell:target cell (E:T). Additional wells containing media only (spontaneous release, SR) or a 1% solution of triton-X 100 detergent (total release, TR) are also prepared. After 4 hours of incubation at 37° C., supernatant from each well is harvested. Released $^{51}$Cr is then measured using a gamma particle counter (Packard Instrument Co., Waltham, Mass.). Each condition is performed in at least triplicate, and the percentage of lysis is calculated using the formula: % Lysis=(ER−SR)/(TR−SR), where ER represents the average $^{51}$Cr released for each experimental condition.

Imaging technologies can be used to evaluate specific trafficking and proliferation of TFPs in tumor-bearing animal models. Such assays have been described, e.g., in Barrett et al., Human Gene Therapy 22:1575-1586 (2011). Briefly, NOD/SCID/γc−/− (NSG) mice are injected IV with cancer cells followed 7 days later with T-cells 4 hour after electroporation with the TFP constructs. The T-cells are stably transfected with a lentiviral construct to express firefly luciferase, and mice are imaged for bioluminescence. Alternatively, therapeutic efficacy and specificity of a single injection of TFP+ T-cells in a cancer xenograft model can be measured as follows: NSG mice are injected with cancer cells transduced to stably express firefly luciferase, followed by a single tail-vein injection of T-cells electroporated with BCMA TFP 7 days later. Animals are imaged at various time points post injection. For example, photon-density heat maps of firefly luciferase positive cancer in representative mice at day 5 (2 days before treatment) and day 8 (24 hours post TFP+ PBLs) can be generated.

Other assays, including those described in the Example section herein as well as those that are known in the art can also be used to evaluate the anti-BCMA TFP constructs of the invention.

Therapeutic Applications

BCMA Associated Diseases and/or Disorders

In one aspect, the invention provides methods for treating a disease associated with BCMA expression. In one aspect, the invention provides methods for treating a disease wherein part of the tumor is negative for BCMA and part of the tumor is positive for BCMA. For example, the antibody or TFP of the invention is useful for treating subjects that have undergone treatment for a disease associated with elevated expression of BCMA, wherein the subject that has undergone treatment for elevated levels of BCMA exhibits a disease associated with elevated levels of BCMA.

In one aspect, the invention pertains to a vector comprising anti-BCMA antibody or TFP operably linked to promoter for expression in mammalian T-cells. In one aspect, the invention provides a recombinant T-cell expressing a BCMA TFP for use in treating BCMA-expressing tumors, wherein the recombinant T-cell expressing the BCMA TFP is termed a BCMA TFP-T. In one aspect, the BCMA TFP-T of the invention is capable of contacting a tumor cell with at least one BCMA TFP of the invention expressed on its surface such that the TFP-T targets the tumor cell and growth of the tumor is inhibited.

In one aspect, the invention pertains to a method of inhibiting growth of a BCMA-expressing tumor cell, comprising contacting the tumor cell with a BCMA antibody or TFP T-cell of the present invention such that the TFP-T is activated in response to the antigen and targets the cancer cell, wherein the growth of the tumor is inhibited.

In one aspect, the invention pertains to a method of treating cancer in a subject. The method comprises administering to the subject a BCMA antibody, bispecific antibody, or TFP T-cell of the present invention such that the cancer is treated in the subject. An example of a cancer that is treatable by the BCMA TFP T-cell of the invention is a cancer associated with expression of BCMA. In one aspect, the cancer is a myeloma. In one aspect, the cancer is a lymphoma. In one aspect, the cancer is an colon cancer.

In some embodiments, BCMA antibodies or TFP therapy can be used in combination with one or more additional therapies. In some instances, such additional therapies comprise a chemotherapeutic agent, e.g., cyclophosphamide. In some instances, such additional therapies comprise surgical resection or radiation treatment.

In one aspect, disclosed herein is a method of cellular therapy wherein T-cells are genetically modified to express a TFP and the TFP-expressing T-cell is infused to a recipient in need thereof. The infused cell is able to kill tumor cells in the recipient. Unlike antibody therapies, TFP-expressing T-cells are able to replicate in vivo resulting in long-term persistence that can lead to sustained tumor control. In various aspects, the T-cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T-cell to the patient.

In some instances, disclosed herein is a type of cellular therapy where T-cells are modified, e.g., by in vitro transcribed RNA, to transiently express a TFP and the TFP-expressing T-cell is infused to a recipient in need thereof. The infused cell is able to kill tumor cells in the recipient. Thus, in various aspects, the T-cells administered to the patient, is present for less than one month, e.g., three weeks, two weeks, or one week, after administration of the T-cell to the patient.

Without wishing to be bound by any particular theory, the anti-tumor immunity response elicited by the TFP-expressing T-cells may be an active or a passive immune response, or alternatively may be due to a direct vs indirect immune response. In one aspect, the TFP transduced T-cells exhibit specific proinflammatory cytokine secretion and potent cytolytic activity in response to human cancer cells expressing the BCMA antigen, resist soluble BCMA inhibition, mediate bystander killing and/or mediate regression of an established human tumor. For example, antigen-less tumor cells within a heterogeneous field of BCMA-expressing tumor may be susceptible to indirect destruction by BCMA-redirected T-cells that has previously reacted against adjacent antigen-positive cancer cells.

In one aspect, the human TFP-modified T-cells of the invention may be a type of vaccine for ex vivo immunization and/or in vivo therapy in a mammal. In one aspect, the mammal is a human.

With respect to ex vivo immunization, at least one of the following occurs in vitro prior to administering the cell into a mammal: i) expansion of the cells, ii) introducing a nucleic acid encoding a TFP to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing a TFP disclosed herein. The TFP-modified cell can be administered to a mammalian recipient to provide a therapeutic benefit. The mammalian recipient may be a human and the TFP-modified cell can be autologous with respect to the recipient. Alternatively, the cells can be allogeneic, syngeneic or xenogeneic with respect to the recipient.

The procedure for ex vivo expansion of hematopoietic stem and progenitor cells is described, e.g., in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T-cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the TFP-modified T-cells of the invention are used in the treatment of diseases, disorders and conditions associated with expression of BCMA. In certain aspects, the cells of the invention are used in the treatment of patients at risk for developing diseases, disorders and conditions associated with expression of BCMA. Thus, the present invention provides methods for the treatment or prevention of diseases, disorders and conditions associated with expression of BCMA comprising administering to a subject in need thereof, a therapeutically effective amount of the TFP-modified T-cells of the invention.

In one aspect the antibodies or TFP-T-cells of the inventions may be used to treat a proliferative disease such as a cancer or malignancy or is a precancerous condition. In one aspect, the cancer is a myeloma. In one aspect, the cancer is a lymphoma. In one aspect, the cancer is a colon cancer. Further, a disease associated with BCMA expression includes, but is not limited to, e.g., atypical and/or non-classical cancers, malignancies, precancerous conditions or proliferative diseases expressing BCMA. Non-cancer related indications associated with expression of BCMA include, but are not limited to, e.g., autoimmune disease, (e.g., lupus), inflammatory disorders (allergy and asthma) and transplantation.

The antibodies or TFP-modified T-cells of the present invention may be administered either alone, or as a pharmaceutical composition in combination with diluents and/or with other components such as IL-2 or other cytokines or cell populations.

The present invention also provides methods for inhibiting the proliferation or reducing a BCMA-expressing cell population, the methods comprising contacting a population of cells comprising a BCMA-expressing cell with an anti-BCMA TFP-T-cell of the invention that binds to the BCMA-expressing cell. In a specific aspect, the present invention provides methods for inhibiting the proliferation or reducing the population of cancer cells expressing BCMA, the methods comprising contacting the BCMA-expressing cancer cell population with an anti-BCMA antibody or TFP-T-cell of the invention that binds to the BCMA-expressing cell. In one aspect, the present invention provides methods for inhibiting the proliferation or reducing the population of cancer cells expressing BCMA, the methods comprising contacting the BCMA-expressing cancer cell population with an anti-BCMA antibody or TFP-T-cell of the invention that binds to the BCMA-expressing cell. In certain aspects, the anti-BCMA antibody or TFP-T-cell of the invention reduces the quantity, number, amount or percentage of cells and/or cancer cells by at least 25%, at least 30%, at least 40%, at least 50%, at least 65%, at least 75%, at least 85%, at least 95%, or at least 99% in a subject with or animal model for multiple myeloma or another cancer associated with BCMA-expressing cells relative to a negative control. In one aspect, the subject is a human.

The present invention also provides methods for preventing, treating and/or managing a disease associated with BCMA-expressing cells (e.g., a cancer expressing BCMA), the methods comprising administering to a subject in need an anti-BCMA antibody or TFP-T-cell of the invention that binds to the BCMA-expressing cell. In one aspect, the subject is a human. Non-limiting examples of disorders associated with BCMA-expressing cells include autoimmune disorders (such as lupus), inflammatory disorders (such as allergies and asthma) and cancers (such as hematological cancers or atypical cancers expressing BCMA).

The present invention also provides methods for preventing, treating and/or managing a disease associated with BCMA-expressing cells, the methods comprising administering to a subject in need an anti-BCMA antibody or TFP-T-cell of the invention that binds to the BCMA-expressing cell. In one aspect, the subject is a human.

The present invention provides methods for preventing relapse of cancer associated with BCMA-expressing cells, the methods comprising administering to a subject in need thereof an anti-BCMA antibody or TFP-T-cell of the invention that binds to the BCMA-expressing cell. In one aspect, the methods comprise administering to the subject in need thereof an effective amount of an anti-BCMA antibody or TFP-T-cell described herein that binds to the BCMA-expressing cell in combination with an effective amount of another therapy.

Combination Therapies

An antibody or TFP-expressing cell described herein may be used in combination with other known agents and therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In some embodiments, the "at least one additional therapeutic agent" includes a TFP-expressing cell. Also provided are T-cells that express multiple TFPs, which bind to the same or different target antigens, or same or different epitopes on the same target antigen. Also provided are populations of T-cells in which a first subset of T-cells express a first TFP and a second subset of T-cells express a second TFP.

A TFP-expressing cell described herein and the at least one additional therapeutic agent can be administered simultaneously, in the same or in separate compositions, or sequentially. For sequential administration, the TFP-expressing cell described herein can be administered first, and the additional agent can be administered second, or the order of administration can be reversed.

In further aspects, a TFP-expressing cell described herein may be used in a treatment regimen in combination with surgery, chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludarabine, cyclosporin, FK506, rapamycin, mycophenolic acid, steroids, FR901228, cytokines, and irradiation. peptide vaccine, such as that described in Izumoto et al. 2008 J Neurosurg 108:963-971.

In one embodiment, the subject can be administered an agent which reduces or ameliorates a side effect associated with the administration of a TFP-expressing cell. Side effects associated with the administration of a TFP-expressing cell include, but are not limited to cytokine release syndrome (CRS), and hemophagocytic lymphohistiocytosis (HLH), also termed Macrophage Activation Syndrome (MAS). Symptoms of CRS include high fevers, nausea, transient hypotension, hypoxia, and the like. Accordingly, the methods described herein can comprise administering a TFP-expressing cell described herein to a subject and further administering an agent to manage elevated levels of a soluble factor resulting from treatment with a TFP-expressing cell. In one embodiment, the soluble factor elevated in the subject is one or more of IFN-γ, TNFα, IL-2 and IL-6. Therefore, an agent administered to treat this side effect can be an agent that neutralizes one or more of these soluble factors. Such agents include, but are not limited to a steroid, an inhibitor of TNFα, and an inhibitor of IL-6. An example of a TNFα inhibitor is etanercept (marketed under the name ENBREL®). An example of an IL-6 inhibitor is tocilizumab (marketed under the name ACTEMRA®).

In one embodiment, the subject can be administered an agent which enhances the activity of a TFP-expressing cell. For example, in one embodiment, the agent can be an agent which inhibits an inhibitory molecule. Inhibitory molecules, e.g., Programmed Death 1 (PD1), can, in some embodiments, decrease the ability of a TFP-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. Inhibition of an inhibitory molecule, e.g., by inhibition at the DNA, RNA or protein level, can optimize a TFP-expressing cell performance. In embodiments, an inhibitory nucleic acid, e.g., an inhibitory nucleic acid, e.g., a dsRNA, e.g., an siRNA or shRNA, can be used to inhibit expression of an inhibitory molecule in the TFP-expressing cell. In an embodiment the inhibitor is a shRNA. In an embodiment, the inhibitory molecule is inhibited within a TFP-expressing cell. In these embodiments, a dsRNA molecule that inhibits expression of the inhibitory molecule is linked to the nucleic acid that encodes a component, e.g., all of the components, of the TFP. In one embodiment, the inhibitor of an inhibitory signal can be, e.g., an antibody or antibody fragment that binds to an inhibitory molecule. For example, the agent can be an antibody or antibody fragment that binds to PD1, PD-L1, PD-L2 or CTLA4 (e.g., ipilimumab (also referred to as MDX-010 and MDX-101, and marketed as YERVOY®; Bristol-Myers Squibb; Tremelimumab (IgG2 monoclonal antibody available from Pfizer, formerly known as ticilimumab, CP-675,206)). In an embodiment, the agent is an antibody or antibody fragment that binds to T-cell immunoglobulin and mucin-domain containing-3 (TIM3). In an embodiment, the agent is an antibody or antibody fragment that binds to Lymphocyte-activation gene 3 (LAG3).

In some embodiments, the agent which enhances the activity of a TFP-expressing cell can be, e.g., a fusion protein comprising a first domain and a second domain, wherein the first domain is an inhibitory molecule, or fragment thereof, and the second domain is a polypeptide that is associated with a positive signal, e.g., a polypeptide comprising an intracellular signaling domain as described herein. In some embodiments, the polypeptide that is associated with a positive signal can include a costimulatory domain of CD28, CD27, ICOS, e.g., an intracellular signaling domain of CD28, CD27 and/or ICOS, and/or a primary signaling domain, e.g., of CD3 zeta, e.g., described herein. In one embodiment, the fusion protein is expressed by the same cell that expressed the TFP. In another embodiment, the fusion protein is expressed by a cell, e.g., a T-cell that does not express an anti-BCMA TFP.

Pharmaceutical Compositions

Pharmaceutical compositions of the present invention may comprise a TFP-expressing cell, e.g., a plurality of TFP-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one embodiment, the pharmaceutical composition is substantially free of, e.g., there are no detectable levels of a contaminant, e.g., selected from the group consisting of endotoxin, *mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

When "an immunologically effective amount," "an anti-tumor effective amount," "a tumor-inhibiting effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T-cells described herein may be administered at a dosage of $10^4$ to $10^9$ cells/kg body weight, in some instances $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., New Eng. J. of Med. 319:1676, 1988).

In certain aspects, it may be desired to administer activated T-cells to a subject and then subsequently redraw blood (or have an apheresis performed), activate T-cells therefrom according to the present invention, and reinfuse the patient with these activated and expanded T-cells. This process can be carried out multiple times every few weeks. In certain aspects, T-cells can be activated from blood draws of from 10 cc to 400 cc. In certain aspects, T-cells are activated from blood draws of 20 cc, 30 cc, 40 cc, 50 cc, 60 cc, 70 cc, 80 cc, 90 cc, or 100 cc.

The administration of the subject compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T-cell compositions of the present invention are administered to a patient by intradermal or subcutaneous injection. In one aspect, the T-cell compositions of the present invention are administered by i.v. injection. The compositions of T-cells may be injected directly into a tumor, lymph node, or site of infection.

In a particular exemplary aspect, subjects may undergo leukapheresis, wherein leukocytes are collected, enriched, or depleted ex vivo to select and/or isolate the cells of interest, e.g., T-cells. These T-cell isolates may be expanded by methods known in the art and treated such that one or more TFP constructs of the invention may be introduced, thereby creating a TFP-expressing T-cell of the invention. Subjects in need thereof may subsequently undergo standard treatment with high dose chemotherapy followed by peripheral blood stem cell transplantation. In certain aspects, following or concurrent with the transplant, subjects receive an infusion of the expanded TFP T-cells of the present invention. In an additional aspect, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for alemtuzumab (CAMPATH®), for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

In one embodiment, the TFP is introduced into T-cells, e.g., using in vitro transcription, and the subject (e.g., human) receives an initial administration of TFP T-cells of the invention, and one or more subsequent administrations of the TFP T-cells of the invention, wherein the one or more subsequent administrations are administered less than 15 days, e.g., 14, 13, 12, 11, 10, 9, 8, 7, 6, 5, 4, 3, or 2 days after the previous administration. In one embodiment, more than one administration of the TFP T-cells of the invention are administered to the subject (e.g., human) per week, e.g., 2, 3, or 4 administrations of the TFP T-cells of the invention are administered per week. In one embodiment, the subject (e.g., human subject) receives more than one administration of the TFP T-cells per week (e.g., 2, 3 or 4 administrations per week) (also referred to herein as a cycle), followed by a week of no TFP T-cells administrations, and then one or more additional administration of the TFP T-cells (e.g., more than one administration of the TFP T-cells per week) is administered to the subject. In another embodiment, the subject (e.g., human subject) receives more than one cycle of TFP T-cells, and the time between each cycle is less than 10, 9, 8, 7, 6, 5, 4, or 3 days. In one embodiment, the TFP T-cells are administered every other day for 3 administrations per week. In one embodiment, the TFP T-cells of the invention are administered for at least two, three, four, five, six, seven, eight or more weeks.

In one aspect, BCMA TFP T-cells are generated using lentiviral viral vectors, such as lentivirus. TFP-T-cells generated that way will have stable TFP expression.

In one aspect, TFP T-cells transiently express TFP vectors for 4, 5, 6, 7, 8, 9, 10, 11, 12, 13, 14, 15 days after transduction. Transient expression of TFPs can be effected by RNA TFP vector delivery. In one aspect, the TFP RNA is transduced into the T-cell by electroporation.

A potential issue that can arise in patients being treated using transiently expressing TFP T-cells (particularly with murine scFv bearing TFP T-cells) is anaphylaxis after multiple treatments.

Without being bound by this theory, it is believed that such an anaphylactic response might be caused by a patient developing humoral anti-TFP response, i.e., anti-TFP antibodies having an anti-IgE isotype. It is thought that a patient's antibody producing cells undergo a class switch from IgG isotype (that does not cause anaphylaxis) to IgE isotype when there is a ten- to fourteen-day break in exposure to antigen.

If a patient is at high risk of generating an anti-TFP antibody response during the course of transient TFP therapy (such as those generated by RNA transductions), TFP T-cell infusion breaks should not last more than ten to fourteen days.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein. Without further description, it is believed that one of ordinary skill in the art can, using the preceding description and the following illustrative examples, make and utilize the compounds of the present invention and practice the claimed methods. The following working examples specifically point out various aspects of the present invention, and are not to be construed as limiting in any way the remainder of the disclosure.

Example 1: TFP Constructs

Anti-BCMA TFP constructs are engineered by cloning an anti-BCMA scFv DNA fragment linked to a CD3 or TCR DNA fragment by either a DNA sequence encoding a short linker (SL): AAAGGGGSGGGGSGGGGSLE (SEQ ID NO:1) or a long linker (LL): AAAIEVMYPP-PYLGGGGSGGGGSGGGGSLE (SEQ ID NO:2) into p510 vector ((System Biosciences (SBI)) at XbaI and EcoR1 sites.

The anti-BCMA TFP constructs generated are p510_antiBCMA_LL_TCRα (anti-BCMA scFv-long linker-human full length T cell receptor α chain), p510_antiBCMA_LL_TCR_αC (anti-BCMA scFv-long linker-human T cell receptor α constant domain chain), p510_antiBCMA_LL_TCRβ (anti-BCMA scFv-long linker-human full length T cell receptor β chain), p510_antiBCMA_LL_TCRβC (anti-BCMA scFv-long linker-human T cell receptor β constant domain chain), p510_antiBCMA_LL_CD3γ (anti-BCMA scFv-long linker-human CD3γ chain), p510_antiBCMA_LL_CD3δ (anti-BCMA scFv-long linker-human CD3δ chain), p510_antiBCMA_LL_CD3ε (anti-BCMA scFv-long linker-human CD3ε chain), p510_antiBCMA_SL_TCRβ (anti-BCMA scFv-short linker-human full length T cell receptor β chain), p510_antiBCMA_SL_CD3γ (anti-BCMA scFv-short linker-human CD3γ chain), p510_antiBCMA_SL_CD3δ (anti-BCMA scFv-short linker-human CD3δ chain), p510_antiBCMA_SL_CD3ε (anti-BCMA scFv-short linker-human CD3ε chain).

The anti-BCMA CAR construct, p510_antiBCMA_28ζ is generated by cloning synthesized DNA encoding anti-BCMA, partial CD28 extracellular domain, CD28 transmembrane domain, CD28 intracellular domain and CD3 zeta into p510 vector at XbaI and EcoR1 sites.

Anti-BCMA TFP constructs were engineered by cloning an anti-BCMA scFv DNA fragment linked to a CD3 DNA fragment by a DNA sequence encoding the linker: GGGGSGGGGSGGGGSLE (SEQ ID NO:5) into p510 vector (SBI) at XbaI and EcoR1 sites. The anti-BCMA TFP constructs generated were p510_antiBCMA_CD3γ (anti-BCMA scFv (or $V_H$H)-linker-human CD3γ chain) and p510_anti-BCMA_CD3ε (anti-BCMA scFv (or $V_H$H)-linker-human CD3ε chain).

Full length BCMA was synthesized and cloned into p514 (SBI) at BamHI and NheI sites to generate the construct p514_BCMA, used to generate stable target cell lines.

Anti-Fibroblast activation protein (FAP) and anti-Carboanhydrase-9 (CAIX) TFP constructs are engineered by cloning an anti-FAP or anti-CAIX scFv DNA fragment linked to a CD3 DNA fragment by a DNA sequence encoding the linker: GGGGSGGGGSGGGGSLE (SEQ ID NO:5) into p510 vector (SBI) at XbaI and EcoR1 sites. The anti-FAP or anti-CAIX TFP constructs that can be generated include p510_antiFAP_CD3γ (anti-FAP scFv-linker-human CD3γ chain) and p510_antiFAP_CD3ε (anti-FAP scFv-linker-human CD3ε chain) and p510_antiCAIX_CD3γ (anti-CAIX scFv-linker-human CD3γ-chain) and p510_antiCAIX_CD3ε (anti-CAIX scFv-linker-human CD3ε chain).

Full length FAP and CAIX can be synthesized and cloned into p514 (SBI) at BamHI and NheI sites to generate the constructs p514_FAP and p514_CAIX, that can be used to generate stable target cell lines.

Exemplary construct sequences are disclosed in Appendix A: Sequences.

Example 2: Antibody Sequences

Generation of Antibody Sequences

The human BCMA polypeptide canonical sequence is UniProt Accession No. Q02223. Provided are antibody polypeptides that are capable of specifically binding to the human BCMA polypeptide, and fragments or domains thereof. Anti-BCMA antibodies can be generated using diverse technologies (see, e.g., (Nicholson et al, 1997). Where murine anti-BCMA antibodies are used as a starting material, humanization of murine anti-BCMA antibodies is desired for the clinical setting, where the mouse-specific residues may induce a human-anti-mouse antigen (HAMA) response in subjects who receive T-cell receptor (TCR) fusion protein (TFP) treatment, i.e., treatment with T-cells transduced with the TFP.BCMA construct. Humanization is accomplished by grafting CDR regions from murine anti-BCMA antibody onto appropriate human germline acceptor frameworks, optionally including other modifications to CDR and/or framework regions. As provided herein, antibody and antibody fragment residue numbering follows Kabat (Kabat E. A. et al, 1991; Chothia et al, 1987).

Generation of scFvs

Human or humanized anti-BCMA IgGs are used to generate scFv sequences for TFP constructs. DNA sequences coding for human or humanized $V_L$ and $V_H$ domains are obtained, and the codons for the constructs are, optionally, optimized for expression in cells from Homo sapiens. The order in which the $V_L$ and $V_H$ domains appear in the scFv is varied (i.e., $V_L$—$V_H$, or $V_H$—$V_L$ orientation), and three copies of the "G4S" or "$G_4$S" subunit $(G_4S)_3$ connect the variable domains to create the scFv domain. Anti-BCMA scFv plasmid constructs can have optional Flag, His or other affinity tags, and are electroporated into HEK293 or other suitable human or mammalian cell lines and purified. Validation assays include binding analysis by FACS, kinetic analysis using Proteon, and staining of BCMA-expressing cells.

Exemplary anti-BMCA CDRs of $V_L$ and $V_H$ domains and the nucleotide sequences encoding them, respectively, are shown below:
Anti-BCMA

```
Anti-BCMA light chain CDR1
Coding Sequence:
                                          (SEQ ID NO: 7)
AAAAGCAGCCAGAGCCTGGTGCATAGCAACGGCAACACCTATCTGCAT.

Amino acid sequence:
                                          (SEQ ID NO: 8)
KSSQSLVHSNGNTYLH.

Anti-BCMA light chain CDR2
Coding Sequence:
                                          (SEQ ID NO: 9)
AAAGTGAGCAACCGCTTTAGC.

Amino acid sequence:
                                          (SEQ ID NO: 10)
KVSNRFS.

Anti-BCMA light chain CDR3
Coding Sequence:
                                          (SEQ ID NO: 11)
GCGGAAACCAGCCATGTGCCGTGGACC Amino acid sequence:
                                          (SEQ ID NO: 12)
AETSHVPWT.

Anti-BCMA heavy chain CDR1
Coding Sequence:
                                          (SEQ ID NO: 13)
AAAGCGAGCGGCTATAGCTTTCCGGATTATTATATTAAC.

Amino acid sequence:
                                          (SEQ ID NO: 14)
KASGYSFPDYYIN.

Anti-BCMA heavy chain CDR2
Coding Sequence:
                                          (SEQ ID NO: 15)
TGGATTTATTTTGCGAGCGGCAACAGCGAATATAACCAGAAATTTACCG
GC.

Amino acid sequence:
                                          (SEQ ID NO: 16)
WIYFASGNSEYNQKFTG.

Anti-BCMA heavy chain CDR3
Coding Sequence:
                                          (SEQ ID NO: 17)
CTGTATGATTATGATTGGTATTTTGATGTG.

Amino acid sequence:
                                          (SEQ ID NO: 18)
LYDYDWYFDV.

Anti-BCMA light chain variable region
Coding Sequence:
                                          (SEQ ID NO: 19)
GATATTGTGATGACCCAGACCCCGCTGAGCCTGAGCGTGACCCCGGGCGA
ACCGGCGAGCATTAGCTGCAAAAGCAGCCAGAGCCTGGTGCATAGCAACG
GCAACACCTATCTGCATTGGTATCTGCAGAAACCGGGCCAGAGCCCGCAG
CTGCTGATTTATAAAGTGAGCAACCGCTTTAGCGGCGTGCCGGATCGCTT
TAGCGGCAGCGGCAGCGGCGCGGATTTTACCCTGAAAATTAGCCGCGTGG
AAGCGGAAGATGTGGGCGTGTATTATTGCGCGGAAACCAGCCATGTGCCG
TGGACCTTTGGCCAGGGCACCAAACTGGAAATTAAAAGC.

Amino acid sequence:
                                          (SEQ ID NO: 20)
DIVMTQTPLSLSVTPGEPASISCKSQSLVHSNGNTYLHWYLQKPGQSPQL
LIYKVSNRFSGVPDRFSGSGSGADFTLKISRVEAEDVGVYYCAETSHVPW
TFGQGTKLEIKS.

Anti-BCMA heavy chain variable region
Coding Sequence:
                                          (SEQ ID NO: 21)
CAGGTGCAGCTGGTGCAGAGCGGCGCGGAAGTGAAAAAACCGGGCGCGAG
CGTGAAAGTGAGCTGCAAAGCGAGCGGCTATAGCTTTCCGGATTATTATA
TTAACTGGGTGCGCCAGGCGCCGGGCCAGGGCCTGGAATGGATGGGCTGG
ATTTATTTTGCGAGCGGCAACAGCGAATATAACCAGAAATTTACCGGCCG
CGTGACCATGACCCGCGATACCAGCAGCAGCACCGCGTATATGGAACTGA
GCAGCCTGCGCAGCGAAGATACCGCGGTGTATTTTTGCGCGAGCCTGTAT
GATTATGATTGGTATTTTGATGTGTGGGGCCAGGGCACCATGGTGACCGT
GAGCAGC.

Amino acid sequence:
                                          (SEQ ID NO: 22)
QVQLVQSGAEVKKPGASVKVSCKASGYSFPDYYINWVRQAPGQGLEWMGW
IYFASGNSEYNQKFTGRVTMTRDTSSTAYMELSSLRSEDTAVYFCASLY
DYDWYFDVWGQGTMVTVSS.

Anti-BCMA $V_H$H 1
Coding Sequence:
                                          (SEQ ID NO: 23)
ATGGCGGTGGTCCTGGCTGCTCTACTACAAGGTGTCCAGGCTCAGGTGCA
CCCGGTGGAGTCTGGGGGAGGCTTGGTGCAGACTGGGGGGTCTCTGAGAC
TCTCCTGTGCAGCCTCTGCTGGTATCTTCAGTATCAATGTCATGGGCTGG
TACCGCCAGGCTCCAGGGAAGCAGCGCGAATTGGTCGCGAGTATAACTAG
TCGTGGTGATACAACGTATGCGAACTCCGTGAAGGGCCGATTCACCATCT
CCAGAGACAACGCCAAGAACACGGTATATCTGCAAATGAACGCCCTGAAA
CCTGAGGACACAGCCGTCTATTACTGTAAATTTAAAGGGGACAGACTATAG
TGGTACATCCACCCAGACCTTCGACAGACAGGGCCAGGGGACCCAGGTCA
CCGTCTCTTCGGAACCCAAGACACCAAAACCACAACCACAACCACAACCA
CAACCACAACCCAATCCTACAACAGAATCCAAGTGTCCCAAATGTCCAGC
CCCTGAGCTCCTGGGAGGGCCCTCAGTCTTCATCTTCCCCCCGAAACCCA
AGGACGTCCTCTCCATC Amino acid sequence:
                                          (SEQ ID NO: 24)
QVHPVESGGGLVQTGGSLRLSCAASAGIFSINVMGWYRQAPGKQRELVAS
ITSRGDTTYANSVKGRFTISRDNAKNTVYLQMNALKPEDTAVYYCNLKGT
DYSGTSTQTFDRQGQGTQVTVSSEPKTPKPQPQPQPQPQPNPTTESKCPK
CPAPELLGGPSVFIFPPKPKDVLSI
```

Anti-BCMA V<sub>H</sub>H1 CDR1

(SEQ ID NO: 25)
INVMG

Anti-BCMA V<sub>H</sub>H1 CDR2

(SEQ ID NO: 26)
SITSRGDTTYANSVKG

Anti-BCMA V<sub>H</sub>H1 CDR3

(SEQ ID NO: 28)
LKGTDYSGTSTQTFDR

Anti-BCMA V<sub>H</sub>H2
QVQLVESGGGLVQPGESLRLSCAASTNIFSISPMGWYRQAPGKQRELVAA

IHGFSTLYADSVKGRFTISRDNAKNTIYLQMNSLKPEDTAVYYCNKVPWG

DYHPRNVYWGQGTQVTVSSEPKTPKPQPQPQPQPQPQPNPTTESKCPKCP

APELLGGPSVFIFPPKPKDVLSI

Anti-BCMA V<sub>H</sub>H2 CDR1

(SEQ ID NO: 29)
ISPMG

Anti-BCMA V<sub>H</sub>H2 CDR2

(SEQ ID NO: 30)
AIHGFSTLYADSVKG

Anti-BCMA V<sub>H</sub>H2 CDR3

(SEQ ID NO: 31)
VPWGDYHPRNVY

Source of TCR Subunits

Subunits of the human T Cell Receptor (TCR) complex all contain an extracellular domain, a transmembrane domain, and an intracellular domain. A human TCR complex contains the CD3-epsilon polypeptide, the CD3-gamma polypeptide, the CD3-delta polypeptide, the CD3-zeta polypeptide, the TCR alpha chain polypeptide and the TCR beta chain polypeptide. The human CD3-epsilon polypeptide canonical sequence is Uniprot Accession No. P07766. The human CD3-gamma polypeptide canonical sequence is Uniprot Accession No. P09693. The human CD3-delta polypeptide canonical sequence is Uniprot Accession No. P043234. The human CD3-zeta polypeptide canonical sequence is Uniprot Accession No. P20963. The human TCR alpha chain canonical sequence is Uniprot Accession No. Q6ISU1. The human TCR beta chain C region canonical sequence is Uniprot Accession No. P01850, a human TCR beta chain V region sequence is P04435.

The human CD3-epsilon polypeptide canonical sequence is:

(SEQ ID NO: 32)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDVMSVATIVIVDICITGGLLLLVYY

WSKNRKAKAKPVTRGAGAGGRQRGQNKERPPPVPNPDYEPIRKGQRDLYS

GLNQRRI.

The human CD3-gamma polypeptide canonical sequence is:

(SEQ ID NO: 33)
MEQGKGLAVLILAIILLQGTLAQSIKGNHLVKVYDYQEDGSVLLTCDAEA

KNITWFKDGKMIGFLTEDKKKWNLGSNAKDPRGMYQCKGSQNKSKPLQVY

YRMCQNCIELNAATISGFLFAEIVSIFVLAVGVYFIAGQDGVRQSRASDK

QTLLPNDQLYQPLKDREDDQYSHLQGNQLRRN.

The human CD3-delta polypeptide canonical sequence is:

(SEQ ID NO: 34)
MEHSTFLSGLVLATLLSQVSPFKIPIEELEDRVFVNCNTSITWVEGTVGT

LLSDITRLDLGKRILDPRGIYRCNGTDIYKDKESTVQVHYRMCQSCVELD

PATVAGIIVTDVIATLLLALGVFCFAGHETGRLSGAADTQALLRNDQVYQ

PLRDRDDAQYSHLGGNWARNK.

The human CD3-zeta polypeptide canonical sequence is:

(SEQ ID NO: 35)
MKWKALFTAAILQAQLPITEAQSFGLLDPKLCYLLDGILFIYGVILTALF

LRVKFSRSADAPAYQQGQNQLYNELNLGRREEYDVLDKRRGRDPEMGGKP

QRRKNPQEGLYNELQKDKMAEAYSEIGMKGERRRGKGHDGLYQGLSTATK

DTYDALHMQALPPR.

The human TCR alpha chain canonical sequence is:

(SEQ ID NO: 36)
MAGTWLLLLLALGCPALPTGVGGTPFPSLAPPIMLLVDGKQQMVVVCLVL

DVAPPGLDSPIWFSAGNGSALDAFTYGPSPATDGTWTNLAHLSLPSEELA

SWEPLVCHTGPGAEGHSRSTQPMHLSGEASTARTCPQEPLRGTPGGALWL

GVLRLLLLFKLLLFDLLLTCSCLCDPAGPLPSPATTTRLRALGSHRLHPAT

ETGGREATSSPRPQPRDRRWGDTPPGRKPGSPVWGEGSYLSSYPTCPAQA

WCSRSALRAPSSSLGAFFAGDLPPPLQAGAA.

The human TCR alpha chain C region canonical sequence is:

(SEQ ID NO: 37)
PNIQNPDPAVYQLRDSKSSDKSVCLFTDFDSQTNVSQSKDSDVYITDKTV

LDMRSMDFKSNSAVAWSNKSDFACANAFNNSIIPEDTFFPSPESSCDVKL

VEKSFETDTNLNFQNLSVIGFRILLLKVAGFNLLMTLRLWSS.

The human TCR alpha chain V region CTL-L17 canonical sequence is:

(SEQ ID NO: 38)
MAMLLGASVLILWLQPDWVNSQQKNDDQQVKQNSPSLSVQEGRISILNCD

YTNSMFDYFLWYKKYPAEGPTFLISISSIKDKNEDGRFTVFLNKSAKHLS

LHIVPSQPGDSAVYFCAAKGAGTASKLTFGTGTRLQVTL.

The human TCR beta chain C region canonical sequence is:

(SEQ ID NO: 39)
EDLNKVFPPEVAVFEPSEAEISHTQKATLVCLATGFFPDHVELSWWVNGK

EVHSGVSTDPQPLKEQPALNDSRYCLSSRLRVSATFWQNPRNHFRCQVQF

-continued
YGLSENDEWTQDRAKPVTQIVSAEAWGRADCGFTSVSYQQGVLSATILYE

ILLGKATLYAVLVSALVLMAMVKRKDF.

The human TCR beta chain V region CTL-L17 canonical sequence is:

(SEQ ID NO: 40)
MGTSLLCWMALCLLGADHADTGVSQNPRHNITKRGQNVTFRCDPISEHNR

LYWYRQTLGQGPEFLTYFQNEAQLEKSRLLSDRFSAERPKGSFSTLEIQR

TEQGDSAMYLCASSLAGLNQPQHFGDGTRLSIL.

The human TCR beta chain V region YT35 canonical sequence is:

(SEQ ID NO: 41)
MDSWTFCCVSLCILVAKHTDAGVIQSPRHEVTEMGQEVTLRCKPISGHNS

LFWYRQTMMRGLELLIVFNNNVPIDDSGMPEDRFSAKMPNASFSTLKIQP

SEPRDSAVYFCASSFSTCSANYGYTFGSGTRLTVV.

Generation of TFPs from TCR Domains and scFvs

The BCMA scFvs are recombinantly linked to CD3-epsilon or other TCR subunits (see 1C) using a linker sequence, such as G$_4$S, (G$_4$S) (G$_4$S)$_3$ or (G$_4$S)$_4$. Various linkers and scFv configurations are utilized. TCR alpha and TCR beta chains were used for generation of TFPs either as full-length polypeptides or only their constant domains. Any variable sequence of TCR alpha and TCR beta chains is allowed for making TFPs.

TFP Expression Vectors

Expression vectors are provided that include: a promoter (Cytomegalovirus (CMV) enhancer-promoter), a signal sequence to enable secretion, a polyadenylation signal and transcription terminator (Bovine Growth Hormone (BGH) gene), an element allowing episomal replication and replication in prokaryotes (e.g., SV40 origin and ColE1 or others known in the art) and elements to allow selection (ampicillin resistance gene and zeocin marker).

Preferably, the TFP-encoding nucleic acid construct is cloned into a lentiviral expression vector and expression validated based on the quantity and quality of the effector T-cell response of TFP.BCMA-transduced T-cells ("BCMA.TFP" or "BCMA.TFP T-cells" or "TFP.BCMA" or "TFP.BCMA T-cells") in response to BCMA+ target cells. Effector T-cell responses include, but are not limited to, cellular expansion, proliferation, doubling, cytokine production and target cell lysis or cytolytic activity (i.e., degranulation).

The TFP.BCMA lentiviral transfer vectors are used to produce the genomic material packaged into the VSVg pseudotyped lentiviral particles. Lentiviral transfer vector DNA is mixed with the three packaging components of VSVg, gag/pol and rev in combination with Lipofectamine reagent to transfect them together into 293 cells. After 24 and 48 hours, the media is collected, filtered and concentrated by ultracentrifugation. The resulting viral preparation is stored at −80 C. The number of transducing units is determined by titration on SupT1 cells. Redirected TFP.BCMA T-cells are produced by activating fresh naive T-cells with anti-CD3x anti-CD28 beads for 24 hrs and then adding the appropriate number of transducing units to obtain the desired percentage of transduced T-cells. These modified T-cells are allowed to expand until they become rested and come down in size at which point they are cryopreserved for later analysis. The cell numbers and sizes are measured using a coulter multisizer III. Before cryopreserving, percentage of cells transduced (expressing TFP.BCMA on the cell surface) and their relative fluorescence intensity of that expression are determined by flow cytometric analysis. From the histogram plots, the relative expression levels of the TFPs are examined by comparing percentage transduced with their relative fluorescent intensity.

In some embodiments multiple TFPs are introduced by T-cell transduction with multiple viral vectors.

Evaluating Cytolytic Activity, Proliferation Capabilities and Cytokine Secretion of Humanized TFP Redirected T Cells The functional abilities of TFP.BCMA T-cells to produce cell-surface expressed TFPs, and to kill target tumor cells, proliferate and secrete cytokines are determined using assays known in the art.

Human PBMCs (e.g., blood from a normal apheresed donor whose naive T-cells are obtained by negative selection for T-cells, CD4+ and CD8+ lymphocytes) are treated with human interleukin-2 (IL-2) then activated with anti-CD3x anti-CD28 beads, e.g., in 10% RPMI at 37° C., 5% CO$_2$ prior to transduction with the TFP-encoding lentiviral vectors. Flow cytometry assays are utilized to confirm cell surface presence of a TFP, such as by an anti-FLAG antibody or an anti-murine variable domain antibody. Cytokine (e.g., IFN-γ) production is measured using ELISA or other assays.

Example 1: Human TFP T-Cell Efficacy in a Human ALL Mouse Model

Primary human ALL cells can be grown in immune compromised mice (e.g., NSG or NOD) without having to culture them in vitro. Likewise, cultured human ALL cell lines can induce leukemia in such mice. ALL-bearing mice can be used to test the efficacy of human TFP.BCMA T-cells, for instance, in the model HALLX5447. The readout in this model is the survival of mice after intravenous (i.v.) infusion of ALL cells in the absence and presence of i.v. administered human TFP.BCMA T-cells.

Example 2: Human TFP T-Cell Treatment in an In Vivo Solid Tumor Xenograft Mouse Model The efficacy of human TFP.BCMA T-cells can also be tested in immune compromised mouse models bearing subcutaneous solid tumors derived from human BCMA-expressing ALL, CLL or NHL human cell lines. Tumor shrinkage in response to human TFP.BCMA T-cell treatment can be either assessed by caliper measurement of tumor size, or by following the intensity of a GFP fluorescence signal emitted by GFP-expressing tumor cells.

Primary human solid tumor cells can be grown in immune compromised mice without having to culture them in vitro. Exemplary solid cancer cells include solid tumor cell lines, such as provided in The Cancer Genome Atlas (TCGA) and/or the Broad Cancer Cell Line Encyclopedia (CCLE, see Barretina et al., Nature 483:603 (2012)). Exemplary solid cancer cells include primary tumor cells isolated from mesothelioma, renal cell carcinoma, stomach cancer, breast cancer, lung cancer, ovarian cancer, prostate cancer, colon cancer, cervical cancer, brain cancer, liver cancer, pancreatic cancer, kidney, endometrial, or stomach cancer. In some embodiments, the cancer to be treated is selected from the group consisting of mesotheliomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas. These mice can be used to test the efficacy of TFP.BCMA T-cells in the human tumor xenograft models (see, e.g., Morton et al., Nat. Procol. 2:247 (2007)). Following an implant or injection of $1\times10^6$-$1\times10^7$ primary cells (collagenase-treated bulk tumor suspensions in EC matrix material) or tumor fragments (primary tumor fragments in EC matrix material) subcutaneously, tumors are allowed to grow to 200-500 mm$^3$ prior to initiation of treatment.

Example 3: Demonstration of Multiplexed TFP Polypeptides, and Use of Multiplexed Humanized TFP Redirected T Cells The TFP polypeptides provided herein are capable of functionally associating with endogenous TCR subunit polypeptides to form functional TCR complexes. Here, multiple TFPs in lentiviral vectors are used to transduce T-cells in order to create a functional, multiplexed recombinant TCR complex. For example, provided is T-cell containing i) a first TFP having an extracellular domain, a transmembrane domain, and an intracellular domain from the CD3-dselta polypeptide and an BCMA-specific scFv antibody fragment, and ii) a second TFP having an extracellular domain, a transmembrane domain, and an intracellular domain from the CD3-gamma polypeptide and a BCMA-specific antibody fragment. The first TFP and second TFP are capable of interacting with each other and with endogenous TCR subunit polypeptides, thereby forming a functional TCR complex.

The use of these multiplexed humanized TFP.BCMA T-cells can be demonstrated in liquid and solid tumors as provided in the Examples above.

Example 4: Preparation of T-Cells Transduced with TFPs

Lentiviral Production

Lentivirus encoding the appropriate constructs are prepared as follows. $5\times10^6$ HEK293FT-cells are seeded into a 100 mm dish and allowed to reach 70-90% confluency overnight. 2.5 μg of the indicated DNA plasmids and 20 μL Lentivirus Packaging Mix (ALSTEM, cat #VP100; see Appendix B3) are diluted in 0.5 mL DMEM or Opti-MEM I Medium without serum and mixed gently. In a separate tube, 30 μL of NanoFect transfection reagent (ALSTEM, cat.no. NF100) is diluted in 0.5 mL DMEM or Opti-MEM I Medium without serum and mixed gently. The NanoFect/DMEM and DNA/DMEM solutions are then mixed together and votrexed for 10-15 seconds prior to incubation of the DMEM-plasmid-NanoFect mixture at room temperature for 15 minutes. The complete transfection complex from the previous step is added dropwise to the plate of cells and rocked to disperse the transfection complex evenly in the plate. The plate is then incubated overnight at 37° C. in a humidified 5% $CO_2$ incubator. The following day, the supernatant is replaced with 10 mL fresh media and supplemented with 20 μL of ViralBoost (500×, ALSTEM, cat.no. VB100). The plates are then incubated at 37° C. for an additional 24 hours. The lentivirus containing supernatant is then collected into a 50 mL sterile, capped conical centrifuge tube and put on ice. After centrifugation at 3000 rpm for 15 minutes at 4° C., the cleared supernatant is filtered with a low-protein binding 0.45 μm sterile filter and virus is subsequently isolated by ultracentrifugation at 25,000 rpm (Beckmann, L8-70M) for 1.5 hours, at 4° C. The pellet is removed and re-suspended in DMEM media and Lentivirus concentrations/titers are established by quantitative RT-PCR, using the Lenti-X qRT-PCR Titration kit (Clontech; catalog number 631235). Any residual plasmid DNA is removed by treatment with DNaseI. The virus stock preparation is either used for infection immediately or aliquoted and stored at −80° C. for future use.

PBMC Isolation

Peripheral Blood Mononuclear Cells (PBMCs) are prepared from either whole blood or buffy coat. Whole blood is collected in 10 mL Heparin vacutainers and either processed immediately or stored overnight at 4° C. Approximately 10 mL of whole anti-coagulated blood is mixed with sterile phosphate buffered saline (PBS) buffer for a total volume of 20 mL in a 50 mL conical centrifuge tube (PBS, pH 7.4, without $Ca^{2+}/Mg^{2+}$). 20 mL of this blood/PBS mixture is then gently overlayed onto the surface of 15 mL of Ficoll-Paque PLUS (GE Healthcare, 17-1440-03) prior to centrifugation at 400 g for 30-40 min at room temperature with no brake application.

Buffy coat is purchased from Research Blood Components (Boston, Mass.). Leucosep tubes (Greiner bio-one) are prepared by adding 15 mL Ficoll-Paque (GE Health Care) and centrifuged at 1000 g for 1 minute. Buffy coat is diluted 1:3 in PBS (pH 7.4, without $Ca^{2+}$ or $Mg^{2+}$). The diluted buffy coat is transferred to Leucosep tube and centrifuged at 1000 g for 15 minutes with no brake application. The layer of cells containing PBMCs, seen at the diluted plasma/Ficoll interface, is removed carefully to minimize contamination by Ficoll. Residual Ficoll, platelets, and plasma proteins are then removed by washing the PBMCs three times with 40 mL of PBS by centrifugation at 200 g for 10 minutes at room temperature. The cells are then counted with a hemocytometer. The washed PBMC are washed once with CAR-T media (AIM V-AlbuMAX (BSA) (Life Technologies), with 5% AB serum and 1.25 μg/mL amphotericin B (Gemini Bioproducts, Woodland, Calif.), 100 U/mL penicillin, and 100 μg/mL streptomycin). Alternatively, the washed PBMC's are transferred to insulated vials and frozen at −80° C. for 24 hours before storing in liquid nitrogen for later use.

T-Cell Activation

PBMCs prepared from either whole blood or buffy coat are stimulated with anti-human CD28 and CD3 antibody-conjugated magnetic beads for 24 hours prior to viral transduction. Freshly isolated PBMC are washed once in CAR-T media (AIM V-AlbuMAX(BSA)(Life Technologies), with 5% AB serum and 1.25 μg/mL amphotericin B (Gemini Bioproducts), 100 U/mL penicillin, and 100 μg/mL streptomycin) without huIL-2, before being re-suspended at a final concentration of $1\times10^6$ cells/mL in CAR-T medium with 300 IU/mL human IL-2 (from a 1000× stock; Invitrogen). If the PBMCs had previously been frozen they are thawed and re-suspended at $1\times10^7$ cells/mL in 9 mL of pre-warmed (37° C.) cDMEM media (Life Technologies), in the presence of 10% FBS, 100 U/mL penicillin, and 100 μg/mL streptomycin, at a concentration of $1\times10^6$ cells/mL prior to washing once in CART medium, re-suspension at $1\times10^6$ cells/mL in CAR-T medium, and addition of IL-2 as described above.

Prior to activation, anti-human CD28 and CD3 antibody-conjugated magnetic beads (Invitrogen) are washed three times with 1 mL of sterile 1×PBS (pH 7.4), using a magnetic rack to isolate beads from the solution, before re-suspension in CAR-T medium, with 300 IU/mL human IL-2, to a final concentration of $4\times10^7$ beads/mL. PBMC and beads are then mixed at a 1:1 bead-to-cell ratio, by transferring 25 µL (1×10⁶ beads) of beads to 1 mL of PBMC. The desired number of aliquots are then dispensed to single wells of a 12-well low-attachment, or non-treated cell culture plate, and incubated at 37° C., with 5% $CO_2$, for 24 hours before viral transduction.

T-Cell Transduction/Transfection and Expansion

Following activation of PBMC cells are incubated for 24 hours at 37° C., 5% $CO_2$. Lentivirus is thawed on ice and 5×10⁶ lentivirus, along with 2 µL of Transplus (Alstem) per mL of media (a final dilution of 1:500) is added to each well of 1×10⁶ cells. Cells are incubated for an additional 24 hours before repeating addition of virus. Alternatively, lentivirus is thawed on ice and the respective virus is added at 5 or 50 MOI in presence of 5 µg/mL polybrene (Sigma). Cells are spinoculated at 100 g for 100 minutes at room temperature. Cells are then grown in the continued presence of 300 IU/mL of human IL-2 for a period of 6-14 days (total incubation time is dependent on the final number of CAR-T-cells required). Cell concentrations are analyzed every 2-3 days, with media being added at that time to maintain the cell suspension at 1×10⁶ cells/mL.

In some instances, activated PBMCs are electroporated with in vitro transcribed (IVT) mRNA. Human PBMCs are stimulated with Dynabeads® (ThermoFisher) at 1-to-1 ratio for 3 days in the presence of 300 IU/ml recombinant human IL-2 (R&D System). The beads are removed before electroporation. The cells are washed and re-suspended in OPTI-MEM® medium (ThermoFisher) at the concentration of 2.5×10⁷ cells/mL. 200 µL of the cell suspension (5×10⁶ cells) are transferred to the 2 mm gap Electroporation Cuvettes Plus™ (Harvard Apparatus BTX) and prechilled on ice. 10 µg of IVT TFP mRNA is added to the cell suspension. The mRNA/cell mixture is then electroporated at 200 V for 20 milliseconds using ECM830 Electro Square Wave Porator (Harvard Apparatus BTX). Immediately after the electroporation, the cells are transferred to fresh cell culture medium (AIM V AlbuMAX (BSA) serum free medium+5% human AB serum+300 IU/ml IL-2) and incubated at 37° C.

Verification of TFP Expression by Cell Staining

Figure 5:
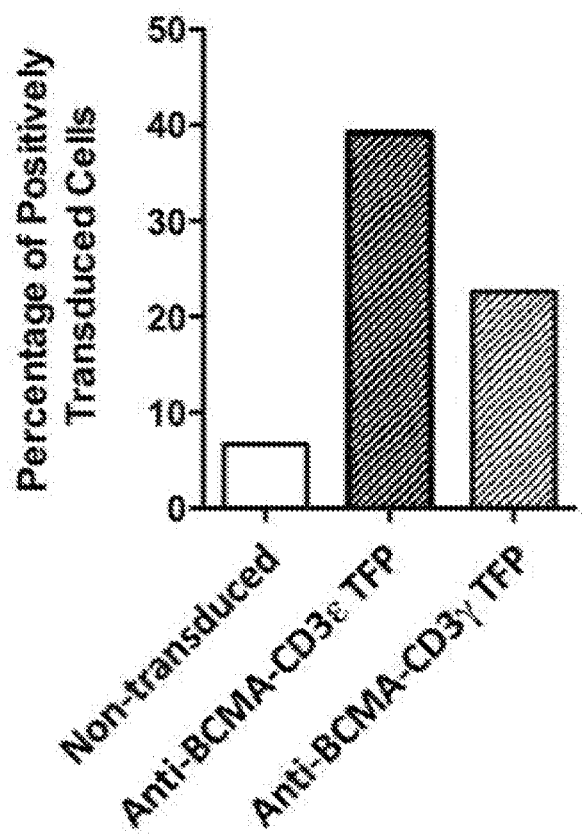
FIG. 5 is an exemplary bar graph depicting surface expression of anti-BCMA TFPs on T-cells after lentiviral transduction. Effector T-cells were either un-transduced or transduced with either anti-BCMA-CD3ε or anti-BCMA-CD3γ TFP constructs. After being expanded for 10 days in IL-2, their surface TFP expression was determined by flow cytometry.

Following lentiviral transduction or mRNA electroporation, expression of anti-BCMA TFPs is confirmed by flow cytometry, using an anti-mouse Fab antibody to detect the murine anti-BCMA scFv. T-cells are washed three times in 3 mL staining buffer (PBS, 4% BSA) and re-suspended in PBS at 1×10⁶ cells per well. For dead cell exclusion, cells are incubated with Live dead aqua (Invitrogen) for 30 minutes on ice. Cells are washed twice with PBS and re-suspended in 50 µL staining buffer. To block Fc receptors, 1 µL of 1:100 diluted normal goat IgG (LifeTechnologies) is added to each tube and incubated in ice for 10 minutes. 1.0 mL FACS buffer is added to each tube, mixed well, and cells are pelleted by centrifugation at 300 g for 5 min. Surface expression of scFv TFPs is detected by biotin-labeled polyclonal goat anti-mouse-F(ab)₂ antibodies (Life Technologies) with biotin-labeled normal polyclonal goat IgG antibodies (Life Technologies) serving as an isotype control. Both antibodies are added at 10 µg/mL in a reaction volume of 100 µL. Cells are then incubated at 4° C. for 45 minutes, washed once, re-suspended in FACS buffer, and blocked with normal mouse IgG (Invitrogen) by adding 100 µL 1:1000 diluted normal mouse IgG to each tube. The cells are then incubated on ice for 10 minutes, washed with stain buffer and re-suspended in 100 µL stain buffer. The cells are then stained by the addition of 1.0 µL phycoerythrin (PE)-labeled streptavidin (BD Biosciences) and APC anti-human CD3 antibody (Clone-UCHT1, BD Biosciences), PerCP/Cy5.5 anti-human CD8 antibody (Clone-SK1, BD Biosciences) and Pacific Blue anti-human CD4 antibody (Clone-RPA-T4, BD Biosciences) are added to each tube. Flow cytometry is performed using LSRFortessa™ X20 (BD Biosciences) and data is acquired using FACS diva software and is analyzed with FlowJo® (Treestar, Inc. Ashland, Oreg.). Between 20% and 40% of the transduced T-cells expressed anti-BCMA TFP, indicating comparable levels of transduction and surface expression of CAR and TFP constructs (FIG. 5).

Verification of TFP Expression by Cell Activation

Following lentiviral transduction or mRNA electroporation, activation of target cells by anti-BCMA TFPs is confirmed by flow cytometry. T cells were transduced with a BCMA positive control scFv (SEQ ID NO:45) attached to CD3ε subunit, and single domain antibody (sdAb) anti-BCMA $V_HH$ 2 (SEQ ID NO:28) in the format CD3ε, CD3γ, TCRβ, and CD28ζ. Transduced T cells (effector cells) and BCMA-positive K562 target cells were co-cultured at a 1:1 ratio overnight. BCMA-negative K562 cells were used as a negative control, as was a non-transduced BCMA-positive T cell culture. Cells were stained as described above for CD25 and CD69, both markers of target cell activation.

Results are shown in FIG. 10. As shown in FIG. 10A (CD25 positive cells) and 10B (CD69 positive cells), all transduced cells were able to activate expression of both CD69 and CD25 in the target cell population (gray bars) compared to the BCMA-negative controls (black bars), especially the cells transduced with the $V_HH$ 2 constructs, which were significantly more activating than the positive control.

Figure 10A:
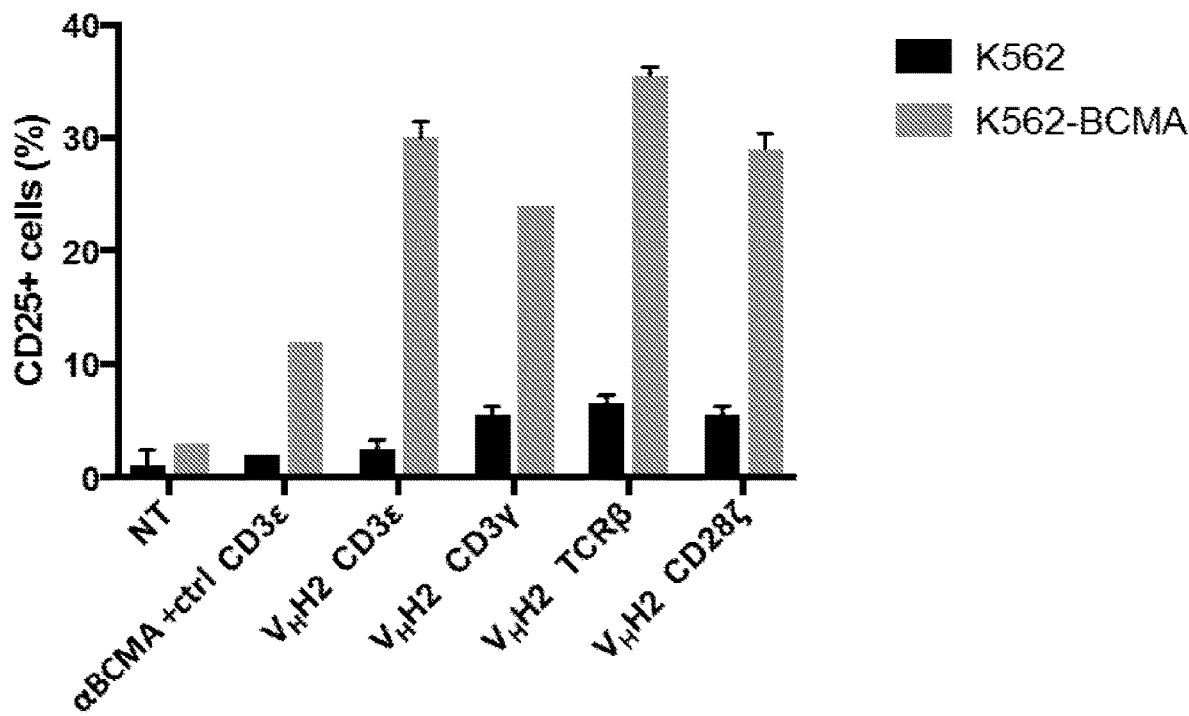
FIG. 10 is a series of graphs showing verification of TFP expression by cell activation. Following lentiviral transduction or mRNA electroporation, activation of target cells by anti-BCMA TFPs is confirmed by flow cytometry. T cells were transduced with a BCMA positive control scFv (SEQ ID NO:45) attached to CD3ε subunit, and single domain antibody (sdAb) anti-BCMA $V_H$H2 (SEQ ID NO:28) in the format CD3ε, CD3γ, TCRβ, and CD2ζ. Transduced T cells and BCMA-positive K562 target cells (gray bars) awere co-cultured at a 1:1 ratio overnight. BCMA-negative K562 cells (black bars) were used as a negative control, as was a non-transduced BCMA-positive T cell culture ("NT"). Cells were stained for CD25 (10A) and CD69 (10B).
FIGS. 10C (CD25 positive cells) and 10D (CD69 positive cells) show similar results for TFP T cells with anti-BCMA scFv2 (SEQ ID NO:43) in the format CD3ε, CD3γ, and TCRβ in the LH orientation, and CD3ε in the HL orientation. All TFPs (in either orientation) were able to activate the BCMA-positive target cells (gray bars), but not BCMA-negative cells (black bars).
In FIG. 10E, cells were transduced with a BCMA positive control scFv (SEQ ID NO:45) attached to CD3ε subunit, and single domain antibody (sdAb) anti-BCMA $V_H$H2 (SEQ ID NO:28) in the format CD3ε, CD3γ, TCRβ, and CD28ζ)
in FIG. 10F, cells were transduced with anti-BCMA scFv2 (SEQ ID NO:43) in the format CD3ε, CD3γ, and TCRβ in the LH orientation, and CD3ε in the HL orientation. As shown in the Figure, all TFP T cells, except the negative control, had elevated levels of granzyme B after coming into contact with BCMA-positive target cells (gray bars) compared to the BCMA-negative cells (black bars)
in FIG. 10G (E:T 3:1) and FIG. 10H (E:T 1:3), cells were transduced with a BCMA positive control scFv1 (SEQ ID NO:45) attached to CD3ε subunit, single domain antibody (sdAb) anti-BCMA $V_H$H2 (SEQ ID NO:28) in the format CD3ε, CD3γ, TCRβ, and anti-BCMA scFv2 (SEQ ID NO:43) in the format CD3ε, CD3γ, and TCRβ in the LH orientation. As shown in both 10G, all constructs except the empty vector were sufficient to reduce the number of tumor cells at a 3:1 ratio of effector cells to T cells. At a 1:3 ratio of effector cells to T cells (10H), all constructs were able to reduce the number of tumor cells with slightly more varying efficacy. Solid bars represent BCMA negative HeLa cells, and empty bars represent BCMA positive cells.
Figure 10B:
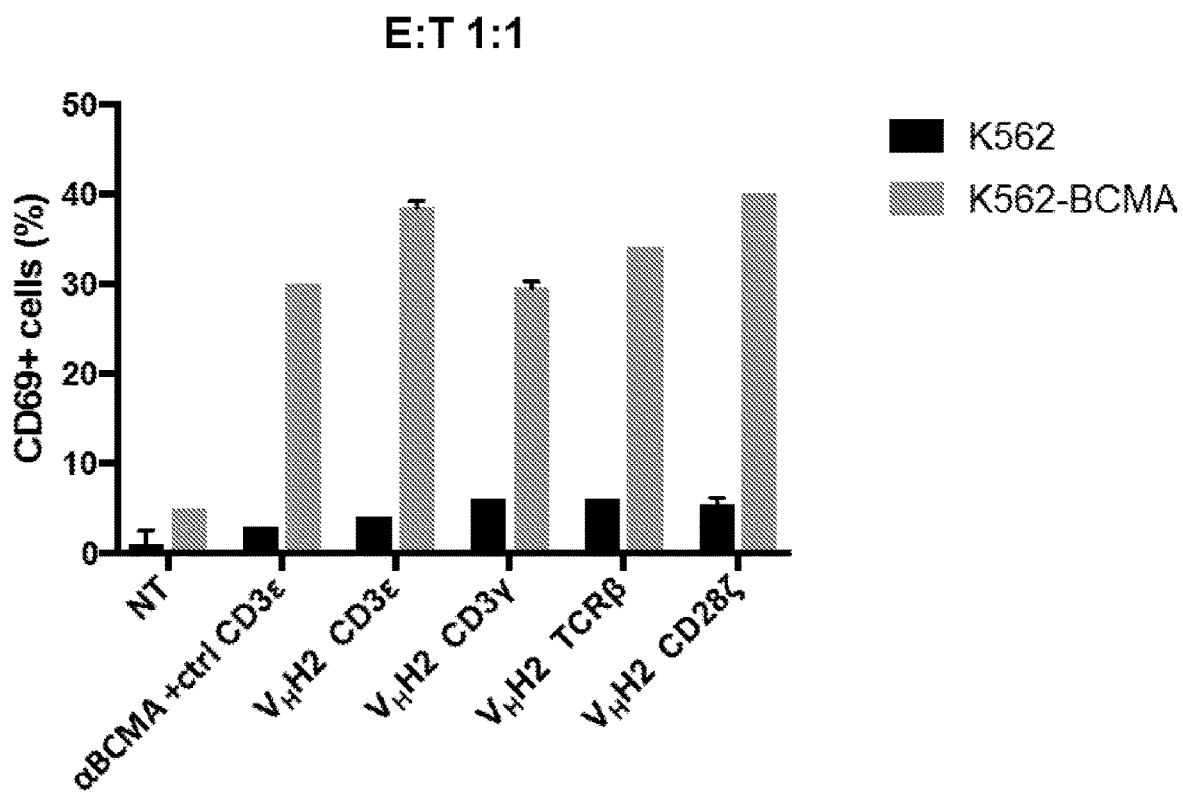
Figure 10C:
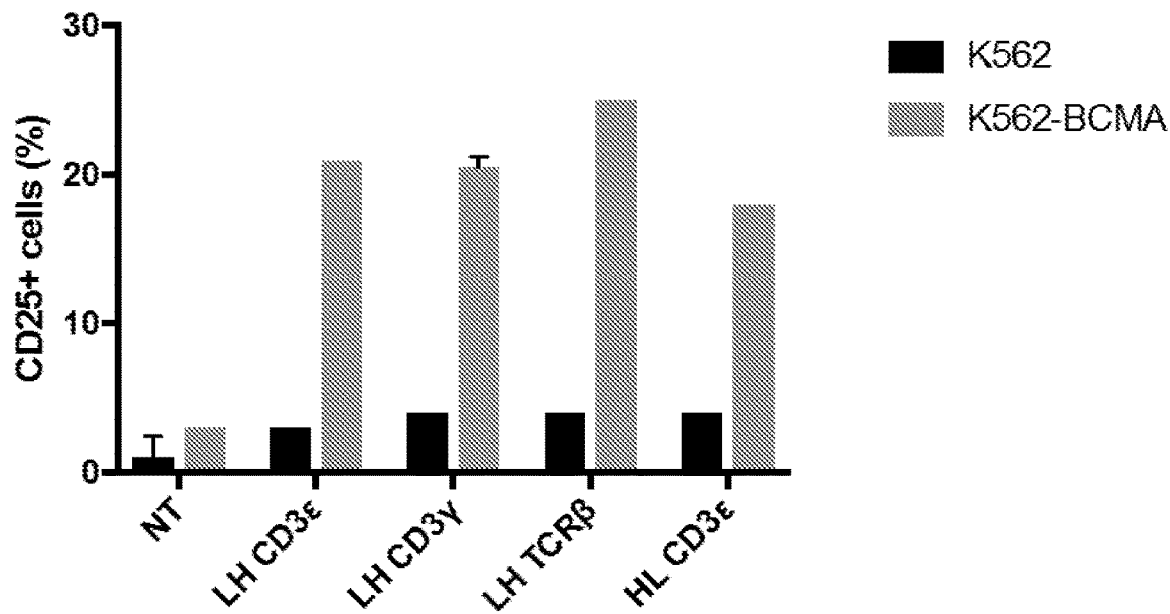
Figure 10D:
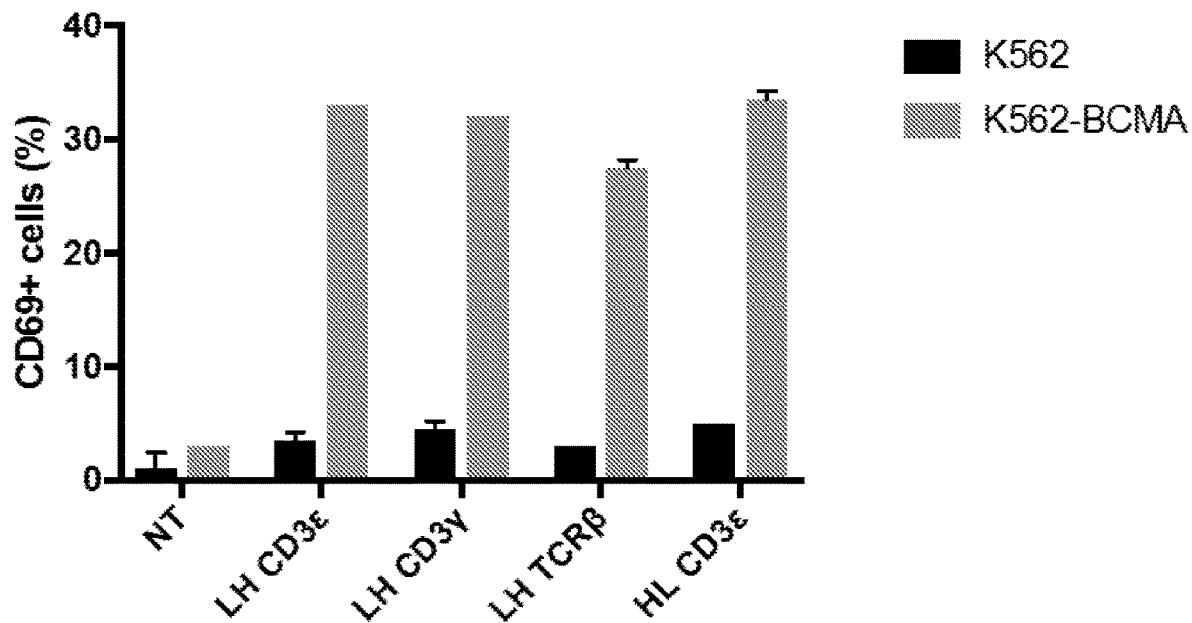

A similar experiment was performed using anti-BCMA scFv 2 (SEQ ID NO:43) in the format CD3ε, CD3γ, and TCRβ in the LH orientation, and CD3ε in the HL orientation. As shown in FIG. 10C (CD25 positive cells) and 10D (CD69 positive cells), all TFPs (in either orientation) were able to activate the BCMA-positive target cells (gray bars).

Next, target cells were stained for granzyme B, a serine protease stored in the granules of cytotoxic lymphocytes, which mediates apoptosis of target cells when secreted. Activation of TFP-T cells is evaluated by intracellular antibody staining and flow cytometry analysis. TFP T cells (transduced with sdAb $V_HH$ 2 and BCMA-positive K562 target cells are prepared as described above and co-cultured 1:1. BCMA-negative cells were used as a control. After cells are fixed, the granzyme B antibody (Alexa Fluor 700™ mouse antiHuman granzyme B, Clone GB11, BD Biosciences Cat #560213) is diluted 1:100 in wash buffer. Cells are resuspended in 100 µl of diluted antibody and incubated at 4° C. for 30 minutes in dark. Cells are washed and analyzed immediately on a BD LSRFortessa® X-20 cell analyzer.

Figure 10E:
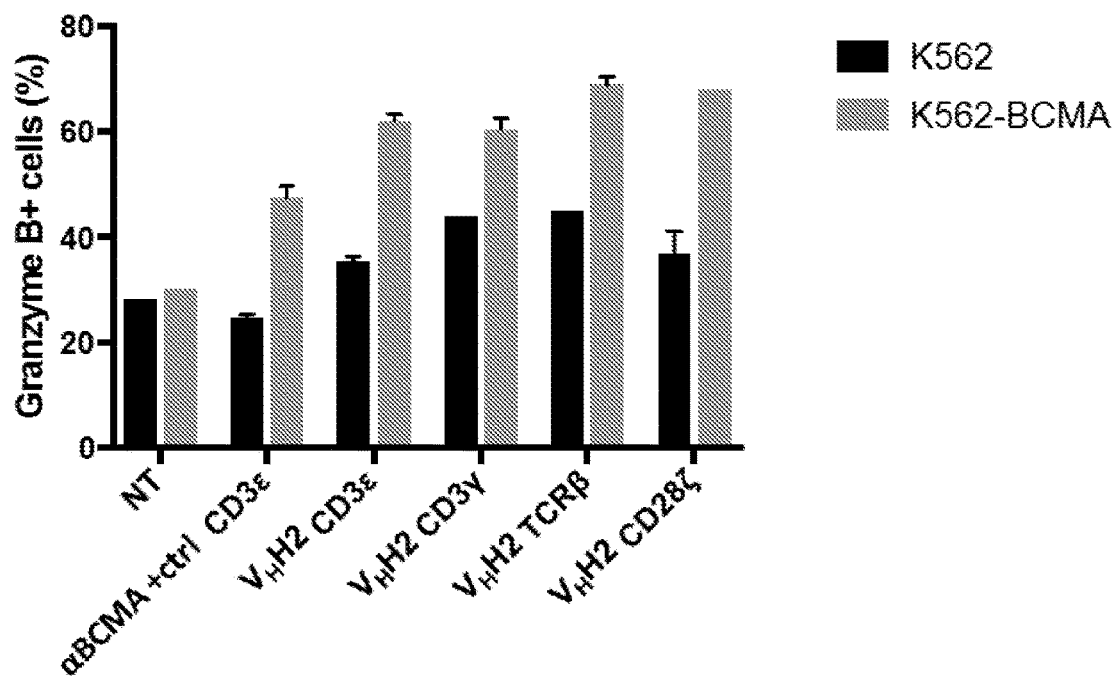
Figure 10F:
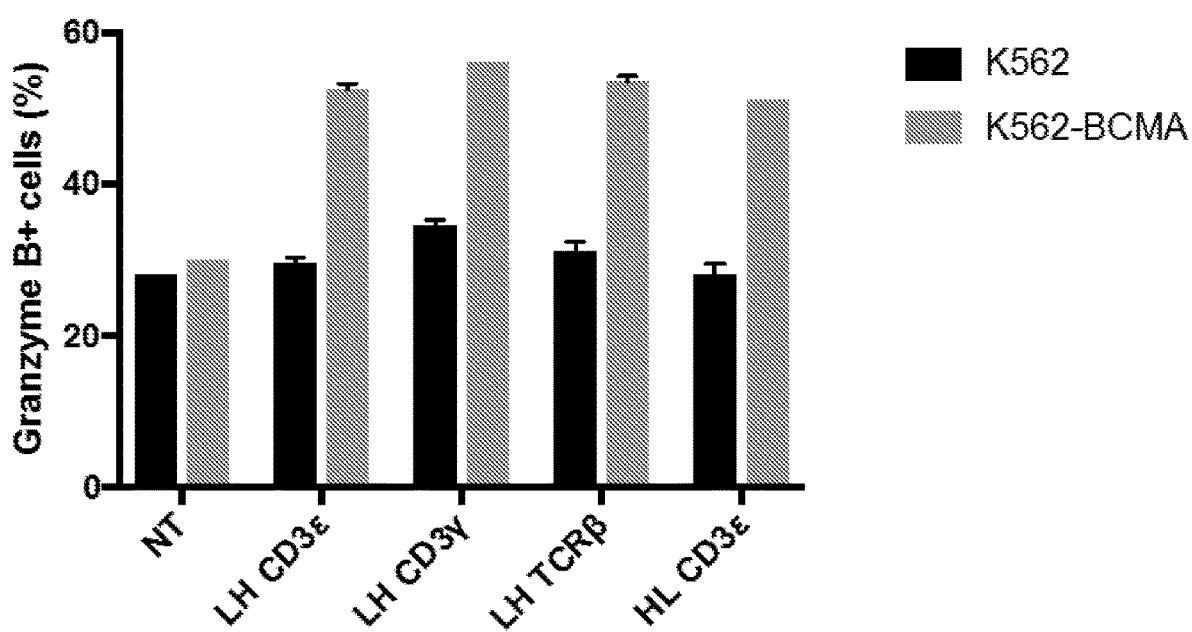

Results are shown in FIG. 10E (anti-BCMA $V_HH$2 TFP T cells) and 10F (anti-BCMA scFv2 TFP T cells) and show granzyme B levels in TFP T cells after contact with BCMA-positive target cells. In FIG. 10E, cells were transduced with a BCMA positive control scFv (SEQ ID NO:45) attached to CD3ε subunit, and single domain antibody (sdAb) anti-BCMA $V_HH$ 2 (SEQ ID NO:28) in the format CD3ε, CD3γ, TCRβ, and CD28ζ; in FIG. 10F, cells were transduced with anti-BCMA scFv 2 (SEQ ID NO:43) in the format CD3ε, CD3γ, and TCRβ in the LH orientation, and CD3ε in the HL orientation. As shown in the Figure, all TFP T cells, except the negative control, had elevated levels of granzyme B after coming into contact with BCMA-positive target cells (gray bars) compared to the BCMA-negative cells (black bars). In FIG. 10G (E:T 3:1) and FIG. 10H (E:T 1:3), cells were transduced with a BCMA positive control scFv1 (SEQ ID NO:45) attached to CD3ε subunit, single domain antibody (sdAb) anti-BCMA V$_H$H2 (SEQ ID NO:28) in the format CD3ε, CD3γ, TCRβ, and anti-BCMA scFv2 (SEQ ID NO:43) in the format CD3ε, CD3γ, and TCRβ in the LH orientation. As shown in both 10G, all constructs except the empty vector were sufficient to reduce the number of tumor cells at a 3:1 ratio of effector cells to T cells. At a 1:3 ratio of effector cells to T cells (10H), all constructs were able to reduce the number of tumor cells with slightly more varying efficacy. Solid bars represent BCMA negative HeLa cells, and empty bars represent BCMA positive cells.

Example 5: Cytotoxicity Assay by Flow Cytometry

Target cells that are either positive or negative for BCMA targets are labelled with the fluorescent dye, carboxyfluorescein diacetate succinimidyl ester (CFSE). These target cells are mixed with effector T-cells that are either un-transduced, transduced with control CAR-T constructs, or transduced with TFPs. After the indicated incubation period, the percentage of dead to live CFSE-labeled target cells and negative control target cells is determined for each effector/target cell culture by flow cytometry. The percent survival of target cells in each T-cell +target cell culture is calculated relative to wells containing target cells alone.

The cytotoxic activity of effector T-cells is measured by comparing the number of surviving target cells in target cells without or with effector T-cells, following co-incubation of effector and target cells, using flow cytometry. In experiments with BCMA TFPs or CAR-T-cells, the target cells are BCMA-positive RPMI-8226 plasmacytoma/myeloma cells (ATCC, CCL-155), while cells used as a negative control are BCMA-negative Raji Burkitt's lymphoma cells (ATCC, CCL-86).

Target cells are washed once, and re-suspended in PBS at $1 \times 10^6$ cells/mL. The fluorescent dye carboxyfluorescein diacetate succinimidyl ester (CFSE) (ThermoFisher) is added to the cell suspension at a concentration of 0.03 µM and the cells are incubated for 20 minutes at room temperature. The labeling reaction is stopped, by adding to the cell suspension with complete cell culture medium (RPMI-1640+10% HI-FBS) at the volume 5 times of the reaction volume, and the cells are incubated for an additional 2 minutes at room temperature. The cells are pelleted by centrifugation and re-suspended in cytotoxicity medium (Phenol red-free RPMI1640 (Invitrogen) plus 5% AB serum (Gemini Bioproducts) at $2 \times 10^5$ cells/mL. Fifty microliters of CFSE labelled-target cell suspension (equivalent to 10,000 cells) are added to each well of the 96-well U-bottom plate (Corning).

Effector T-cells transduced with anti-BCMA TFP constructs, together with non-transduced T-cells as negative controls, are washed and suspended at $2 \times 10^6$ cells/mL, or $1 \times 10^6$ cells/mL in cytotoxicity medium. 50 µL of effector T-cell suspensions (equivalent to 100,000 or 50,000 cells) are added to the plated target cells to reach the effector-to-target ratio of 10-to-1 or 5-to-1, respectively, in a total volume of 100 µL. The cultures are then mixed, spin down, and incubated for 4 hours at 37° C., 5% $CO_2$. Immediately following this incubation, 7AAD (7-aminoactinomycin D) (BioLegend®) is added to the cultured cells as recommended by the manufacturer, and flow cytometry is performed with a BD Fortessa X-20 (BD Biosciences). Analysis of flow cytometric data is performed using FlowJo® software (TreeStar, Inc.).

The percentage of survival for RPMI-8226 target cells is calculated by dividing the number of alive RPMI-8226 target cells (CFSE+7-AAD-) in sample with effector T-cells and target cells, by the number of alive RPMI-8226 (CFSE+7-AAD-) cells in the sample with target cells alone. The cytotoxicity for effector cells is calculated as the percentage of killing for RPMI-8226=100%–percentage of survival for RPMI-8226 cells.

T-cells transduced with an anti-BCMA 28t CAR construct may demonstrate cytotoxicity against BCMA-expressing cells, when compared to T-cells that are either non-transduced or are transduced with a non-BCMA-specific CAR control. However, T-cells transduced with anti-BCMA-CD3ε may induce more efficient cytotoxicity against the targets than the anti-BCMA CAR control. Anti-BCMA-CD3γ TFPs may also mediate robust cytotoxicity that is greater than that observed with anti-BCMA-CAR at effector:target ratios between 5 and 10:1. Some cytotoxicity may be observed with anti-BCMA-TCRα and anti-BCMA-TCRβ TFPs. Similar results may be obtained with anti-BCMA TFPs constructed with an alternative hinge region. Once again, cytotoxicity against BCMA-expressing target cells may be greater with anti-BCMA-CD3ε or anti-BCMA-CD3γ TFP-transduced T-cells than with anti-BCMA-CAR-transduced T-cells.

T-cells electroporated with mRNA encoding TFPs specific for BCMA may also demonstrate robust cytotoxicity against BCMA-expressing cells. While no significant killing of the BCMA-negative cells may be seen with either control or anti-BCMA TFP constructs, BCMA-specific killing of BCMA-expressing cells may be observed by T-cells transduced with either anti-BCMA-CD3ε SL, or anti-BCMA-CD3γ SL TFPs.

Figure 6:
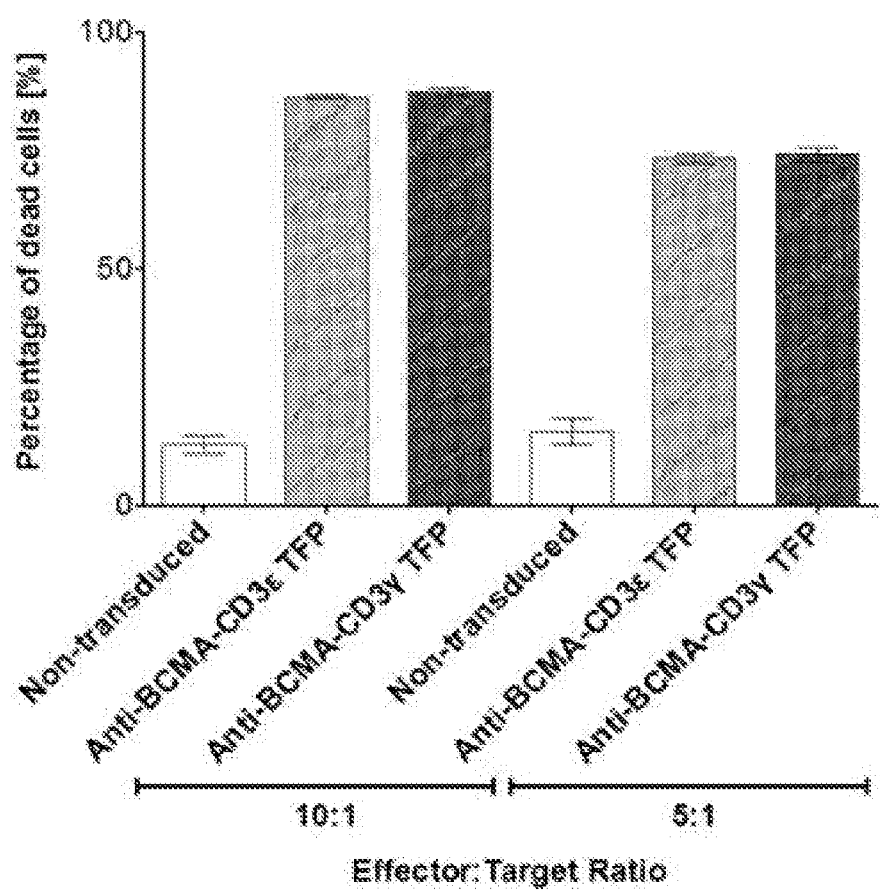
FIG. 6 is an exemplary bar graph depicting killing of BCMA-expressing RPMI8226 target cells by anti-BCMA TFPs. Transduced effector T-cells were expanded for 12 days prior to incubation for 4 hours with $1\times10^4$ RPMI8226 target cells at E:T ratios of 10:1, or 5:1. The percentage cytotoxicity was determined in a flow-cytometric cytotoxicity assay.

T-cells transduced with TFPs specific for B-cell maturation antigen (BCMA) also demonstrated robust cytotoxicity against BCMA-expressing RPMI8226 cells. T-cells transduced with anti-BCMA-CD3ε or anti-BCMA-CD3γ TFPs efficiently mediated cytotoxicity against the BCMA-expressing RPMI8226 target cells. At 10:1 ratio of effectors to target cells, almost 100% of the target cells were killed (FIG. 6).

Similar experiments can be carried out with FAP.TFP and CAIX.TFP constructs.

Example 6: Cytotoxicity by Real Time Cytotoxicity Assay

Anti-BCMA TFPs may also demonstrate superior cytotoxicity to anti-BCMA CARs in the real-time cytotoxicity assay (RTCA) format. The RTCA assay measures the electrical impedance of an adherent target cell monolayer, in each well of a specialized 96-well plate, in real time and presents the final readout as a value called the cell index. Changes in cell index indicate disruption of the target cell monolayer as a result of killing of target cells by co-incubated T-cell effectors. Thus, the cytotoxicity of the effector T-cells can be evaluated as the change in cell index of wells with both target cells and effector T-cells compared to that of wells with target cells alone.

Target cells for RTCA are HeLa cells expressing BCMA (BCMA-HeLa) with parental, non-transduced, HeLa cells as negative controls. The DNA encoding full-length human BCMA or BCMA is synthesized by GeneArt® (ThermoFisher) and inserted into the multiple cloning site of dual-promoter lentiviral vector pCDH514B (System Biosciences) carrying neomycin as selection marker, under the control of EF1a promoter. Lentivirus carrying either the BCMA or BCMA encoding vector is then packaged. HeLa cells are transduced with BCMA-lentivirus for 24 hours and then selected with G418 (1 mg/mL). The expression of BCMA by the transduced BCMA-HeLa is confirmed by FACS analysis with anti-human BCMA antibodies (BioLegend, clone #19A2; Miltenyi, clone #REA315).

Adherent target cells are cultured in DMEM, 10% FBS, 1% Antibiotic-Antimycotic (Life Technologies). To prepare the RTCA, 50 µL of RPMI medium is added into the appropriate wells of an E-plate (ACEA Biosciences, Inc, Catalog #: JL-10-156010-1A). The plate is then placed into a RTCA MP instrument (ACEA Biosciences, Inc.) and the appropriate plate layout and assay schedule entered into the RTCA 2.0 software as described in the manufacturers manual. Baseline measurement is performed every 15 minutes for 100 measurements. $1 \times 10^4$ target cells in a 100 µL volume are then added to each assay well and the cells are allowed to settle for 15 minutes. The plate is returned to the reader and readings are resumed.

The next day, effector T-cells are washed and re-suspended in cytotoxicity media (Phenol red-free RPMI1640 (Invitrogen) plus 5% AB serum (Gemini Bioproducts; 100-318)). The plate is then removed from the instrument and the effector T-cells, suspended in cytotoxicity medium (Phenol red-free RPMI1640+5% AB serum), are added to each well at 100,000 cells or 50,000 cells to reach the effector-to-target ratio of 10-to-1 or 5-to-1, respectively. The plate is then placed back to the instrument. The measurement is carried out for every 2 minutes for 100 measurements, and then every 15 minutes for 1,000 measurements.

In the RTCA assay, killing of BCMA-transduced cells may be observed by T-cells transduced with anti-BCMA-28 CAR-transduced T-cells, as demonstrated by a time-dependent decrease in the cell index following addition of the effector cells relative to cells alone or cells co-incubated with T-cells transduced with a control CAR construct. However, target cell killing by anti-BCMA-CD3ε TFP-expressing T-cells may be deeper and more rapid than that observed with the anti-BCMA CAR. For example, within 4 hours of addition of T-cells transduced with anti-BCMA-CD3ε TFP, killing of the BCMA-expressing target cells may be essentially complete. Little or no killing may be observed with T-cells transduced with a number of TFP constructs comprising other CD3 and TCR constructs. Similar results may be obtained with anti-BCMA TFPs constructed with an alternative hinge region. Cytotoxicity against BCMA-transduced target cells may be greater with anti-BCMA-CD3ε or anti-BCMA-CD3γ TFP-transduced T-cells than with anti-BCMA-CAR-transduced T-cells.

Figure 7A:
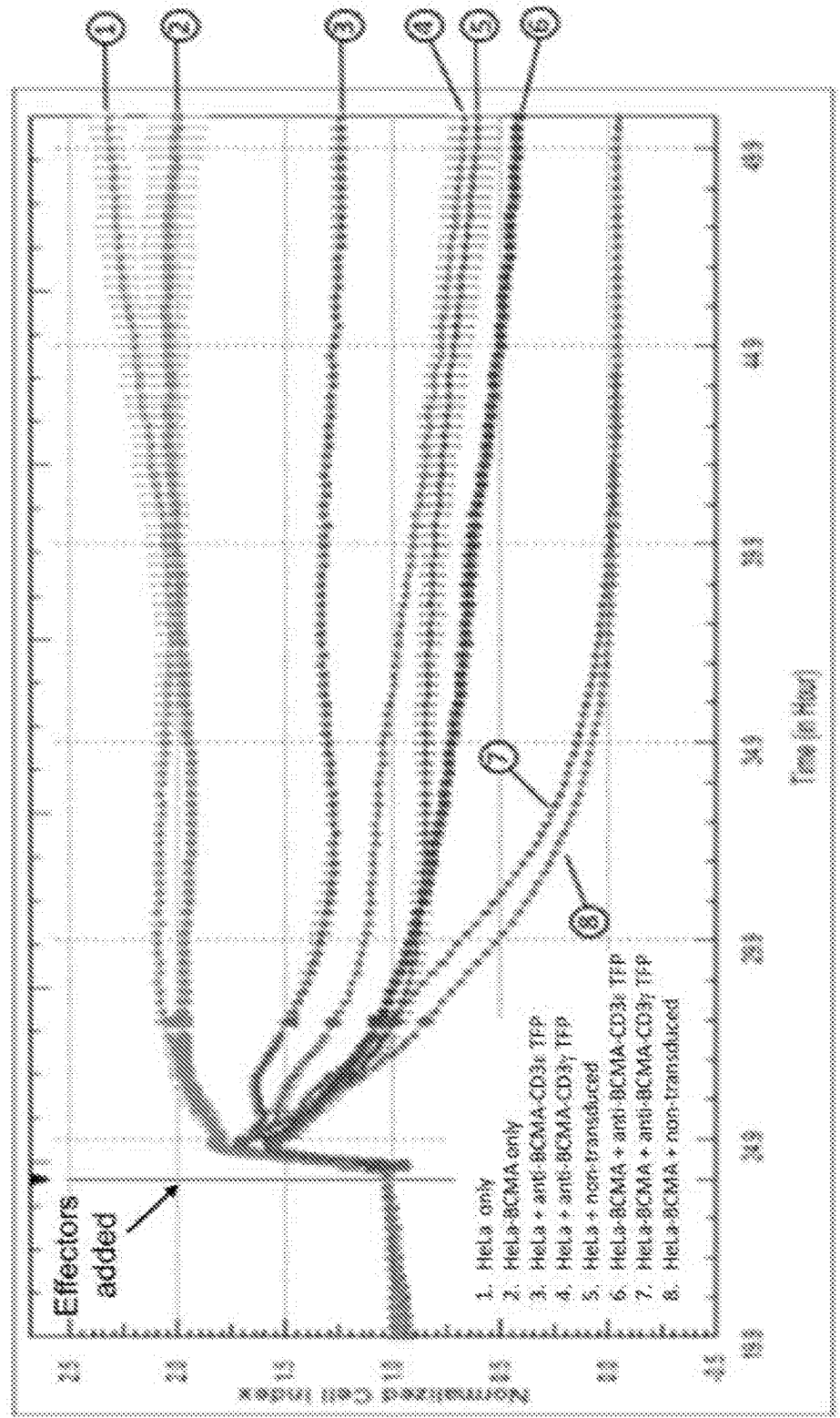
FIG. 7A is an exemplary graph depicting killing of BCMA-transduced HeLa target cells by anti-BCMA TFPs over time. Effector T-cells that were either non-transduced or transduced with either anti-BCMA-CD3ε or anti-BCMA-CD3γ TFPs were expanded for 7 days prior to incubation with either $1\times10^4$ HeLa or HeLa-BCMA target cells. The cell index, indicative of cytotoxicity, was determined in a RTCA assay. The assay was repeated with anti-BCMA $V_H$H2 (SEQ ID NO:28) in the format CD3ε, CD3γ, TCRβ, and CD28ζ, at an E:T ratio of 5:1 (FIG. 7B), 1:1 (FIG. 7C) and 1:5 (FIG. 7D); and with anti-BCMA scFv2 (SEQ ID NO:43) in the format CD3ε, CD3γ, and TCRβ in the LH orientation, and CD3ε in the HL orientation at an E:T ratio of 5:1 (FIG. 7E), 1:1 (FIG. 7F) and 1:5 (FIG. 7G).

T-cells transduced with anti-BCMA TFPs also demonstrated robust cytotoxicity against BCMA-expressing RPMI8226 cells. As shown in FIG. 6, T-cells transduced with anti-BCMA ($V_H$2 in CD3ε or CD3γ format) TFPs efficiently mediated cytotoxicity against the BCMA-expressing RPMI8226 target cells. At an effector to target ratio of 10:1, almost 100% of the target cells were killed (FIG. 7).

The cytotoxic activity of TFP-transduced T-cells may be dose-dependent with respect to the amount of virus (MOI) used for transduction. Increased killing of BCMA-cells may be observed with increasing MOI of anti-BCMA-CD3ε TFP lentivirus, further reinforcing the relationship between TFP transduction and cytotoxic activity.

Example 7: IL-2 and IFN-γ Secretion by ELISA

Another measure of effector T-cell activation and proliferation associated with the recognition of cells bearing cognate antigen is the production of effector cytokines such as interleukin-2 (IL-2) and interferon-gamma (IFN-γ).

ELISA assays for human IL-2 (catalog #EH2IL2, Thermo Scientific) and IFN-γ catalog #KHC4012, Invitrogen) are performed as described in the product inserts. 50 µL of reconstituted standards or samples in duplicate are added to each well of a 96 well plate followed by 50 µL of Biotinylated Antibody Reagent. Samples are mixed by gently tapping the plate several times. 50 µL of Standard Diluent is then added to all wells that did not contain standards or samples and the plate is carefully sealed with an adhesive plate cover prior to incubation for 3 hours at room temperature (20-25° C.). The plate cover is then removed, plate contents are emptied, and each well is filled with Wash Buffer. This wash procedure is repeated a total of 3 times and the plate is blotted onto paper towels or other absorbent material. 100 µL of prepared Streptavidin-HRP Solution is added to each well and a new plate cover is attached prior to incubation for 30 minutes at room temperature. The plate cover is again removed, the plate contents are discarded, and 100 µL of TMB Substrate Solution is added into each well. The reaction is allowed to develop at room temperature in the dark for 30 minutes, after which 100 µL of Stop Solution is added to each well. Evaluate the plate. Absorbance is measured on an ELISA plate reader set at 450 nm and 550 nm within 30 minutes of stopping the reaction. 550 nm values are subtracted from 450 nm values and IL-2 amounts in unknown samples are calculated relative to values obtained from an IL-2 standard curve.

Alternatively, 2-Plex assays are performed using the Human Cytokine Magnetic Buffer Reagent Kit (Invitrogen, LHB0001M) with the Human IL-2 Magnetic Bead Kit (Invitrogen, LHC0021M) and the Human IFN-γ Magnetic Bead Kit (Invitrogen, LHC4031M). Briefly, 25 µL of Human IL-2 and IFN-γ antibody beads are added to each well of a 96 well plate and washed using the following guidelines: two washes of 200 µL 1× wash solution, placing the plate in contact with a Magnetic 96-well plate Separator (Invitrogen, A14179), letting the beads settle for 1 minute and decanting the liquid. Then, 50 µL of Incubation Buffer is added to each well of the plate with 100 µL of reconstituted standards in duplicates or 50 µL of samples (supernatants from cytotoxicity assays) and 50 µL of Assay Diluent, in triplicate, for a total volume of 150 µL. Samples are mixed in the dark at 600 rpm with an orbital shaker with a 3 mm orbital radius for 2 hours at room temperature. The plate is washed following the same washing guidelines and 100 µL of human IL-2 and IFN-γ biotinylated detector antibody is added to each well. Samples are mixed in the dark at 600 rpm with an orbital shaker with a 3 mm orbital radius for 1 hour at room temperature. The plate is washed following the same washing guidelines and 100 µL of Streptavidin-R-Phycoerythrin is added to each well. Samples are mixed in the dark at 600 rpm with an orbital shaker with a 3 mm orbital radius for 30 minutes at room temperature. The plate is washed 3 times using the same washing guidelines and after decanting the liquid the samples are re-suspended in 150 µL of 1× wash solution. The samples are mixed at 600 rpm with an orbital shaker with a 3 mm orbital radius for 3 minutes and stored over night at 4° C. Afterwards, the plate is washed following the same washing guidelines and the samples are re-suspended in 150 µL of 1× wash solution.

The plate is read using the MAGPIX System (Luminex) and xPONENT software. Analysis of the data is performed using MILLIPLEX Analyst software, which provides the standard curve and cytokine concentrations.

Relative to non-transduced or control CAR-transduced T-cells, T-cells transduced with anti-BCMA TFPs may produce higher levels of both IL-2 and IFN-γ when co-cultured with either cells that endogenously express BCMA or BCMA-transduced cells. In contrast, co-culture with BCMA negative cells or non-transduced cells, may result in little or no cytokine release from TFP-transduced T-cells. Consistent with the previous cytotoxicity data, anti-BCMA TFPs constructed with an alternative hinge region may generate similar results upon co-culture with BCMA-bearing target cells.

In agreement with the previous cytotoxicity data, anti-BCMA ($V_HH2$) in CD3ε and CD3γ formats may produce the highest IL-2 and IFN-γ levels of the TFP constructs. However, cytokine production by T-cells transduced with anti-BCMA-CD3ε and anti-BCMA-CD3γ TFPs may be comparable to that of T-cells expressing anti-BCMA-28 CAR, despite the TFPs demonstrating much higher levels of target cell killing. The possibility that TFPs may more efficiently kill target cells than CARs, but release comparable or lower levels of pro-inflammatory cytokines, represents a potential advantage for TFPs relative to CARs since elevated levels of these cytokines have been associated with dose-limiting toxicities for adoptive CAR-T therapies.

Figure 8A:
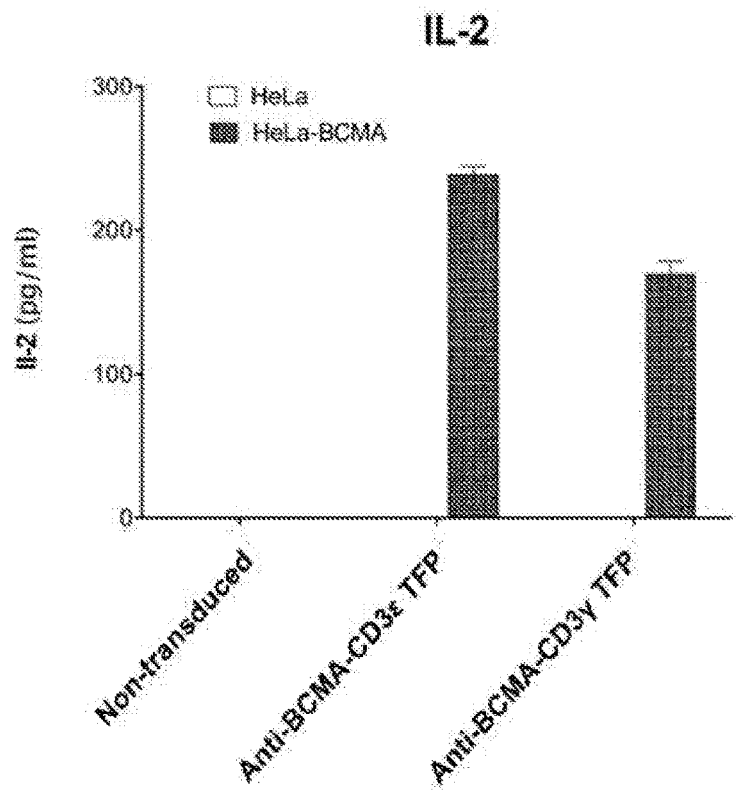
FIG. 8A is an exemplary graph depicting IL-2 release by T-cells transduced with anti-BCMA TFPs in response to BCMA-bearing target cells. Effector T-cells that were either non-transduced or transduced with either anti-BCMA-CD3ε or anti-BCMA-CD3γ TFPs were expanded for 7 days prior to incubation with either $1\times10^4$ HeLa or HeLa-BCMA target cells. IL-2 production was determined by 2-plex Luminex.
Figure 8B:
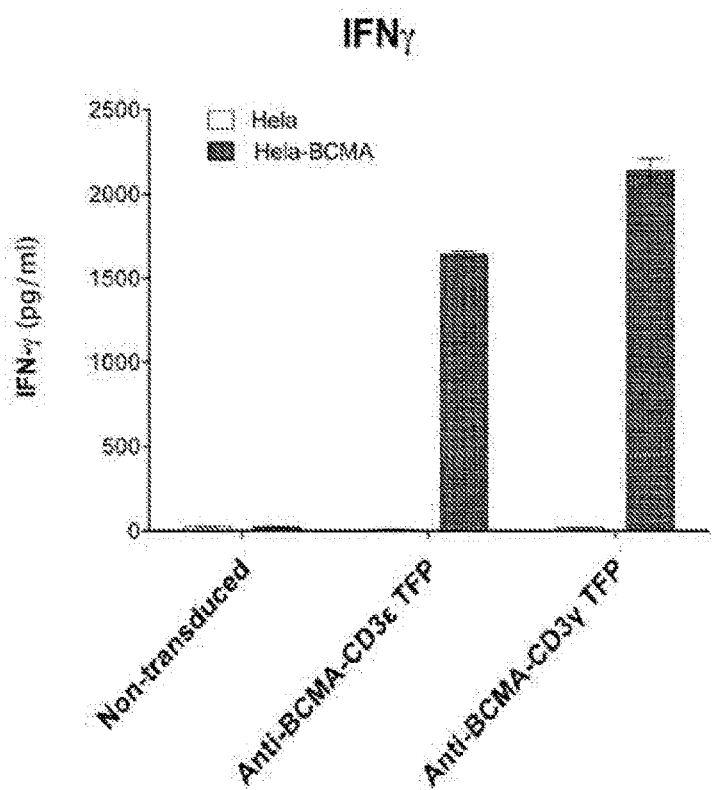
FIG. 8B is an exemplary graph depicting IFN-γ release by T-cells transduced with anti-BCMA TFPs in response to BCMA-bearing target cells. Effector T-cells that were either non-transduced or transduced with either anti-BCMA-CD3ε or anti-BCMA-CD3γ TFPs were expanded for 7 days prior to incubation with either $1\times10^4$ HeLa or HeLa-BCMA target cells. IFN-γ production was determined by 2-plex Luminex.

T-cells transduced with anti-BCMA-CD3ε or anti-BCMA-CD3γ TFPs also produced IL-2 and IFN-γ upon co-culture with BCMA-HeLa but not control HeLa cells that did not express BCMA (FIG. 8).

Example 10: CD107a Exposure by Flow Cytometry

An additional assay for T-cell activation is surface expression of CD107a, a lysosomal associated membrane protein (LAMP-1) that is located in the membrane of cytoplasmic cytolytic granules in resting cells. Degranulation of effector T-cells, a prerequisite for cytolytic activity, results in mobilization of CD107a to the cell surface following activation-induced granule exocytosis. Thus, CD107a exposure provides an additional measure of T-cell activation, in addition to cytokine production, that correlates closely with cytotoxicity.

Target and effector cells are separately washed and re-suspended in cytotoxicity medium (RPMI+5% human AB serum+1% antibiotic antimycotic). The assay is performed by combining $2 \times 10^5$ effectors cells with $2 \times 10^5$ target cells in a 100 μL final volume in U-bottom 96-well plates (Corning), in the presence of 0.5 μL/well of PE/Cy7-labelled anti-human CD107a (LAMP-1) antibody (Clone-H4A3, BD Biosciences). The cultures are then incubated for an hour at 37° C., 5% $CO_2$. Immediately following this incubation, 10 μL of a 1:10 dilution of the secretion inhibitor monensin (1000× solution, BD GolgiStop™) is carefully added to each well without disturbing the cells. The plates are then incubated for a further 2.5 hours at 37° C., 5% $CO_2$. Following this incubation, the cells are stained with APC anti-human CD3 antibody (Clone-UCHT1, BD Biosciences), PerCP/Cy5.5 anti-human CD8 antibody (Clone-SK1, BD Biosciences) and Pacific Blue anti-human CD4 antibody (Clone-RPA-T4, BD Biosciences) and then incubated for 30 minutes at 37° C., 5% $CO_2$. The cells are then washed 2× with FACS buffer (and resuspended in 100 μL FACS buffer and 100 ul IC fix buffer prior to analysis.

Exposure of CD107a on the surface of T-cells is detected by flow cytometry. Flow cytometry is performed with a LSRFortessa™ X20 (BD Biosciences) and analysis of flow cytometric data is performed using FlowJo software (Treestar, Inc. Ashland, Oreg.). The percentage of CD8+ effector cells, within the CD3 gate, that are CD107 +ve is determined for each effector/target cell culture.

Consistent with the previous cytotoxicity and cytokine data, co-culture of BCMA-expressing target cells with effector T-cells transduced with anti-BCMA-2K CAR may induce an increase in surface CD107a expression relative to effectors incubated with BCMA-ve target cells. In comparison, under the same conditions, anti-BCMA-CD3ε LL or anti-BCMA-CD3γ LL TFP-expressing effectors may exhibit a 5 to 7-fold induction of CD107a expression. Anti-BCMA TFPs constructed with an alternative hinge region may generate similar results upon co-culture with BCMA-bearing target cells.

Figure 9:
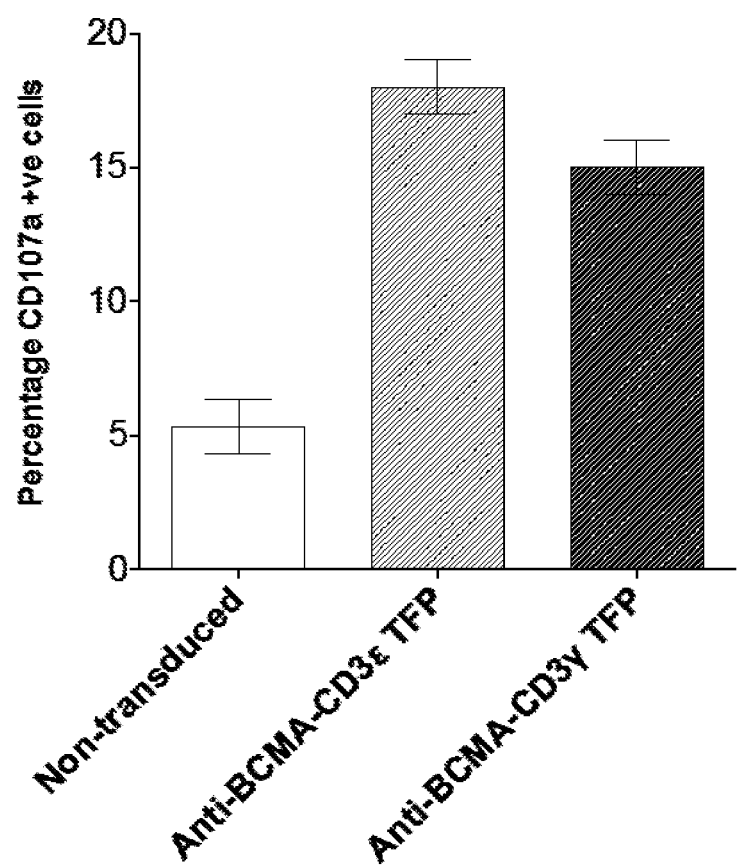
FIG. 9 is an exemplary graph depicting degranulation of T-cells transduced with anti-BCMA TFPs in response to BCMA-bearing target cells. Effector T-cells that were either non-transduced or transduced with 50 MOI of either anti-BCMA-CD3ε or anti-BCMA-CD3γ TFPs were expanded for 13 days prior to incubation with $1\times10^4$ of the indicated BCMA +ve RPMI8226 target cells. The percentage of CD107+ cells in the CD3+CD8+ gate was determined.

Relative to non-transduced T-cells, cells transduced with anti-BCMA-CD3ε or anti-BCMA-CD3γ TFPs exhibited an increase in surface expression of CD107a upon co-culture with BCMA +ve RPMI8226 cells (FIG. 9). These results indicate that TFP-transduced effector T-cells become activated and degranulate upon exposure to target cells expressing their cognate antigen.

Example 8: In Vivo Mouse Efficacy Studies

To assess the ability of effector T-cells transduced with anti-BCMA (scFv1, SEQ ID NO:45) TFPs to achieve anti-tumor responses in vivo, effector T-cells transduced with anti-BCMA-CD3ε TFP, anti-BCMA-28ζ CAR, or anti-BCMA-41BBζ TFP were adoptively transferred into NOD/SCID/IL-2Rγ-/- (NSG-JAX) mice that are inoculated with BCMA+ RPMI-8226 multiple myeloma cell line (ATCC Cat #CRM-CCL-155). human cancer cell lines. Non-transduced T cells were used as a control.

Materials and Methods

RPMI-8226 Maintenance and Expansion

RPMI-8226 multiple myeloma cell line was obtained from ATCC (Catalog number CRM-CCL-155). These cells were transfected with luciferase to produce RPMI-8226 Luc lines. Cells were passaged every 2-3 days in RPMI 1640 media (Corning, Catalog number 10-041-CV), supplemented with 10% HI FBS (Invitrogen, Catalog #10438-026, lot #1785079) and 1% antibiotics (Life Technologies, Catalog number 15240-062).

Lentivirus Generation

Lentiviruses were prepared by transient transfection of 293TN Producer Cell Line (System Biosciences, Inc., LV900A-1). TFP/CAR constructs were generated using Anti-BCMA single chain fragment variable (scFv) fused to CD3 epsilon chain (in TFPs) or CD28z or 41BBz (in CARs).

T Cell Isolation and Lentivirus Transduction

PBMCs were purified from whole blood (Hemacare, Donor 12, lot #W313716040526) using Ficoll®-Paque PLUS (GE Healthcare, 17-1440-03).

T cells were activated using DynaBeads® (Gibco, Catalog #00415447, lot #1785079) at 1:1 ratio and were maintained in AimV media (Life Technologies, Catalog number 31035025) in 5% human AB serum (Gemini Products, Catalog #100-318, lot #H605oo1), and 1% antibiotics (Life Technologies, Catalog number 15240-062) in presence of 300 IU/ml IL-2 (Peprotech, Catalog number 200-02, lot #051512). Dynabead activated T cells were transduced with lentivirus at 10 MOI (based on titers in Jurkat cell line) for Anti-BCMA-CD3ε TFP, Anti-BCMA-CD28ζ CAR and Anti-BCMA-41BBζ CAR and 510-vector alone control virus in presence of polybrene (5 ug/ml, Millipore #TR-1003-G) and spinoculation at 100 G for 100 minutes. A total of two rounds of transductions were performed at 24 hour and 48 hour post T cell activation. Cells were expanded for 11 days and frozen.

Transduction Efficiency Determination.

Transduction efficiency was determined by flow cytometry. T cells were stained using anti-CD3 APC, Clone: UCHT1 (BD Biosciences, Catalog number 561811 lot 5090862), anti-CD4-Pacific blue, Clone: RPAT4 (Biolegend, Catalog number 300521 lot B231611), anti-CD8-APCCY7, Clone: SKI (BD Biosciences, Catalog number 557834 lot 6082865), and/or goat anti mouse FAB (Invitrogen, Catalog number 31803 lot SC2362539). In addition, cells were stained with Zenon-labelled (Thermofisher, Catalogue number Z25055A Lot 1851333) BCMA-Fc protein to detect surface expression of TFPs and CARs. Cells were analyzed using BD-LSRII Fortessa® X20.

In Vitro Functional Assays

All in vitro functional assays were performed at day 9 post activation.

Luciferase Assay:

T cells were cocultured with HeLa-cell line overexpressing truncated CD19 and luciferase (BCMA negative targets) or HeLa-cell line overexpressing BCMA and luciferase (BCMA positive targets) at different effector (E): target (T) ratios (3:1 and 1:3) for 24 hours. Cells were lysed and subjected to luciferase assay (SOP 002) using manufacturer's instructions (Promega, Catalog number E1500).

Real-Time Cytotoxicity Assay (RTCA):

T cells were co-cultured with above mentioned target cells at different E:T ratios. The cytotoxicity is determined by measuring electronic impedance of cell sensor electrodes on 96-well plates (E-Plate 96) via the xCELLigence® RTCA MP (Multiple Plate) Instrument. The final readout is displayed as cell index. Changes in cell index indicate disruption of target cell monolayer as a result of killing of target cells by co-incubated T cells. Culture supernatants were collected following centrifugation for cytokine analysis and stored at −80 C until further analysis.

Cytokine Measurement

Culture supernatants from RTCA assays were analyzed for cytokine release using Human Cytokine/Chemokine Magnetic Bead Panel.

ELISA assays for Human IL-2 and IFNγ were performed as described in the product inserts. Data was collected on Magpixγ Luminex® xMAP® Technology and measured in pg/ml amounts.

In Vivo Studies

A NOD/SCID (NSG) mouse model was used to conduct an in vivo potency study. Female NOD/SCID/IL-2Rγ−/− (NSG-JAX) mice, at least 6 weeks of age prior to the start of the study, are obtained from The Jackson Laboratory (stock number 005557) and acclimated for 3 days before experimental use. Human BCMA-expressing cell lines for inoculation are maintained in log-phase culture prior to harvesting and counting with trypan blue to determine a viable cell count. On the day of tumor challenge, the cells are centrifuged at 300 g for 5 minutes and re-suspended in pre-warmed sterile PBS at either 0.5-1×$10^6$ cells/100 μL. 3×$10^6$ RPMI-8226-Luc cells were injected subcutaneously (s.c.) into NSG mice. 19 days post tumor inoculation, T cells were administered at 15×$10^6$ cells per mouse i.v. There were 7 animals per group. Bioluminescent imaging was performed on days 3, 7, 14, 21, 28 and 35 of study. Tumor volumes were measured by caliper measurements two days per week. Detailed clinical observations on the animals are recorded daily until euthanasia. Body weight measurements are made on all animals weekly until death or euthanasia. All animals are euthanized 35 days after adoptive transfer of test and control articles. Any animals appearing moribund during the study are euthanized at the discretion of the study director in consultation with a veterinarian Efficient TFP and CAR Surface Expression on T Cells Surface expression of scFv2 on TFP or CAR T cells was evaluated. TFP or CAR T cells were prepared by transducing DynaBead® stimulated T cells using various lentivirus constructs. Transduced T cells were cultured for 7 days and were subjected to flow cytometry analysis. TFP and CAR surface expression as evidenced by anti-Fab or BCMA-Fc staining was between 40-50% in all groups. TFP and CAR T cells had comparable surface expression of scFv (FIG. 11).

TFP and CAR T Cells Function In Vitro

Figure 11A:
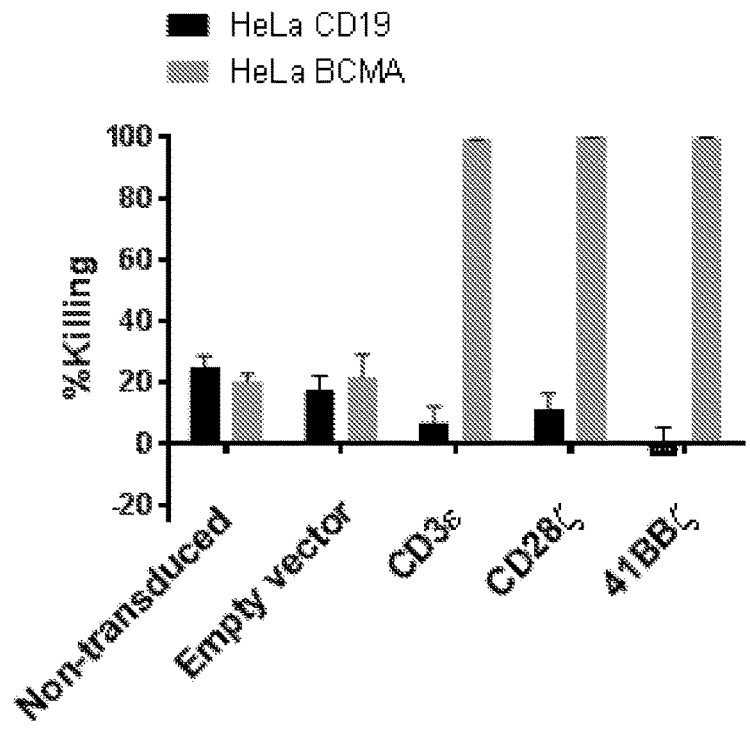
FIG. 11 is a series of graphs showing in vitro analysis of anti-BCMA scFv1 TFP T cells and their efficacy in an in vivo multiple myeloma model. TFP T cells in CD3ε format or CAR T cells in CD28ζ or 41BBζ format were tested for their cytolytic activity by culturing T cells with luciferase expressing HeLa-CD19 (negative control) or HeLa-BCMA tumor target cells at an effector to target cell ratio of 3:1 (FIG. 11A) or 1:3 (FIG. 11B) ratios for 24 hours. A luciferase assay was performed and % killing was calculated relative to target cells alone (as evidenced by the non-transduced T cells or empty vector T cells). TFP or CAR T cells were also tested for cytolytic function by Real-Time Cytotoxicity Assay (RTCA). T cells were co-cultured with BCMA-positive target cells (HeLa-BCMA) or BCMA negative tumor targets (HeLa-CD19) at 1:3 (FIG. 11C) or 1:3 (FIG. 11D) E:T ratios. Cellular impedance as indicated by cell index values was measured to determine cytotoxic potential. Effector T cells that were either non-transduced or transduced with anti-BCMA TFP or CAR constructs as listed above were incubated with BCMA-positive target cells (HeLa-BCMA) or BCMA negative target cells (HeLa-CD19) at 3:1 and 1:3 E:T ratios in an RTCA as described above. Cytokines IFN-γ (FIG. 11E) and IL-2 (FIG. 11F) released in cellular supernatants were measured.
Figure 11B:
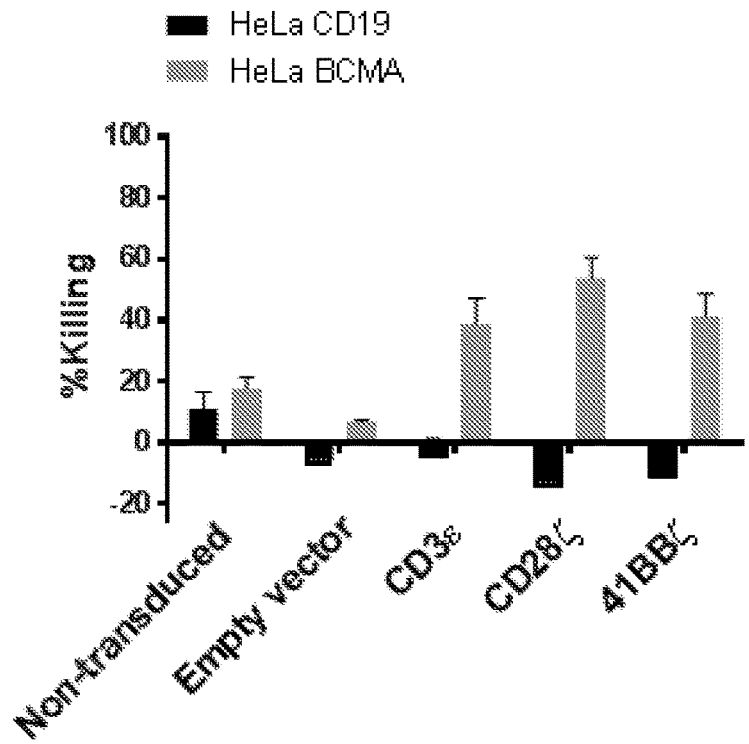

The effector function of TFP or CAR transduced T cells was evaluated by two different cytotoxicity assays. In the first assay, non-transduced T cells, 510-empty vector control, TFP or CAR T cells were cocultured with HeLa-BCMA-Luciferase expressing target cells at various ratios (3:1 (FIG. 11A) and 1:3 (FIG. 11B) Effector:Target). HeLa-CD19 Luciferase expressing cells served as BCMA-negative controls. All T cells efficiently cleared the BCMA-positive target cells at 3:1 (98% to 99% dead cells). At lower E:T ratio of 1:3, cytotoxicity observed was between 38% to 53% (FIG. 11B). No killing was noted in the nontransduced (NT) or 510-vector only control groups.

Figure 11D:
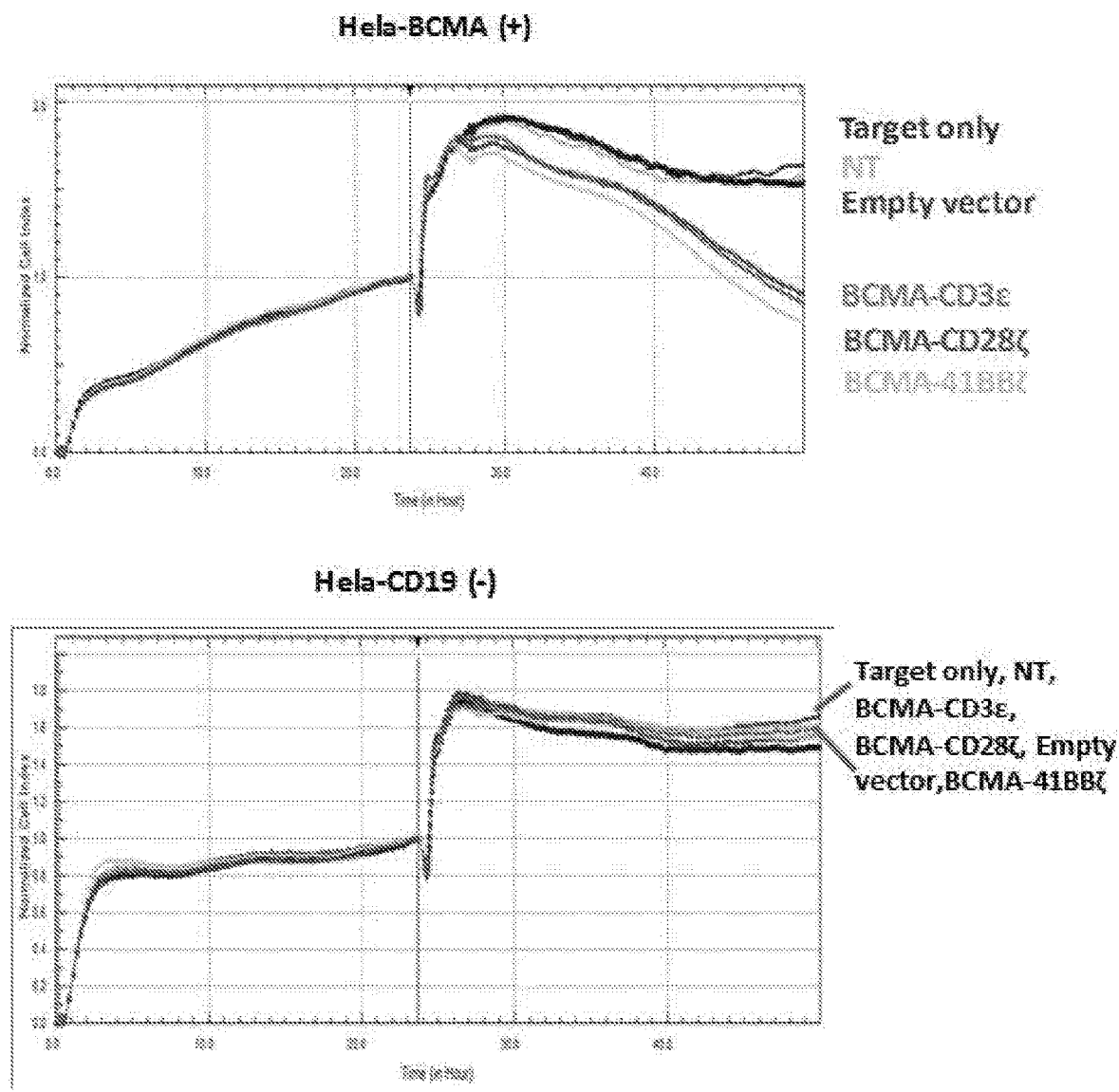

The cytotoxicity of anti-BCMA TFPs or CARs was also measured by real-time cytotoxicity assay (RTCA) which measures electrical impedance of the target cell monolayer in a specialized 96-well format, in real-time. In this assay, robust killing was observed in TFP or CAR transduced groups at 3:1 E:T ratio (FIG. 11C) as indicated by a time-dependent decrease in cell index following the addition of transduced T cells. Target cells were cleared within 10 hours of T cell addition. The 41BBζ group showed the highest killing kinetics followed by TFP and CD28ζ CAR. Nonetheless, all the groups killed target cells at the end of a 24 h period. At the 1:3 E:T ratio, killing was slower and tumor cells were not efficiently cleared by any group. No killing was observed by the NT or 510-vector only group. Hela-CD19 luciferase cells served as negative controls and continued to grow even after addition of T cells (FIG. 11D).

Figure 11E:
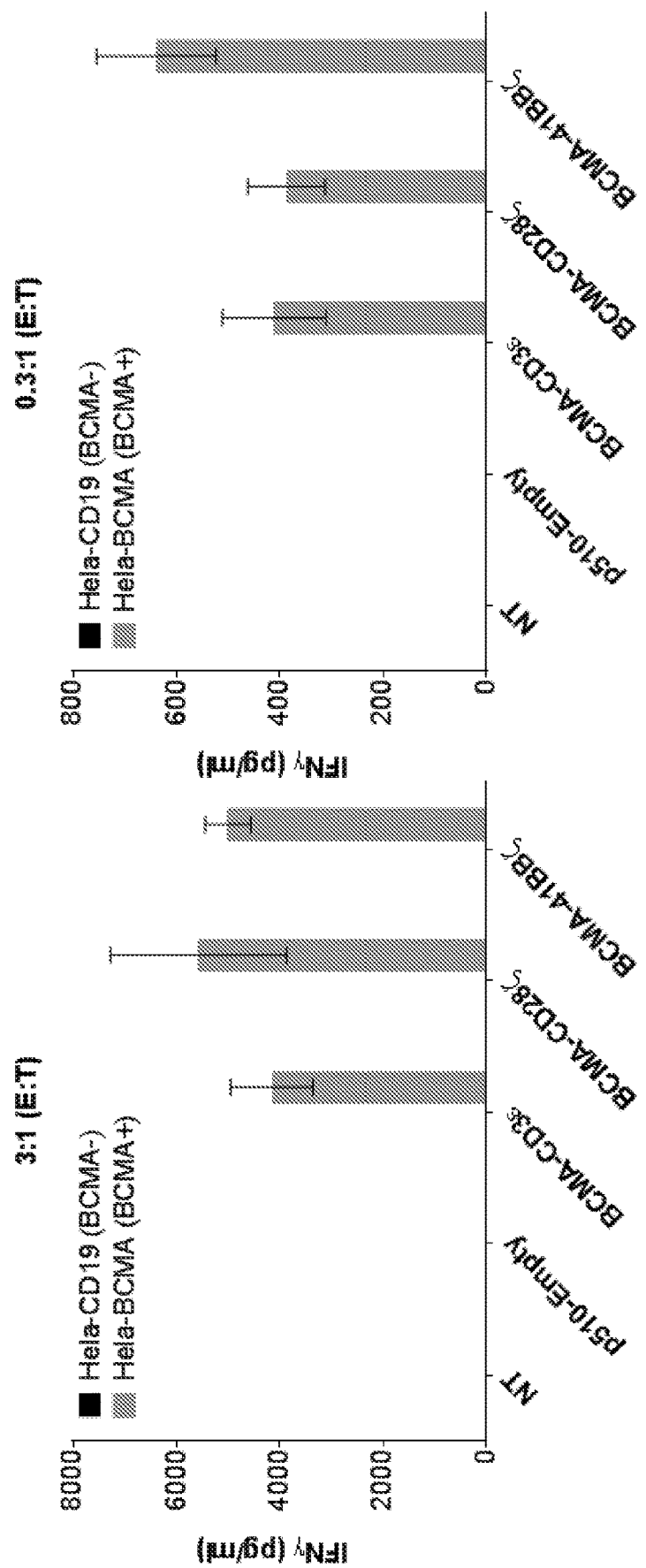
Figure 11F:
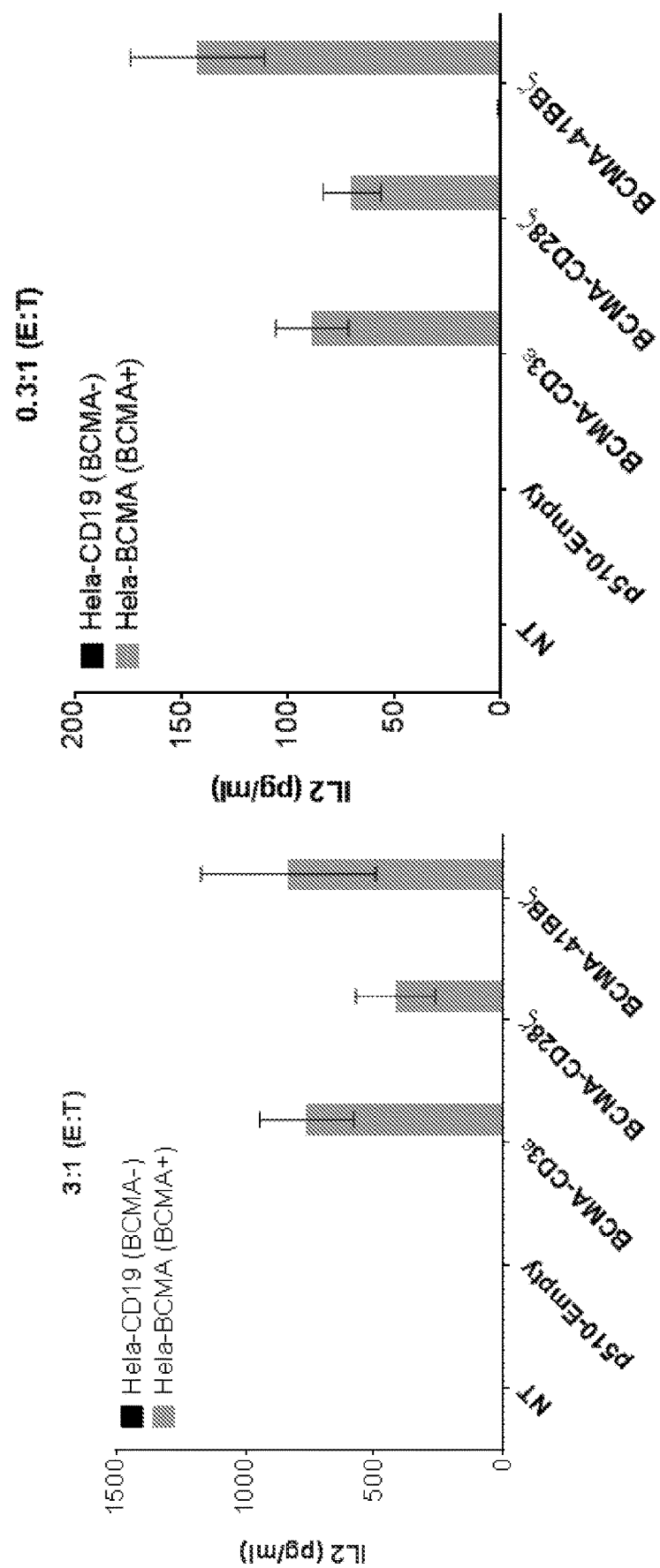

Another measure of effector T cell activation and proliferation is the production of cytokines such as IFNγ and IL-2. Culture supernatants from the RTCA assay above were analyzed for cytokine release using 2-plex Luminex® kit (EMD Millipore). As shown in FIGS. 11E (IFNγ) and 11F (IL-2), both TFP and CAR transduced T cells produced high levels of IFNγ and IL-2 at 3:1 and 1:3 E:T ratios when co-cultured with HeLa cells expressing BCMA, relative to non-transduced or 510-empty vector control cells. Most notably, the 41BBζ group produced more cytokines at the 1:3 E:T ratio.

Anti-BCMA TFP and CAR T Cells Demonstrate Anti-Tumor Efficacy In Vivo

Figure 12A:
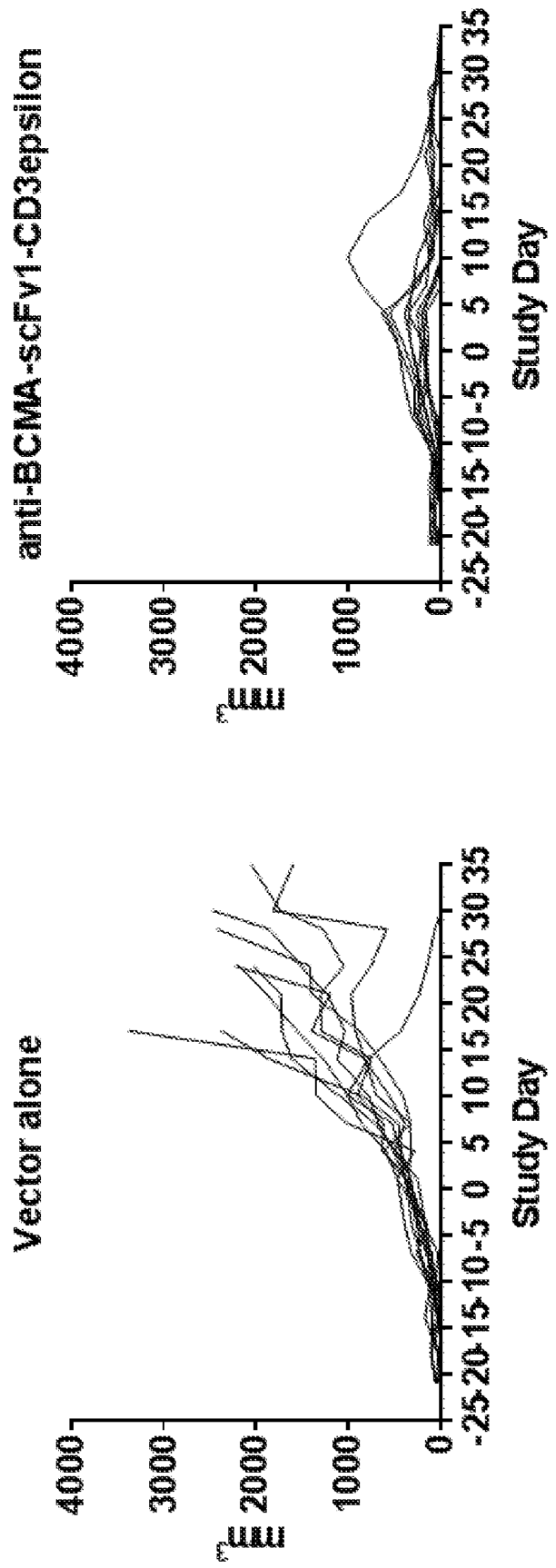
FIG. 12 is a series of graphs showing the in vivo efficacy of scFv2 (in HL format) and $V_H$H2 TFP T cells. Mice were inoculated with RPMI-8226 tumor cells and then treated using empty vector T cells as a negative control and scFv1-CD3ε TFP T cells as a positive control (FIG. 12A); $V_H$H2 TFP T cells in epsilon, gamma, and beta format (FIG. 12B), and scFv2 TFP T cells in epsilon, gamma and beta format (FIG. 12C). Each line in each graph represents one mouse. Data represent tumor volume in mm3 over time in days. Day 0 represents the day of the start of treatment, three weeks after inoculation with tumor cells.
Figure 12B:
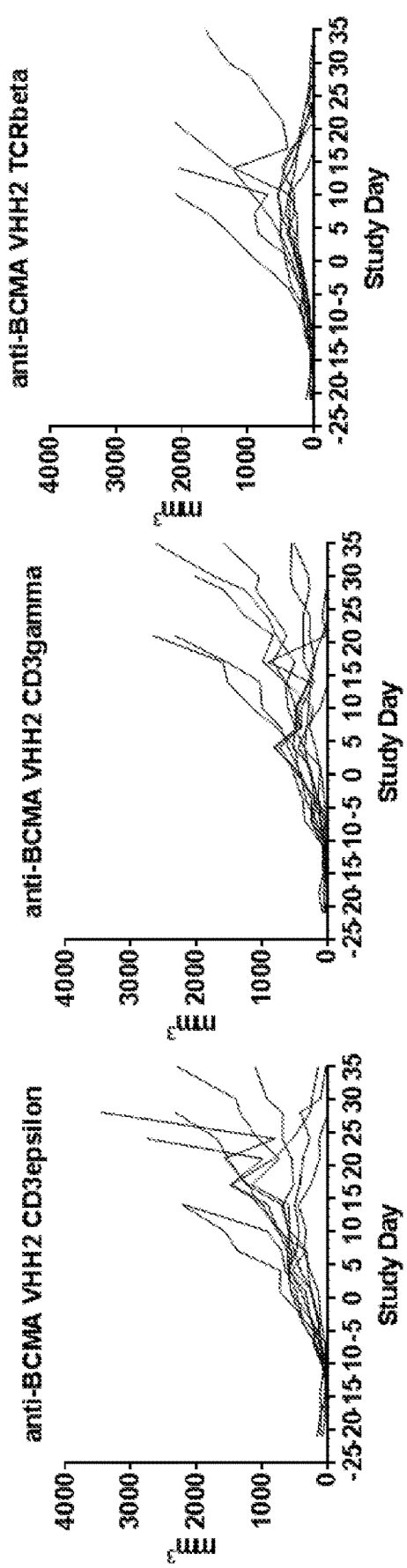
Figure 12C:
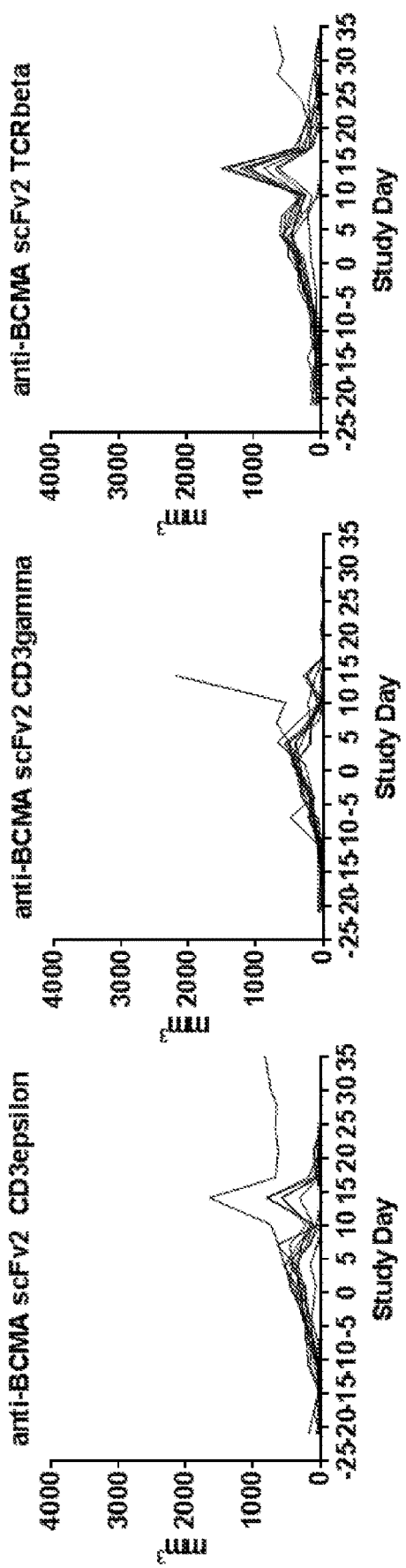

To evaluate the in vivo efficacy of scFv2 (in HL format) and $V_H$H2 TFP T cells, in vivo studies were performed as described above using empty vector T cells as a negative control and scFv1-CD3ε TFP T cells as a positive control (FIG. 12A); $V_H$H2 TFP T cells in epsilon, gamma, and beta format (FIG. 12B), and scFv2 TFP T cells in epsilon, gamma and beta format (FIG. 12C). Each line in each graph represents one mouse. As shown in FIG. 12A, mice treated with vector only T cells had tumors that grew over time, whereas the positive control was able to reduce or eradicate tumors in mice. As shown in FIG. 12B, a number of the mice showed a reduction in tumor size after treatment with VHH2

TFP T cells, as did the mice treated with scFv2 TFP T cells shown in FIG. 12C. Notably, in FIG. 12B, the BH10-CD3ε and CD3γ groups co-expressed PD1, TIM3 and LAG3 exhaustion markers at the time of injection.

Figure 13A:
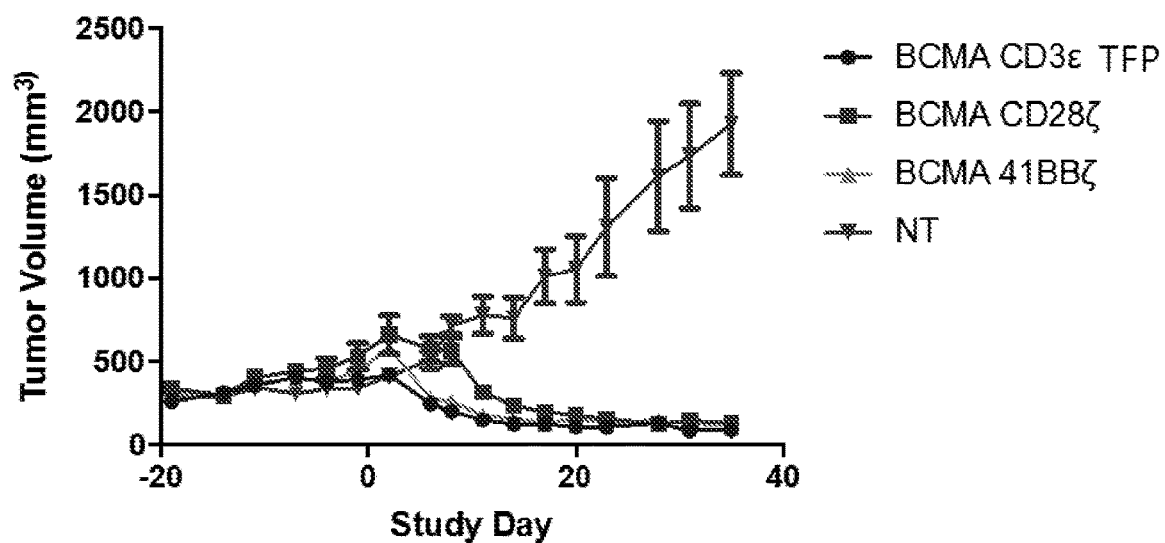
FIG. 13 is a series of graphs showing in vivo efficacy of the TFP and CAR T cells used in FIG. 11 above. To evaluate the potency of TFP vs CARs, RPMI8226 multiple myeloma cells and a NSG mouse model were used. A significant decrease in tumor volumes was observed in TFP and CAR T groups beginning at day 8 after T cell injection (FIG. 13A). Tumor burden as assessed by average radiance of the tumors was significantly decreased in all groups compared to controls (FIG. 13B). In addition, the TFP and 41BBζ CAR T cell groups displayed increased survival compared to CD28ζ CAR T group (FIG. 13C).
Figure 13B:
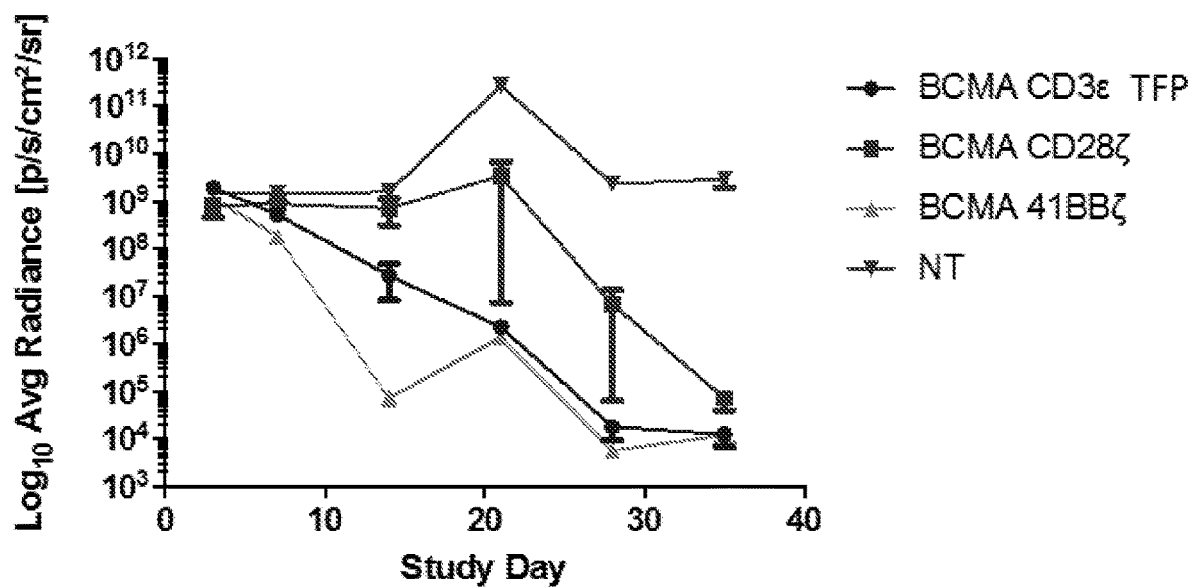
Figure 13C:
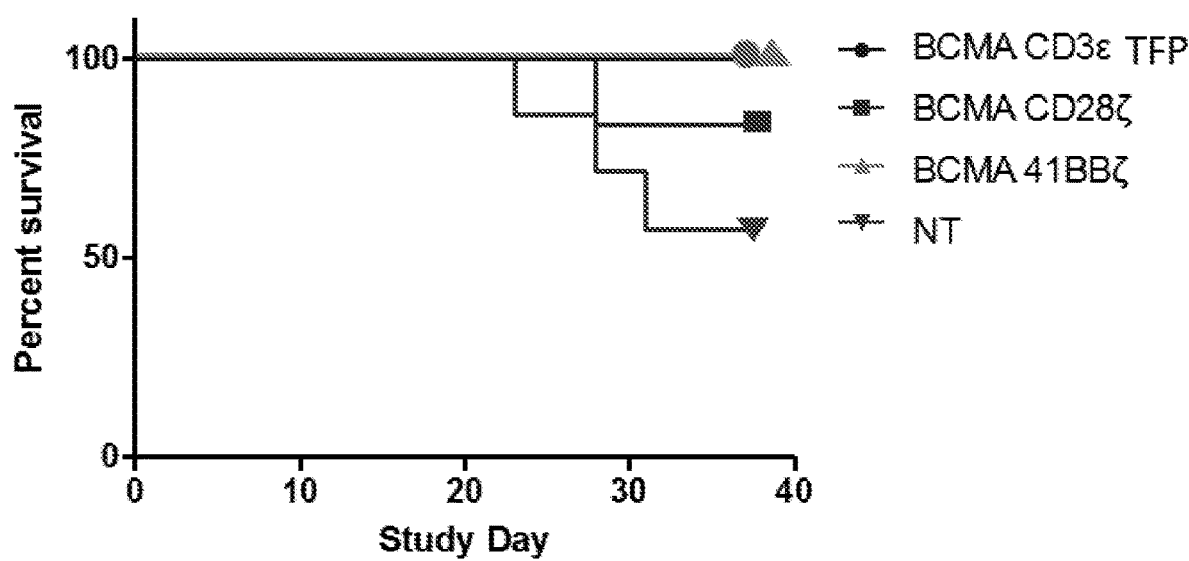

To evaluate the potency of TFP vs CARs, RPMI8226 multiple myeloma cells and a NSG mouse model were used. RPMI8226 cells were injected at $3\times10^6$ cells per mouse. T cells frozen at day 11 were thawed and recovered for 24 h before in vivo injection at $15\times10^6$ cells per mouse. A significant decrease in tumor volumes was observed in TFP and CAR T groups beginning at day 8 after T cell injection (FIG. 13A). This trend was maintained till day 37, at which time the study was terminated due to absence of tumors. Tumor burden as assessed by average radiance of the tumors was significantly decreased in all groups compared to controls (FIG. 13B). In addition, the TFP and 41BBζ CAR T cell groups displayed increased survival compared to CD28ζ CAR T group (FIG. 13C). These results demonstrate that anti-BCMA-TFP and CAR T cells are potent in killing multiple myeloma tumor cells in vivo.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

APPENDIX

| | | |
|---|---|---|
| 1 | Linker 1 (SL) | AAAGGGGSGGGGSGGGGSLE |
| 2 | Linker 2 (LL) | AAAIEVMYPPPYLGGGGSGGGGSGGGGSLE |
| 3 | Linker 3 | GGGGSGGGGS |
| 4 | Linker 4 | GGTGGCGGAGGTTCTGGAGGTGGAGGTTCC |
| 5 | Linker 5 | GGGGSGGGGSGGGGSLE |
| 6 | p514_BCMA (DNA) | ACGCGTGTAGTCTTATGCAATACTCTTGTAGTCTTGCAACATGGTA<br>ACGATGAGTTAGCAACATGCCTTACAAGGAGAGAAAAAGCACCGT<br>GCATGCCGATTGGTGGAAGTAAGGTGGTACGATCGTGCCTTATTAG<br>GAAGGCAACAGACGGGTCTGACATGGATTGGACGAACCACTGAAT<br>TGCCGCATTGCAGAGATATTGTATTTAAGTGCCTAGCTCGATACAT<br>AAACGGGTCTCTCTGGTTAGACCAGATCTGAGCCTGGGAGCTCTCT<br>GGCTAACTAGGGAACCCACTGCTTAAGCCTCAATAAAGCTTGCCTT<br>GAGTGCTTCAAGTAGTGTGTGCCCGTCTGTTGTGTGACTCTGGTAA<br>CTAGAGATCCCTCAGACCCTTTTAGTCAGTGTGGAAAATCTCTAGC<br>AGTGGCGCCCGAACAGGGACCTGAAAGCGAAAGGGAAACCAGAG<br>CTCTCTCGACGCAGGACTCGGCTTGCTGAAGCGCGCACGGCAAGA<br>GGCGAGGGGCGGCGACTGGTGAGTACGCCAAAAATTTTGACTAGC<br>GGAGGCTAGAAGGAGAGAGATGGGTGCGAGAGCGTCAGTATTAAG<br>CGGGGGAGAATTAGATCGCGATGGGAAAAAATTCGGTTAAGGCCA<br>GGGGGAAAGAAAAAATATAAATTAAAACATATAGTATGGGCAAGC<br>AGGGAGCTAGAACGATTCGCAGTTAATCCTGGCCTGTTAGAAACAT<br>CAGAAGGCTGTAGACAAATACTGGGACAGCTACAACCATCCCTTC<br>AGACAGGATCAGAAGAACTTAGATCATTATATAATACAGTAGCAA<br>CCCTCTATTGTGTGCATCAAAGGATAGAGATAAAAGACACCAAGG<br>AAGCTTTAGACAAGATAGAGGAAGAGCAAAACAAAAGTAAGACC<br>ACCGCACAGCAAGCGGCCACTGATCTTCAGACCTGGAGGAGGAGA<br>TATGAGGGACAATTGGAGAAGTGAATTATATAAATATAAAGTAGT<br>AAAAATTGAACCATTAGGAGTAGCACCCACCAAGGCAAAGAGAAG<br>AGTGGTGCAGAGAGAAAAAAGAGCAGTGGGAATAGGAGCTTTGTT<br>CCTTGGGTTCTTGGGAGCAGCAGGAAGCACTATGGGCGCAGCGTC<br>AATGACGCTGACGGTACAGGCCAGACAATTATTGTCTGGTATAGTG<br>CAGCAGCAGAACAATTTGCTGAG<br>GGCTATTGAGGCGCAACAGCATCTGTTGCAACTCACAGTCTGGGC<br>ATCAAGCAGCTCCAGGCAAGAATCCTGGCTGTGGAAAGATACCTA<br>AAGGATCAACAGCTCCTGGGGATTTGGGGTTGCTCTGGAAAACTCA<br>TTTGCACCACTGCTGTGCCTTGGAATGCTAGTTGGAGTAATAAATC<br>TCTGGAACAGATTTGGAATCACACGACCTGGATGGAGTGGGACAG<br>AGAAATTAACAATTACACAAGCTTAATACACTCCTTAATTGAAGAA<br>TCGCAAAACCAGCAAGAAAAGAATGAACAAGAATTATTGGAATTA<br>GATAAATGGGCAAGTTTGTGGAATTGGTTTAACATAACAAATTGGC<br>TGTGGTATATAAAATTATTCATAATGATAGTAGGAGGCTTGGTAGG<br>TTTAAGAATAGTTTTTGCTGTACTTTCTATAGTGAATAGAGTTAGGC<br>AGGGATATTCACCATTATCGTTTCAGACCCACCTCCCAACCCCGAG<br>GGGACCCGACAGGCCCGAAGGAATAGAAGAAGAAGGTGGAGAGA<br>GAGACAGAGACAGATCCATTCGATTAGTGAACGGATCTCGACGGT<br>ATCGGTTAACTTTTAAAAGAAAAGGGGGGATTGGGGGGTACAGTG<br>CAGGGGAAAGAATAGTAGACATAATAGCAACAGACATACAAACTA<br>AAGAATTACAAAAACAAATTACAAAATTCAAAATTTTATCGATACT<br>AGTATTATGCCCAGTACATGACCTTATGGGACTTTCCTACTTGGCA<br>GTACATCTACGTATTAGTCATCGCTATTACCATGGTGATGCGGTTTT<br>GGCAGTACATCAATGGGCGTGGATAGCGGTTTGACTCACGGGGAT<br>TTCCAAGTCTCCACCCCATTGACGTCAATGGGAGTTTGTTTTGGCA<br>CCAAAATCAACGGGACTTTCCAAAATGTCGTAACAACTCCGCCCCA |

APPENDIX

```
TTGACGCAAATGGGCGGTAGGCGTGTACGGTGGGAGGTTTATATA
AGCAGAGCTCGTTTAGTGAACCGTCAGATCGCCTGGAGACGCCATC
CACGCTGTTTTGACCTCCATAGAAGATTCTAGAGCTAGCGCCGCCA
CCATGCTCCAGATGGCTGGCCAGTGCAGCCAGAACGAGTACTTCG
ACAGCCTGCTGCACGCCTGCATCCCTTGCCAGCTGCGGTGCAGCAG
CAACACCCCACCCCTGACCTGCCAGCGGTACTGCAACGCCAGCGTG
ACCAACAGCGTGAAGGGCACCAACGCCATCCTGTGGACCTGCCTG
GGCCTGAGCCTGATCATCAGCCTGGCCGTGTTCGTGCTGATGTTCC
TGCTGCGGAAGATCAACAGCGAGCCCTGAAGGACGAGTTCAAGA
ACACCGGCAGCGGCCTGCTGGGCATGGCCAACATCGACCTGGAAA
AGAGCCGGACCGGCGACGAGATCATCCTGCCCAGAGGCCTGGAGT
ACACCGTGGAAGAGTGTACCTGCGAGGACTGCATCAAGAGCAAGC
CCAAGGTGGACAGCGACCACTGCTTCCCTCTGCCCGCCATGGAAGA
GGGCGCCACCATCCTGGTGACAACAAAGACCAACGACTACTGCAA
GAGCCTGCCTGCCGCCCTGAGCGCCACCGAGATCGAGAAGTCCAT
CAGCGCCAGATGAGGATCCGCGGCCGCAAGGATCTGCGATCGCTC
CGGTGCCCGTCAGTGGGCAGAGCGCACATCGCCCACAGTCCCCGA
GAAGTTGGGGGGAGGGGTCGGCAATTGAACGGGTGCCTAGAGAAG
GTGGCGCGGGGTAAACTGGGAAAGTGATGTCGTGTACTGGCTCCG
CCTTTTTCCCGAGGGTGGGGGAGAACCGTATATAAGTGCAGTAGTC
GCCGTGAACGTTCTTTTTCGCAACGGGTTTGCCGCCAGAACACAGC
TGAAGCTTCGAGGGGCTCGCATCTCTCCTTCACGCGCCCGCCGCCC
TACCTGAGGCCGCCATCCACGCCGGTTGAGTCGCGTTCTGCCGCCT
CCCGCCTGTGGTGCCTCCTGAACTGCGTCCGCCGTCTAGGTAAGTT
TAAAGCTCAGGTCGAGACCGGGCCTTTGTCCGGCGCTCCCTTGGAG
CCTACCTAGACTCAGCCGGCTCTCCACGCTTTGCCTGACCCTGCTTG
CTCAACTCTACGTCTTTGTTTCGTTTTCTGTTCTGCGCCGTTACAGA
TCCAAGCTGTGACCGGCGCCTACGTCGAGATGATTGAACAAGATG
GATTGCACGCAGGTTCTCCGGCCGCTTGGGTGGAGAGGCTATTCG
GCTATGACTGGGCACAACAGACAATCGGCTGCTCTGATGCCGCCGT
GTTCCGGCTGTCAGCGCAGGGGCGCCCGGTTCTTTTTGTCAAGACC
GACCTGTCCGGTGCCCTGAATGAACTGCAGGACGAGGCAGCGCGG
CTATCGTGGCTGGCCGCGACGGGCGTTCCTTGCGCAGCTGTGCTCG
ACGTTGTCACTGAAGCGGGAAGGGACTGGCTGCTATTGGGCGAAG
TGCCGGGGCAGGATCTCCTGTCATCTCACCTTGCTCCTGCCGAGAA
AGTATCCATCATGGCTGATGAATGCGGCGGCTGCATACGCTTGAT
CCGGCTACCTGCCCATTCGACCACCAAGCGAAACATCGCATCGAGC
GAGCACGTACTCGGATGGAAGCCGGTCTTGTCGATCAGGATGATCT
GGACGAAGAGCATCAGGGGCTCGCGCCAGCCGAACTGTTCGCCAG
GCTCAAGGCGCGCATGCCCGACGGCGAGGATCTCGTCGTGACCCA
TGGCGATGCCTGCTTGCCGAATATCATGGTGGAAAATGGCCGCTTT
TCTGGATTCATCGACTGTGGCCGGCTGGGTGTGGCGGACCGCTATC
AGGACATAGCGTTGGCTACCCGTGATATTGCTGAAGAGCTTGGCGG
CGAATGGGCTGACCGCTTCCTCGTGCTTTACGGTATCGCCGCTCCC
GATTCGCAGCGCATCGCCTTCTATCGCCTTCTTGACGAGTTCTTCTG
ACTCGACAATCAACCTCTGGATTACAAAATTTGTGAAAGATTGACT
GGTATTCTTAACTATGTTGCTCCTTTTACGCTATGTGGATACGCTGC
TTTAATGCCTTTGTATCATGCTATTGCTTCCCGTATGGCTTTCATTTT
CTCCTCCTTGTATAAATCCTGGTTGCTGTCTCTTTATGAGGAGTTGT
GGCCCGTTGTCAGGCAACGTGGCGTGGTGTGCACTGTGTTTGCTGA
CGCAACCCCCACTGGTTGGGGCATTGCCACCACCTGTCAGCTCCTT
TCCGGGACTTTCGCTTTCCCCCTCCCTATTGCCACGGCGGAACTCAT
CGCCGCCTGCCTTGCCCGCTGCTGGACAGGGGCTCGGCTGTTGGGC
ACTGACAATTCCGTGGTGTTGTCGGGGAAATCATCGTCCTTTCCTT
GGCTGCTCGCCTGTGTTGCCACCTGGATTCTGCGCGGGACGTCCTT
CTGCTACGTCCCTTCGGCCCTCAATCCAGCGGACCTTCCTTCCCGCG
GCCTGCTGCCGGCTCTGCGGCCTCTTCCGCGTCTTCGCCTTCGCCCT
CAGACGAGTCGGATCTCCCTTTGGGCCGCCTCCCCGCCTGGTACCT
TTAAGACCAATGACTTACAAGGCAGCTGTAGATCTTAGCCACTTTT
TAAAAGAAAAGGGGGGACTGGAAGGGCTAATTCACTCCCAACGAA
GATAAGATCTGCTTTTTGCTTGTACTGGGTCTCTCTGGTTAGACCAG
ATCTGAGCCTGGGAGCTCTCTGGCTAACTAGGGAACCCACTGCTTA
AGCCTCAATAAAGCTTGCCTTGAGTGCTTCAAGTAGTGTGTGCCCG
TCTGTTGTGTGACTCTGGTAACTAGAGATCCCTCAGACCCTTTTAGT
CAGTGTGGAAAATCTCTAGCAGTAGTAGTTCATGTCATCTTATTAT
TCAGTATTTATAACTTGCAAAGAAATGAATATCAGAGAGTGAGAG
GAACTTGTTTATTGCAGCTTATAATGGTTACAAATAAAGCAATAGC
ATCACAAATTTCACAAATAAAGCATTTTTTTCACTGCATTCTAGTTG
TGGTTTGTCCAAACTCATCAATGTATCTTATCATGTCTGGCTCTAGC
TATCCCGCCCCTAACTCCGCCCATCCCGCCCCTAACTCCGCCCAGTT
CCGCCCATTCTCCGCCCCATGGCTGACTAATTTTTTTTATTTATGCA
GAGGCCGAGGCCGCCTCGGCCTCTGAGCTATTCCAGAAGTAGTGA
GGAGGCTTTTTTGGAGGCCTAGACTTTTGCAGAGACGGCCCAAATT
CGTAATCATGGTCATAGCTGTTTCCTGTGTGAAATTGTTATCCGCTC
ACAATTCCACACAACATACGAGCCGGAAGCATAAAGTGTAAAGCC
TGGGGTGCCTAATGAGTGAGCTAACTCACATTAATTGCGTTGCGCT
CACTGCCCGCTTTCCAGTCGGGAAACCTGTCGTGCCAGCTGCATTA
```

APPENDIX

| | | |
|---|---|---|
| | | ATGAATCGGCCAACGCGCGGGGAGAGGCGGTTTGCGTATTGGGCG<br>CTCTTCCGCTTCCTCGCTCACTGACTCGCTGCGCTCGGTCGTTCGGC<br>TGCGGCGAGCGGTATCAGCTCACTCAAAGGCGGTAATACGGTTATC<br>CACAGAATCAGGGGATAACGCAGGAAAGAACATGTGAGCAAAAG<br>GCCAGCAAAAGGCCAGGAACCGTAAAAAGGCCGCGTTGCTGGCGT<br>TTTTCCATAGGCTCCGCCCCCTGACGAGCATCACAAAAATCGACG<br>CTCAAGTCAGAGGTGGCGAAACCCGACAGGACTATAAAGATACCA<br>GGCGTTTCCCCCTGGAAGCTCCCTCGTGCGCTCTCCTGTTCCGACCC<br>TGCCGCTTACCGGATACCTGTCCGCCTTTCTCCCTTCGGGAAGCGT<br>GGCGCTTTCTCATAGCTCACGCTGTAGGTATCTCAGTTCGGTGTAG<br>GTCGTTCGCTCCAAGCTGGGCTGTGTGCACGAACCCCCCGTTCAGC<br>CCGACCGCTGCGCCTTATCCGGTAACTATCGTCTTGAGTCCAACCC<br>GGTAAGACACGACTTATCGCCACTGGCAGCAGCCACTGGTAACAG<br>GATTAGCAGAGCGAGGTATGTAGGCGGTGCTACAGAGTTCTTGAA<br>GTGGTGGCCTAACTACGGCTACACTAGAAGGACAGTATTTGGTATC<br>TGCGCTCTGCTGAAGCCAGTTACCTTCGGAAAAAGAGTTGGTAGCT<br>CTTGATCCGGCAAACAAACCACCGCTGGTAGCGGTGGTTTTTTTGT<br>TTGCAAGCAGCAGATTACGCGCAGAAAAAAAGGATCTCAAGAAGA<br>TCCTTTGATCTTTTCTACGGGGTCTGACGCTCAGTGGAACGAAAAC<br>TCACGTTAAGGGATTTTGGTCATGAGATTATCAAAAAGGATCTTCA<br>CCTAGATCCTTTTAAATTAAAAATGAAGTTTTAAATCAATCTAAAG<br>TATATATGAGTAAACTTGGTCTGACAGTTACCAATGCTTAATCAGT<br>GAGGCACCTATCTCAGCGATCTGTCTATTTCGTTCATCCATAGTTGC<br>CTGACTCCCCGTCGTGTAGATAACTACGATACGGGAGGGCTTACCA<br>TCTGGCCCCAGTGCTGCAATGATACCGCGAGACCCACGCTCACCGG<br>CTCCAGATTTATCAGCAATAAACCAGCCAGCCGGAAGGGCCGAGC<br>GCAGAAGTGGTCCTGCAACTTTATCCGCCTCCATCCAGTCTATTAA<br>TTGTTGCCGGGAAGCTAGAGTAAGTAGTTCGCCAGTTAATAGTTTG<br>CGCAACGTTGTTGCCATTGCTACAGGCATCGTGGTGTCACGCTCGT<br>CGTTTGGTATGGCTTCATTCAGCTCCGGTTCCCAACGATCAAGGCG<br>AGTTACATGATCCCCCATGTTGTGCAAAAAAGCGGTTAGCTCCTTC<br>GGTCCTCCGATCGTTGTCAGAAGTAAGTTGGCCGCAGTGTTATCAC<br>TCATGGTTATGGCAGCACTGCATAATTCTCTTACTGTCATGCCATCC<br>GTAAGATGCTTTTCTGTGACTGGTGAGTACTCAACCAAGTCATTCT<br>GAGAATAGTGTATGCGGCGACCGAGTTGCTCTTGCCCGGCGTCAAT<br>ACGGGATAATACCGCGCCACATAGCAGAACTTTAAAAGTGCTCAT<br>CATTGGAAAACGTTCTTCGGGGCGAAAACTCTCAAGGATCTTACCG<br>CTGTTGAGATCCAGTTCGATGTAACCCACTCGTGCACCCAACTGAT<br>CTTCAGCATCTTTTACTTTCACCAGCGTTTCTGGGTGAGCAAAAAC<br>AGGAAGGCAAAATGCCGCAAAAAAGGGAATAAGGGCGACACGGA<br>AATGTTGAATACTCATACTCTTCCTTTTTCAATATTATTGAAGCATT<br>TATCAGGGTTATTGTCTCATGAGCGGATACATATTTGAATGTATTT<br>AGAAAAATAAACAAATAGGGGTTCCGCGCACATTTCCCCGAAAAG<br>TGCCACCTGACGTCTAAGAAACCATTATTATCATGACATTAACCTA<br>TAAAAATAGGCGTATCACGAGGCCCTTTCGTCTCGCGCGTTTCGGT<br>GATGACGGTGAAAACCTCTGACACATGCAGCTCCCGGAGACGGTC<br>ACAGCTTGTCTGTAAGCGGATGCCGGGAGCAGACAAGCCCGTCAG<br>GGCGCGTCAGCGGGTGTTGGCGGGTGTCGGGGCTGGCTTAACTATG<br>CGGCATCAGAGCAGATTGTACTGAGAGTGCACCATATGCGGTGTG<br>AAATACCGCACAGATGCGTAAGGAGAAAATACCGCATCAGGC<br>GCCATTCGCCATTCAGGCTGCGCAACTGTTGGGAAGGGCGATCGGT<br>GCGGGCCTCTTCGCTATTACGCCAGCTGGCGAAAGGGGGATGTGCT<br>GCAAGGCGATTAAGTTGGGTAACGCCAGGGTTTTCCCAGTCACGAC<br>GTTGTAAAACGACGGCCAGTGCCAAGCTG |
| 7 | anti-BCMA<br>scFv 1 light<br>chain CDR1<br>(DNA) | AAAAGCAGCCAGAGCCTGGTGCATAGCAACGGCAACACCTATCTG<br>CAT |
| 8 | anti-BCMA<br>scFv 1 light<br>chain CDR1<br>(amino acid) | KSSQSLVHSNGNTYLH |
| 9 | anti-BCMA<br>scFv 1 light<br>chain CDR2<br>(DNA) | AAAGTGAGCAACCGCTTTAGC |
| 10 | anti-BCMA<br>scFv 1 light<br>chain CDR2<br>(amino acid) | KVSNRFS |

| APPENDIX | | |
|---|---|---|
| 11 | anti-BCMA scFv 1 light chain CDR3 (DNA) | GCGGAAACCAGCCATGTGCCGTGGACC |
| 12 | anti-BCMA scFv 1 light chain CDR3 (amino acid) | AETSHVPWT |
| 13 | anti-BCMA scFv 1 heavy chain CDR1 (DNA) | AAAGCGAGCGGCTATAGCTTTCCGGATTATTATATTAAC |
| 14 | anti-BCMA scFv1 heavy chain CDR1 (amino acid) | KASGYSFPDYYIN |
| 15 | anti-BCMA scFv 1 heavy chain CDR2 (DNA) | TGGATTTATTTTGCGAGCGGCAACAGCGAATATAACCAGAAATTTA CCGGC |
| 16 | anti-BCMA scFv 1 heavy chain CDR2 (amino acid) | WIYFASGNSEYNQKFTG |
| 17 | anti-BCMA scFv 1 heavy chain CDR3 (DNA) | CTGTATGATTATGATTGGTATTTTGATGTG |
| 18 | anti-BCMA scFv 1 heavy chain CDR3 (amino acid) | LYDYDWYFDV |
| 19 | Anti-BCMA light chain variable region (DNA) | GATATTGTGATGACCCAGACCCCGCTGAGCCTGAGCGTGACCCCGG GCGAACCGGCGAGCATTAGCTGCAAAAGCAGCCAGAGCCTGGTGC ATAGCAACGGCAACACCTATCTGCATTGGTATCTGCAGAAACCGG GCCAGAGCCCGCAGCTGCTGATTTATAAAGTGAGCAACCGCTTTAG CGGCGTGCCGGATCGCTTTAGCGGCAGCGGCAGCGGCGCGGATTTT ACCCTGAAAATTAGCCGCGTGGAAGCGGAAGATGTGGGCGTGTAT TATTGCGCGGAAACCAGCCATGTGCCGTGGACCTTTGGCCAGGGCA CCAAACTGGAAATTAAAAGC |
| 20 | Anti-BCMA light chain variable region (amino acid) | DIVMTQTPLSLSVTPGEPASISCKSSQSLVHSNGNTYLHWYLQKPGQSP QLLIYKVSNRFSGVPDRFSGSGSGADFTLKISRVEAEDVGVYYCAETS HVPWTFGQGTKLEIKS |
| 21 | Anti-BCMA heavy chain variable region (DNA) | CAGGTGCAGCTGGTGCAGAGCGGCGCGGAAGTGAAAAAACCGGGC GCGAGCGTGAAAGTGAGCTGCAAAGCGAGCGGCTATAGCTTTCCG GATTATTATATTAACTGGGTGCGCCAGGCGCCGGGCCAGGGCCTGG AATGGATGGGCTGGATTTATTTTGCGAGCGGCAACAGCGAATATA ACCAGAAATTTACCGGCCGCGTGACCATGACCCGCGATACCAGCA GCAGCACCGCGTATATGGAACTGAGCAGCCTGCGCAGCGAAGATA CCGCGGTGTATTTTTGCGCGAGCCTGTATGATTATGATTGGTATTTT GATGTGTGGGGCCAGGGCACCATGGTGACCGTGAGCAGC |
| 22 | Anti-BCMA heavy chain variable region (amino acid) | QVQLVQSGAEVKKPGASVKVSCKASGYSFPDYYINWVRQAPGQGLE WMGWIYFASGNSEYNQKFTGRVTMTRDTSSSTAYMELSSLRSEDTAV YFCASLYDYDWYFDVWGQGTMVTVSS |
| 23 | Anti-BCMA V$_H$H 1 DNA | ATGGCGGTGGTCCTGGCTGCTCTACTACAAGGTGTCCAGGCTCAGG TGCACCCGGTGGAGTCTGGGGGAGGCTTGGTGCAGACTGGGGGGT CTCTGAGACTCTCCTGTGCAGCCTCTGCTGGTATCTTCAGTATCAAT GTCATGGGCTGGTACCGCCAGGCTCAGGGAAGCAGCGCGAATTG GTCGCGAGTATAACTAGTCGTGGTGATACAACGTATGCGAACTCCG TGAAGGGCCGATTCACCATCTCCAGAGACAACGCCAAGAACACGG TATATCTGCAAATGAACGCCCTGAAACCTGAGGACACAGCCGTCTA TTACTGTAATTTAAAGGGGACAGACTATAGTGGTACATCCACCCAG ACCTTCGACAGACAGGGCCAGGGGACCCAGGTCACCGTCTCTTCG |

APPENDIX

| | | |
|---|---|---|
| | | GAACCCAAGACACCAAAACCACAACCACAACCACAACCA<br>CAACCCAATCCTACAACAGAATCCAAGTGTCCCAAATGTCCAGCCC<br>CTGAGCTCCTGGGAGGGCCCTCAGTCTTCATCTTCCCCCCGAAACC<br>CAAGGACGTCCTCTCCATC |
| 24 | Anti-BCMA<br>V$_H$H 1<br>Amino Acid | MAVVLAALLQGVQAQVHPVESGGGLVQTGGSLRLSCAASAGIFSINV<br>MGWYRQAPGKQRELVASITSRGDTTYANSVKGRFTISRDNAKNTVYL<br>QMNALKPEDTAVYYCNLKGTDYSGTSTQTFDRQGQGTQVTVSSEPKT<br>PKPQPQPQPQPQPNPTTESKCPKCPAPELLGGPSVFIFPPKPKDVLSI |
| 25 | Anti-BCMA<br>V$_H$H1 CDR1 | INVMG |
| 26 | Anti-BCMA<br>V$_H$H1 CDR2 | SITSRGDTTYANSVKG |
| 27 | Anti-BCMA<br>V$_H$H1 CDR3 | LKGTDYSGTSTQTFDR |
| 28 | Anti-BCMA<br>V$_H$H 2<br>Amino Acid | QVQLVESGGGLVQPGESLRLSCAASTNIFSISPMGWYRQAPGKQRELV<br>AAIHGFSTLYADSVKGRFTISRDNAKNTIYLQMNSLKPEDTAVYYCNK<br>VPWGDYHPRNVYWGQGTQVTVSSEPKTPKPQPQPQPQPQPNPTTE<br>SKCPKCPAPELLGGPSVFIFPPKPKDVLSI |
| 29 | Anti-BCMA<br>V$_H$H2 CDR1 | ISPMG |
| 30 | Anti-BCMA<br>V$_H$H2 CDR2 | AIHGFSTLYADSVKG |
| 31 | Anti-BCMA<br>V$_H$H2 CDR3 | VPWGDYHPRNVY |
| 32 | human CD3-ε | MQSGTHWRVLGLCLLSVGVWGQDGNEEMGGITQTPYKVSISGTTVIL<br>TCPQYPGSEILWQHNDKNIGGDEDDKNIGSDEDHLSLKEFSELEQSGY<br>YVCYPRGSKPEDANFYLYLRARVCENCMEMDVMSVATIVIVDICITG<br>GLLLLVYYWSKNRKAKAKPVTRGAGAGGRQRGQNKERPPPVPNPDY<br>EPIRKGQRDLYSGLNQRRI |
| 33 | human CD3-γ | MEQGKGLAVLILAIILLQGTLAQSIKGNHLVKVYDYQEDGSVLLTCDA<br>EAKNITWFKDGKMIGFLTEDKKKWNLGSNAKDPRGMYQCKGSQNKS<br>KPLQVYYRMCQNCIELNAATISGFLFAEIVSIFVLAVGVYFIAGQDGVR<br>QSRASDKQTLLPNDQLYQPLKDREDDQYSHLQGNQLRRN |
| 34 | human CD3-δ | MEHSTFLSGLVLATLLSQVSPFKIPIEELEDRVFVNCNTSITWVEGTVG<br>TLLSDITRLDLGKRILDPRGIYRCNGTDIYKDKESTVQVHYRMCQSCV<br>ELDPATVAGIIVTDVIATLLLALGVFCFAGHETGRLSGAADTQALLRN<br>DQVYQPLRDRDDAQYSHLGGNWARNKS |
| 35 | human CD3-ζ | MKWKALFTAAILQAQLPITEAQSFGLLDPKLCYLLDGILFIYGVILTAL<br>FLRVKFSRSADAPAYQQGQNQLYNELNLGRREEYDVLDKRRGRDPE<br>MGGKPQRRKNPQEGLYNELQKDKMAEAYSEIGMKGERRRGKGHDG<br>LYQGLSTATKDTYDALHMQALPPR |
| 36 | human TCR α-<br>chain | MAGTWLLLLLALGCPALPTGVGGTPFPSLAPPIMLLVDGKQQMVVC<br>LVLDVAPPGLDSPIWFSAGNGSALDAFTYGPSPATDGTWTNLAHLSLP<br>SEELASWEPLVCHTGPGAEGHSRSTQPMHLSGEASTARTCPQEPLRGT<br>PGGALWLGVLRLLLFKLLLFDLLLTCSCLCDPAGPLPSPATTTRLRAL<br>GSHRLHPATETGGREATSSPRPQPRDRRWGDTPPGRKPGSPVWGEGS<br>YLSSYPTCPAQAWCSRSALRAPSSSLGAFFAGDLPPPLQAGA |
| 37 | human TCR α-<br>chain C region | PNIQNPDPAVYQLRDSKSSDKSVCLFTDFDSQTNVSQSKDSDVYITDK<br>TVLDMRSMDFKSNSAVAWSNKSDFACANAFNNSIIPEDTFFPSPESSC<br>DVKLVEKSFETDTNLNFQNLSVIGFRILLLKVAGFNLLMTLRLWSS |
| 38 | human TCR α-<br>chain V region<br>CTL-L17 | MAMLLGASVLILWLQPDWVNSQQKNDDQQVKQNSPSLSVQEGRISIL<br>NCDYTNSMFDYFLWYKKYPAEGPTFLISISSIKDKNEDGRFTVFLNKS<br>AKHLSLHIVPSQPGDSAVYFCAAKGAGTASKLTFGTGTRLQVTL |
| 39 | human TCR β-<br>chain C region | EDLNKVFPPEVAVFEPSEAEISHTQKATLVCLATGFFPDHVELSWWVN<br>GKEVHSGVSTDPQPLKEQPALNDSRYCLSSRLRVSATFWQNPRNHFR<br>CQVQFYGLSENDEWTQDRAKPVTQIVSAEAWGRADCGFTSVSYQQG<br>VLSATILYEILLGKATLYAVLVSALVLMAMVKRKDF |
| 40 | human TCR β-<br>chain V region<br>CTL-L17 | MGTSLLCWMALCLLGADHADTGVSQNPRHNITKRGQNVTFRCDPISE<br>HNRLYWYRQTLGQGPEFLTYFQNEAQLEKSRLLSDRFSAERPKGSFST<br>LEIQRTEQGDSAMYLCASSLAGLNQPQHFGDGTRLSIL |

| | | |
|---|---|---|
| 41 | human TCR β-<br>chain V region<br>YT35 | MDSWTFCCVSLCILVAKHTDAGVIQSPRHEVTEMGQEVTLRCKPISGH<br>NSLFWYRQTMMRGLELLIYFNNNVPIDDSGMPEDRFSAKMPNASFST<br>LKIQPSEPRDSAVYFCASSFSTCSANYGYTFGSGTRLTVV |
| 42 | human BCMA<br>canonical<br>polypeptide<br>sequence | MLQMAGQCSQNEYFDSLLHACIPCQLRCSSNTPPLTCQRYCNASVTNS<br>VKGTNAILWTCLGLSLIISLAVFVLMFLLRKINSEPLKDEFKNTGSGLL<br>GMANIDLEKSRTGDEIILPRGLEYTVEECTCEDCIKSKPKVDSDHCFPL<br>PAMEEGATILVTTKTNDYCKSLPAALSATEIEKSISAR |
| 43 | anti-BCMA<br>scFv 2 | DIVMTQSQRFMTTSVGDRVSVTCKASQSVDSNVAWYQQKPRQSPKA<br>LIFSASLRFSGVPARFTGSGSGTDFTLTISNLQSEDLAEYFCQQYNNYPL<br>TFGAGTKLELKGGGGSGGGGSSGGGSQVQLQQSGGGLVQPGGSLKLS<br>CAASGIDFSRYWMSWVRRAPGKGLEWIGEINPDSSTINYAPSLKDKFII<br>SRDNAKNTLYLQMSKVRSEDTALYYCASLYYDYGDAMDYWGQGTS<br>VTVSS |
| 44 | linker for anti-<br>BCMA scFv 1 | GGGGSGGGGSSGGGS |
| 45 | anti-BCMA<br>scFv 1 | QVQLVQSGAEVKKPGASVKVSCKASGYSFPDYYINWVRQAPGQGLE<br>WMGWIYFASGNSEYNQKFTGRVTMTRDTSSSTAYMELSSLRSEDTAV<br>YFCASLYDYDWYFDVWGQGTMVTVSSGGGGSGGGGSGGGGSDIVM<br>TQTPLSLSVTPGEPASISCKSSQSLVHSNGNTYLHWYLQKPGQSPQLLI<br>YKVSNRFSGVPDRFSGSGSGADFTLKISRVEAEDVGVYYCAETSHVP<br>WTFGQGTKLEIKS |

What is claimed is:

1. A recombinant nucleic acid encoding a T-cell receptor (TCR) fusion protein (TFP) comprising:
   (a) a TCR subunit comprising
      (i) at least a portion of a TCR extracellular domain, and
      (ii) a TCR intracellular domain comprising a stimulatory domain from an intracellular signaling domain of a TCR chain; and
   (b) an antibody domain comprising an antigen binding domain that is an anti-BCMA binding domain comprising
      (i) a CDR1 sequence as set forth in SEQ ID NO: 29, a CDR2 sequence as set forth in SEQ ID NO: 30, and a CDR3 sequence as set forth in SEQ ID NO: 31; or
      (ii) a CDR1 sequence as set forth in SEQ ID NO: 25, a CDR2 sequence as set forth in SEQ ID NO: 26, and a CDR3 sequence as set forth in SEQ ID NO: 27;
   wherein the TCR subunit and the antibody domain are operatively linked, and
   wherein the TFP incorporates into a functional TCR when expressed in a T-cell.

2. The recombinant nucleic acid of claim 1, wherein the anti-BCMA binding domain is connected to an extracellular domain of the TCR subunit by a linker.

3. The recombinant nucleic acid of claim 2, wherein the linker comprises $(G_4S)_n$, wherein G is glycine, S is serine, and n is an integer from 1 to 4.

4. The recombinant nucleic acid of claim 1, wherein the anti-BCMA binding domain comprises a single domain antibody.

5. The recombinant nucleic acid of claim 4, wherein the single domain antibody is a VHH domain.

6. The recombinant nucleic acid of claim 1, wherein the anti-BCMA binding domain comprises a CDR1 sequence as set forth in SEQ ID NO: 29, a CDR2 sequence as set forth in SEQ ID NO: 30, and a CDR3 sequence as set forth in SEQ ID NO: 31.

7. The recombinant nucleic acid of claim 6, wherein the anti-BCMA binding domain comprises a sequence as set forth in SEQ ID NO: 28.

8. The recombinant nucleic acid of claim 1, wherein the anti-BCMA binding domain comprises a CDR1 sequence as set forth in SEQ ID NO: 25, a CDR2 sequence as set forth in SEQ ID NO: 26, and a CDR3 sequence as set forth in SEQ ID NO: 27.

9. The recombinant nucleic acid of claim 8, wherein the anti-BCMA binding domain comprises a sequence as set forth in SEQ ID NO: 24.

10. The recombinant nucleic acid of claim 1, wherein the TCR intracellular domain comprises a stimulatory domain from an intracellular signaling domain of CD3 gamma.

11. The recombinant nucleic acid of claim 10, wherein the TCR subunit comprises a sequence identical to amino acids 23-182 of SEQ ID NO: 33.

12. The recombinant nucleic acid of claim 1, wherein the TCR intracellular domain comprises a stimulatory domain from an intracellular signaling domain of CD3 delta.

13. The recombinant nucleic acid of claim 12, wherein the TCR subunit comprises a sequence identical to amino acids 22-171 of SEQ ID NO: 34.

14. The recombinant nucleic acid of claim 1, wherein the TCR intracellular domain comprises a stimulatory domain from an intracellular signaling domain of CD3 epsilon.

15. The recombinant nucleic acid of claim 14, wherein the TCR subunit comprises a sequence identical to amino acids 23-207 of SEQ ID NO: 32.

16. The recombinant nucleic acid of claim 1, wherein the antibody domain is a mammalian antibody domain or a humanized antibody domain.

17. The recombinant nucleic acid of claim 1, wherein the TFP lacks a costimulatory domain.

18. A human T cell comprising the recombinant nucleic acid of claim 1.

19. A pharmaceutical composition comprising
   (a) the human T cell of claim 18; and
   (b) a pharmaceutically acceptable excipient.

* * * * *